United States Patent
Tabor

(10) Patent No.: US 9,132,202 B2
(45) Date of Patent: Sep. 15, 2015

(54) COMPOSITIONS AND METHODS FOR GENETIC MODIFICATION OF CELLS HAVING COSMETIC FUNCTION TO ENHANCE COSMETIC APPEARANCE

(76) Inventor: Aaron T. Tabor, Winston-Salem, NC (US)

( * ) Notice: Subject to any disclaimer, the term of this patent is extended or adjusted under 35 U.S.C. 154(b) by 105 days.

(21) Appl. No.: 13/383,612

(22) PCT Filed: Jul. 15, 2010

(86) PCT No.: PCT/US2010/042051
§ 371 (c)(1),
(2), (4) Date: Jan. 12, 2012

(87) PCT Pub. No.: WO2011/008904
PCT Pub. Date: Jan. 20, 2011

(65) Prior Publication Data
US 2012/0115938 A1     May 10, 2012

Related U.S. Application Data

(60) Provisional application No. 61/226,518, filed on Jul. 17, 2009.

(51) Int. Cl.
| | |
|---|---|
| A61K 31/70 | (2006.01) |
| C07H 21/04 | (2006.01) |
| C07K 1/00 | (2006.01) |
| C12N 15/09 | (2006.01) |
| C12N 15/63 | (2006.01) |
| A61K 48/00 | (2006.01) |
| C07K 14/475 | (2006.01) |
| C12N 15/79 | (2006.01) |

(52) U.S. Cl.
CPC .............. *A61K 48/005* (2013.01); *A61K 48/00* (2013.01); *C07H 21/04* (2013.01); *C07K 14/475* (2013.01); *C12N 15/63* (2013.01); *C12N 15/79* (2013.01)

(58) Field of Classification Search
CPC ..... A61K 48/00; A61K 48/005; C07H 21/04; C07K 14/475; C12N 15/63; C12N 15/79
USPC .............. 514/44 R; 435/320.1, 455; 530/350; 536/23.5
See application file for complete search history.

(56) References Cited

U.S. PATENT DOCUMENTS

| | | |
|---|---|---|
| 2003/0068297 A1 | 4/2003 | Jain |
| 2007/0066552 A1 | 3/2007 | Clarke et al. |
| 2007/0224150 A1* | 9/2007 | Chung |
| 2008/0119433 A1 | 5/2008 | Tabor |
| 2008/0234194 A1* | 9/2008 | Brem et al. |
| 2009/0270487 A1* | 10/2009 | Wyatt et al. |
| 2010/0184158 A1* | 7/2010 | Williams |

FOREIGN PATENT DOCUMENTS

WO      WO 90/08771    * 8/1990

OTHER PUBLICATIONS

Uzan et al., 2005, Geneseq Accession No. AEB13002, computer printout pp. 3-5.*
Gorecki, D., 2001, Expert Opin. Emerging Drugs, 6(2): 187-198.*
Bennett, J., 2003, Gene Therapy, vol. 10, p. 977-982.*
Thomas et al., 2003, Nature Reviews/ Genetics, vol. 4, p. 346-358.*
Lebedeva et al., 2003, Seminars in Cancer Biology, vol. 12, p. 169-178.*
Kodama et al., 2006, Current Medicinal Chemistry, vol. 13, p. 2155-2161.*
Skolnick et al., 2000, Trends in Biotech, vol. 18, p. 34-39.*
Tomasinsig et al., 2005, Current Protein and Peptide Science, vol. 6, p. 23-34.*
Smallwood et al., 2002, Virology, vol. 304, p. 135-145.*
Chattopadhyay et al., 2004, Virus Research, vol. 99, p. 139-145.*
http://www.uniprot.org/uniprot/P21781.
International Search Report issued in PCT/US2010/042051 on Sep. 17, 2010.

* cited by examiner

*Primary Examiner* — Shin Lin Chen
(74) *Attorney, Agent, or Firm* — Bibby, McWilliams & Kearney PLLC; John Weatherspoon; Shilpa Ghurye

(57) ABSTRACT

Disclosed are methods and compositions to genetically modify substantially intact cells having cosmetic function to enhance the cosmetic appearance in mammals so as to enhance and/or maintain a biochemical and/or physiological process that has a positive effect on cosmetic appearance. The methods and compositions may provide cosmetic benefits such as reduced skin sagging, increased skin thickness, reduced wrinkles, increased skin thickness and collagen content, increased skin tone and elasticity, increased skin hydration, and improved skin texture and color.

13 Claims, 23 Drawing Sheets

COLA1A - MAIN PROCOLLAGEN

SEQ ID NO: 1
CDS                120..4514
polyA_signal       4763..4775
polyA_site         4798
polyA_signal       5891..5896
polyA_site         5921

```
   1 agcagacggg agtttctcct cggggtcgga gcaggaggca cgccggagtgt gaggccacgc
  61 atgagcggac gctaaccccc tccccagcca caaagagtct acatgtctag ggtctagaca
 121 tgttcagctt tgtggacctc cggctcctgc tcctcttagc ggccaccgcc ctcctgacgc
 181 acggccaaga ggaaggccaa gtcgagggcc aagacgaaga catcccacca atcacctgcg
 241 tacagaacgg cctcaggtac catgaccgag acgtgtggaa acccgagccc tgccggatct
 301 gcgtctgcga caacggcaag gtgttgtgcg atgacgtgat ctgtgacgag accaagaact
 361 gccccggcgc cgaagtcccc gagggcgagt gctgtccccg ctgccccgac ggctcagagt
 421 cacccaccga ccaagaaacc accggcgtcg agggacccaa gggagacact ggccccccgag
 481 gcccaagggg accgcaggc ccccctggcc gagatggcat ccctggacag cctggacttc
 541 ccgaccccc cggaccccc ggacctcccg gaccccctgg cctcggagga aactttgctc
 601 cccagctgtc ttatggctat gatgagaaat caaccggagg aatttccgtg cctggcccca
 661 tgggtccctc tggtcctcgt ggtccccctg gccccctgg tgcacctggt ccccaaggct
 721 tccaaggtcc ccctggtgag cctggcgagc ctggagcttc aggtcccatg ggtccccgag
 781 gtccccagg tccccctgga aagaatggag atgatgggga agctggaaaa cctggtcgtc
 841 ctggtgagcg tgggcctcct gggcctcagg gtgctcgagg attgcccgga acagctggcc
 901 tccctggaat gaagggacac agaggtttca gtggtttgga tggtgccaag ggagatgctg
 961 gtcctgctgg tcctaagggt gagcctggca gccctggtga aaatggagct cctggtcaga
1021 tgggccccg tggcctgcct ggtgagagag tcgccctgg agcccctggc cctgctggtg
1081 ctcgtggaaa tgatggtgct actggtgctg ccgggcccc tggtcccacc ggccccgctg
1141 gtcctcctgg cttccctggt gctgttggtg ctaaggggtga agctggtccc caagggcccc
1201 gaggctctga aggtcccag ggtgtgcgtg gtgagcctgg ccccctggc cctgctggtg
1261 ctgctggccc tgctggaaac cctggtgctg atggacagcc tggtgctaaa ggtcccaatg
1321 gtgctcctgg tattgctggt gctcctgggct tccctggtgc ccgaggcccc tctgaccccc
1381 agggccccgg cggccctcct ggtccccaagg gtaacagcgg tgaacctggt gctcctggca
1441 gcaaaggaga cactggtgct aagggagagc ctggcccgt tggtgttcaa ggaccccctg
1501 gcccctgctgg agaggaagga aagcgaggag ctcgaggtga acccggaccc actggcctgc
1561 ccggaccccc tggcgagcgt ggtggacctg gtagccgtgg tttccctggc gcagatggtg
1621 ttgctggtcc caagggtccc gctggtgaac gtggttctcc tggccccgct ggccccaaag
1681 gatctcctgg tgaagctggt cgtccccgtg aagctgtct gcctggtgcc aagggtctga
1741 ctggaagccc tggcagccct ggtcctgatg gcaaaactgg ccccccttggt cccgccggtc
1801 aagatggtcg ccccgaccc caggcccac ctggtgcccg tggtcaggct ggtgtgatgg
1861 gattccctgg acctaaaggt gctgctgag agccccggcaa ggctggagag cgaggtgttc
1921 ccggaccccc tggcgctgtc ggtcctgctg gcaaagatga gaggctgga gctcagggac
1981 ccctggccc tgctggtccc gctggcgaga gaggtgaaca aggccctgct ggctccccccg
2041 gattccaggg tctccctggt cctctggtc tccaggtga agcaggcaaa cctggtgaac
2101 agggtgttcc tggagacctt ggcgcccctg gccctctgg agcaagaggc gagagaggtt
2161 tccctggcga gcgtggtgtg caaggtcccc ctggtcctgc tggaccccga ggggccaacg
2221 gtgctcccgg caacgatggt gctaagggtg atgctggtgc ccctggagct cccggtagcc
2281 agggcgcccc tggcctttcag ggaatgcctg gtgaacgtgg tgcagctggt cttcagggc
2341 ctaagggtga cagaggtgat gctggtccca aggtgctga tggctctcct ggcaaagatg
2401 gcgtccgtgg tctgaccggc cccattggtc tccctggccc tgctggtgcc cctggtgaca
2461 aggtgaaag tggtccccagc ggccctgctg gtcccactgg agctcgtggt gcccccggag
2521 accgtggtga gcctggtccc cccggccctg ctggctttgc tggccccct ggtgctgacg
2581 gccaacctgg tgctaaaggc gaacctggtg atgctggtgc caaaggcgat gctggtcccc
2641 ctgggcctgc cggacccgct ggaccccctg gccccattgg taatgttggt gctcctggag
```

FIG. 1A

```
2701 ccaaaggtgc tcgcggcagc gctggtcccc ctggtgctac tggtttccct ggtgctgctg
2761 gccgagtcgg tcctcctggc ccctctggaa atgctggacc ccctggcccet cctggtcctg
2821 ctggcaaaga aggcggcaaa ggtccccgtg gtgagactgg ccctgctgga cgtcctggtg
2881 aagttggtcc ccctggtccc cctggccctg ctggcgagaa aggatcccct ggtgctgatg
2941 gtcctgctgg tgctcctggt actcccgggc ctcaaggtat tgctggacag cgtggtgtgg
3001 tcggcctgcc tggtcagaga ggagagagag gcttccctgg tcttcctggc ccctctggtg
3061 aacctggcaa acaaggtccc tctggagcaa gtggtgaacg tggtccccccc ggtcccatgg
3121 gcccccctgg attggctgga cccctggtg aatctggacg tgagggggct cctgctgccg
3181 aaggttcccc tggacgagac ggtctcctg gcgccaaggg tgaccgtggt gagaccggcc
3241 ccgctggacc ccctggtgct cctggtgctc ctggtgcccc tggccccgtt ggccctgctg
3301 gcaagagtgg tgatcgtggt gagactggtc ctgctggtcc cgccggtccc gtcggccccg
3361 tcggcgcccg tggccccgcc gcaccccaag gccccgtgg tgacaagggt gagacaggcg
3421 aacagggcga cagaggcata aagggtcacc gtggcttctc tggcctccag ggtccccctg
3481 gccctcctgg ctctcctggt gaacaaggtc cctctggagc ctctggtcct gctggtcccc
3541 gaggtcccce tggctctgct ggtgctcctg gcaaagatgg actcaacggt ctccctggcc
3601 ccattgggcc cctggtcct cgcggtcgca ctggtgatgc tggtcctgtt ggtccccccg
3661 gccctcctgg acctcctggt cccctggtc ctcccagcgc tggtttcgac ttcagcttcc
3721 tgccccagcc acctcaagag aaggctcacg atggtggccg ctactaccgg gctgatgatg
3781 ccaatgtggt tcgtgaccgt gacctcgagg tggacaccac cctcaagagc ctgagccagc
3841 agatcgagaa catccggagc ccagagggaa gccgcaagaa ccccgcccgc acctgccgtg
3901 acctcaagat gtgccactct gactggaaga gtggagagta ctggattgac cccaaccaag
3961 gctgcaacct ggatgccatc aaagtctict gcaacatgga gactggtgag acctgcgtgt
4021 accccactca gcccagtgtg gcccagaaga actggtacat cagcaagaac cccaaggaca
4081 agaggcatgt ctcgttcggc gagagcatga ccgatggatt ccagttcgag tatggcggcc
4141 agggctccga ccctgccgat gtggccatcc agctgacctt cctgcgcctg atgtccaccg
4201 aggcctccca gaacatcacc taccactgca gaacagcgt ggcctacatg gaccagcaga
4261 ctggcaacct caagaaggcc ctgctcctca agggctccaa cgagatcgag atccgcgccg
4321 agggcaacag ccgcttcacc tacagcgtca ctgtcgatgg ctgcacgagt cacaccggag
4381 cctggggcaa gacagtgatt gaatacaaaa ccaccaagtc ctcccgcctg cccatcatcg
4441 atgtggcccc cttggacgtt ggtgcccag accaggaatt cggcttcgac gttggccctg
4501 tctgcttcct gtaaactccc tccatcccaa cctggctccc tcccacccaa ccaactttcc
4561 ccccaacccg gaacagaca agcaacccaa actgaacccc ccaaaaagcc aaaaaatggg
4621 agacaatttc acatggactt tggaaaatat ttttttcctt tgcattcatc tctcaaactt
4681 agtttttatc tttgaccaac cgaacatgac caaaaaccaa aagtgcattc aaccttacca
4741 aaaaaaaaaa aaaaaaaaaa agaataaata aataagtttt taaaaaagga agcttggtcc
4801 acttgcttga agacccatgc ggggtaagt ccctttctgc ccgttgggtt atgaaacccc
4861 aatgctgccc tttctgctcc ttctccaca ccccccttgg cctcccctcc actccttccc
4921 aaatctgtct ccccagaaga cacaggaaac aatgtattgt ctgcccagca atcaaaggca
4981 atgctcaaac acccaagtgg cccccaccct cagcccgctc ctgcccgccc agcaccccca
5041 ggccctgggg acctggggtt ctcagactgc caaagaagcc ttgccatctg gcgctcccat
5101 ggctcttgca acatctcccc ttcgttttg aggggtcat gccgggggag ccaccagccc
5161 ctcactgggt tcggaggaga gtcaggaacg gccacgacaa agcagaaaca tcggatttgg
5221 ggaacgcgtg tcatcccttg tgccgcagcc tgggcgggag agactgttct gttctgttcc
5281 ttgtgtaact gtgttgctga aagactacct cgttcttgtc ttgatgtgtc accgcggcaa
5341 ctgcctgggg gcggggatgg gggcagggtg gaagcggctc cccattttta taccaaaggt
5401 gctacatcta tgtgatgggt ggggtgggga gggaatcact ggtgctatag aaattgagat
5461 gccccccag gccagcaaat gttcctttt gttcaaagtc tatttttatt ccttgatatt
5521 ttttctttct ttttttttt ttttgtggat ggggactgt gaattttct aaaggtgcta
5581 tttaacatgg gaggagagcg tgtgcgctcc agcccagccc gctgctcact ttccaccctc
5641 tctccacctg cctctggctt ctcaggcctc tgctctccga cctctctcct ctgaaaccct
5701 cctccacagc tgcagcccat cctcccggct ccctcctagt ctgtcctgcg tcctctgtcc
5761 ccgggtttca gagacaactt cccaaagcac aaagcagttt ttccctaggg gtgggaggaa
5821 gcaaaagact ctgtacctat tttgtatgtg tataataatt tgagatgttt ttaattattt
5881 tgattgctgg aataaagcat gtggaaatga cccaaacata a
```

FIG. 1B

SEQ ID NO: 2

MFSFVDLRLLLLLAATALLTHGQEEGQVEGQDEDIPPITCVQNGLRYHDRDVWKPEPCRICVCDNGKVLCDDVICD
ETKNCPGAEVPEGECCPVCPDGSESPTDQETTGVEGPKGDTGPRGPRGPAGPPGRDGIPGQPGLPGPPGPPGPPGP
PGLGGNFAPQLSYGYDEKSTGGISVPGPMGPSGPRGLPGPPGAPGPQGFQGPPGEPGEPGASGPMGPRGPPGPPGK
NGDDGEAGKPGRPGERGPPGPQGARGLPGTAGLPGMKGHRGFSGLDGAKGDAGPAGPKGEPGSPGENGAPGQMGPR
GLPGERGRPGAPGPAGARGNDGATGAAGPPGPTGPAGPPGFPGAVGAKGEAGPQGPRGSEGPQGVRGEPGPPGPAG
AAGPAGNPGADGQPGAKGANGAPGIAGAPGFPGARGPSGPQGPGGPPGPKGNSGEPGAPGSKGDTGAKGEPGPVGV
QGPPGPAGEEGKRGARGEPGPTGLPGPPGERGGPGSRGFPGADGVAGPKGPAGERGSPGPAGPKGSPGEAGRPGEA
GLPGAKGLTGSPGSPGPDGKTGPPGPAGQDGRPGPPGPPGARGQAGVMGFPGPKGAAGEPGKAGERGVPGPPGAVG
PAGKDGEAGAQGPPGPAGPAGERGEQGPAGSPGFQGLPGPAGPPGEAGKPGEQGVPGDLGAPGPSGARGERGFPGE
RGVQGPPGPAGPRGANGAPGNDGAKGDAGAPGAPGSQGAPGLQGMPGERGAAGLPGPKGDRGDAGPKGADGSPGKD
GVRGLTGPIGPPGPAGAPGDKGESGPSGPAGPTGARGAPGDRGEPGPPGPAGFAGPPGADGQPGAKGEPGDAGAKG
DAGPPGPAGPAGPPGPIGNVGAPGAKGARGSAGPPGATGFPGAAGRVGPPGPSGNAGPPGPPGPAGKEGGKGPRGE
TGPAGRPGEVGPPGPPGPAGEKGSPGADGPAGAPGTPGPQGIAGQRGVVGLPGQRGERGFPGLPGPSGEPGKQGPS
GASGERGPPGPMGPPGLAGPPGESGREGAPAAEGSPGRDGSPGAKGDRGETGPAGPPGAPGAPGAPGPVGPAGKSG
DRGETGPAGPAGPVGPVGARGPAGPQGPRGDKGETGEQGDRGIKGHRGFSGLQGPPGPPGSPGEQGPSGASGPAGP
RGPPGSAGAPGKDGLNGLPGPIGPPGPRGRTGDAGPVGPPGPPGPPGPPGPPSAGFDFSFLPQPPQEKAHDGGRYY
RADDANVVRDRDLEVDTTLKSLSQQIENIRSPEGSRKNPARTCRDLKMCHSDWKSGEYWIDPNQGCNLDAIKVFCN
METGETCVYPTQPSVAQKNWYISKNPKDKRHVWFGESMTDGFQFEYGGQGSDPADVAIQLTFLRLMSTEASQNITY
HCKNSVAYMDQQTGNLKKALLLKGSNEIEIRAEGNSRFTYSVTVDGCTSHTGAWGKTVIEYKTTKSSRLPIIDVAP
LDVGAPDQEFGFDVGPVCFL

5' OLIGO WITH NheI-Kozak-ORF:

SEQ ID NO: 3

5' GATCGCTAGCGCCGCCACCATGTTCAGCTTTGTGGACCTCCGGCTCCTGC 3'

3' OLIGO WITH HindIII-stop_ORF:

SEQ ID NO: 4

5' CGATAAGCTTTTACAGGAAGCAGACAGGGCCAACGTCGAAGCCG 3'

FIG. 1C

ELASTIN: MAIN SKIN "TROPOELASTIN"

SEQ ID NO: 5

CDS             1..2274

```
   1 atggcgggtc tgacggcggc ggccccgcgg cccggagtcc tcctgctcct gctgtccatc
  61 ctccacccct ctcggcctgg aggggtccct ggggccattc tggtggagt tcctggagga
 121 gtcttttatc caggggctgg tctcggagcc cttggaggag gagcgctggg gcctggaggc
 181 aaacctctta agccagttcc cggagggctt gcgggtgctg gccttgggc agggctcggc
 241 gccttccccg cagttacctt tccgggggct ctggtgcctg gtggagtggc tgacgctgct
 301 gcagcctata aagctgctaa ggctggcgct gggcttggtg gtgtcccagg agttggtggc
 361 ttaggagtgt ctgcaggtgc ggtggttcct cagcctggag ccggagtgaa gcctgggaaa
 421 gtgccgggtg tggggctgcc aggtgtatac ccaggtggcg tgctcccagg agctcggttc
 481 cccggtgtgg gggtgctccc tggagttccc actggagcag gagttaagcc caaggctcca
 541 ggtgtaggtg gagcttttgc tggaatccca ggagttggac cctttggggg accgcaacct
 601 ggagtcccac tggggtatcc catcaaggcc cccaagctgc ctggtggcta tggactgccc
 661 tacaccacag ggaaactgcc ctatggctat gggcccgag gagtggctgg tgcagcgggc
 721 aaggctggtt acccaacagg gacaggggtt ggcccccagg cagcagcagc agcggcagct
 781 aaagcagcag caaagttcgg tgctggagca gccggagtcc tccctggtgt tggagggct
 841 ggtgttcctg gcgtgcctgg ggcaattcct ggaattgag gcatcgcagg cgttgggact
 901 ccagctgcag ctgcagctgc agcagcagcc gctaaggcag ccaagtatgg agctgctgca
 961 ggcttagtgc ctggtgggcc aggctttggc ccgggagtag ttggtgtccc aggagctggc
1021 gttccaggtg ttggtgtccc aggagctggg attccagttg tccaggtgc tgggatccca
1081 ggtgctgcgg ttccagggg tgtgtcacca gaagcagctg ctaaggcagc tgcaaaggca
1141 gccaaatacg gggccaggcc cggagtcgga gttggaggca ttcctactta cggggttgga
1201 gctgggggct ttcccggctt tggtgtcgga gtcggaggta tccctggagt cgcaggtgtc
1261 cctagtgtcg gaggtgttcc cggagtcgga ggtgtcccgg agttggcat tcccccgaa
1321 gctcaggcag cagctgccgc caaggctgcc aagtacgag tggggacccc agcagctgca
1381 gctgctaaag cagccgccaa agccgcccag tttgggttag ttcctggtgt cggcgtggct
1441 cctggagttg gcgtggctcc tggtgtcggt gtggctcctg gagttggctt ggctcctgga
1501 gttggcgtgg ctcctggagt tggtgtggct cctggcgttg gcgtggctcc cggcattggc
1561 cctggtggag ttgcagctgc agcaaaatcc gctgccaagg tggctgccaa agcccagctc
1621 cgagctgcag ctgggcttgg tgctggcatc cctggacttg gagttggtgt cggcgtccct
1681 ggacttggag ttggtgctgg tgttcctgga cttggagttg gtgctggtgt tcctggcttc
1741 ggggcaggtg cagatgaggg agttaggcgg agcctgtccc ctgagctcag ggaaggagat
1801 ccctcctcct ctcagcacct ccccagcacc ccctcatcac ccagggtacc tggagccctg
1861 gctgccgcta aagcagccaa atatggagca gcagtgcctg gggtccttgg agggctcggg
1921 gctctcggtg gagtaggcat cccaggcgt gtggtgggag ccggacccgc cgccgccgct
1981 gccgcagcca aagctgctgc caaagccgcc cagtttggcc tagtgggagc cgctgggctc
2041 ggaggactcg gagtcggagg gcttggagtt ccaggtgttg gggccttgg aggtatacct
2101 ccagctgcag ccgctaaagc agctaaatac ggtgctgctg gccttggagg tgtcctaggg
2161 ggtgccgggc agttcccact tggaggagtg gcagcaagac ctggcttcgg attgtctccc
2221 attttcccag gtggggcctg cctggggaaa gcttgtggcc ggaagagaaa atga
```

FIG. 2A

SEQ ID NO: 6

MAGLTAAAPRPGVLLLLLSILHPSRPGGVPGAIPGGVPGGVFYPGAGLGALGGGALGPGGKPLKPVPGGLAGAGLGA
GLGAFPAVTFPGALVPGGVADAAAAYKAAKAGAGLGGVPGVGGLGVSAGAVVPQPGAGVKPGKVPGVGLPGVYPGGV
LPGARFPGVGVLPGVPTGAGVKPKAPGVGGAFAGIPGVGPFGGPQPGVPLGYPIKAPKLPGGYGLPYTTGKLPYGYG
PGGVAGAAGKAGYPTGTGVGPQAAAAAAAKAAAKFGAGAAGVLPGVGGAGVPGVPGAIPGIGGIAGVGTPAAAAAAA
AAAKAAKYGAAAGLVPGGPGFGPGVVGVPGAGVPGVGVPGAGIPVVPGAGIPGAAVPGVVSPEAAAKAAAKAAKYGA
RPGVGVGGIPTYGVGAGGFPGFGVGVGGIPGVAGVPSVGGVPGVGGVPGVGISPEAQAAAAAKAAKYGVGTPAAAAA
KAAAKAAQFGLVPGVGVAPGVGVAPGVGVAPGVGLAPGVGVAPGVGVAPGVGVAPGIGPGGVAAAAKSAAKVAAKAQ
LRAAAGLGAGIPGLGVGVGVPGLVGAGVPGLGVGAGVPGFGAGADEGVRRSLSPELREGDPSSSQHLPSTPSSPRV
PGALAAAKAAKYGAAVPGVLGGLGALGGVGIPGGVVGAGPAAAAAAAKAAAKAAQFGLVGAAGLGGLGVGGLGVPGV
GGLGGIPPAAAAKAAKYGAAGLGGVLGGAGQFPLGGVAARPGFGLSPIFPGGACLGKACGRKRK

5' OLIGO WITH NheI-Kozak-ORF:

SEQ ID NO: 7

5'  GATCGCTAGCGCCGCCACCATGGCGGGTCTGACGGCGGCGGCCCCGCGG   3'

SEQ ID NO: 8

5'  GCTAAGATCTTCATTTTCTCTTCCGGCCACAAGCTTTCCCCAGG   3'

FIG. 2B

EC-SOD (SOD3)

SEQ ID NO: 9

| | |
|---|---|
| CDS | 664..1386 |
| polyA_signal | 1965..1970 |
| polyA_site | 1984 |

```
   1 ggatccagag atttagattt tttataagct ttcctgccac cgaaacgggt gtttgggacc
  61 tcacgaggcc ctgttcattc ttcgtcgctg cgctccccac tctgtactgg atgcatttac
 121 tgacgttgtt gtctccgtcc ccagagtatg aaccccaag gtgactcatg cagctgtggg
 181 tgcccggcat acagcatggt gactggaatg gatgagcacc caataaacat ttgttgcagg
 241 aatgcaggag gacgggcagg ccagcaagca ggctgcctgg ttttccccac atgggctttt
 301 ctgggaaaga agagcttcta tttttggaaa gggctgctat gattgagaaa agttcatggc
 361 agcaaaaaaa ggacagacgt cgggagggaa acactcctag ttctcccaga caacacattt
 421 tttaaaaaga ctccttcatc tctttaataa taacggtaac gacaatgaca atgatgatta
 481 cttatgagtg cggctagtgc cagccactgt gttgtcactg ggcgagtaat gatctcattg
 541 gatcttcacg gtgggcgtgc ggggctccag ggacagcctg cgttcctggg ctggctgggt
 601 gcagctctct tttcaggaga gaaagctctc ttggaggagc tggaaaggtg cccgactcca
 661 gcc atg ctgg cgctactgtg ttcctgcctg ctcctggcag ccggtgcctc ggacgcctgg
 721 acgggcgagg actcggcgga gcccaactct gactcggcgg agtggatccg agacatgtac
 781 gccaaggtca cggagatctg gcaggaggtc atgcagcggc gggacgacga cggcacgctc
 841 cacgccgcct gccaggtgca gccgtcggcc acgctggacg ccgcgcagcc ccgggtgacc
 901 ggcgtcgtcc tcttccggca gcttgcgccc cgcgccaagc tcgacgcctt cttcgccctg
 961 gagggcttcc cgaccgagcc gaacagctcc agccgcgcca tccacgtgca ccagttcggg
1021 gacctgagcc agggctgcga gtccaccggg ccccactaca acccgctggc cgtgccgcac
1081 ccgcagcacc cgggcgactt cggcaacttc gcggtccgcg acggcagcct ctggaggtac
1141 cgcgccggcc tggccgcctc gctcgcgggc ccgcactcca tcgtgggccg ggccgtggtc
1201 gtccacgctg gcgaggacga cctgggccgc ggcggcaacc aggccagcgt ggagaacggg
1261 aacgcgggcc ggcggctggc ctgctgcgtg gtgggcgtgt gcgggcccgg gctctgggag
1321 cgccaggcgc gggagcactc agagcgcaag aagcggcggc gcgagagcga gtgcaaggcc
1381 gcc tga gcgc ggccccacc cggcggcggc cagggacccc cgaggccccc ctctgccttt
1441 gagcttctcc tctgctccaa cagacacctt ccactctgag gtctcacctt cgcctctgct
1501 gaagtctccc cgcagccctc tccacccaga ggtctcccta taccgagacc caccatcctt
1561 ccatcctgag gaccgcccca accctcggag ccccccactc agtaggtctg aaggcctcca
1621 tttgtaccga aacaccccgc tcacgctgac agcctcctag gctccctgag gtacctttcc
1681 acccagaccc tccttcccca ccccataagc cctgagactc ccgcctttga cctgacgatc
1741 ttcccccttc ccgccttcag gttcctccta ggcgctcaga ggccgctctg ggggttgcc
1801 tcgagtcccc ccaccctcc ccacccacca ccgctcccgc ggcaagccag cccgtgcaac
1861 ggaagccagg ccaactgccc cgcgtcttca gctgtttcgcatccaccgcc accccactga
1921 gagctgctcc tttgggggaa tgtttggcaa cctttgtgtt acagattaaa aattcagcaa
1981 ttca
```

FIG. 3A

SEQ ID NO: 10

MLALLCSCLLLAAGASDAWTGEDSAEPNSDSAEWIRDMYAKVTEIWQEVMQRRDDDGTLHAACQVQPSATLDAAQPR
VTGVVLFRQLAPRAKLDAFFALEGFPTEPNSSSRAIHVHQFGDLSQGCESTGPHYNPLAVPHPQHPGDFGNFAVRDG
SLWRYRAGLAASLAGPHSIVGRAVVVHAGEDDLGRGGNQASVENGNAGRRLACCVVGVCGPGLWERQAREHSERKKR
RRESECKAA

5' OLIGO WITH NheI-Kozak-ORF:

SEQ ID NO: 11

5'  GATCGCTAGCGCCGCCACCATGCTGGCGCTACTGTGTTCCTGCCTGCTCCTGGCAG  3'

3' OLIGO WITH HindIII-stop_ORF:

SEQ ID NO: 12

OLIGO SEQUENCE (46-mer):

5'  CGATAAGCTTTTCAGGCGGCCTTGCACTCGCTCTCGCGCCGCCGCTT  3'

FIG. 3B

TIMP-1
SEQ ID NO: 13

| | |
|---|---|
| CDS | 193..816 |
| sig_peptide | 193..261 |
| mat_peptide | 262..813 |
| polyA_signal | 893..898 |
| polyA_site | 911 |
| polyA_site | 916 |

```
  1 tttcgtcggc ccgccccttg gcttctgcac tgatggtggg tggatgagta atgcatccag
 61 gaagcctgga ggcctgtggt tccgcaccc gctgccaccc ccgcccctag cgtggacatt
121 tatcctctag cgctcaggcc ctgccgccat cgccgcagat ccagcgccca gagagacacc
181 agagaaccca ccatggcccc ctttgagccc ctggcttctg gcatcctgtt gttgctgtgg
241 ctgatagccc ccagcagggc ctgcacctgt gtcccacccc acccacagac ggccttctgc
301 aattccgacc tcgtcatcag ggccaagttc gtggggacac cagaagtcaa ccagaccacc
361 ttataccagc gttatgagat caagatgacc aagatgtata agggttcca agccttaggg
421 gatgccgctg acatccggtt cgtctacacc cccgccatgg agagtgtctg cggatacttc
481 cacaggtccc acaaccgcag cgaggagttt ctcattgctg gaaaactgca ggatggactc
541 ttgcacatca ctacctgcag ttttgtggct ccctggaaca gcctgagctt agctcagcgc
601 cggggcttca ccaagaccta cactgttggc tgtgaggaat gcacagtgtt tccctgttta
661 tccatcccct gcaaactgca gagtggcact cattgcttgt ggacggacca gctcctccaa
721 ggctctgaaa agggcttcca gtcccgtcac cttgcctgcc tgcctcggga gccagggctg
781 tgcacctggc agtccctgcg gtcccagata gcctgaatcc tgcccggagt ggaagctgaa
841 gcctgcacag tgtccaccct gttcccactc ccatctttct tccggacaat gaaataaaga
901 gttaccaccc agcagaaaaa aaaaaaaaaa a
```

SEQ ID NO: 14

MAPFEPLASGILLLLWLIAPSRACTCVPPHPQTAFCNSDLVIRAKFVGTPEVNQTTLYQRYEIKMTKMYKGFQALGD
AADIRFVYTPAMESVCGYFHRSHNRSEEFLIAGKLQDGLLHITTCSFVAPWNSLSLAQRRGFTKTYTVGCEECTVFP
CLSIPCKLQSGTHCLWTDQLLQGSEKGFQSRHLACLPREPGLCTWQSLRSQIA

*5' OLIGO WITH NheI-Kozak-ORF:*

SEQ ID NO: 15

5'  GATCGCTAGCGCCGCCACCATGGCCCCCTTTGAGCCCCTGGCTTCTGGCATCCTG  3'

*3' OLIGO WITH HindIII-stop_ORF:*

SEQ ID NO: 16

5'  CGATAAGCTTTCAGGCTATCTGGGACCGCAGGGACTGCCAGGTGCA  3'

FIG. 4

COL1A2

SEQ ID NO: 17

```
   1 atgctcagct tgtggatac gcggactttg ttgctgcttg cagtaacctt atgcctagca
  61 acatgccaat ctttacaaga ggaaactgta agaaagggcc cagccggaga tagaggacca
 121 cgtggagaaa ggggtccacc aggcccccca ggcagagatg gtgaagatgg tcccacaggc
 181 cctcctggtc cacctggtcc tcctggcccc cctggtctcg gtgggaactt tgctgctcag
 241 tatgatggaa aaggagttgg acttggccct ggaccaatgg gcttaatggg acctagaggc
 301 ccacctggtg cagctggagc cccaggccct caaggtttcc aaggacctgc tggtgagcct
 361 ggtgaacctg gtcaaactgg tcctgcaggt gctcgtggtc cagctggccc tcctggcaag
 421 gctggtgaag atggtcaccc tggaaaaccc ggacgacctg gtgagagagg agttgttgga
 481 ccacagggtg ctcgtggttt ccctggaact cctggacttc ctggcttcaa aggcattagg
 541 ggacacaatg gtctggatgg attgaaggga cagcccggtg ctcctggtgt gaagggtgaa
 601 cctggtgccc ctggtgaaaa tggaactcca ggtcaaacag gagcccgtgg gcttcctggt
 661 gagagaggac gtgttggtgc ccctggccca gctggtgccc gtggcagtga tggaagtgtg
 721 ggtcccgtgg gtcctgctgg tcccattggg tctgctggcc ctccaggctt cccaggtgcc
 781 cctggcccca agggtgaaat tggagctgtt ggtaacgctg gtcctgctgg tcccgccggt
 841 ccccgtggtg aagtgggtct tccaggcctc tccggccccg ttggacctcc tggtaatcct
 901 ggagcaaacg gccttactgg tgccaagggt gctgctgcc ttcccggcgt tgctggggct
 961 cccggcctcc ctggaccccg cggtattcct ggccctgttg gtgctgccgg tgctactggt
1021 gccagaggac ttgttggtga gcctggtcca gctggctcca aggagagag cggtaacaag
1081 ggtgagcccg gctctgctgg gccccaaggt cctcctggtc ccagtggtga agaaggaaag
1141 agaggcccta atgggggaagc tggatctgcc ggccctccag gacctcctgg gctgagaggt
1201 agtcctggtt ctcgtggtct tcctggagct gatggcagag ctggcgtcat gggccctcct
1261 ggtagtcgtg gtgcaagtgg ccctgctgga gtccgaggac ctaatggaga tgctggtcgc
1321 cctggggagc ctggtctcat gggacccaga ggtcttcctg gttcccctgg aaatatcggc
1381 cccgctggaa aagaaggtcc tgtcggcctc cctggcatcg acggcaggcc tggcccaatt
1441 cgcccagctg gagcaagagg agagcctggc aacattggat tccctggacc caaaggcccc
1501 actggtgatc ctggcaaaaa cggtgataaa ggtcatgctg gtcttgctgg tgctcggggt
1561 gctccaggtc ctgatggaaa caatggtgct cagggacctc ctggaccaca gggtgttcaa
1621 ggtggaaaag gtgaacaggg tcccccctggt cctccaggct tccagggtct gcctggcccc
1681 tcaggtcccg ctggtgaagt tggcaaacca ggagaaaggg gtctccatgg tgagtttggt
1741 ctccctggtc ctgctggtcc aagaggggaa cgcggtcccc caggtgagag tggtgctgcc
1801 ggtcctactg gtcctattgg aagccgaggt cctctggac cccagggcc tgatggaaac
1861 aagggtgaac ctggtgtggt tggtgctgtg ggcactgctg gtccatctgg tcctagtgga
1921 ctcccaggag agaggggtgc tgctggcata cctggaggca aggagaaaa gggtgaacct
1981 ggtctcagag gtgaaattgg taaccctggc agagatggtg ctcgtggtgc tcctggtgct
2041 gtaggtgccc ctggtcctgc tggagccaca ggtgaccggg gcgaagctgg ggctgctggt
2101 cctgctggtc ctgctggtcc tcggggaagc cctggtgaac gtggtgaggt cggtcctgct
2161 ggccccaatg gatttgctgg tcctgctggt gctgctggtc aacctggtgc taaaggagaa
2221 agaggagcca aaggccctaa gggtgaaaac ggtgttgttg gtcccacagg ccccgttgga
2281 gctgctggcc cagctggtcc aaatggtccc ccggtcctg ctggaagtcg tggtgatgga
2341 ggcccccctg gtatgactgg tttccctggt gctgctggac ggactggtcc cccaggaccc
2401 tctggtattt ctggccctcc tggtcccct ggtcctgctg ggaaagaagg gcttcgtggt
2461 cctcgtggtg accaaggtcc agttggccga actggagaag taggtgcagt tggtccccct
2521 ggcttcgctg gtgagaaggg tccctctgga gaggctggta ctgctggacc tcctggcact
2581 ccaggtcctc agggtcttct tggtgctcct ggtattctgg gtctccctgg ctcgagaggt
2641 gaacgtggtc taccaggtgt tgctggtgct gtgggtgaac ctggtcctct ggcattgcc
2701 ggccctcctg gggcccgtgg tcctcctggt gctgtgggta gtcctggagt caacggtgct
2761 cctggtgaag ctggtcgtga tggcaaccct gggaacgatg gtccccccag gcgcgatggt
2821 caacccggac acaagggaga gcgcggttac cctggcaata ttggtcccgt tggtgctgca
2881 ggtgcacctg gtcctcatgg ccccgtgggt cctgctggca aacatggaaa ccgtggtgaa
2941 actggtcctt ctggtcctgt tggtcctgct ggtgctgttg gccaagagg tcctagtggc
3001 ccacaaggca ttcgtggcga taagggagag cccggtgaaa aggggcccag aggtcttcct
```

FIG. 5A 3061 ggcttaaagg gacacaatgg attgcaaggt ctgcctggta tcgctggtca ccatggtgat
3121 caaggtgctc ctggctccgt gggtcctgct ggtcctaggg gccctgctgg tccttctggc
3181 cctgctggaa aagatggtcg cactggacat cctggtacag ttggacctgc tggcattcga
3241 ggccctcagg gtcaccaagg ccctgctggc cccctggtc ccctggccc tcctggacct
3301 ccaggtgtaa gcggtggtgg ttatgacttt ggttacgatg gagacttcta cagggctgac
3361 cagcctcgct cagcaccttc tctcagaccc aaggactatg aagttgatgc tactctgaag
3421 tctctcaaca accagattga gaccttctt actcctgaag gctctagaaa gaacccagct
3481 cgcacatgcc gtgacttgag actcagccac ccagagtgga gcagtggtta ctactggatt
3541 gaccctaacc aaggatgcac tatggatgct atcaaagtat actgtgattt ctctactggc
3601 gaaacctgta tccgggccca acctgaaaac atcccagcca agaactggta taggagctcc
3661 aaggacaaga aacacgtctg gctaggagaa actatcaatg ctggcagcca gtttgaatat
3721 aatgtagaag gagtgacttc caaggaaatg gctacccaac ttgccttcat gcgcctgctg
3781 gccaactatg cctctcagaa catcacctac cactgcaaga acagcattgc atacatggat
3841 gaggagactg gcaacctgaa aaaggctgtc attctacagg gctctaatga tgttgaactt
3901 gttgctgagg gcaacagcag gttcacttac actgttcttg tagatggctg ctctaaaaag
3961 acaaatgaat ggggaaagac aatcattgaa tacaaaacaa ataagccatc acgcctgccc
4021 ttccttgata ttgcaccttt ggacatcggt ggtgctgacc aggaattctt tgtggacatt
4081 ggcccagtct gtttcaaata a SEQ ID NO: 18
MLSFVDTRTL LLLAVTLCLA TCQSLQEETV RKGPAGDRGP RGERGPPGPP
GRDGEDGPTG PPGPPGPPGP PGLGGNFAAQ YDGKGVGLGP GPMGLMGPRG
PPGAAGAPGP QGFQGPAGEP GEPGQTGPAG ARGPAGPPGK AGEDGHPGKP
GRPGERGVVG PQGARGFPGT PGLPGFKGIR GHNGLDGLKG QPGAPGVKGE
PGAPGENGTP GQTGARGLPG ERGRVGAPGP AGARGSDGSV GPVGPAGPIG
SAGPPGFPGA PGPKGEIGAV GNAGPAGPAG PRGEVGLPGL SGPVGPPGNP
GANGLTGAKG AAGLPGVAGA PGLPGPRGIP GPVGAAGATG ARGLVGEPGP
AGSKGESGNK GEPGSAGPQG PPGPSGEEGK RGPNGEAGSA GPPGPPGLRG
SPGSRGLPGA DGRAGVMGPP GSRGASGPAG VRGPNGDAGR PGEPGLMGPR
GLPGSPGNIG PAGKEGPVGL PGIDGRPGPI GPAGARGEPG NIGFPGPKGP
TGDPGKNGDK GHAGLAGARG APGPDGNNGA QGPPGPQGVQ GGKGEQGPAG
PPGFQGLPGP SGPAGEVGKP GERGLHGEFG LPGPAGPRGE RGPPGESGAA
GPTGPIGSRG PSGPPGPDGN KGEPGVVGAV GTAGPSGPSG LPGERGAAGI
PGGKGEKGEP GLRGEIGNPG RDGARGAPGA VGAPGPAGAT GDRGEAGAAG
PAGPAGPRGS PGERGEVGPA GPNGFAGPAG AAGQPGAKGE RGAKGPKGEN
GVVGPTGPVG AAGPAGPNGP PGPAGSRGDG GPPGMTGFPG AAGRTGPPGP
SGISGPPGPP GPAGKEGLRG PRGDQGPVGR TGEVGAVGPP GFAGEKGPSG
EAGTAGPPGT PGPQGLLGAP GILGLPGSRG ERGLPGVAGA VGEPGPLGIA
GPPGARGPPG AVGSPGVNGA PGEAGRDGNP GNDGPPGRDG QPGHKGERGY
PGNIGPVGAA GAPGPHGPVG PAGKHGNRGE TGPSGPVGPA GAVGPRGPSG
PQGIRGDKGE PGEKGPRGLP GLKGHNGLQG LPGIAGHHGD QGAPGSVGPA
GPRGPAGPSG PAGKDGRTGH PGTVGPAGIR GPQGHQGPAG PPGPPGPPGP
PGVSGGGYDF GYDGDFYRAD QPRSAPSLRP KDYEVDATLK SLNNQIETLL
TPEGSRKNPA RTCRDLRLSH PEWSSGYYWI DPNQGCTMDA IKVYCDFSTG
ETCIRAQPEN IPAKNWYRSS KDKKHVWLGE TINAGSQFEY NVEGVTSKEM
ATQLAFMRLL ANYASQNITY HCKNSIAYMD EETGNLKKAV ILQGSNDVEL
VAEGNSRFTY TVLVDGCSKK TNEWGKTIIE YKTNKPSRLP FLDIAPLDIG
GADQEFFVDI GPVCFK

FIG. 5B

*5' OLIGO WITH NheI-Kozak-ORF:*

SEQ ID NO: 19

5' GATCGCTAGCGCCGCCACCATGctcagctttgtggatacgcggactttgttgctgctt 3'

*3' OLIGO WITH HindIII-stop_ORF:*

SEQ ID NO: 20

5' CGATAAGCTTTTATTTGAAACAGACTGGGCCAATGTCCACAAAGAATTCCT 3'

FIG. 5C (SEQ ID NO: 23)

MHKWILTWILPTLLYRSCFHIICLVGTISLACNDMTPEQMATNVNCSSPER
HTRSYDYMEGGDIRVRRLFCRTQWYLRIDKRGKVKGTQEMKNNYNIME
IRTVAVGIVAIKGVESEFYLAMNKEGKLYAKKECNEDCNFKELILENHYN
TYASAKWTHNGGEMFVALNQKGIPVRGKKTKKEQKTAHFLPMAIT

FIG. 16A (SEQ ID NO: 24)

```
acgcgctcac acacagagag aaaatccttc tgcctgttga tttatggaaa caattatgat      60
tctgctggag aacttttcag ctgagaaata gtttgtagct acagtagaaa ggctcaagtt     120
gcaccaggca gacaacagac atggaattct tatatatcca gctgttagca acaaaacaaa     180
agtcaaatag caaacagcgt cacagcaact gaacttacta cgaactgttt ttatgaggat     240
ttatcaacag agttatttaa ggaggaatcc tgtgttgtta tcaggaacta aaaggataag     300
gctaacaatt tggaagagc aagtactctt tcttaaatca atctacaatt cacagatagg      360
aagaggtcaa tgacctagga gtaacaatca actcaagatt cattttcatt atgttattca     420
tgaacacccg gagcactaca ctataatgca caaatggata ctgacatgga tcctgccaac     480
tttgctctac agatcatgct tcacattat ctgtctagtg ggtactatat ctttagcttg      540
caatgacatg actccagagc aaatggctac aaatgtgaac tgttccagcc ctgagcgaca     600
cacaagaagt tatgattaca tggaaggagg ggatataaga gtgagaagac tcttctgtcg     660
aacacagtgg tacctgagga tcgataaaag aggcaaagta aaagggaccc aagagatgaa     720
gaataattac aatatcatgg aaatcaggac agtggcagtt ggaattgtgg caatcaaagg     780
ggtggaaagt gaattctatc ttgcaatgaa caaggaagga aaactctatg caaagaaaga     840
atgcaatgaa gattgtaact tcaaagaact aattctggaa accattaca acacatatgc       900
atcagctaaa tggacacaca acggagggga aatgtttgtt gccttaaatc aaaaggggat     960
tcctgtaaga ggaaaaaaaa cgaagaaaga acaaaaaaca gcccactttc ttcctatggc    1020
aataacttaa ttgcatatgg tatataaaga acccagttcc agcagggaga tttctttaag    1080
tggactgttt tctttcttct caaaattttc tttcctttta ttttttagta atcaagaaag    1140
gctggaaaaa ctactgaaaa actgatcaag ctggacttgt gcatttatgt ttgttttaag    1200
acactgcatt aaagaaagat ttgaaagta tacacaaaaa tcagatttag taactaaagg    1260
ttgtaaaaaa ttgtaaaact ggttgtacaa tcatgatgtt agtaacagta atttttttct    1320
taaattaatt taccctaag agtatgttag atttgattat ctgataatga ttatttaaat    1380
attcctatct gcttataaaa tggctgctat aataataata atacagatgt tgttatataa    1440
```

FIG. 16B ns and Methods for Genetic Modification of Cells Having Cosmetic Function to Enhance Cosmetic Appearance

CROSS-REFERENCE TO RELATED APPLICATIONS

This application is a National Phase of PCT International Patent Application No. PCT/US2010/042051, filed Jul. 15, 2010, which claims Priority to U.S. Provisional Patent Application No. 61/226,518, filed Jul. 17, 2009, in the United States Patent and Trademark Office, the disclosures of which are incorporated herein by reference.

BACKGROUND OF THE INVENTION

1. Field of the Invention

Compositions and methods for cosmetic genetic modification of cells that have cosmetic function are provided. Compositions and methods are also provided for determining, using various animal models, whether expression and/or levels of skin proteins and other biomolecules such as collagen, elastin, extracellular matrix proteins, proteoglycans, growth factors has a cosmetic rejuvenation effect on the skin, and for evaluating the cosmetic genetic modification of substantially intact cells having a cosmetic function.

2. Description of the Related Art

Expression and/or levels of skin proteins and other biomolecules such as collagen, elastin, extracellular matrix proteins, proteoglycans, growth factors, endogenous antioxidant enzymes, and/or DNA repair enzymes, may decline substantially with age, to produce undesirable changes in cosmetic appearance. For example, fibroblast and kertinocyte responsiveness to growth factor stimulation may decline with age. In contrast, certain proteins may increase to produce undesirable changes in skin and other cells having cosmetic function. For example, matrix metalloproteinase-1 (MMP-1) protein may increase in skin cells; as MMP-1 accelerates collagen breakdown, the build-up of MMP-1 can be detrimental to the skin.

Age-related changes may include sagging, thinning, or wrinkling of the skin. There are topical compositions that are formulated to improve the appearance of skin, but generally, such formulations require frequent and multiple applications (i.e., once or twice daily year round). Alternatively, invasive intervention (e.g., plastic surgery, laser resurfacing, and injection procedures) may help to reduce sagging and wrinkling of the skin. Still, many individuals are reluctant to undergo a surgical procedure for a non-therapeutic (i.e., cosmetic) reason. Thus, there is a need for cosmetic compositions and methods that offer a more permanent solution than many skin creams can offer, but that do not require plastic surgery or other types of invasive intervention.

Genetic therapy can provide a targeted approach for the improvement, treatment and maintenance of cells having cosmetic function. For example, certain genes appear to be involved in skin tissue maintenance and repair. Numerous growth factors, including epidermal growth factor (EGF), transforming growth factor (e.g., TGF-beta), fibroblast growth factor (FGF), insulin-like growth factor (IGF-1), keratinocyte growth factor (KGF), vascular endothelial growth factor (VEGF), and PDGF may be involved in wound healing (see e.g., Grazul-Bilska et al., Drugs of Today, 2003, 39:787-800; S. Werner and R. Grose; Physiol. Rev., 83:835-870, 2003). For example, a mixture of vascular endothelial growth factor (VEGF), platelet-derived growth factor (PDGF), insulin-like growth factor (IGF-1), granulocyte/macrophage colony-stimulating factor (GM-CSF), interleukin (IL-8, IL-6), tumor necrosis factor (TNF-alpha), transforming growth factor (TGB-beta) and matrix proteins may be used to improve wound healing (reviewed in Jimenez and Jimenez, Am. J. Surgery, 2004, 187:56S-64S). Also, insulin-like growth factor (IGF-1) may be used to increase muscle hypertrophy (Barton-Davis et al., Acta Physiol. Scand., 1999, 167:301-305). Thus, improving the production and function of specific proteins by molecular targeting of the genome of cells involved in cosmetic function may provide a means to improve the longevity and health of such cells.

SUMMARY OF THE INVENTION

Certain embodiments of the present invention address such cosmetic problems associated with aging and other unwanted changes that can occur in skin and other cells that have cosmetic function.

Certain embodiments of the present invention provide methods for cosmetic genetic modification of cells that have cosmetic function, and compositions for improving the cosmetic appearance of cells that have cosmetic function.

Other embodiments of the present invention provide compositions and methods for determining, using various animal models, whether expression and/or levels of skin proteins and other biomolecules such as collagen, elastin, extracellular matrix proteins, proteoglycans, growth factors has a cosmetic rejuvenation effect on the skin, and for evaluating the cosmetic genetic modification of substantially intact cells having a cosmetic function.

As disclosed herein, embodiments of the methods and compositions of the present invention may comprise polynucleotide constructs that encode for nucleic acids and/or polypeptides that may act to improve and/or maintain the appearance of such cells. Alternatively or additionally, compositions comprising isolated polypeptides or biologically active derivatives thereo may be used.

Thus, embodiments of the present invention address the problem of cosmetic degeneration of skin and other cells that have cosmetic function, and may provide compositions and methods for genetic modification of cells having cosmetic function. The present invention may be embodied in a variety of ways.

In one embodiment, the present invention may comprise a method for the cosmetic genetic modification of substantially intact cells having a cosmetic function in a subject comprising administering polynucleotide encoding at least one of a nucleic acid or a polypeptide involved in maintaining the cells having cosmetic function to a least a portion of the cells such that the nucleic acid or polypeptide is expressed in the cells having cosmetic function to enhance and/or maintain a biochemical and/or physiological process that has a positive effect on cosmetic appearance. In an embodiment, the polypeptide comprises a keratinocyte growth factor or a biologically active derivative thereof. For example, in certain embodiments the polynucleotide comprises nucleotides 446 to 1030 of SEQ ID NO: 24 or a sequence that is at least 70%, 75%, 80%, 85%, 90%, 95%, 96%, 97% 98%, or 99% identical to nucleotides 446 to 1030 of SEQ ID NO: 24 or a polynucleotide that encodes a protein having the sequence of SEQ ID NO: 23 or a sequence that is at least 70%, 75%, 80%, 85% 90%, 95%, 96%, 97%, 98%, or 99% identical to SEQ ID NO: 23.

In another embodiment, the present invention comprises a composition for genetically modifying substantially intact cells having cosmetic function in a subject. The composition may comprise an isolated polynucleotide encoding at least one of a nucleic acid or a polypeptide involved in maintaining cells having cosmetic function. Or, the composition may comprise a polypeptide involved in maintaining cells having cosmetic function. In an embodiment, the polypeptide comprises a keratinocyte growth factor or a biologically active derivative thereof. For example, in certain embodiments the polynucleotide comprises nucleotides 446 to 1030 of SEQ ID NO: 24 or a sequence that is at least 70%, 75%, 80%, 85%, 90%, 95%, 96%, 97%, 98%, or 99% identical to nucleotides 446 to 1030 of SEQ ID NO: 24 or a polynucleotide that encodes a protein having the sequence of SEQ ID NO: 23 or a sequence that is at least 70%, 75%, 80%, 85%, 90%, 95%, 96%, 97%, 98%, or 99% identical to SEQ ID NO: 23.

The composition may further comprise a carrier for administration of the polynucleotide or polypeptide to a least a portion of the subject's cells having cosmetic function. In an embodiment the composition is formulated such that upon administration to a subject, the nucleic acid or polypeptide is expressed in the cells having cosmetic function so as to enhance and/or maintain a biochemical and/or physiological process that has a positive effect on cosmetic appearance.

In certain embodiments, the methods and compositions of the present invention may result in expression of a plurality of proteins to enhance and/or maintain a biochemical and/or physiological process that has a positive effect on cosmetic appearance. For example, expression of a first protein or polypeptide that is involved in cosmetic appearance (e.g., by application to cells of polynucleotide that expresses a keratinocyte growth factor or other polypeptide) may trigger endogenous expression of a second protein or polypeptide (e.g., a collagen or other polypeptide) so as to enhance and/or maintain a biochemical and/or physiological process that has a positive effect on cosmetic appearance.

Thus, embodiments of the present invention may comprise methods and compositions for the cosmetic genetic modification of cells having cosmetic function. In certain embodiments, the present invention may comprise methods and compositions for the in vivo transfection of recombinant polynucleotide constructs into cells having cosmetic function. In other embodiments, the invention may comprise methods and compositions for the ex vivo transfection of recombinant polynucleotide constructs into cells having cosmetic function followed by injection of the transfected cells into the skin or other cells that have cosmetic function. In yet other embodiments, polypeptides may be used in the methods and compositions of the present invention.

The recombinant constructs may encode for a variety of biomolecules that may be used to enhance the expression of proteins and other biomolecules that are beneficial to cells having a cosmetic function. In an embodiment, the composition may comprise a polypeptide. Or, the construct may comprise a recombinant DNA molecule that encodes for a polypeptide or other biomolecule that may modify the activity of genes in cells having cosmetic function. For example, in alternate embodiments, the polynucleotide may encode for a collagen polypeptide, an elastin polypeptide, a TIMP-1 polypeptide, a superoxide dismutase polypeptide, and/or a keratinocyte growth factor (KGF) polypeptide.

Or, the recombinant constructs may encode for regulatory nucleic acid molecules, as for example, antisense oligodeoxynucleotides, or inhibitory RNAs (RNAi), ribozymes, triplex helix-forming oligonucleotides (TFOs) or peptide nucleic acid (PNA) that impact genes in cells having cosmetic function, as for example by downregulating expression of collagen and elastin degrading enzymes (e.g., matrix metalloproteinases, collagenases, gelatinases, elastases, stromelysins, serine proteases and/or membrane-type type MMPs). For example, antisense oligodeoxynucleotides targeted against cysteine-rich 61 (CYR61/CCN1) which normally suppresses collagen 1 expression, and antisense oligodeoxynucleotides targeted against matrix metalloproteinases (MMPs) which normally accelerate collagen and elastin breakdown may be used.

In alternate embodiments, the polynucleotide construct may encode for a growth factor that improves cosmetic appearance. For example, the polynucleotide construct may encode for keratinocyte growth factor (KGF). In other embodiments, the the polynucleotide construct may encode for insulin-like growth factor 1 (IGF-1), platelet derived growth factor (PDGF), hepatocyte growth factor (HGF), and/or transforming growth factor beta (TGF-beta).

The methods and compositions of the present invention may produce "genetic face and/or body lift" without the need for invasive procedures. Such genetic modifications may restore or enhance a biochemical and/or physiological process that has a positive effect on cosmetic appearance (e.g. boosting collagen, elastin and/or superoxide dismutase production), or may reduce a skin cell process that has a negative cosmetic appearance (e.g. increased inhibition of collagenases by increased expression of inhibitors).

Other embodiments and further details regarding various aspects of the present invention are set forth in the following description and claims. It is to be understood that the invention is not limited in its application to the details set forth in the following description and claims, but is capable of other embodiments and of being practiced or carried out in various ways.

BRIEF DESCRIPTION OF THE DRAWINGS

These and/or other aspects and advantages of the invention will become apparent and more readily appreciated from the following description of the embodiments, taken in conjunction with the accompanying drawings of which:

FIGS. 1A-1C depict the following: sequences for procollagen DNA (COL1A1) (SEQ ID NO: 1) (FIGS. 1A and 1B); protein (SEQ ID NO: 2) (FIG. 1C); and primers used to subclone the procollagen cDNA into Pcdna3.1 zeo vector (FIG. 1C), where the 5' subcloning primer (SEQ ID NO: 3) includes a Nhe I restriction enzyme site (underlined) and a Kozak sequence (underlined bold font), and the 3' subcloning primer (SEQ ID NO: 4) includes a Hind II restriction enzyme site (underlined) and an open reading frame (ORF) stop sequence (bold underlined font) in accordance with an embodiment of the present invention; cds=coding sequence.

FIGS. 2A-2B depict the following: sequences for elastin DNA (SEQ ID NO: 5) (FIG. 2A); protein (SEQ ID NO: 6) (FIG. 2B); and primers used to subclone the elastin cDNA into Pcdna3.1 zeo vector (FIG. 2B), where the 5' subcloning primer (SEQ ID NO: 7) includes a Nhe I restriction enzyme site (underlined) and a Kozak sequence (bold font), and the 3' subcloning primer (SEQ ID NO: 8) includes a Bgl II restriction enzyme site (underlined) and an ORF stop sequence (bold underlined font) in accordance with an embodiment of the present invention.

FIGS. 3A-3B depict the following: sequences for superoxide dismutase 3 (SOD3) DNA (SEQ ID NO: 9) (FIG. 3A); protein (SEQ ID NO: 10) (FIG. 3B); and primers used to subclone the SOD3 cDNA into Pedna3.1 zeo vector (FIG. 3B), where the 5' subcloning primer (SEQ ID NO: 11) includes a Nhe I restriction enzyme site (underlined) and a Kozak sequence (underlined bold font), and the 3' subcloning primer (SEQ ID NO: 12) includes a Hind III restriction enzyme site (underlined) and an ORF stop sequence (underlined bold font) in accordance with an embodiment of the present invention.

FIG. 4 depicts the following: sequences for TIMP-1 DNA (SEQ ID NO: 13); protein (SEQ ID NO: 14); and primers used to subclone the TIMP-1 cDNA into Pedna3.1 zeo vector, where the 5' subcloning primer (SEQ ID NO: 15) includes a Nhe I restriction enzyme site (underlined) and a Kozak sequence (underlined bold font), and the 3' subcloning primer (SEQ ID NO: 16) includes a Hind III restriction enzyme site (underlined) and an ORF stop sequence (underlined bold font) in accordance with an embodiment of the present invention.

FIGS. 5A-5C depict the following: sequences for COL1A2 DNA (SEQ ID NO: 17) (FIGS. A and B); protein (SEQ ID NO: 18) (FIG. B); and primers used to subclone the COL1A2 cDNA into Pedna3.1 zeo vector (FIG. C), where the 5' subcloning primer (SEQ ID NO: 19) includes a Nhe I restriction enzyme site (underlined) and a Kozak sequence (underlined bold font), and the 3' subcloning primer (SEQ ID NO: 20) includes a Hind III restriction enzyme site (underlined) and an ORF stop sequence (underlined bold font) in accordance with an embodiment of the present invention.

FIGS. 16A-16B depict the following: the amino acid sequence of KGF-1 (FIG. 16A) and the nucleotide sequence of KGF-1 (also known as FGF-7 or KGF-1/FGF-7) (FIG. 16B) in accordance with an embodiment of the present invention.

DETAILED DESCRIPTION OF THE EMBODIMENTS

Definitions

Figure 6:
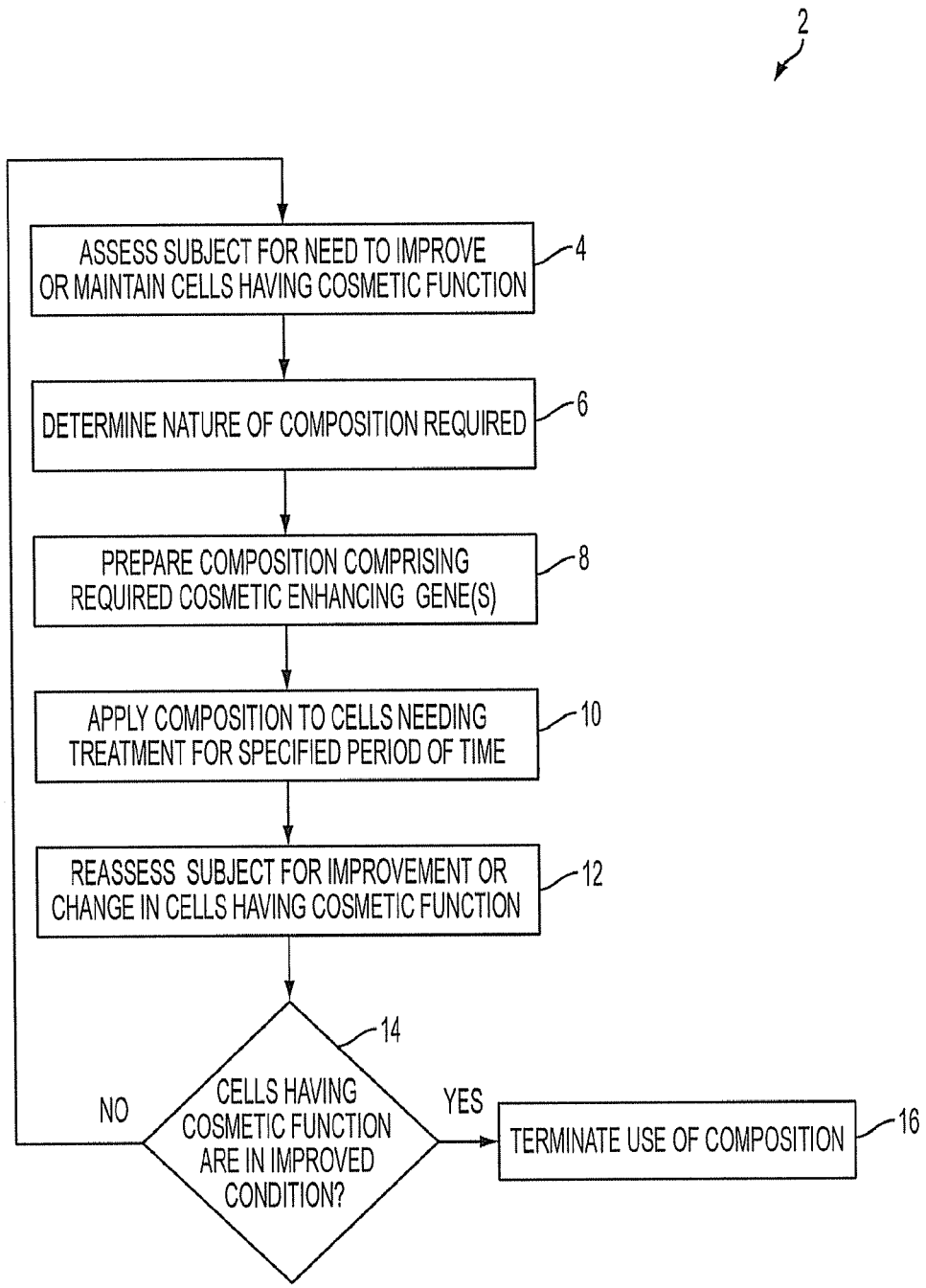
FIG. 6 depicts an example of a method used to treat cells having cosmetic function in a subject in accordance with an embodiment of the present invention.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10. Additionally, any reference referred to as being "incorporated herein" is to be understood as being incorporated in its entirety.

It is further noted that, as used in this specification, the singular forms "a," "an," and "the" include plural referents unless expressly and unequivocally limited to one referent. The term "or" is used interchangeably with the term "and/or" unless the context clearly indicates otherwise.

Also, as used herein, a subject is a mammal who may require treatment to maintain and/or to improve the condition of any cells having cosmetic function. Such subjects may include animals (e.g., animals who may have a skin condition) and humans. The subject may be a human. The subject may comprise a post-menopausal female. Or the subject may be a non-human mammal as for example, pets that may have a need for treatment of the skin, nails, hair, and/or fur.

As used herein, cells that have cosmetic function include skin, fat, muscle, connective tissue, and nerve cells found in the epidermis, dermis and subcutaneous layers, including the nail root or nail bed, nail matrix and nail plate, and scalp, hair follicles and hair strands, as well as muscles found under the subcutaneous fat layer and the tongue; cells in the teeth and gums; cells in the bones, including facial bones; and cells found in the eye including the iris and stroma covering the iris.

As used herein, "epidermal tissue" comprises tissue derived from the ectoderm. The ectoderm is the outermost germ layer of metazoan embryos, developing into epidermal and nervous tissue. Epidermal tissue includes skin, nails, and hair.

As used herein, "skin" is composed of the epidermis and the dermis. The outermost epidermis in skin consists of stratified squamous epithelium with an underlying basement membrane. The epidermis in skin does not contain any blood vessels, but receives nutrients by diffusion from the dermis. The main types of cells that make up the epidermis are keratinocytes. Also, melanocytes and Langerhans cells are present. The epidermis can be further subdivided into the following layers from outermost to innermost: corneum, lucidum, granulosum, spinosum, and basal. The dermis lies below the epidermis and includes blood vessels, nerves, hair follicles, smooth muscle, glands and lymphatic tissue. Also, fibroblasts are commonly found in the dermis and secrete an extracellular matrix rich collage, elastin, hyaluronic acid and other macromolecules. Below the dermis lies the subcutaneous layer containing fat-filled cells called adipose cells, larger blood vessels and larger nerves. Muscles are found below the subcutaneous fat. The skin structure is attached via connective tissues to the muscles. Connective tissues also anchor the skin, fat and muscles to underlying bone tissues. Excessive fat in the subcutaneous layer in the attachment areas cause a dimpled "cellulite" appearance.

As used herein, "substantially intact cells" comprise cells that are not torn, cut or punctured as a result of trauma. The cells may, however, include cells that have been treated with a laser, or by chemical peel, or by dermabrasion or other cosmetic enhancing treatments.

Unless defined otherwise, all technical and scientific terms used herein have the same meaning as commonly understood by one of ordinary skill in the art. Practitioners are particularly directed to *Current Protocols in Molecular Biology* (Ansubel) for definitions and terms of the art. Abbreviations for amino acid residues are the standard 3-letter and/or 1-letter codes used in the art to refer to one of the 20 common L-amino acids.

The term "recombinant" as used herein in relation to a polynucleotide intends a polynucleotide of semisynthetic, or synthetic origin, or encoded by cDNA or genomic DNA ("gDNA") such that it is not entirely associated with all or a portion of a polynucleotide with which it is associated in nature.

As used herein, the term "polypeptide" refers to a polymer of amino acids and does not refer to a specific length of the product. Thus, peptides, oligopeptides, and proteins are included within the definition of polypeptide and could be as short as two amino acids. This term also does not exclude post-expression modifications of the polypeptide, for example, glycosylations, acetylations, phosphorylations and the like. Included within the definition are, for example, polypeptides containing one or more analogs of an amino acid (including, for example, unnatural amino acids), polypeptides with substituted linkages, as well as other modifications known in the art, both naturally occurring and non-naturally occurring. As is known in the art, "proteins", "peptides," "polypeptides" and "oligopeptides" are chains of amino acids (typically L-amino acids) whose alpha carbons are linked through peptide bonds formed by a condensation reaction between the carboxyl group of the alpha carbon of one amino acid and the amino group of the alpha carbon of another amino acid. Typically, the amino acids making up a protein are numbered in order, starting at the amino terminal residue and increasing in the direction toward the carboxy terminal residue of the protein.

A "nucleic acid" is a polynucleotide such as deoxyribonucleic acid (DNA) or ribonucleic acid (RNA). The term is used to include single-stranded nucleic acids, double-stranded nucleic acids, and RNA and DNA made from nucleotide or nucleoside analogues. The term "polynucleotide"0 as used herein refers to a DNA molecule, a RNA molecule or its complementary strand thereof. A polynucleotide molecule can be single or double stranded.

DNA molecules may be identified by their nucleic acid sequences, which are generally presented in the 5' to 3' direction, wherein 5' and 3' indicate the linkages formed between the 5'-phosphate group of one nucleotide and the 3'-hydroxyl group of the next. For a sequence presented in the 5'-3' direction, its complement is the DNA strand which hybridizes to that sequence according to the Watson-Crick base pairing model. Thus, the sequence of the complement is defined by the sequence of the original strand, such that adenine base-pairs with thymine, and cytosine base-pairs with guanine.

As used herein, a small inhibitory RNA is a double-stranded RNA of about 20-30 nucleotides than associated with proteins to form an RNA-induced silencing complex (RISC) that may direct the siRNA to the target RNA sequence. The ds siRNA may then unwind, leaving the antisense strand to signal degradation of the mRNA sequence by endonucleases and exonucleases. In order to obtain lasting therapeutic effects, the RNAi sequence may be expressed long term, preferably under a constitutive promoter. To obtain dsRNA from a vector, it may be expressed as a short hairpin RNA (shRNA), in which there is a sense strand, a hairpin loop region and an antisense strand (Miyagishi et al., *J Gene Med* 6:715-723, 2004).

As used herein, the term "upstream" refers to a residue that is N-terminal to a second residue where the molecule is a protein, or 5' to a second residue where the molecule is a nucleic acid. Also as used herein, the term "downstream" refers to a residue that is C-terminal to a second residue where the molecule is a protein, or 3' to a second residue where the molecule is a nucleic acid. Also, the terms "portion" and "fragment" are used interchangeably to refer to parts of a polypeptide, nucleic acid, or other molecular construct.

The term "vector" refers to a nucleic acid molecule that may be used to transport a second nucleic acid molecule into a cell. In one embodiment, the vector allows for replication of DNA sequences inserted into the vector. The vector may comprise a promoter to enhance and/or maintain expression of the nucleic acid molecule in at least some host cells. Vectors may replicate autonomously (extrachromasomally) or may be integrated into a host cell chromosome. In one embodiment, the vector may comprise an expression vector capable of producing a protein or a nucleic acid derived from at least part of a nucleic acid sequence inserted into the vector.

As is known in the art, conditions for hybridizing nucleic acid sequences to each other can be described as ranging from low to high stringency. Generally, highly stringent hybridization conditions refer to washing hybrids in low salt buffer at high temperatures. Hybridization may be to filter bound DNA using hybridization solutions standard in the art such as 0.5M NaHPO$_4$, 7% sodium dodecyl sulfate (SDS), at 65° C., and washing in 0.25 M NaHPO$_4$, 3.5% SDS followed by washing 0.1× SSC/0.1% SDS at a temperature ranging from room temperature to 68° C. depending on the length of the probe (see e.g. Ausubel, F. M. et al, *Short Protocols in Molecular Biology*, 4$^{th}$ Ed., Chapter 2, John Wiley & Sons, N.Y). For example, a high stringency wash comprises washing in 6× SSC/0.05% sodium pyrophosphate at 37° C. for a 14 base oligonucleotide probe, or at 48° C. for a 17 base oligonucleotide probe, or at 55° C. for a 20 base oligonucleotide probe, or at 60° C. for a 25 base oligonucleotide probe, or at 65° C. for a nucleotide probe about 250 nucleotides in length. Nucleic acid probes may be labeled with radionucleotides by end-labeling with, for example, [gamma-$^{32}$P]ATP, or incorporation of radiolabeled nucleotides such as [alph-$^{32}$P]dCTP by random primer labeling. Alternatively, probes may be labeled by incorporation of biotinylated or fluorescein labeled nucleotides, and the probe detected using Streptavidin or anti-fluorescein antibodies.

The terms "identity" or "percent identical" refers to sequence identity between two amino acid sequences or between two nucleic acid sequences. Percent identity can be determined by aligning two sequences and refers to the number of identical residues (i.e., amino acid or nucleotide) at positions shared by the compared sequences. Sequence alignment and comparison may be conducted using the algorithms standard in the art (e.g. Smith and Waterman, 1981, *Adv. Appl. Math.* 2:482; Needleman and Wunsch, 1970, *J. Mol. Biol.* 48:443; Pearson and Lipman, 1988, *Proc. Natl. Acad. Sci., USA,* 85:2444) or by computerized versions of these algorithms (Wisconsin Genetics Software Package Release 7.0, Genetics Computer Group, 575 Science Drive, Madison, Wis.) publicly available as BLAST and FASTA. Also, ENTREZ, available through the National Institutes of Health, Bethesda Md., may be used for sequence comparison. In one embodiment, the percent identity of two sequences may be determined using GCG with a gap weight of 1, such that each amino acid gap is weighted as if it were a single amino acid mismatch between the two sequences. For example, the term at least 90% identical thereto includes sequences that range from 90 to 99.99% identity to the indicated sequences and includes all ranges in between. Thus, the term at least 90% identical thereto includes sequences that are 91, 91.5, 92, 92.5, 93, 93.5, 94, 94.5, 95, 95.5, 96, 96.5, 97, 97.5, 98, 98.5, 99, 99.5 percent identical to the indicated sequence. Similarly the term "at least 70% identical includes sequences that range from 70 to 99.99% identical, with all ranges in between. The determination of percent identity is determined using the algorithms described here.

As used herein, "homology" refers to the degree of sequence identity between a first sequence and a second sequence (protein or nucleic acid). Typically, the sequence identity between two homologous sequences will be at least 50%. In alternate embodiments, the sequence identity will be no less than 60%; or no less than 75%; or no less than 80%; or at least 90%. In other embodiments, the sequence identity between the two sequences will be at least 95%, or at least 98%, or at least 99%. Also, as used herein, the term "homologue" means a polypeptide having a degree of homology with the wild-type amino acid sequence. Homology comparisons can be conducted by eye, or more usually, with the aid of readily available sequence comparison programs. These commercially available computer programs can calculate percent homology between two or more sequences (e.g. Wilbur, W. J. and Lipman, D. J., 1983, *Proc. Natl. Acad. Sci. USA,* 80:726-730). For example, homologous sequences may be taken to include an amino acid sequences which in alternate embodiments are at least 75% identical, 85% identical, 90% identical, 95% identical, or 98% identical to each other.

A biologically active or functional derivative (and/or analogue) of any polypeptide includes a polypeptide that has been modified by one or more of an amino acid modification, insertion, deletion, or substitution that does not substantially affect its properties. For example, the biologically active derivative or analog can include conservative amino acid substitutions. Also, a biologically active derivative may comprise a fragment of the native polypeptide. Preferably, the derivative or analog has increased activity or stability compared to native polypeptide. For example, the derivative or analog can include conservative amino acid substitutions. Muteins, analogues and derivatives may be generated using conventional techniques. In an embodiment, the derivative may have increased activity compared to native polypeptide. For example, in certain embodiments, the derivative or analog may comprise at least a 2-fold increase, or at least a 5-10 fold increase, or at least a 20-fold increase.

A "mutein" is polypeptide variant with one or more amino acids altered to produce a desired characteristic, such as to replace a cysteine residue with a non-disulfide bond forming amino acid.

Muteins, analogues and derivatives may be generated using conventional techniques. For example, PCR mutagenesis can be used. While the following discussion refers to DNA, it is understood that the technique also finds application with RNA. An example of a PCR technique is described in WO 92/22653. Another method for making analogs, muteins, and derivatives, is cassette mutagenesis based on the technique described by Wells, Gene, (1985) 34:315.

The terms "analog" or "derivative" in reference to the polypeptides of the present invention also refers to truncations, variants, alleles and derivatives thereof. Where applicable, these terms encompass the bioactivities of "mature" polypeptides or functional isoforms. Thus, polypeptides that are identical or contain at least 60%, preferably 70%, more preferably 80%, and most preferably 90% sequence identity to the mature protein or functional isoform wherever derived, from human or nonhuman sources are included within this definition. The analogs may further include peptides having one or more peptide mimics, also known as peptoids, that possess the bioactivity of the protein. Included within the definition are also polypeptides containing one or more analog amino acid (including, for example, unnatural amino acids, etc.), polypeptides with substituted linkages, as well as other modifications known in the art, both naturally occurring and nonnaturally occurring. The term polypeptide also does not exclude post-expression modifications of the polypeptide, for example, glycosylations, acetylations, phosphorylations and the like.

Thus, the analogues and/or derivatives of polypeptides used to modulate cells having cosmetic function may contain amino acid substitutions, deletions, or insertions. The amino acid substitutions can be conservative amino acid substitutions or substitutions to eliminate non-essential amino acid residues such as to alter a glycosylation site, a phosphorylation site, an acetylation site, or to minimize misfolding by substitution or deletion of one or more cysteine residues that are not necessary for function.

As used herein, the term "conserved residues" refers to amino acids that are the same among a plurality of proteins having the same structure and/or function. A 5 region of conserved residues may be important for protein structure or function. Thus, contiguous conserved residues as identified in a three-dimensional protein may be important for protein structure or function. To find conserved residues, or conserved regions of 3-D structure, a comparison of sequences for the same or similar proteins from different species, or of individuals of the same species, may be made. Conservative amino acid substitutions are generally those that preserve the general charge, hydrophobicity/hydrophilicity and/or steric bulk of the amino acid substituted, for example, substitutions between the members of the following groups are conservative substitutions: Gly/Ala, Val/Ile/Leu, Asp/Glu, Lys/Arg, Asn/Gln, Ser/Cys/Thr and Phe/Trp/Tyr.

An "expression vector" is a polynucleotide that is operable in a desired host cell and capable of causing the production of a gene of interest in that host cell.

A "regulatory sequence" refers to a polynucleotide sequence that is necessary for regulation of expression of a coding sequence to which the polynucleotide sequence is operably linked. The nature of such regulatory sequences may differ depending upon the host organism. Such regulatory sequences generally include, for example, a promoter, and/or a transcription termination sequence. The term "regulatory sequence" may also include additional components the presence of which are advantageous, for example, a secretory leader sequence for secretion of the polypeptide attached thereto.

"Operably linked" refers to a juxtaposition wherein the components so described are in a relationship permitting them to function in their intended manner. A regulatory sequence is "operably linked" to a coding sequence when it is joined in such a way that expression of the coding sequence is achieved under conditions compatible with the regulatory sequence. Operably linked sequences may have additional nucleotides (or amino acids in a peptide) positioned between the two components of interest.

As used herein, "terminators" are regulatory sequences, such as polyadenylation and transcription termination sequences, located 3' or downstream of the stop codon of the coding sequences.

As used herein, "recombinant host cells," "host cells," "cells," "cell cultures," and other such terms denote, for example, microorganisms, insect cells, and mammalian cells, that can be or have been used as recipients for introduction of recombinant vector or other transfer DNA, and include the progeny of the cell that has been transformed.

"Transformation" or "transfection," as used herein, refers to the transfer of an exogenous polynucleotide into a host cell, irrespective of the method used for the transfer, which can be, for example, by infection, direct uptake, transduction, F-mating, injection, microinjection or electroporation. The exogenous polynucleotide may be maintained as a non-integrated vector, for example, in some cases, a plasmid, or alternatively, may be integrated into the host genome.

"Purified" and "isolated" in reference to a polypeptide or a nucleotide sequence means that the indicated molecule is present in substantial absence of other biological macromolecules of the same species or type. In alternate embodiments, the term "purified" as used herein refers to at least 75% by weight; or at least 85% by weight, or at least 95% by weight or at least 98% by weight, of biological macromolecules of the same type.

A "pharmaceutically acceptable carrier," is any carrier that is used by persons in the art for administration into a human that does not itself induce any undesirable side effects such as the production of antibodies, fever, etc.

The term "treating" or "treat" refers to improving, or preventing the worsening of a condition (e.g., wrinkles in the skin), or improving the subject's condition. In certain embodiments, the term "treatment" may refer to a full spectrum of treatments for a given condition relating to cosmetic appearance for which the subject may have, including alleviation of one symptom or most of the symptoms resulting from that condition.

An "effective amount," as used herein refers to that amount that is effective for production of a desired result. This amount varies, for example, depending upon the health and physical condition of the individual to be treated, the capacity of the individual's immune system to synthesize antibodies, the degree of protection desired, the formulation, the attending physician's assessment of the medical situation, and other relevant factors.

As used herein, "in vivo transfection" or "in vivo incorporation" refers to the process where the biomolecule of interest is introduced into a cell in a living body. The term includes transfection of naked polynucleotides, or polynucleotides that include an additional moiety or carrier into cells. Methods used for in vivo transfection are described in detail herein.

As used herein, "ex vivo transfection" or "ex vivo incorporation" refers to the process where the biomolecule of interest is introduced into a cell that is outside of a living body. The term includes transfection of naked polynucleotides, or polynucleotides that include an additional moiety or carrier into cells. Methods used for ex vivo transfection are described in detail herein.

As used herein, a polypeptide involved in maintaining cells having cosmetic function may be any peptide as described herein that can improve the production of biomolecules that can enhance the health or longevity of such cells. As is known in the art, the peptide and gene sequences for such proteins are available on public databases.

As used herein, the term "platelet derived growth factor" or "PDGF" includes the PDGF A chain polypeptide and the PDGF B chain polypeptide and to the AA, BB, and AB dimers, and biologically active fragments, analogs, and derivatives thereof as described in U.S. Pat. No. 5,187,263; Waterfield et al., Nature 304:35-39 (1983); Wang et al., J. Biol. Chem. 259: 10645-48(1984), Antoniades et al., Biochem. Pharm. 33: 2833-38 (1984); and Westermark et al., Proc. Natl. Acad. Sci. USA 83:7197-7200 (1986); U.S. Pat. No. 5,219,759. A polypeptide "having the biological activity of PDGF" refers to a polypeptide having the same or increased capability of preferentially stimulating the growth of cells of the dermis layer of the skin. Such a polypeptide can be a full-length PDGF, a fragment of PDGF, an analog of PDGF bearing amino acid substitution, deletion or addition or a derivative of PDGF, such as that described in U.S. Pat No. 5,149,792 and EP 458 959 B1; and U.S. Pat. Nos. 4,769,328; 4,801,542; 4,766,073; 4,849,407; 4,845,075; 4,889,919; 5,045,633; and 5,128,321.

As used herein, the term "keratinocyte growth factor" or "KGF" refers to a member of a group of structurally distinct proteins known as FGFs that display varying degrees of sequence homology, suggesting that they are encoded by a related family of genes. The FGFs share common receptor sites on cell surfaces. KGF, for example, can bind to FGFR-3. The term "keratinocyte growth factor" or "KGF" refers to any one of a mature polypeptide and biologically active fragments, analogs, and derivatives thereof as described in, for example, WO 90/08771 and WO 95/01434. A polypeptide "having the biological activity of KGF" refers to a polypeptide having the same or increased capability of preferentially stimulating the growth of cells of the epidermis layer of the skin. Such a polypeptide can be a full-length KGF, a fragment of KGF, an analog of KGF bearing an amino acid substitution, deletion, or addition; or a derivative of KGF as described in WO 90/08771, and WO 95/01434.

The term "insulin-like growth factor" as used herein encompasses IGF-I and IGF-II in their substantially purified, native, recombinantly produced, or chemically synthesized forms, and includes biologically active fragments, analogues, muteins, including C-terminal deletion muteins, and derivatives thereof that retain IGF activity and/or ability to bind the IGF receptors, as described in, for example, EP 135 094, WO 85/00831, U.S. Pat. No. 4,738,921, WO 92/04363, U.S. Pat. No. 5,158,875, EP 123 228, and EP 128 733. Also included are IGF-I and IGF-II in their substantially purified, native, recombinantly produced, or chemically synthesized forms, and includes biologically active fragments, analogues, muteins, including C-terminal deletion muteins, and derivatives thereof that retain IGF activity and/or ability to bind the IGF receptors, as described in, for example, EP 135 094, WO 85/00831, U.S. Pat. No. 4,738,921, WO 92/04363, U.S. Pat. No. 5,158,875, EP 123 228, and EP 128 733. A polypeptide "having the biological activity of IGF" refers to a polypeptide having the same or increased capability of acting as growth factor capable of insulin-like effects such as, for example, stimulation of phosphorylation of specific tyrosine residues within the cytoplasmic domain of the receptor to which it binds as described in WO 93/98826, or, in some cases, for example, mitogenic effects on certain cells as described in EP 0 128 733. Such a polypeptide can be full-length IGF, a fragment of IGF, an analog of IGF bearing an amino acid substitution, deletion, or addition, or any derivative of IGF.

As used herein, the term "insulin like growth factor binding protein (IGFBP)" refers to a binding protein identified to bind an IGF binding protein as described and identified in Keifer et al, J. Biol. Chem. 266: 9043-9 (1991), Camacho-Hubner et al, J. Biol. Chem. 267: 11949-56 (1992), McCusker and Clemens, THE INSULIN LIKE GROWTH FACTORS: STRUCTURE AND BIOLOGICAL FUNCTIONS, Oxford Univ. Press, N.Y. pp. 110-150 (1992). A polypeptide "having the biological activity of IGFBP" refers to a polypeptide having about the same or an increased capability of acting as an IGF binding protein by binding and transporting IGF to tissue and cells where IGF—can have a biological effect. As there are presently at least six IGFBPs known, many of which significantly different from the other IGFBPs, specific qualities regarding the biological activity of a given IGFBP does not include necessarily the entire group of IGF binding proteins. Thus, the biological activity of an IGFBP may have some similarities to other IGFBPs, but may also have distinctions that identify it as a unique IGFBP.

As used herein, "full-length PDGF" or "mature PDGF" and "full-length KGF" or "mature KGF" and "full-length IGF" or "mature IGF", and "full length IGFBP" and "mature IGFBP" refers to the respective native polypeptide as found in human or other mammalian tissues.

As used herein, the term "collagen" refers to a member of a large group of at least 28 structurally related proteins (Collagen I-XXVIII) that display varying degrees of sequence homology, suggesting that they are encoded by a related family of genes. Collagens are the main fibrous polypeptides composing extracellular matrices and structural support of the skin, including the dermis and dermal-epidermal junction, and other body tissues. These proteins form a variety of structurally and functionally important supramolecular assemblies. (See e.g., Pihlajamaa T., New tools for the study of an old collagen characterization of the human COL9A1, COL9A2 and COL9A3 genes and production of human type IX collagen as a recombinant protein. Collagen Research Unit, Biocenter Oulu and Department of Medical Biochemistry, University of Oulu, FIN-90220 Oulu, Finland, 2000, Oulu, Finland). Collagens are characterized by a triple helix consisting of three identical or different polypeptides, called alpha chains. Collagen is characterized by division into two major structural groups i.e. fibrillar and non-fibrillar. The group of fibrillar, or fibril-forming, collagens consists of types I, II, III, V and XI.

Collagen types I, II and III are referred to as the major fibrillar collagens, implying abundance in a number of tissues. Type I collagen is expressed in most connective tissues and it is the most abundant type of all, being the major structural component of skin, bone, tendon and ligaments. Type I collagen is mostly present in the form of heterotrimers of two $\alpha 1(I)$ chains and one $\alpha 2(I)$ chain, encoded by the COL1A1 and COL1A2 genes, respectively. Type II is the major collagenous component of cartilage, the vitreous humour and the intervertebral disc, and is also detected in the inner ear and transiently in numerous other tissues during development. It is a homotrimer of three $\alpha 1(II)$ chains encoded by the COL2A1 gene. Type III collagen is also a homotrimer, consisting of $\alpha 1(III)$ chains. It is expressed in most tissues that contain type I collagen, but not in bone or tendon. Type III is an abundant component of elastic tissues, including the skin, blood vessels, gut and lung, and can be assembled into heterotypic fibrils with type I collagen. Instead of forming fibrils, the non-fibrillar collagens serve various other functions. Characteristically their triple helix is divided into several segments on account of noncollagenous interruptions. The non-fibrillar collagens may be divided into six subgroups in terms of their structure or function. Important network-forming collagens include types IV, VI, and VII. Type IV collagen networks are present in all basement membranes at numerous locations in the body. In most locations this supporting and controlling network contains $\alpha 1(IV)$ and $\alpha 2(IV)$ chains, but certain basement membranes, e.g. glomerular membranes, also include $\alpha 3(IV)$, $\alpha 4(IV)$, $\alpha 5(IV)$ and $\alpha 6(IV)$ chains. The collagenous region of these $\alpha$ chains is about 1400 amino acids long with numerous short interruptions. The genes encoding these polypeptides form an interesting exception among the generally randomly located collagen genes as they are located pairwise on three chromosomes in a head-to-head fashion. Type VI collage is a heterotrimer of $\alpha 1(VI)$, $\alpha 2(VI)$ and $\alpha 3(VI)$ chains consisting of a short triple helix flanked by large globular N and C-terminal domains. It is the only collagen aggregating into beaded microfilaments, which are to be found on the cell surface and around collagen fibres in most connective tissues and may serve to anchor the cells to the macromolecular framework of the ECM. Type VII collagen forms anchoring fibrils upon dimerization and lateral association of homotrimeric $\alpha 1(VII)3$ molecules. These fibrils link the epithelial basement membrane to the underlying ECM in skin, cornea and several other epithelial tissues. The highly interrupted triple helix of type VII is the longest among all the collagens, and the gene COL7A1 encoding it has the highest number of exons of the known genes, i.e. 108. Thus, in alternate embodiments, the collagen peptides used in the methods and compositions of the present invention and/or whose expression is increased using the methods and compositions of the present invention can be full-length collagen, a fragment of collagen, or a functional analog of collagen. Such collagens can include type I (genes COL1A1 and COL1A2; the most abundant collagen in the body), II (genes COL2A1; hyaline cartilage), III (gene COL3A1; found in granulation tissue), IV (genes COL4A1, COL4A2, COL4A3, COL4A4, COL4A5, COL4A6; found in basal lamina and eye lens), V (genes COL5A1, COL5A2, COL5A3; found in interstitial tissue), VI (genes COL6A1, COL6A2, COL6A3; found in interstitial tissue), VII (gene C0L7A1; found in dermal epidermal junctions), VIII (genes COL8A1 and COL8A2; found in endothelial cells), IX (genes COL9A1, COL9A2, COL9A3; FACIT collagen associated with type II and XI fibrils), X (gene COL10A1; mineralizing cartilage), XI (genes COL11A1 and COL11A2; found in cartilage), XII (gene COL12A1; FACIT collagen found in type I fibrils), XIII (gene COL13A1; a transmembrane collagen that interacts with certain integrins and fibronectin), XIV (gene COLI4A1; a FACIT collagen), XV (gene COL 15A1), XVI (gene COL 16A1), XVII (gene COL 17A1; a type of transmembrane collagen), XVIII (gene COL 18A1), XIX (gene COL 19A1; a 10 FACIT collagen), XX (gene COL 20A1), XXI (gene COL21A; a FACIT collagen), XXII (gene COL 22A1), XXIII (gene COL 23A1), XXIV (gene COL 24A1), XXV (gene COL 25A1) XXVI (gene COL 26A1), XXVIII (gene COL 27A1), and XVIII (gene COL 28A1). Many of the types of collagen that are important to cosmetic cell function may be used in the methods and compositions of the present invention.

As used herein, the term "elastin" refers to a tropoelastin or mature elastin polypeptide. Elastin is a key extracellular matrix protein that is critical to the elasticity
and resilience of many vertebrate tissues including skin large arteries, lung, ligament, tendon, skin, and elastic cartilage (see Mithieux and Weiss, 2005, Elastin, Advances in Protein Chemistry, Vol 70, p437). The human gene encoding tropoelastin is a single copy localized to 7q11.2 region. The primary transcript is approximately 40 kb in length and contains small exons interspersed between large introns giving rise to an unusually low exon/intron ratio. This sequence codes for an mRNA of ~3.5 kb, which consists of a ~2.2 kb coding segment and a relatively large, 1.3 kb 30 untranslated region. The human tropoelastin gene contains 34 exons. Tropoelastin is distinguished by an exon periodicity where functionally distinct hydrophobic and crosslinking domains are encoded in separate alternating exons. All the exons exist as multiples of three nucleotides and the exon-intron borders are always split in the same way. The first nucleotide of a codon is found at the 30 junction, while the second and third nucleotides are present at the 50 border of exons. The primary transcript of 30 tropoelastin undergoes extensive alternative splicing. As the splitting of codons at the exon-intron borders is consistent throughout the molecule, alternative splicing occurs in a cassette-like fashion with maintenance of the coding sequence. This results in the translation of multiple heterogeneous tropoelastin isoforms. At least seven human exons are known to be alternatively spliced: 22, 23, 24, 26A, 30, 32, and 33. Alternative splicing of individual exons may be used to tailor the structural function of the protein in different tissues. It appears to be developmentally regulated and tissue-specific with age-related changes in isoform ratios observed in all species that have been investigated. The most frequently observed human tropoelastin isoform lacks exon 26A, which is reportedly only expressed in certain disease states. Three human disorders have been linked to mutations or deletions of the tropoelastin gene: cutis laxa, supravalvular aortic stenosis, and Williams-Beuren syndrome.

As used herein, the term "TIMP" refers to a member of a group of at least 4 structurally related proteins (Tissue inhibitor of matrix metalloproteinase-1, -2, -3 and -4 (TIMP-1, TIMP-2, TIMP-3 and TIMP-4)) that display varying degrees of sequence homology, suggesting that they are encoded by a related family of genes. TIMPs are critical to limiting extracellular matrix breakdown by inhibiting collagenases, gelatinases, and the like (matrix metalloproteinases (MMPs)). An essential feature of all TIMPs is that they have 12 conserved cysteine residues, with conserved relative spacing, and the presence of a 23 to 29 amino acid leader sequence, which is cleaved to produce a mature protein. Crystal structures for TIMPs, and MMP-TIMP complexes such as TIMP-1 in complex with MMP-3 and TIMP-2 with MT1-MMP have been described. TIMPs have the shape of an elongated, contiguous wedge consisting of the N-terminal and the C-terminal halves of the polypeptide chains opposing each other (Gomis-Ruth et al. 1997). In complexes with MMPs, TIMPs bind with their edge into the entire length of the active-site cleft of MMPs.

TIMP-1 protein is a 184 amino acid glycoprotein with a molecular mass of 28.5 kDa. It contains two possible N-glycosylation sites. The TIMP-1 promoter contains 10 Sp1, six AP-1, six PEA3, 12 AP-2 sites and five CCAAT boxes, in addition to a putative binding site for the transcription factor leader-binding protein 1 (LBP-1). The upstream TIMP-1 element-1 (UTE-1) is also essential for TIMP-1 transcription. The promoter contains two novel repressive elements, and an unidentified Ets-related factor to suppress transcription (Dean et al. 2000). TIMP-1 protein has been detected in human dentin and cementum. In addition, human osteoblasts secrete TIMP-1 constitutively.

TIMP-2 is a nonglycosylated 194 amino acid protein of 21 kDa molecular mass. It has an extended negatively charged C-terminus. The TIMP-2 promoter contains several regulatory elements including five Sp1, two AP-2, one AP-1 and three PEA-3 binding sites. TIMP-2 is transcribed into two mRNAs of 1.2 and 3.8 kb. Human osteoblasts and chondrocytes secrete TIMP-2.

The TIMP-3 polypeptide sequence is 37% and 42% similar to the sequences of TIMP-1 and TIMP-2, respectively. The TIMP-3 protein has 188 amino acids. It has a conserved glycosylation site near the C-terminus. Characterisation of the human recombinant TIMP-3 reveals that it has both a 27 kDa glycosylated and a 24 kDa unglycosylated species. TIMP-3 is localised to the ECM in both its glycosylated and unglycosylated forms. The TIMP-3 gene has four Sp1 sites, but no TATA-box in the promoter. Three TIMP-3 mRNA species of 2.4, 2.8 and 5.5 kb are transcribed from the gene, and are constitutively expressed by human chondrocytes.

TIMP-4 is a 195 amino acid polypeptide with molecular mass of 22 kDa. The TIMP-4 polypeptide is 37% identical to TIMP-1 and 51% identical to TIMP-2 and -3. TIMP-4 is the most neutral TIMP protein under physiological conditions (pH 7.4), having an isoelectric point of 7.34, compared with values of 8.00, 6.45 and 9.04 for 15 human TIMP-1, TIMP-2 and TIMP-3, respectively. The TIMP-4 gene is transcribed into 1.4 kb mRNA species. Of the calcified tissues, TIMP-4 has been detected in human cartilage.

Each TIMP binds with both a different rate of interaction and affinity to a target MMP, usually in 1:1 or 2:2 stoichiometrical fashions. TIMP-1 inhibits MMP-1, 20 MMP-3 and MMP-9 more effectively than TIMP-2. TIMP-2 inhibits proMMP-2 over 10-fold more effectively than TIMP-1. However, TIMP-2 has a bi-functional effect on MMP-2 since MT-MMP mediated proMMP-2 activation requires a tiny amount of TIMP-2 to make activation progress, whereas a greater concentration of TIMP-2 inhibits MMP-2. TIMP-3 inhibits at least MMP-2 and MMP-9, whereas TIMP-4 is a good inhibitor for all classes of MMPs without remarkable preference for specific MMPs. TIMP-4 regulates MMP-2 activity both by inhibiting MT1-MMP and by inhibiting activated MMP-2.

While TIMPs usually inhibit already active MMP, gelatin-binding MMPs are an exception, since TIMP reversibly binds to the proforms of both MMP-2 and MMP-30 9. Later, TIMP may be dissociated from the complex, and proMMP activation is allowed to proceed. For example, TIMP-1 binds to the proMMP-9, and further proMMP-9 activation by MMP-3 is prevented until TIMP-1 is inactivated in the complex, e.g. by neutrophil elastase, which does not destruct proMMP-9. However, TIMP-2 may also inhibit the active form of MMP-9. Active MMP-13 is an example of an MMP, which is inhibited by all types of TIMPs, and MMP-19 is inhibited by all TIMPs, except TIMP-1. The activity of soluble MMP-16 is inhibited by TIMP-2 and TIMP-3, but not TIMP-1.

As used herein, "MMPs" comprise a family of at least 28 secreted or transmembrane enzymes collectively capable of processing and degrading various ECM proteins. Of these, at least 22 MMPs have so far been found to be expressed in human tissues. MMPs share high protein sequence homology and have defined domain structures and thus, according to their structural properties, MMPs are classified either as secreted MMPs or membrane anchored MMPs, which are further divided into eight discrete subgroups. Secreted MMPs include minimal-domain MMPs, simple hemopexin domain-containing MMPs, gelatin-binding MMPs, furin-activated secreted MMPs and vitronectin-like insert MMPs, while membrane bound MMPs include type I transmembrane MMPs, glycosyl-phosphatidyl inositol (GPI)-linked MMPs and type II transmembrane MMPs.

Crystal structures of MMPs further uncovered the exact domain organization, polypeptide fold and main specificity determinants. To data, crystal structures of the catalytic domains of human MMP-1, MMP-2, MMP-3, MMP-7, MMP-8, MMP-9, MMP-11, MMP-12, MMP-13 and MMP-14, in addition to porcine full length MMP-1 and human proMMP-2 have been resolved.

The third level of restricting the proteolytic activities of MMPs includes endogenous tissue inhibitors of MMPs (TIMPs). TIMPs specifically inhibit active forms of MMPs, and in some cases, latent MMPs as well, and disturbance in this balance may lead to pathological situations in tissues. Active MMPs may also be inactivated by α-macroglobulins, particularly α2-macroglobulin. Recent findings indicate that serine proteinase inibitor, tissue factor pathway inhibitor-2 (TFPI-2), inhibits MMP-1, MMP-2, MMP-9 and MMP-13 (Herman et al. 2001). Calcium-binding proteoglycans (N-Tes, testican-1 or testican-3) are able to inhibit MT1- or MT3-MMP mediated proMMP-2 activation. In addition, there are many exogenous inhibitors. Some examples include flavonols in green tea such as epigallocatechin-3-gallale or catechins, which inhibit MMP-2, MMP-9, MMP-12 activities and proMMP-2 activation. Several synthetic inhibitors are also good inhibitors of MMPs activities. A polypeptide "having the biological activity of TIMP" refers to a polypeptide having the same or increased capability of preferentially inhibiting MMPs. Such a polypeptide can be a full-length TIMP, a fragment of TIMP, an analog of TIMP bearing an amino acid substitution, deletion, or addition; or a derivative of TIMP.

As used herein, the term "elafin" refers to a mature elafin polypeptide (see e.g., Francart, et. al., 1997, Solution Structure of R-elafin, a Specific Inhibitor of Elastase, J. Mol. Biol. (1997) 268; 666-677). A polypeptide "having the biological activity of elafin" refers to a polypeptide having the same or increased capability of preferentially inhibiting elastase. Such a polypeptide can be a full-length elafin, a fragment of elafin, an analog of elafin bearing an amino acid substitution, deletion, or addition; or a derivative of elafin as described in U.S. Pat. No. 5,734,014. Elafin is also commonly called "skin-derived antileukoproteinase; elastase inhibitor; and SKALP). Elafin is a 57 amino acid residue peptide (6 kDa) that was first isolated from scales of patients with psoriasis. Elafin is a specific inhibitor of human leukocyte elastase (HLE) and porcine pancreatic elastase, and of proteinase-3, three enzymes that possess the ability to cleave the important connective tissue protein elastin. It has no inhibition effect on other serine proteinases such as trypsin, plasmin, a chymotrypsin, and cathepsin G. The binding of elafin to its target is very tight with dissociation constants. Elafin is believed to play an important protective role against destructive degradation by excessive elastases of the structural integrity of elastin-containing tissues and is therefore a compound of potentially therapeutical value in elastase-mediated disorders. Recently, elafin has been shown to protect elastin from UV-induced elastolytic degradation by physically binding to elastin fibers. Elafin gene sequences are publicly available.

As used herein, the term "superoxide dismutase" or "SOD" refers to a member of a group of at least 3 structurally related enzymatic proteins (SOD 1-3) that display varying degrees of sequence homology, suggesting that they are encoded by a related family of genes. Superoxide dismutase catalyzes the dismutation of superoxide into oxygen and hydrogen peroxide. As such, it is an important antioxidant defense in nearly all cells exposed to oxygen. In humans, three forms of superoxide dismutase are present. SOD1 is located in the cytoplasm, SOD2 in the mitochondria and SOD3 is extracellular. The first is a dimer (consists of two units), while the others are tetramers (four subunits). SOD1 and SOD3 contain copper and zinc, while SOD2 has manganese in its reactive centre. The genes are located on chromosomes 21, 6 and 4, respectively (21q22.1, 6q25.3 and 4p15.3-p15.1). SOD has been shown to prevent telomere shortening in fibroblasts, convert myofibrossed into fibroblasts, and reduce fibrotic scarring in skin post-irradiation (Serra, et. al., 2003. J Biol Chem. Feb 28;278(9):6824-30; Vozenin-Brotons. et. al., 2001. Free Radic Biol Med. Jan 1;30(1):30-42). The SOD 1 and SOD 2 gene sequences are publicly available.

As used herein, the term "heat shock proteins" or "HSPs" refers to a member of a large group of structurally related proteins that display varying degrees of sequence homology, suggesting that they are encoded by a related family of genes. Heat shock proteins (Hsps) are highly conserved constitutive and induced proteins that may be found in cells from bacteria to human beings (S. Lindquist, Ann. Rev. Biochem 55, 1151 (1986)). Constitutive Hsps can be critical to many diverse cellular functions. There are six major groups of Hsps that are grouped based upon molecular size. The groups are: (a) 20-30 kDa; (b) 40-50 kDa; (c) 50-60 kDa; (d) 70 kDa; (e) 90 kDa; and (f) 100-110 kDa (Minowada G et al., J. Clin. Invest., 95, 3 (1995); Morris S D, Clin. Exper. Dermatol., 27, 220 (2001)). The inducible forms of Hsps may be elicited by a variety of stressors, including elevated temperature (M. Schlesinger et al., Cold Spring Harbor Laboratory, 1982), heavy metals (M. Schlesinger et al., Alan R. Liss, Inc., 137 (1989)), amino acid analogs (P. Kelley and M. Schlesinger, Cell 15, 1277 (1978); L. Hightower, J. Cell. Physiol. 102, 407 (1980)), oxidate radicals (M. Ashburner, Chromosoma 31, 356 (1970); J. Compton and B. McCarthy, Cell 14, 191 (1978)), ischemia or return from anoxia (S. Guttman, Cell 22, 299 (1980); M. Ashburner and J. Bonner, Cell 17, 241 (1979)), mechanical trauma (L. Hightower and F. White, Cold Spring Harbor Laboratory, 369 (1982); D. Gower et al., J. Cell Biol. 103, 291 (1986)), and the presence of abnormal proteins in the cell (J. Ananthan et al., Science 232, 522 (1986)). The unifying functional characteristic of heat shock proteins is to act to maintain normal cellular function under non-ideal conditions.

Hsps may be expressed constitutively in normal or resting skin cells where they may play an important role in several important biological processes. For example, Hsps in skin may act as molecular chaperones (Maytin E V, J. Invest. Dermatol., 104, 448 (1995)), and/or to effect the rapid upregulation of stress proteins in response to environmental stressors (Welch W J, Physiol. Rev., 72, 1063 (1992)). Several Hsps are expressed in skin cells. Hsp 72 is constitutively expressed in keratinocytes, (see e.g., Trautinger F et al., J. Invest. Dermatol., 101, 334 (1993); Charveron M et al., Cell Biol. Toxicol., 11, 161 (1995); and Laplante A et al., J. Histochem. Cytochem., 46, 1291 (1998)). Also, Hsps 27, 47, 60, 90, and 110 may be present in normal epidermis (Wilson N et al., J. Cutan. Pathol., 27, 176 (2000)). Each of these Hsps appear to have specific functions within normal tissue. For example, Hsp 27 stabilizes actin, whereas Hsp 90 acts both as a molecular chaperone, and/or may activate certain transcription factors (Charveron M el al., Cell Biol. Toxicol., 11, 161 (1995)). Hsp 27 in skin tissue may also control differentiation of cells in developing skin (Jantschitsch C et al., Br. J. Dermatol., 139, 247 (1998)).

There is evidence that Hsps can be exchanged between cells (L. Hightower and P. Guidon, J. Cell. Physiol. 138, 257 (1989); M. Tytell et al., Brain Res. 363, 161 (1986); M. Tytell, Int. J. Hyperhermia, 21, 4450455 (2005)). Thus, it is possible that the effects of Hsps may not be limited to the cell in which the lisp is expressed, but may extend to neighboring cells.

Genetic Modification of Cells Having Cosmetic Function

Thus, the present invention relates to methods and compositions for genetic modification of cells having cosmetic function to enhance cosmetic appearance. The present invention may be embodied in a variety of ways.

In one embodiment, the invention may comprise a method for the cosmetic genetic modification of substantially intact cells having a cosmetic function in a subject comprising: administering a polynucleotide encoding at least one of a nucleic acid or a polypeptide involved in maintaining the cells having cosmetic function to a least a portion of the cells such that the nucleic acid or polypeptide is expressed in the cells having cosmetic function to enhance and/or maintain a biochemical and/or physiological process that has a positive effect on cosmetic appearance.

In another embodiment, the present invention comprises an isolated polynucleotide encoding at least one of a nucleic acid or a polypeptide involved in 25 maintaining the cells having cosmetic function. In an embodiment, the isolated nucleotide is applied to cells, such that the nucleic acid or polypeptide may be expressed in the cells having cosmetic function to enhance and/or maintain a biochemical and/or physiological process that has a positive effect on cosmetic appearance.

In another embodiment, the present invention comprises an isolated polypeptide or an isolated polynucleotide involved in maintaining the cells having cosmetic function. For example, in certain embodiments, the present invention comprises an isolated polypeptide or an isolated polynucleotide having as described herein. Thus, in alternate embodiments of the methods and compositions of the present invention, the isolated polynucleotide may comprise SEQ ID NO: 1, SEQ ID NO: 5, SEQ ID NO: 9, SEQ ID NO: 13, SEQ ID NO: 17, or nucleotides 446 to 1030 of SEQ ID NO: 24, or the complement of SEQ ID NO: 1, SEQ ID NO: 5, SEQ ID NO: 9, SEQ ID NO: 13, SEQ ID NO: 17, or SEQ ID NO: 24, or a sequence that is at least 70%, 85%, 80%, 90%, 95%, 96%, 97%, 98%, or 99% identical to SEQ ID NO: 1, SEQ ID NO: 5, SEQ ID NO: 9, SEQ ID NO: 13, SEQ ID NO: 17, or nucleotides 446 to 1030 of SEQ ID NO: 24, or at least 70%, 85%, 80%, 90%, 95%, 96%, 97%, 98%, or 99% identical to the complement of SEQ ID NO: 1, SEQ ID NO: 5, SEQ ID NO: 9, SEQ ID NO: 13, SEQ ID NO: 17, or and/or nucleotides 446 to 1030 of SEQ ID NO: 24.

In other embodiments, the isolated polynucleotide may comprise SEQ ID NO: 2 (procollagen COL1A1), SEQ ID NO: 6 (elastin), SEQ ID NO: 10 (superoxide dismutase 3), SEQ ID NO: 14 (TIMP-1) SEQ ID NO: 18 (COL1A2), SEQ ID NO: 23 (KGF-1) or a sequence that is at least 70%, 85%, 80%, 90%, 95%, 96%, 97%, 98%, or 99% identical to a polypeptide of SEQ ID NO: 2, SEQ ID NO: 6, SEQ ID NO: 10, SEQ ID NO: 14, SEQ ID NO: 18, or SEQ ID NO: 23. Or a polypeptide having these sequences may be used. The sequences of these nucleotides and polypeptides are shown in FIGS. 1-5 and 16.

In yet other embodiments, the present invention may comprise a composition for genetically modifying substantially intact cells having cosmetic function in a subject. The composition may comprise a polynucleotide encoding at least one of a nucleic acid or a polypeptide involved in maintaining cells having cosmetic function; and a carrier for administration of the polynucleotide to a least a portion of the subject's cells having cosmetic function such that the nucleic acid or polypeptide is expressed in the cells having cosmetic function so as to enhance and/or maintain a biochemical and/or physiological process that has a positive effect on cosmetic appearance. Or, the composition may comprise a polypeptide involved in maintaining cells having cosmetic function; and a carrier for administration of the polynucleotide to a least a portion of the subject's cells having cosmetic function such that the nucleic acid or polypeptide is expressed in the cells having cosmetic function so as to enhance and/or maintain a biochemical and/or physiological process that has a positive effect on cosmetic appearance.

A variety of polypeptides may be targeted to enhance and/or maintain a biochemical and/or physiological process that has a positive effect on cosmetic appearance. For example, in certain embodiments, the polynucleotide used in the methods and compositions of the present invention encodes a keritinocyte growth factor. In an embodiment, the polypeptide comprises a keratinocyte growth factor or a biologically active derivative thereof. For example, in certain embodiments the polynucleotide comprises nucleotides 446 to 1030 of SEQ ID NO: 24, or the complement of nucleotides 446 to 1030 of SEQ ID NO: 24, or a sequence that is at least 70%, 75%, 80%, 85%, 90%, 95%, 96%, 97%, 98%, or 99% identical to nucleotides 446 to 1030 of SEQ ID NO: 24 or the complement thereof, or a polynucleotide that encodes a protein having the sequence of SEQ ID NO: 23 or a sequence that is at least 70%, 75%, 80%, 85%, 90%, 95%, 96%, 97%, 98%, or 99% identical to SEQ ID NO: 23.

In other embodiments, the polynucleotide encodes a collagen polypeptide or polypeptides (e.g., COL1A1 and COL1A2). Or, the polynucleotide may encode an elastin polypeptide. In other embodiments, the polynucleotide may encode a TIMP-1 polypeptide. Or, the polynucleotide may encode a SOD polypeptide. In yet other embodiments, the polypeptide may comprise at least one of a transforming growth factor, a platelet derived growth factor, a vascular endothelial growth factor, an insulin-like growth factor, a heptocyte growth factor, a vascular endothelial growth factor, a fibroblast growth factor, an epidermal growth factor, a platelet derived endothelial cell growth factor, a connective tissue growth factor, a granulocyte-macrophage colony-stimulating factor, a macrophage colony stimulating factor, a growth hormone, TSP-1, TSP-2, a collagen protein, TIMP-1, a superoxide dismutase, an elastin, or a hypoxia inducible factor, or a biologically active derivative thereof.

Thus, in alternate embodiments of the methods and compositions of the present invention, the polynucleotide may comprise SEQ ID NO: 1, SEQ ID NO: 5, SEQ ID NO: 9, SEQ ID NO: 13, or SEQ ID NO: 17, or the complement of SEQ ID NO: 1, SEQ ID NO: 5, SEQ ID NO: 9, SEQ ID NO: 13, SEQ ID NO: 17, and/or 30 nucleotides 446 to 1030 of SEQ ID NO: 24 or a sequence that is at least 70%, 85%, 80%, 90%, 95%, 96%, 97%, 98%, or 99% identical to SEQ ID NO: 1, SEQ ID NO: 5, SEQ ID NO: 9, SEQ ID NO: 13, or SEQ ID NO: 17, and/or nucleotides 446 to 1030 of SEQ ID NO: 24 or the complement of SEQ ID NO: 1, SEQ ID NO: 5, SEQ ID NO: 9, SEQ ID NO: 13, SEQ ID NO: 17 and/or nucleotides 446 to 1030 of SEQ ID NO: 24.

In other embodiments, the polynucleotide of the methods and compositions of the present invention may encode for a polypeptide of SEQ ID NO: 2 (procollagen COL1A1), SEQ ID NO: 6 (elastin), SEQ ID NO: 10 (superoxide dismutase 3), SEQ ID NO: 14 (TIMP-1) or SEQ ID NO: 18 (COL1A2), SEQ ID NO: 23 (KGF-1) or a sequence that is at least 70%, 85%, 80%, 90%, 95%, 96%, 97%, 98%, or 99% identical to a polypeptide of SEQ ID NO: 2, SEQ ID NO: 6, SEQ ID NO: 10, SEQ ID NO: 14, SEQ ID NO: 18, or SEQ ID NO: 23. Or a polypeptide having these sequences may be used. The sequences of these nucleotides and polypeptides are shown in FIGS. 1-5 and 16.

In certain embodiments of the methods and compositions of the present invention, the polynucleotide comprises, or is inserted into, a plasmid or a viral vector. For example, the polynucleotide may maintained as a extrachromosomal plasmid in at least a portion of the transfected cells. In certain embodiments, the gWIZ™ vector, commercially available from Gelantis may be used. Or, pVAX-BEST from Invitrogen may be used.

The methods and compositions of the present invention may comprise delivery of a single agent or multiple agents to cells. In one embodiment, at least two different polypeptides or nucleic acid molecules are administered to the cells.

The polynucleotide of the methods and compositions of the present invention may comprise a recombinant construct that is designed to express the polypeptide in cells having cosmetic function. Thus, as described in more detail herein, the polynucleotide encoding a nucleic acid or polypeptide involved in maintaining the cells having a cosmetic function may be operably linked to a constitutive or an inducible promoter. In an embodiment, the promoter is not ubiquitously expressed, but is expressed in the cells having cosmetic function. Additionally or alternatively, the polynucleotide encoding a nucleic acid or polypeptide involved in maintaining the cells having a cosmetic function may be operably linked to an enhancer. Also, in yet other embodiments, the polynucleotide encoding a nucleic acid or polypeptide involved in maintaining the cells having a cosmetic function may be operably linked to at least one of a functional poly A sequence, an intron, a cleavage sequence, a stop sequence, or a cap site.

A variety of cells having a cosmetic function may be targeted using the methods and compositions of the present invention. In alternate embodiments, the modified cells having a cosmetic function comprise at least one of keratinocytes, fibroblasts, adipocytes, or myofibrils.

A variety of methods may be used to administer the nucleic acid (i.e., polynucleotide) constructs of the present invention. In one embodiment, the polynucleotide is introduced as naked DNA into the cells having a cosmetic function. In certain embodiments, the carrier comprises at least one of liposomes, nanoparticles, an emulsion, a thixogel, or an organoleptic gel. Thus, in alternate embodiments, the polynucleotide is introduced into the cells having a cosmetic function using a carrier comprising at least one of liposomes, nanoparticles, an emulsion, a thixogel, or an organoleptic gel. Or, the polynucleotide may be introduced into the cells having a cosmetic function via a water-in-oil emulsion or an oil-in-water emulsion. In yet other embodiments, the polynucleotide is introduced into the cells having a cosmetic function via at least one of particle mediated transfer (e.g., gold particles, microsheres), voltage driven transfer, radio frequency ablation-mediated transfer, ultrasound, or microneedles.

FIG. 6 shows an embodiment of an example method 2 of the present invention. For example, the method may comprise the step 4 of assessing the subject for the need to improve or maintain cells having cosmetic function. The assessment may be done by a dermatologist or another health care professional. Or, the assessment may be performed by the subject (i.e., a self-assessment).

Next, the method may comprise the step 6 of determining the nature of the treatment that is required. Again, the assessment may be done by a dermatologist or another health care professional. Or, the assessment may be performed by the subject (i.e., a self-assessment).

The method may further comprise the step 8 of preparing (or selecting) a composition comprising the required therapeutic gene or mixture thereof. In an embodiment, this step may be performed at least initially by a dermatologist or another health care professional. Once the appropriate composition has been selected, an assessment may be performed by the subject (i.e., a self-assessment). For example, the subject may perform an assessment as to which of the available skin care genetic products to purchase.

The method may additionally comprise the step 10 of applying the composition to the cells or tissue needing treatment. In an embodiment, the composition may be applied for a period of time as is required to improve and/or maintain the cells having cosmetic function. As described in more detail herein, the exact dosage and time period of treatment may vary depending upon the condition of the subject and the nature of the composition applied.

The method may also comprise the step 12 of reassessing the subject to determine if there has been an improvement in the subject's cells having cosmetic function. If it is determined that the cells having cosmetic function have an improved appearance 14-YES the subject may choose to terminate the use of the composition 16. If, however, it is determined that the cells having cosmetic function do not have an improved appearance 14-NO the subject may choose to repeat the procedure, perhaps using a different composition.

Thus, embodiments of the present invention comprise methods and compositions for the genetic modification of cells having cosmetic function. In certain embodiments, the present invention may comprise methods and/or compositions for the in vivo or ex vivo transfection of recombinant nucleic acid constructs into cells having cosmetic function. The recombinant constructs may be incorporated into cells having cosmetic function either as extrachromosomal elements or may insert directly into the genome.

In other embodiments, the methods and/or compositions may provide polypeptides or other biomolecules directly (i.e, without the need for expression of the gene). For example, a mixture of growth factors that may enhance or maintain cells that have cosmetic function may be used. For example, in alternate embodiments, the polynucleotides may comprise keratinocyte growth factor (KGF), insulin-like growth factor 1 (IGF-1), and/or transforming growth factor beta (TGF-beta), and/or mixtures of these peptides as discussed in detail herein. Or, other peptides may be used.

Or, the recombinant constructs may encode for regulatory polynucleotides, as for example antisense RNA or inhibitory RNAs (RNAi) to enhance and/or maintain a biochemical and/or physiological process that has a positive effect on cosmetic appearance.

The methods and or compositions of the present invention may be utilized to enhance and/or maintain and/or improve the cosmetic appearance of a subject and/or a subject's tissue and/or cells having a cosmetic function. A variety of biological molecules and/or physiological processes may be modulated using the methods and/or compositions of the present invention. In certain embodiments, the cosmetic benefits provided by the methods and compositions of the present invention may include at least one of the following: reduced skin sagging; increased skin thickness; increased skin volume; reduced wrinkle number; reduced wrinkle length, reduced wrinkle depth; increased skin tightness, firmness, tone, or elasticity; increased skin hydration and ability to retain moisture, water flow (e.g. aquaporine channel production) and osmotic balance.

Modulation of at least one of a variety of biomolecules having expression in cells that have cosmetic function may result upon treatment with the compositions and/or methods of the present invention. For example, use of the methods and compositions of the present invention may also, in certain embodiments, result in increased skin proteins. Or, use of the methods and compositions of the present invention may result in increased levels of skin lipids, such as membrane lipids, lamellar body lipids, secreted intercellular lipids. Thus, in certain embodiments, use of the methods and/or compositions of the present invention may result in increased extracellular matrix, and/or adhesion and communication polypeptides, including but not limited to collagens, elastins, keratins (including keratin intermediate filaments), fibronectins, proteoglycans, laminins, integrins, decorin, lumican, fibromodufin (and other are small leucin-rich repeat proteoglycans (SLRP's)), Tenascin E, neurofilaments, nestins, desmins, vimentins, peripherins, ceramides, cholesterol, phospholipids, sphingolipids, "Natural Moisturizing Factor" (NMF), and glycosaminoglycans (GAGs) such as hyaluronic acid and dermatan sulfate.

In yet other embodiments, use of the methods and/or compositions of the present invention may result in increased skin cell energy production, utilization and conservation; improved oxygen utilization; improved skin cell life (e.g. longer living fibroblasts) and/or life cycle (e.g. reduced senescence). Embodiments of use of the methods and/or compositions of the present invention may additionally or alternatively result in at least one of improved skin cell immunity defense, heat shock/stress response, antioxidant defense capacity to neutralize free radicals (e.g. reactive oxygen or carbonyl species), and/or toxic defense (e.g. environmental pollutants); improved protection and recovery from ultraviolet rays. In yet other embodiments, use of the methods and/or compositions of the present invention may result in improved skin cell communication (e.g. neuropeptide mediated communication) and skin cell innervation; improved skin cell cohesion/adhesion (e.g. desmosome integrity); improved calcium mineral and other mineral metabolism; improved skin cell turnover (e.g. desquamation); and/or improved skin cell circadian rhythms.

Use of the method and compositions of the present invention may, in certain embodiments result in at least one of improved skin texture, smoothness, softness radiance, glow. For example, in certain embodiments, use of the method and/or compositions of the present invention may result in at least one of reduced discolorations and unevenness of skin color including redness, hyperpigmentation (e.g., melasma) and hypopigmentation.

Yet other embodiments of the use of the methods and compositions of the present invention may result in at least one of improved blood vessel health including improved vascular integrity (i.e. less leakage of discoloring blood products into skin), improved vascular tone, improved breakdown of discoloring blood by-products (e.g. improved hemosidirin breakdown, bilirubin processing and improved UGT1a enzyme function) and reduced "spider veins" and "varicose veins." In yet other embodiments, use of the methods and compositions of the present invention may result in improved DNA, RNA, mitochondrial, membrane and other skin cell organelle health; improved adipogenesis to increase fat amounts to keep skin plumped and the face or other body areas looking full, defined or rounded; improved dermal-epidermal junction ("DEJ"). For example, one of the most evident and reproducible biological feature of aging skin is the flattening of the dermal-epidermal junction. This process may occur as a consequence of a rarification and reduction of dermal papillae. For example, between the age of 30 and 90 years, a more than 50% decrease in the interdigitation between these skin layers may take place (see e.g., Kirstin et al., Phytochemistry and Photobiology, 2005, 81:581-587).

There may be certain biomolecules that may be over-expressed in cells having cosmetic function. Thus, in yet other embodiments, use of the methods and/or compositions of the present invention may be used to reduce such detrimental biomolecules. For example, embodiments of the methods and/or compositions of the present invention may result in increased lipolysis to reduce "cellulite" and "dimpling" of skin; as well as to reduce abdominal and/or total body fat. Or, the methods and/or compositions of the present invention may also be used to result in reduced pore size; reduced dryness and/or flaking; reduced oiliness and acne. Embodiments of the methods and/or compositions of the present invention may also be used to result in decreased contraction of muscles, smooth muscle cells and myofibrils (e.g. to reduce expression wrinkles), or increased contraction of muscles, smooth muscle cells and myofibrils (e.g. to reduce sagging); and increased size of skin cells (e.g. hypertrophied facial muscles to prevent a "hollowed" face look). Additionally, cells having cosmetic function (e.g., skin cells) may be modified for the purpose of maintaining cosmetic appearance despite UV light damage (e.g. enhanced endonuclease, photolyase, heat shock proteins, metallothionein, and superoxide dismutase expression levels for an increased endogenous "sunscreen" to protect cosmetic appearance) and other environmental aggressions (e.g. pollutants and irritants).

Yet other embodiments of the methods and/or compositions of the present invention may be used to increase pigmentation (e.g. sun tan without UV exposure for a sunless tan) or alternatively, decrease pigmentation (e.g. "whitening"). Additionally, skin cells may be modified for the purpose of producing permanent or temporary color and pigmentation changes (e.g. changing color of hair or iris) including fluorescence, iridescence, phosphorescence, reflectance, refraction, photoluminescence, chemiluminescence, and/or bioluminescence (e.g. luciferase and luciferin reaction). Additionally, cosmetic improvement and cosmetic maintenance benefits upon treatment with the methods and/or compositions of the present invention may include at least one of the following: reduced scar formation post-trauma; improved post-laser resurfacing repair of the skin; increased protection from sun-sensitizing drugs such as ACCUTANE®, anti-depressants, RETIN-A MICRO®, and the like; reduced photoaging damage; improved cosmetic appearance and healing after laser resurfacing/pulsed light therapy or any similar method that uses light, laser, radio waves, electromagnetic, ultrasound waves and the like to treat skin cells; improved cosmetic appearance and healing post-dermabrasion procedures, post-chemical peels (large variety of chemical peels); scar reduction (proactive and retroactive), and post-injectable procedures including BOTOX®, Restylane, Juviderm and the like.

Although the methods and/or compositions of the present invention may, in certain embodiments, be used on skin, other types of cells having cosmetic function may also be targeted. For example, nail-related cells may be modified for improved nails and cuticles with faster growth rate, reduced splitting and breaking, improved length and thickness, decreased ridging and flaking, decreased roughness and dullness, and better coloration. Also, hair-related cells may be modified for faster growth rate, lower growth rate, reduced split ends, flaking and breaking, improved manageability, reduced dullness, improved shine and sheen, increased density (thicker), decreased density (thinner), ablation, increased length and thickness and improved softness. Any one of the above cosmetic improvements may produce the secondary benefit of greater self-confidence and enhanced mood in a subject.

Thus, in certain embodiments, the invention provides in vivo or ex vivo methods for increasing expression of cosmetic enhancing and/or maintaining nucleic acids or polypeptides in cells having cosmetic function. For example, the method may comprise administering a polynucleotide encoding at least one of a nucleic acid or a polypeptide involved in maintaining the cells having cosmetic function to a least a portion of the cells such that the nucleic acid or polypeptide is expressed in the cells having cosmetic function to enhance and/or maintain a biochemical and/or physiological process that has a positive effect on cosmetic appearance.

A variety of genes that encode for a variety of proteins may be used in the methods and compositions of the present invention. In certain embodiments of the methods and compositions of the present invention, the polynucleotide construct may encode for an antisense RNA or a siRNA as a means to inhibit expression of the protein. For example, reduced expression of certain growth factors may result in reduced inflammation in or near the cell having cosmetic function. Also, reduced expression of certain MMP proteins may result in increased collagen levels in the cells. In certain embodiments, the siRNA may inhibit expression of other genes to improve the cosmetic appearance of cells.

In an embodiment, the nucleic acid, or polypeptide(s) encoded by the transfected recombinant polynucleotide, may comprise a keratinocyte growth factor (e.g., KFG-1 or KFG-2), and/or KGF receptors and cofactors or a fragment thereof. Alternatively or additionally, the nucleic acid, or polypeptide(s) encoded by the transfected recombinant polynucleotide, may comprise at least one a transforming growth factor (TFG-alpha, TFG-beta$_{1-4}$, other known TGF-beta proteins) and/or TGF receptors or cofactors or a fragment thereof. Alternatively or additionally, the nucleic acid, or polypeptide(s) encoded by the transfected recombinant polynucleotide, may comprise an insulin-like growth factor (e.g., IGF-1, IGF-2) or a fragment thereof. Alternatively or additionally, the nucleic acid, or polypeptide(s) encoded by the transfected recombinant polynucleotide, may comprise at least one of a platelet derived growth factors (e.g., PDGF-AA, PDGF-AB, PDGF-BB, PDGF-CC) or a fragment thereof.

In other embodiments, the nucleic acid, or polypeptide(s) encoded by the transfected recombinant polynucleotide, may comprise at least one of the following polypeptides or fragments thereof: a vascular endothelial growth factor (e.g. VEGF-A or VEGF-C); a hepatocyte growth factor; a fibroblast growth factor (e.g., FGF-1, FGF-2, FGF-3, or FGF-22); an epidermal growth factor (e.g., EGF; Heparin-binding-EGF); a platelet derived endothelial cell growth factor (PD-ECGF); a connective tissue growth factor (e.g., CTGF-1, CTGF-2); a granulocyte-macrophage colony-stimulating factor (GMCSF); a monocyte colony stimulating factor (MCSF); a granulocyte colony-stimulating factor (GCSF); a growth hormone (GH); an anti-angiogenic factors (e.g. Ang-1, soluble platelet factor-4, thrombospondins such as TSP-1 and TSP-2, an antagonist of urokinase plasminogen astivator/receptor, e.g., uPA/uPAR, angiostatin, endostatin and vasostatin); a transcription factor Egr-1, or a hypoxia inducible factor (HIF-1-alpha). Other encoded polypeptides or nucleic acids may be used in the compositions and methods of the present invention may comprise polypeptides having enzymatic function for synthesis, degradation, repair and antioxidant protection, polypeptides with structural function including extracellular matrix proteins, polypeptides with cellular adhesion and communication function, factors, cofactors, receptors for the expressed polypeptides, and promoters for non-transfected genomic polynucleotides encoding polypeptides active in skin cells. For example, the polypeptides or nucleic acids used in the compositions and methods of the present invention may comprise, or encode (or be complementary to a nucleotide that encodes) for polypeptides or fragments thereof of neurotrophins (e.g. nerve growth factors (NGFs), neurotrophin-3 (NT-3), NT-4 and brain-derived neurotrophic factor (BDNF), tumor necrosis factors (TNFs), hepatocyte growth factors (HGFs), interferons (INFs), interleukins (ILs—e.g. IL-1, IL-2, IL6, IL-8 and IL-10), angiopoietins, scatter factors (SFs), chemokines (CCs), activins (part of TGF-beta family), adipokines (e.g. leptin, interleukin 6 (IL-6), other cytokines, adiponectin, complement components, adipsin, plasminogen activator inhibitor-1 (PAI-1), proteins of the renin-angiotensin system (RAS) and others), bone morphogenetic proteins (BMPs).

In yet other embodiments, the polynucleotide may encode (or be complementary to a nucleotide that encodes) for a CCN protein family peptide (e.g. cysteine-rich (CYR61/CNN1), a connective tissue growth factor CNN2, Nov, WISP-1, WISP-2, and WISP-3), integrin alpha(6)beta(1), cell surface heparan sulfate proteoglycans (HSPGs), focal adhesion kinase, paxillin, and/or Rac, p42/p44 MAPKs, or a fragment or biologically active derivative thereof. Or, siRNAs or antisense molecules to these genes may be used.

In yet other embodiments, the polynucleotide may encode (or be complementary to a nucleotide that encodes) at least one of the following polypeptides (or biologically active derivative or fragments thereof): a signal transducer and/or activators of transcription (STATs), a thyroid hormone (TH), a thyroid stimulating hormone (TSH), prolactin, parathyroid hormone (PTH), a Parathyroid hormone-related protein (PTHrP), a thyrotropin releasing hormone (TRH), neuropeptides, (e.g. endorphin) tazorac induced genes (TIGs), cellular retinoic acid-binding proteins (CRABPs), procollagen, collagen (all forms), proline hydroxylase and other enzymes involved in collagen synthesis (e.g. hydroxylysyl galactosyltransferase and galactosylhydroxylysyl glucosyltransferase), repair/maintenance and degration, tropoelasin, elastin, lysyl oxidase and other enzymes involved in elastin synthesis, repair/maintenance and degradation, fibrillins, fibulins, superoxide dismutase (e.g., SOD 1, 2 and 3), glutathione peroxidase (GSH-Px), catalase (CAT), peroxiredoxin VI, haem-oxygenase (HO), thioprotein reductase, antioxidant protein 2 (Aop2), metallothionein (MT), glutathione (GSH), ubiquinol (coenzyme Q), calnexin, enzymes involved in keratinocyte desquamation (e.g. cathepsins such as Cathepsin-D and Cathepsin-G and transglutaminases), fibronectins, laminins, integrin, cadherins, lectin cell adhesion molecules (LEC-CAMs), aquaporins, actins, involucrins, loricrins, (pro)filaggrin, keratin/cytokeratins, desmoplakins, envoplakins, periplakins, annexins, enzymes involved in the synthesis, maintenance/repair and degradation of extracellular matrix, cellular adhesion and cellular communications (e.g. enzymes involved in the synthesis of laminin, fibronectin and keratins), DNA synthesis, repair/maintenance and degradation enzymes (e.g., endonucleases, photolyase, telomerase, and others (ERCC3, PCNA, RPA, XPA, p53, all of which are decreased with age; Goukassian et al., FASEB J., 2000, 14, 1325-1334) and telomere 3-prime overhang sequence (T-oligos), stress response and chaperone proteins and related elements/activators/factors (e.g. heat shock protein 27, heat shock protein 47, heat shock protein 60, heat shock protein 70, alphaB-crystalline, Grp78, Grp94, heal shock element (HSE) by heat shock transcription factors and co-factors (e.g. HSF1, 2, 4), cysteine string protein (csp), BAG-1, Hip, CHIP, Hop and Tpr-2), enzymes involved in synthesis, repair/maintenance and degradation of ceramides and ceramide derivatives (e.g. serine palmitoyl transferase, B-galactocerebrosidase, glucocerebrosidase, acid/neutral/alkaline SMASE (sphingomyelinase), acid ceramidase, SM deacylase, GCdeacylase, pSAP, glucosylceramide synthase, ceramide synthase and sphingomyelin synthase), enzymes involved in synthesis, repair/maintenance and degradation of hyaluronic acid (e.g. hyaluron/hyaluronan synthases 1-3 and others), enzymes involved in cholesterol synthesis, maintenance/repair and degradation, enzymes involved in fatty acid, triacylglyceride, phospholipids, plasmalogen, sphingolipid, and elcosanoid (including the arachidonic acid cascade, prostaglandins and leukotrienes) synthesis, maintenance/repair and degradation, retinoic acid receptors, steroid receptors, hormone receptors (e.g. estrogen receptors), thyroid receptors, vitamin D receptors, peroxisomal proliferators-activated receptors (PPARs), farnesol-activated receptors (FXR), liver-activated receptor (LXR), matrix metalloproteinases (MMPs including collagenases (MMP-1), gelatinases (e.g., MMP-2 and MMP-9), elastases, stromelysins, serine proteases and membrane-type MMPSs), tissue inhibitors of metalloproteinases (TIMPs).

In yet other embodiments, the polynucleotide may encode (or be complementary to a nucleotide that encodes) a polypeptide or nucleic acid that encodes for at least a fragment of a serine proteinase inhibitors (e.g. skin-derived anti-leukoproteinase (SKALP), also known as elafin (preproelafin and proelafin included) and secretory leukocyte protease inhibitor (SLPI)), MSX (synonyms inclue CHOX-8; GHOX-8; HOMEOBOX PROTEIN MSX-2; HOX-8; HOX-8.1; HOX8; MSH HOMEO BOX HOMOLOG 2; MSX-1; MSX-2; MSX1; and QUOX-7), SMAD pathway, Smad3, c-ski, and extracellular signal-regulated kinase ½, cardiac repeat protein, estrogen-responsive B box protein (EBBP), IGF-binding proteins (IGFBPs), vitronectin, follistatin, RAC1, ADAMTS1 Proteinase, amphiphysin-1, transcription factor AP-1, cJun, cFos, beta-amyloid precursor protein (sAPP), Beta-catenin, CHL1, Corticotropin-releasing hormone (CRH), DJ-1, sterol-regulatory element binding proteins (e.g. SREBP-1 and SREBP-2), Phosphatidylinositol 3-Kinase (PI3K), stearoyl-CoA desaturase (SCD), fatty acid synthase, hydroxymethylglutaryl-CoA synthase (HMGCS), CCAAT/enhancer binding protein alpha (C/EBPalpha), C/EBPdelta, FAS, stearoyl coenzyme A desaturase-1 (SCD-1), enzymes involved in estrogen synthesis (e.g. aromatase), fibroblast growth factor homologous factor (FHF) polypeptides, decorin, lumican, fibromodulin (and other small leucine-rich repeat proteoglycans), versican, biglycan, aggrecan, brevican, galectins (e.g. galectin-3 and galectin-7), heparin sulfate, perlecan, syndecan-1, chondroiton sulfate, JUN-regulated factors (e.g. pleiotrophin (PTN) and stromal cell-derived factor 1 (SDF-1)), CXCR4 (SDF-1 receptor), anti-apoptotic proteins (e.g. Bcl2 and survivin), transcription factor nuclear factor (NF)-kappaB, nitric oxide synthase, enzymes involved in the synthesis and degradation of catecholamines, Mitogen-activated protein kinase (MAPK), transcription factor NF-E2-related factors (e.g. Nrf2 and Nrf3), p21-activated protein kinase 4 (PAK4), enzymes involved in the synthesis of sphingosylphosphorylcholine (SPC), lipases, lipid-mobilizing peptides (e.g. beta-lipotropin and "lipolytic peptide A and peptide B"), amphiregulin, tyrosinase and other enzymes involved in melanin, eumelanin and pheomelanin synthesis and degradation, melanocortins (pituitary peptide hormones that include adrenocorticotropin (ACTH) and the alpha, beta and gamma melanocyte-stimulating hormones (MSH), prohormone proopiomelanocortin, a-MSH, ACTH, endothelin 1, camp, PKCb, bey1, bey2, bey3, human melanocortin-1 receptor (MC1R), OCA1 (tyrosinase, TYR), OCA2 (OCA2), OCA3 (tyrosinase-related protein 1, TYRP1), and OCA4 (membrane-associated transporter protein, MATP), c-Jun N-terminal kinase kinase kinases (JNKKK polypeptides e.g. MLK4, PAK4, PAK5 and YSK2), Hif1-alpha regulated genes (e.g. BNIP3, hypoxia-induced gene 1, adenylate kinase 4, galactokinase, galectin-3, gelsolin, RhoA, Rho kinase, heterogeneous nuclear ribonucleoprotein H1 and splicing factor and REV3), alpha-SMA, S1-P, GRO-alpha/CXCR-1, erbB, HGF activator (HGFA), keratinocyte proline-rich protein (KPRP), neurotransmitters and neurotransmitter blockers (e.g. GABA (gamma-aminobutyric acid)), acetylcholine blockers, Waglerin 1 and Curare.

In yet other embodiments, the polynucleotide of the methods and/or compositions of the present invention may encode (or be complementary to a nucleotide that encodes) at least one of the following polypeptides (or fragments thereof): alpha 1-antitrypsin (an irreversible neutrophil elastase inhibitor that improves vein strength for varicose veins) that in certain embodiments, may be coupled with MMP-2 inhibition (MMP-2 is high in varicose vein tissues), Hormone-sensitive lipase (HSL), Protein Kinase A (activates HSL), Triglyceride lipase (ATGL), CGI-58 (a recently identified coactivator of ATGL that stimulates TG hydrolase activity in wild-type and HSL-deficient WAT but not in ATGL-deficient WAT suggesting that ATGL is the sole target for CGI-58 mediated activation of adipose lipolysis; together, ATGL and HSL are responsible for more than 95% of the TG hydrolase activity present in murine WAT). Additionally known lipases, atrial natriuretic peptides, trypsin, alpha-chymotrypsin, skin anti-microbial peptides to fight infection and acne (e.g. SLPI, lysozyme, and defensins), upstream transcription factor-1 (USF-1), DeltaNp63alpha, Sirt1, angiotensin (Ang) II type 1 (AT1) and type 2 (AT2) receptors, angiotensin II, SHP-1 (Src homology 2-containing protein-tyrosine phosphatase-1), and/or prostacyclin synthase (PGIS) may be encoded by, or targeted by antisense constructs of the present invention.

Additionally, the gene constructs of this present invention may comprise a polynucleotide (or fragment thereof) that encodes (or is complementary to a nucleotide that encodes) at least one of the following polypeptides (or fragments thereof) involved in cosmetic improvement or cosmetic maintenance: actin, procollagen or collagen fragments (e.g. KTTKS, polylysine peptides), tropoelastin or elastin fragments, laminin fragments, fibronectin fragments, Matrixyl™ (Pal-KTTKS), Matrixyl 3000™ (Pal-GHK and Pal-GQPR), RonaCare ASCIII™, CPC Peptide™, Collaxyl™, Peptide Vinci 01™, ALDENINE™, Ameliox™(carnosine di-peptide), ANT-ARCTICINE™, BIOPEPTIDE CL™, BioPeptide-EL™, Kappa Elastin™, SYN®-COLL, thrombospondin TSP-1 fragment) MYOXINOL™, DERMAXYL™, copper peptides (GHK-Cu), CYTOKINOL® LS 9028, Peptamide 6™, RIGIN™, KOLLAREN™, (hepatocyte growth factor (HGF) active fragment), Eyeliss™, Haloxyl™, Dipeptide 2, Dermican (TSH fragment), and numerous soy-derived peptides and the like such as those listed in the CFTA's cosmetic ingredient INCI database. Additional topically applied peptides that can relax muscles include SYN®-AKE (Waglerin 1 mimic), VIALOX™ (Curare mimic), ARGIRELINE™ (Acetyl Hexapeptide-3), Leuphasyl™, and SNAP-8™ (same as SNAP-25). Additional, polypeptides having activity in skin are described in U.S. Pat. No. 6,586,185.

In yet other embodiments, the polynucleotide may encode for nucleic acid and/or polypeptide that acts to decrease, slow and/or delay senescence in cells having a cosmetic function such as peptides described in U.S. Pat. No. 6,953,664, so as to enhance and/or maintain a biochemical and/or physiological process that has a positive effect on cosmetic appearance.

In yet other embodiments, the polynucleotide may encode for an antibody to a protein in cells having a cosmetic function so as to enhance and/or maintain a biochemical and/or physiological process that has a positive effect on cosmetic appearance.

Combinations of Polypeptides

Also, the polynucleotide delivered by the constructs of the present invention may, in certain embodiments, comprise a polynucleotide that encodes for combinations of two or more polypeptides or nucleic acids. For example, combinations of certain growth factors may show a synergistic improvement in wound healing as compared to singly applied growth factors (see e.g., Lynch, 1999; J. Clin. Invest., 84:640-646; Jeschke et al., 2004, Gene Therapy 11:847-855; Sprugel et al., Wound Repair Regen., 2004, 12:67-79; Endocrine Reviews, 2002; 24:737-767; Nabarro, J. D., 1987, Clin. Endocrinol., 26:481-512; Ristow et al., 1988, J. Cell Physiol., 137:277-284; O'Keefe et al., 1988, J. Invest. Dermatol., 90:2-7; Cook et al., J. Cell Physiol., 146:277-189). Also, the constructs may be administered such that the polypeptides are expressed in a 1:1 ratio. Or, other ratios (e.g., 2:1, 3:1, 4:1, 5:1, 10:1, 20:1, 50:1, 100:1, 500:1, or 1000:1 for each of the proteins may be used.

For example, in an embodiment, the combination may comprise a PGDF and an IGF. The PGDF may comprise any one of the known PDGF isoforms. Similarly, the IGF may comprise any one of the known isoforms. The constructs may be administered such that the polypeptides are expressed in a 1:1 ratio. Or, other ratios (e.g., 2:1, 3:1, 4:1, 5:1, 10:1, 20:1, 50:1, 100:1, 500:1, or 1000:1 for each of the proteins may be used. In one example embodiment, the constructs are administered to result in about 2:1 ratio (by weight) of PDGF-BB and IGF-1. Or other combinations of PDGF and/or IGF and/or other ratios may be used. Similarly, a combination of a PDGF and a TGF-alpha may be used. Or, combinations of HGF and IGF may be used. In yet other embodiments, a combination of PDGF and a basic FGF may be used, or a combination of HGF and basic FGF may be used. In yet another embodiment, a combination of GH and IGF-1 or IGF-II may be used.

In certain embodiments, the construct, or constructs may encode for more than two proteins. For example, in some embodiments, a combination of PDGF with several other growth factors may be used. In an embodiment, PDGF in combination with KGF, IGF and IGFBP may be used. Or, sub-combinations of these growth factors may be used.

Removal of Degraded Collagen and/or Other Debris

In yet other embodiments, the polynucleotide constructs of the present invention may encode for proteins that help to remove degraded biomolecules as a means to maintain and/or improve synthesis of intact biomolecules that are important to enhancing and/or maintaining a physiological process that has positive effect on cosmetic appearance. For example, in one embodiment, the construct may encode for MMP-2 and/or MMP-9 to remove collagen debris from MMP-1. The use of these constructs may then be followed by the use of constructs that encode for the formation of new collagen. Such constructs may, in certain embodiments encode for growth factors, collagen and/or TIMP-1.

Receptors

Additionally, polynucleotide delivered by the constructs of the present invention may, in certain embodiments, comprise a polynucleotide that encodes for a receptor or combination of receptors for the polypeptides, growth factors and other biomolecules (e.g., required co-factors or transcription factors) in cells having cosmetic function (e.g. KGF receptors, TGF receptors, FGF receptors such as FGFRiiib, etc.) to enhance and/or maintain a biochemical and/or physiological process that has a positive effect on cosmetic appearance.

Nature of Expression

The constructs of the present invention may be administered into one or more types of cells having a cosmetic function in the mammal, for example transfection of undifferentiated "stem" or "basal" skin cells, differentiating skin cells at various stages, and terminally differentiated skin cells. In an embodiment, the technique may provide for the stable transfer of the nucleic acid to the genome of the cells, so that the nucleic acid or polypeptide may be expressed long-term by the cells. Once incorporated into the genome of a stem cell, the polynucleotide that encodes at least one of a nucleic acid or a polypeptide involved in the maintaining the cells having cosmetic function to enhance and/or maintain a biochemical and/or physiological process that has a positive effect on cosmetic appearance may be heritable and expressible by its cell progeny such as keratinocyte or fibroblast cells derived from undifferentiated stem or basal cells. For example, an integrative vector may be used (e.g., retroviruses, lentivirus, AAV, "Sleeping Beauty" transposons, or bacterial phage integrases, such as $\phi$C31, and the like, such that the targeted cell is any cell having cosmetic function.

In other embodiments, the technique may provide for the transient transfer of the nucleic acid to the cells having cosmetic function, so that the nucleic acid or polypeptide may be expressed transiently by the cells. In alternate embodiments, such expression may be for seconds, minutes, hours, days, weeks, months or years.

In other embodiments, expression is transient due to the biology of the cell. In the case of skin cells, cell turnover may result in loss of the modified cells upon terminal differentiation such as differentiating keratinocyte cells that move upward toward the outer periphery of the epidermis to form squames which are eventually lost via desquamation. Or, the stem cells may be modified, but the nucleic acid or a polypeptide that enhances a biochemical and/or physiological process that has a positive effect on cosmetic appearance may not be expressed until some stage of the skin cell differentiation. Thus, although the genetic modification is maintained in the stem cell line, the expression of the nucleic acid or a polypeptide may depend on the developmental stage of the progeny cell, thereby allowing the modification to be transient based on differentiation stage, (i.e., either limited to the stem cell stage, or to a differentiated cell stage).

In certain embodiments, the expressed nucleic acid and/or polypeptide may exert paracrine and/or autocrine effects in cells having a cosmetic function between any combination of stem cells, differentiating cells and differentiated cells. For example, transfected dermal fibroblast stem cells may express and secrete growth factors (e.g. Keratinocyte Growth Factor (KGF)) that have an autocrine effect on differentiating keratinocytes in the epidermis. As another example, transfected differentiating keratinocytes in the epidermis may express and secrete growth factors (e.g. Transforming Growth Factor-alpha) that have an autocrine effect on other differentiating keratinocytes in the epidermis. Additionally, the expressed nucleic acid and/or polypeptide may be designed to change a normal paracrine function to an autocrine function. For example, dermal fibroblasts normally express and secrete Keratinocyte Growth Factor (KGF) which subsequently diffuses to the epidermal keratinocytes to exert a paracrine effect. However, epidermal keratinocytes can be transfected with KGF-encoding construct so that subsequent expression and secretion of KGF is changed to an autocrine function instead of KGF's normal paracrine function.

Sites of Administration

The constructs of the present invention may be administered into one or more sites of a subject to enhance and/or maintain a biochemical and/or physiological process that has a positive effect on cosmetic appearance. Sites of administration may include the forehead, scalp, hair follicles, upper eyelids, lower eyelids, eyebrows, eyelashes, infraorbital and periorbital areas (including typical "crows feet" areas), temples, nose, nose bridge, cheeks, tongue, nasolabial folds, lips and periobicular areas including "jowls" area, jaw line, ears, neck, breasts, under triceps, back of hands, back, abdomen, sides, buttocks, front and back of thighs, knees and other areas of tissue having a cosmetic function in the subject. In an embodiment, the constructs may be injected into the blood and expression of the polypeptide of interest targeted to a particular subset of cells having a cosmetic function as for example by the use of receptor-mediated delivery system or via tissue-specific regulatory sequences (e.g. promotors and/or signal sequences).

Celebrity Genes

In certain embodiments, the sequences of the constructs of the present invention can be derived from "celebrities" and public figures such as well-known actors, actresses, musicians, painters, authors, politicians, royalty, athletes, business leaders, ministers, activists, scientists, heroes, and the like, living or deceased from any available DNA source, or from such celebrities' familial blood relative line (e.g., from the daughter of a famous singer). In other embodiments, the construct sequences of the present invention can be derived from commonly known polymorphisms from the general mammalian population; from a mammal other than the mammal receiving the cosmetic modification (e.g. construct copies from a wife applied to a husband and vice versa); autologous from the same skin cell area or from a preferred skin cell area to the modification area; blood relative of the mammal being transfected (e.g., construct copies from a child applied to a parent); marital partner or companion of the mammal being transfected; other nationality or "race" (e.g. construct copies from French men used for transfection of American men); opposite gender (e.g. women may desire constructs from a famous male actor); or construct sequences from any non-mammalian sources (e.g algae, yeast, fungi, viruses, plants, fish and insects).

Molecular Constructs

In certain embodiments, the introduction and subsequent expression of the constructs of the present invention may be enhanced by molecular methods known in the art, including the use of gene construct alterations including modified internucleotides, targeted expression vectors (e.g. to keratinocyte and fibroblast stem cells), nuclear targeting, use of cell-specific, or developmentally regulated promoters and other elements (e.g., enhancer elements). The constructs of the present invention may comprise additional molecular elements to promote the expression and/or proper functioning of the polynucleotide or polypeptide involved in enhancing and/or maintaining cells having a cosmetic function.

Thus, in some embodiments, the constructs may comprise constitutive or inducible promoters operably linked to the nucleic acid that encodes for a polynucleotide or polypeptide involved in maintenance of cells having a cosmetic function so as to enhance and/or maintain a biochemical and/or physiological process that has a positive effect on cosmetic appearance.

In other embodiments, the constructs may comprise enhancer elements operably linked to the polynucleotide or polypeptide involved in maintenance in the cells having a cosmetic function so as to enhance and/or maintain a biochemical and/or physiological process that has a positive effect on cosmetic appearance.

Additionally or alternatively, the constructs may comprise cleavage site sequences, intron sequences, cap sites, or functional polyA elements operably linked to the polynucleotide or polypeptide involved in maintaining cells having a cosmetic function so as to enhance and/or maintain a biochemical and/or physiological process that has a positive effect on cosmetic appearance.

Methods of Administration

The constructs of the present invention may be administered to cells having cosmetic function using transfection methods known in the art. Numerous techniques are known in the art for the introduction of genes into cells and may be used in accordance with the present invention, provided that the necessary developmental and physiological functions of the recipient cells are not disrupted.

Methods for genetic transformation of cells having cosmetic function may include lipid-based delivery systems such as liposomes or biphasic vesicles. Also, emulsions used to permeate the cells having cosmetic function such as cationic nanoparticles, ethanol-in-fluorocarbon microemulsions, or water-in-oil and oil-in-water nanoemulsions may be used.

Or, concatemers may be used. Concatemers, constructed in vitro by treatment of mature DNA with T4-ligase also have an increased activity in transfection, as the transrerction does not have a requirement for more than one molecule per transfection event as is typically found for transfection smaller DNAs perhaps because the structure of the ends of the transfecting molecules play an important role intransfection.

In yet other embodiments, particle-mediated transfer may be used. In certain embodiments, electromagnetic radiation may be used to stimulate the ability of the constructs of the present invention to permeate cells having cosmetic function. Such methods may include the use of radio frequency to form microchannels, electroporation, iontophoresis, or the use of electroincoporation. Administration may also employ physical delivery as for example microinjection of naked DNA. The technique employed may allow for transient expression of the polynucleotide or polypeptide involved in skin maintenance or repair.

Or, techniques for long-lasting gene expression may be used. For example, molecular techniques such as infection with a viral or bacteriophage vector containing the nucleic acid sequences of interest may be employed. Also other techniques such as cell fusion, chromosome-mediated gene transfer, microcell-mediated gene transfer, spheroplast fusion, or transposons, are encompassed by the methods and compositions of the present invention. As is known in the art, chemical and physical (e.g., heat, pre-treatment microdermabrasion and occlusion) permeation enhancers may be used with any of the methods and compositions of the present invention.

Thus, embodiments of the present invention recognize the potential for the genetic modification of cells having cosmetic function as a means to improve the cosmetic appearance of the subject. Genetic modification of cells having cosmetic function may provide the means to either transiently or permanently modify such cells.

Genes That May be Used to Modulate Skin Maintenance and/or Cosmetic Appearance

Undesirable changes in cosmetic appearance, such as sagging, thinning, or wrinkling of the skin is typically the result of the substantial and steady decline in the expression of skin proteins such as collagen, elastin, or other extracellular matrix proteins and proteoglycans. Therefore, replacing these proteins or preventing the decline of these proteins becomes a potentially effective strategy to maintain or improve the appearance and health of the skin. The examples described herein describe the design of five recombinant vector constructs that encode proteins designed to improve the stability of the extracellular matrix and support the improved appearance of the skin. These are collagen, elastin, EC-SOD, TIMP-1 and keratinocyte growth factor (e.g., KGF-1). The role of these proteins in skin physiology is discussed in detail below.

Other proteins and/or peptides may also be provided using the methods and compositions of the present invention. For example, skin cells are known to express a variety of proteins and other factors that may be important to the repair and maintenance of the tissue. Thus, keratinocytes are known to produce interleukins (IL-1-alpha, IL-1-beta, IL-1ra, IL-3, IL-6, IL-8, IL-10, and IL-18), granulocyte colony-stimulating factor (G-CSF), monocyte colony-stimulating factor (M-CSF), and granulocyte/monocyte colony-stimulating factor (GM-CSF), transforming growth factors (TGF-alpha and TGF-beta), platelet-derived growth factor (PDGF), hepatocyte growth factor (HGF), vascular endothelial growth factor (VEGF), tumor necrosis factor (TNF-alpha), interferon (e.g., INF-alpha, beta, and gamma), insulin-like growth factor (IGF-1), and fibroblast growth factors (basic FGF, FGF-22). Also, fibroblasts are known to produce keratinocyte growth factors (KGF-1, KGF-2), TGF-beta-1, TGF-beta-2, and TGF-beta-3, connective tissue growth factor (CTGF), FGF-2 (basic), PDGF-A, IGF-1, VEGF, hepatocyte growth factor (HGF), IL-6, IL-8, TNF-alpha, GM-CSF ad G-CSF, FGF-22, and IGF-1. In another embodiment, the polynucleotide of interest is the HIF-1-alpha transcription factor. Also, it has been described that Egr-1 transcription factor polypeptides, or a biologically active fragment thereof, or nucleotides encoding such peptides, may be used to treat wounds (U.S. Pat. No. 6,689,758). Thus, any of these polypeptides, or functional derivatives thereof, may be used alone or in combination, in embodiments of the methods and/or compositions of the present invention.

Collagen

In an embodiment, the polypeptide involved in maintaining a cell having a cosmetic function so as to enhance and/or maintain a biochemical and/or physiological process that has a positive effect on cosmetic appearance may be a collagen polypeptide or a functional derivative thereof. Collagens are the main fibrous protein composing the extracellular matrices of the body's tissues. Type I collagen is the major extracellular matrix (ECM) component of human skin and is a triple-stranded helical structure composed of two α-1 and one α-2 chains (Myllyharju and Kivirikko, 2001, Ann. Med., 33:7-21). These procollagen chains are synthesized by fibroblasts in the skin and other tissues throughout the body. Once synthesized, the procollagen chains are cleaved to allow for aggregation and formation of larger collagen fibrils that make up a critical component of the ECM. Degradation or insufficient production of procollagen fibers leads to a loss of structural integrity of the ECM and results in physical changes in the overlying tissues such as the skin.

The loss or degradation of collagen is a normal part of aging, but it also is one of the major changes observed in photodamaged skin (Lavker, 1995, Cutaneous Aging: chronologic versus photoaging, In Photaging, Ed., Gilchrest, B. A., Cambridge Mass., Blackwell Science, pp. 123-135; Fligiel et al., 2003, J. Invest. Dermatol., 120:842-848; Varani et al., 2001, Am. J. Pathol., 158:931-942). It has been reported that sustained down-regulation of collagen synthesis occurs in ages, sun-protected skin (Varani et al., 2000, J. Invest. Dermatol., 114:480-486) and in photodamaged skin (Griffiths et al., 1993, N. Engl. J. Med., 329:530-535). A number of mechanisms elucidating the causes for collagen loss during normal aging and as a result of photodamage have been proposed with increases in matrix metalloproteinases (MMPs) and decreases in skin fibroblast numbers (e.g., Fisher et al., 1996, Nature, 379:335-338; Fisher et al., 1997, N. Eng. J. Med., 337:1419-1428; Millis et al., 1992, Exp. Cell Res., 201:373-379; Burke et al., 1994, Exp. Gerontol., 29:37-53; Varani et al., 2000). Another mechanism at least partly responsible for the loss of collagen is the age-related decrease in collagen synthesis by skin fibroblasts. Thus, it has been demonstrated that compared to young skin, aged skin exhibited a lower amount of type I procollagen and that young fibroblasts synthesize more type I procollagen compared to young fibroblasts (Varani et al., 2006). In this study, a reduction in type I procollagen synthesis and content was associated with a more open space between collagen bundles and less contact between fibroblasts and collagen fibrils, suggesting less mechanical tension on fibroblasts. Earlier research demonstrated that when mechanical tension is reduced, collagen production may decline and production of MMPs may increase (Lambert et al., 1992, Lab. Invest. 66:444-451; Delvoye et al., 1991, J. Invest. Dermatol., 97:898-902). Thus, age-related reduction in fibroblast collagen synthesis may lead to reduced mechanical tension in the ECM, which further reduces collagen production (Varani et al., 2006). By replenishing the skin with copies of the type I procollagen gene, collagen production may be enhanced, providing the potential for improved mechanical tension in the ECM, which may subsequently enhance collagen production from existing fibroblasts.

Elastin

In an embodiment, the polypeptide involved in maintaining a cell having a cosmetic function so as to enhance and/or maintain a biochemical and/or physiological process that has a positive effect on cosmetic appearance may be an elastin polypeptide or a functional derivative thereof. Elastin is another critically important component of the ECM that provides elasticity and resilience to the skin (reviewed by Mithleux and Weiss, 2005, Adv. Protein Chem., 70:437-461). Elastin is formed through synthesis and lysyl oxidase—medicated crosslinking of its precursor molecule, tropoelastin. Elastin is a durable molecule that makes of about 90% of elastic fibers and constitutes 2-5% of the dry weight of skin. The formation of elastin and elastic fibers occurs primarily during fetal development and shortly after birth. With the exception of responses to injury, little elastin is synthesized during adulthood. While the main function of elastin is to provide elasticity to tissues, the elastin-laminin receptor (ELR) has been reported to be involved with skin fibroblast proliferation (Groult et al., 1991, Cell Biochem. Funct., 9:171-182). Normal ageing has been associated with the degradation and loss of elastic fibers (Braverman et al., 1982, J. Invest. Dermatol., 78:434-443; Ashcroft et al., 1997a, J. Pathol., 183:80-89). It has been reported that in individuals between 30-50 years of age, the formation of cysts and lacunae were the main abnormality (Braverman et al., 1982). The formation of porous fibers was observed in individuals between 50-70 years old, but became more frequent in people over 70 years of age. Similarly, it has been shown that the sun-protected skin of older subjects had fragmented elastin fibers in the sub-epidermal area with additional fragmented elastin fibers below the sub- epidermal layer (Ashcroft et al., 1997a). More recent studies have confirmed a decrease in skin elastin content with age. It has been reported that the elastin staining intensity of sun-protected skin decreased from 49% in the $1^{st}$ decade of life to 30% in the $9^{th}$ decade of life (El-Domyati et al., 2002, Exp. Dermatol., 11:398-405). Similarly, it has been reported that there is a 51% reduction in elastin content of buttock (sun-protected) skin between 20 and 80 years of age (Seite et al., 2006, J. Eur. Acad. Dermatol. Venereol., 20:980-987). Interestingly, these authors also reported a 44% reduction in elastin content of facial skin (severe sun exposure) between 50 and 70 years of age, though no change in elastin content was observed in forearm skin (moderate sun exposure). This loss of skin elastin with age is one of the primary factors associated with the loss of elasticity and resilience of the skin, leading to wrinkling and sagging. Providing exogenous copies of the elastin gene may enhance new elastin production and help offset the normal loss of elastin seen with aging. This in turn may help improve the appearance of the skin.

Tissue Inhibitor of Metalloproteinase-1 (TIMP-1)

In an embodiment, the polypeptide involved in maintaining a cell having a cosmetic function so as to enhance and/or maintain a biochemical and/or physiological process that has a positive effect on cosmetic appearance may be a Tissue Inhibitor of Metalloproteinase-1 (TIMP-1) or a functional derivative thereof. Matrix metalloproteinases (MMPs) are a group of enzymes (collagenases, gelatinases, and stromelysins) involved in the digestion and reorganization of the ECM (Woessner, 1994, Ann. NY Acad. Sci., 732:11-30) and are present in abundance in the skin (reviewed by Kahari and Saarialho-Kere, 1997, Exp. Dermatol., 6:199-214). MMP activity is regulated by tissue inhibitors of metalloproteinases (TIMPs) (Birkedal et al., 1993, Crit. Rev. Oral Biol. Med., 4:197-250). The overall turnover rate of the ECM is a function of the ratio of MMP to TIMP activity in the tissue.

During normal, chronological aging, MMP levels, particularly MMP-1, in the skin increase (Ashcroft et al., 1997b, Cell Tissue Res., 290:581-591; Varani et al., 2000). A similar increase in skin MMP levels is observed with photoaging (Fisher et al., 1996, 1997). Models of photoaging using ultraviolet (UV) light-induced aging of the skin demonstrate that MMP-1 may be the major enzyme responsible for collagen degradation in the skin (Brennnan et al., 2003, Photochem. Photobiol., 78:43-48). In contrast to increasing MMP concentrations, TIMP-1 levels in the skin may decrease with the normal aging (Ashcroft et al., 1997c, J. Pathol., 183:169-178). This combination of increasing levels of MMP and the decreasing levels of TIMP-1 with normal aging, can lead to an overall loss of the skin's collagen content. With the loss of collagen and subsequent loss of its supporting ECM, the skin shows the typical outward signs of aging including the appearance of lines and wrinkles and the loss of firmness. Recent studies have reported that various MMP inhibitors may reduce facial skin wrinkling and support collagen production (McDaniel et al., 2005, J. Cosmetic Derm., 4:167-173; Moon et al., 2006, Phytomedicine 13:707-711; Park et al., 2006, Photochem Photobiol., 82:574-578). As a result of these kinds of data, cosmetic ingredients such as EquiStat (Engelhard) and ECM-Protect (Atrium Biotechnologies) to inhibit skin MMP activity have been marketed successfully.

By treating with TIMP-1 cDNA plasmid constructs, embodiments of the present invention may enhance TIMP-1 synthesis. By increasing TIMP-1 production, the skin may be able to reduce the effects of endogenous MMPs on the skin. When both the collagen gene construct, discussed above, and the TTMP-1 gene construct are delivered simultaneously, embodiments of the methods and or compositions of the present invention can generate a two-pronged approach to improving the appearance of the skin. On one hand, the collagen gene construct should enhance collagen production to provide additional support to the skin's ECM, while administration of the TIMP-1 construct will protect both the new and existing collagen from degradation through MMP activity.

Extracellular Superoxide Dismutase (SOD-3)

In certain embodiments, the polypeptide involved in maintaining a cell having a cosmetic function so as to enhance and/or maintain a biochemical and/or physiological process that has a positive effect on cosmetic appearance may be an Extracellular Superoxide Dismutase (SOD-3) or a functional derivative thereof. The skin, as well as many other tissues, contains an endogenous antioxidant enzyme system that consists of three potent enzymes, superoxide dismuatase (SOD), glutathione peroxidase (GPX), and catalase (Steenvoorden et al., 1997, J. Photochem Photobiol B: Biology 41:1-10; Afaq and Mukhtar, 2001, J. Photochem Photobiol B: Biology, 63:61-69). SOD functions to catalyze the reduction of superoxide anion to the less toxic hydrogen peroxide, which is subsequently reduced to water and oxygen by GPX and catalase.

Changes in these enzymes have been reported during aging and photoaging. It has been demonstrated that SOD and catalase were higher in the epidermis than the dermis, while GPX was higher in the dermis than the epidermis in both young and old human skin (Rhie et al., 2001, J. Invest. Dermatol., 117:1212-1217). No significant changes were detected in SOD or GPX with natural or photoaging; however, catalase increased in the epidermis and decreased in the dermis of both natural and photoaged skin (Rhie et al., 2001). In contrast, others have demonstrated a substantial reduction in all three antioxidant enzymes in the stratum corneum and a reduction in CuZn-SOD in the epidermis in response to photoaging (Sander et al., 2002, J. Invest. Dermatol., 118:618-625). This loss of antioxidant enzyme activity coincided with increases in oxidized proteins in the upper dermis of photoaged skin.

Superoxide dismutase is present in the skin in three forms (Cu/Zn-SOD, Mn-SOD, and EC-SOD). Recent studies have reported that EC-SOD may be of particular importance for antioxidant and anti-aging benefits. Extracellular SOD mRNA is present in both the dermis and epidermis, though higher in the dermis, while EC-SOD protein was located in both the epidermis and dermis at high levels (Choung et al., 2004, Exp. Dermatol., 13:691-699). It was demonstrated that EC-SOD mRNA expression is enhanced by exposure to both UVA and UVB (Choung et al., 2004). Others have examined the expression of antioxidant genes in fibroblasts under normoxia and hyperoxia conditions (Serra et al., 2003, J. Biol. Chem., 278:6824-6830). In these studies, hyperoxia induced EC-SOD gene expression, particularly in fibroblasts with high antioxidant capacity. Furthermore, EC-SOD expression was inversely correlated with telomere shortening such that increased expression of EC-SOD was associated with slower telomere shortening, resulting in the extended replicative lifespan of fibroblasts (Serra et al., 2003). Extracellular SOD has also been shown to have direct protective effects on type I collagen. It has been demonstrated that EC-SOD binds directly to type I collagen via its C-terminal heparin-binding region (Petersen et al., 2004, J. Biol. Chem., 279:13705-13710). Additionally, these authors reported that the bound EC-SOD prevented the oxidative fragmentation of type I collagen. In addition to potential skin benefits, EC-SOD has been reported to have anti-inflammatory effects (Ha et al., 2006, Biochem. Biophys. Res. Comm., 348:450-458), to reduce chemically induced tumor formation (Kim et al., 2005, Oncol. Res., 15:333-341), to alleviate some symptoms of collagen-induced arthritis (Iyama et al., 2001, Arthritis Rheum., 44:2160-2167; Ross et al., 2004, Arthritis Rheum., 50:3702-3711)

Exogenously administered EC-SOD gene in a topical formulation is likely to have a similar effect to the over-expression of endogenous EC-SOD mRNA, i.e. enhance EC-SOD production, enhance cellular antioxidant capacity and enhance cellular lifespan. By enhancing the lifespan and antioxidant capacity of skin fibroblasts, these cells will be more functionally capable of producing and maintaining the ECM necessary for good skin health. Furthermore, the direct protective action of EC-SOD on collagen may help protect existing collagen from oxidative damage associated with aging and photoaging.

KGF

In an embodiment, the polypeptide involved in maintaining a cell having a cosmetic function so as to enhance and/or maintain a biochemical and/or physiological process that has a positive effect on cosmetic appearance may be a keratinocyte growth factor (KGF). KGF-1 (or FGF-7) is a heparin-binding growth factor that can promote the proliferation, migration, and morphogenesis of epithelial cells (see e.g., au dem Keller, Eur. J. Cell Biol., 2004, 11-12, 607-612). Also, KGF can stimulate production of collagen and/or elastin, both of which are important for maintaining healthy skin and other tissue that has a cosmetic function. The carboxy-terminal two thirds of this 26-28 kDa protein is 30-45% identical to eight other proteins in the FGF family (Rubin et al., Cell Biol. Int., 1995, 19, 399-411). KGF is produced by a variety of mesenchymal cells, but does not appear to be produced by epithelial cells. Epithelial cells express the high affinity KGF receptor, FGFR1-IIIb, which is the only FGF receptor bound by KGF (Grazu-Bilska et al., 2003; Werner et al., Cytokin Growth Factor Rev., 1998, 9, 153-65). KGF may work in combination with other growth factors. Thus, non-viral liposomal transfer of KGF cDNA into wounds resulted in increased expression of VEGF and IGF-1 (Grazu-Bilska et al., 2003). In an embodiment, KGF may be administered in a large enough amount to cause IGF-1, VEGF and PDGF expression.

KGF-2 (also known as either FGF-12), has 57% homology to KGF. Levels of KGF-2 increase wound healing similar to KGF-1. Also, a truncated form of KGF, $KGF_{des1-23}$, that has increased mitogenic activity has been described (U.S. Pat. No. 5,677,278). Repifermin is a truncated form of recombinant human KGF-2 that has been used in the healing of chronic venous stasis ulcers (Robson et al., Wound Repair Regen., 2001, 9, 347-52; Flicker, Mol. Med. Today, 1998, 4, 229). Also, recent evidence has demonstrated that dendritic gamma-delta epidermal T cells (DETCs) produce FGF-7 and FGF-12, which contribute to keratinocyte proliferation during would healing (Baum and Arpey, Dematol. Surg., 2005, 31, 674-686; Born et al., Nat. Med., 2002, 8, 560-1; Jaeson, Science, 2002, 296:747-9).

For example, polynucleotide constructs that encode KGF-1, KGF-2, and analogues thereof are described in U.S. Pat. Nos. 5,731,170, 5,677,278, 5,814,605, 6,228,839, and 6,916,786. Such sequences may be used in the polynucleotide constructs of the present invention as well as truncated versions such as Kepivance® (palifermin) which differs from endogenous human KGF in that the first 23 N-terminal amino acids have been deleted to improve stability.

IGF

In an embodiment, the polypeptide involved in maintaining a cell having a cosmetic function so as to enhance and/or maintain a biochemical and/or physiological process that has a positive effect on cosmetic appearance may be an insulin-like growth factor (IGF). Insulin-like growth factors are primarily produced in the liver, but may be produced by all cells via autocrine mechanisms. IGF-1 and IGF-2 may be involved in the regulation of tissue growth, development, and regeneration (see e.g., Grazul-Bilska et al., 2003). IGF-1 and PDGF may act together to accelerate healing of skin wounds, bone regeneration and periodontal wounds. For example, the delivery of very small amounts of IGF-1 cDNA via liposomes increased the rate of re-epithelialization in rats with burn wounds (Pierre et al., J. Burn Care Rehab., 1997, 18, 287-91; Jeschke et al., Gene Therapy, 1999, 6, 1015-1020). IGF-I may interact with growth hormone in a synergistic manner (Meyer et al., J. Trauma, 1996, 41, 1008-12). IGF-1 may also, in certain embodiments, increase fat levels in cells. This may be beneficial for increasing the "plumpness" of the tissue, as for example, in facial skin or lips.

TGF-beta

In an embodiment, the polypeptide involved in maintaining a cell having a cosmetic function so as to enhance and/or maintain a biochemical and/or physiological process that has a positive effect on cosmetic appearance may be transforming growth factor-beta (TGF-beta). TGF-beta is synthesized by several cell types, including platelets, macrophages, lymphocytes, fibroblasts, bone cells, and keratinocytes. TGF-beta may stimulate production of fibronectin and collagen by fibroblasts and can increase the incorporation of these proteins into the extracellular matrix (Servoid, Clin. Pod. Med. Surg., 1991, 8, 937-53). Local applications of TGF-beta have beneficial effects on wound healing (Graham et al., J. Wound Care, 1998, 7, 536-40). Thus, TGF-beta may be involved in strengthening and modeling of skin tissue.

HIF-1

In an embodiment, the polypeptide involved in maintaining a cell having a cosmetic function so as to enhance and/or maintain a biochemical and/or physiological process that has a positive effect on cosmetic appearance may be a hypoxia inducible factor (HIF-1). HIF-1 is a DNA binding protein that can activate expression of genes that have an HIF-1 binding site. Examples of genes activated by HIF-1 include VEGF, erythropoietin, and glycolytic genes. HIF-1 is composed of two subunits, HIF-1-alpha and HIF-1-beta. In has been found that variants of either subunit may be used to inactivate HIF-1, by forming a nonfunctional HIF-1 dimer. Thus, in alternate embodiments, the nucleic acid or polypeptide involved in maintaining a cell having a cosmetic function is a polynucleotide that encodes for polypeptides that encode HIF-1-alpha, HIF-1-beta, variants thereof, or a nucleic acid comprising the HIF-1 binding site. Examples of such sequences are found in U.S. Pat. No. 5,882,914).

Other Polypeptides Involved in Skin Function

In an embodiment, the polypeptide involved in maintaining a cell having a cosmetic function so as to enhance and/or maintain a biochemical and/or physiological process that has a positive effect on cosmetic appearance may be Epidermal Growth Factor (EGF). EGF is a 6 kDa molecule that has about 30% amino acid homology with TGF-alpha. EGF is produced by platelets and is present in high concentrations during wound healing. EGF may increase the rate of epithelialization of wounds and ma reduce scarring by preventing excess wound contraction. EGF may work in combination with KFG, PDGF and/or other growth factors to maintain and/or repair skin tissue.

In another embodiment, the polypeptide involved in maintaining a cell having a cosmetic function so as to enhance and/or maintain a biochemical and/or physiological process that has a positive effect on cosmetic appearance may be a member of the fibroblast growth factor family (FGF). The FGF family comprises several related polypeptides, including acidic FGF (aFGF or FGF-1), basic FGF (bFGF or FGF-2), several oncogenes (int-2, hst/K-FGF, FGF-5) and KGF (discussed above). The fibroblast growth factors believed to be most important in skin are FGF-1, FGF-2, and KGF. In other embodiments, FGF-10 and/or FGF-22 may be used (see e.g., au dem Keller, *Eur. J. Cell Biol.*, 2004, 11-12, 607-612). FGFs may stimulate angiogenesis, as well as the proliferation and/or migration of many cells involved in wound healing, including capillary endothelial cells, vascular endothelial cells, fibroblasts, keratinocytes, epithelial cells, and specialized cell types such as chondrocytes and myoblasts. Also, FGF-2 may stimulate collagen synthesis, epithelialization and fibronectin and proteolycan synthesis (see e.g., Grazu-Bilska, 2003).

In another embodiment, the polypeptide involved in maintaining a cell having a cosmetic function so as to enhance and/or maintain a biochemical and/or physiological process that has a positive effect on cosmetic appearance is platelet-derived growth factor (e.g., PDGF AA, AB, BB, CC and others). PDGF is a potent mitogen for cells of mesenchymal origin and has been shown to promote wound healing. PDGF promotes collagenase production in fibroblasts, thereby facilitating migration of fibroblasts and remodeling of the wound matrix. For example, it has been found that ex vivo modification of keratinocytes to over-express platelet-derived growth factor (PDGF) can enhance wound healing (Eming et at., *Hum. Gene Ther.*, 1998, 9, 529-539). Also In yet another embodiment, the polypeptide involved in maintaining a cell having a cosmetic function so as to enhance and/or maintain a biochemical and/or physiological process that has a positive effect on cosmetic appearance may be vascular endothelial growth factor (VEGF). VEGF is highly conserved and shares structural homology with PDGF. VEGF is an endothelial cell-specific mitogen and chemoattractant with potent in vivo angiogenic activity (see e.g., Grazu-Bilska, 2003) which may be important for skin cell maintenance and repair.

In yet another embodiment, the polypeptide involved in maintaining a cell having a cosmetic function so as to enhance and/or maintain a biochemical and/or physiological process that has a positive effect on cosmetic appearance is hepatocyte growth factor (HGF) (see Ono et al., *J Surg Res.* 2004 Jul;120(1):47-55) Hepatocyte growth factor (HGF) has a number of biological activities, e.g., mitogenic, motogenic, antiapoptotic, antifibrous, and morphogenic. It also has angiogenic and angioprotective activities for endothelial cells.

In yet other embodiments, the polypeptide involved in maintaining a cell having a cosmetic function so as to enhance and/or maintain a biochemical and/or physiological process that has a positive effect on cosmetic appearance is at least one of connective tissue growth factors (CTFG-1, CTFG-2), granulocyte-macrophage colony-stimulating factor (GMCSF) (see e.g. U.S. Pat. No. 6,689,351 describing treatment of wounds with GMCSF), macrophage colony stimulating factor (MCSF), growth hormone (GH). Also, the polypeptide involved in a cell having a cosmetic function so as to enhance and/or maintain a biochemical and/or physiological process that has a positive effect on cosmetic appearance may comprise an anti-angiogenic polypeptide, such as TSP-1 or TSP-2 (see e.g., U.S. Pat. No. 6,712,617). Other polypeptides and factors active in cells having a cosmetic function such as those described above, and in U.S. Pat. No. 6,586,185, incorporated by reference in its' entirety herein, may be used as well.

Molecular Constructs and Methods of Making

In various embodiments, the gene of interest is produced by recombinant DNA technology. A recombinant DNA molecule comprising a polynucleotide encoding at least one of a nucleic acid or a polypeptide involved in maintaining a cell having a cosmetic function so as to enhance and/or maintain a biochemical and/or physiological process that has a positive effect on cosmetic appearance can be made and expressed by conventional gene expression technology using methods well-known in the art. In this way, the polypeptide or polynucleotide of interest having the appropriate flanking sequences may be produced in large quantities.

Each of the polynucleotides or polypeptides used in the methods and compositions described herein include biologically active derivatives, analogs and/or fragments that retain the biological activity of the full-length polynucleotide or polypeptide. Such derivative or analogs may include post-translationally modified polypeptides, for example, analogues generated by glycosylation, acetylation, or phosphorylation of the polypeptide. Or, polynucleotide analogues may be made by chemically synthesizing a nucleotide molecule with modified residues. Polypeptide analogs can be also made by conventional techniques of amino acid substitution, deletion, or addition, as for example, by site-directed mutagenesis. In one embodiment, a fragment of the gene of interest can be made by deleting either nucleotides and/or amino acid residues from the nucleic acid or a polypeptide involved in skin maintenance and/or treatment, respectively, as is known in the art.

The polynucleotide encoding at least one of a nucleic acid or a polypeptide involved in maintaining a cell having a cosmetic function so as to enhance and/or maintain a biochemical and/or physiological process that has a positive effect on cosmetic appearance can be propagated and/or expressed in a prokaryotic or eukaryotic expression system. In alternate embodiments, a bacterial, mammalian, yeast, or insect cell system may be used for propagation of the recombinant construct.

In one embodiment, a polynucleotide encoding at least one of a nucleic acid or a polypeptide involved in maintaining a cell having a cosmetic function so as to enhance and/or maintain a biochemical and/or physiological process that has a positive effect on cosmetic appearance can be expressed as a fusion protein by linking, in the correct frame and orientation, the coding sequence of the nucleic acid of a polypeptide involved in maintaining a cell having a cosmetic function to the coding sequence of another molecule. The fusion protein may be designed to increase the stability or the correct processing of the nucleic acid or a polypeptide involved in maintaining a cell having a cosmetic function. Or, the nucleic acid or a polypeptide involved in maintaining a cell having a cosmetic function so as to enhance and/or maintain a biochemical and/or physiological process that has a positive effect on cosmetic appearance can be conjugated to other molecules suitable for its intended use. For example, the nucleic acid or a polypeptide involved in maintaining a cell having a cosmetic function so as to enhance and/or maintain a biochemical and/or physiological process that has a positive effect on cosmetic appearance can be conjugated to a binding partner to a receptor that is recognized by the cell of interest.

The practice of the present invention will employ, unless otherwise indicated, conventional techniques of molecular biology, microbiology, recombinant DNA, and immunology, which are within the skill of the art. Such techniques are explained fully in the literature, including Sambrook, et al., *Molecular Cloning: A Laboratory Manual* 2nd ed. (Cold Spring Harbor Laboratory Press, 1989); *DNA Cloning, Vol. I and II*, D. N Glover ed. (IRL Press, 1985); B. Perbal, *A Practical Guide To Molecular Cloning*, Wiley (1984); *Gene Transfer Vectors For Mammalian Cells*, J. H. Miller and M. P. Calos eds. (Cold Spring Harbor Laboratory, 1987); *Methods In Enzymology*, Vol. 154 and 155, Wu and Grossman, eds., and Wu, ed., respectively (Academic Press, 1987). p Recombinant constructs comprising the nucleic acid or a polypeptide involved in maintaining a cell having a cosmetic function so as to enhance and/or maintain a biochemical and/or physiological process that has a positive effect on cosmetic appearance can be made by well-known recombinant techniques. In this regard, the sequence of interest may be operably linked to one or more regulatory sequences in a suitable vector in a proper reading frame and orientation. Thus, the sequence of interest may be inserted, for example, into a mammalian vector for expression in mammalian cells.

Figure 7:
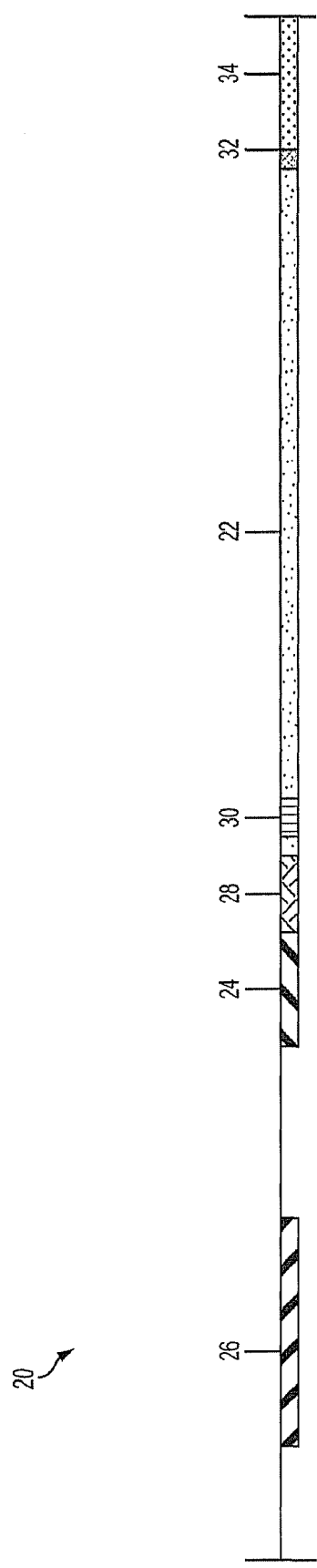
FIG. 7 depicts example recombinant DNA molecules in accordance with an embodiment of the present invention.

FIG. 7 shows an example recombinant construct 20 of the present invention. The recombinant construct may comprise a DNA molecule that encodes for a protein or polypeptide 22 involved in maintaining a cell having a cosmetic function so as to enhance and/or maintain a biochemical and/or physiological process that has a positive effect on cosmetic appearance. Or, the construct may comprise a polynucleotide (e.g., antisense RNA or siRNA) that may be used to regulate expression of polypeptide involved in maintaining a cell having a cosmetic function so as to enhance and/or maintain a biochemical and/or physiological process that has a positive effect on cosmetic appearance.

In an embodiment, the coding sequence of a polypeptide involved in maintaining a cell having a cosmetic function so as to enhance and/or maintain a biochemical and/or physiological process that has a positive effect on cosmetic appearance is derived from a complementary DNA (cDNA) made by reverse transcription of cellular RNA from a host cell known to express the gene of interest as described in the Examples herein, or using other methods known in the art.

As shown in FIG. 7, in certain embodiments, the recombinant construct may comprise a regulatory sequence such as a promoter 24 and/or an enhancer element 26. Thus, a regulatory sequence comprising a promoter 24 that is operable in the host cell of interest may then be linked to cDNA sequence using molecular techniques. Other regulatory sequences can also be used, such as one or more of an enhancer sequence 26, a ribosome binding site 28, an intron with functional splice donor and acceptance sites, a signal sequence for directing secretion of the recombinant polypeptide 30, a termination sequence 32, a polyadenylation signal and/or polyadenylation sequence 34, other transcription terminator sequences, and a sequence homologous to the host cell genome. Other sequences, such as an origin of replication, can be added to the vector as well to optimize expression of the desired product. Also, a selectable marker may be included in the vector for selection of the presence thereof in the transformed host cells.

The regulatory sequences may be derived from various sources. For example, one or more of them can be normally associated with the coding sequence, or may be derived from, or homologous with, regulator systems present in the host cell (e.g., a keratinocyte). Alternatively, the promoter may be derived from a gene that is turned on in response to compounds or conditions that promote degeneration of a cell having a cosmetic function, such as UV light or certain chemicals. The various components of the expression vector can be linked together directly or, via linkers that constitute sites of recognition by restriction enzymes as is known in the art.

Any promoter that would allow expression of the nucleic acid that encodes for a polynucleotide or a polypeptide involved in maintaining a cell having a cosmetic function so as to enhance and/or maintain a biochemical and/or physiological process that has a positive effect on cosmetic appearance can be used in the present invention. For example, mammalian promoter sequences that can be used herein are those from mammalian viruses that are highly expressed and that have a broad host range.

The promoter may be a promoter that is expressed constitutively in most mammalian cells such as the PKG promoter. Examples of suitable regulatable elements which make possible constitutive expression in eukaryotes are promoters which are recognized by the RNA polymerase III or viral promoters, CMV enhancer, CMV promoter, SV40 promoter or LTR promoters, e.g. from MMTV (mouse mammary tumor virus (e.g., Lee et al., 1981, *Nature*, 214, 228-232) and other viral promoter and activator sequences, derived from, for example, HBV, HCV, HSV, HPV, EBV, HTLV or HIV. Examples of regulatable elements which make possible regulatable expression in eukaryotes are the tetracycline operator in combination with a corresponding repressor (Gossen M., et al., 1994, *Curr. Opin. Biotechnol.*, 5, 516-20).

In an embodiment, the expression of the gene of interest genes takes place under the control of tissue-specific promoters. In alternate embodiments, the tissue-specific promoters that may be used include skin-specific promoters such as, for example, the human K10 promoter (Bailleul et al., 1990, *Cell*, 62, 697-708; Sawamura et al., J. Invest. Dermatol., 1999, 112:828-830), the human K14 promoter (Vassar et al., 1989, *Proc. Natl. Acad. Sci. USA*, 86, 1563-67), the human Involucrin promoter (Carroll et al., 1993, Proc. Natl., Acad. Sci., 90:10270-10274), the bovine cytokeratin IV promoter, or other human keratin promoters (e.g., K1 and K5) (Bryne et al., 1994, Development, 120: 2369-2383).

Alternatively, the promoter may be a promoter that is turned on at a particular time in the cell cycle or developmental phase. For example, the constructs may comprise regulatable elements which make possible tissue-specific expression in eukaryotes, such as promoters or activator sequences from promoters or enhancers of those genes which code for proteins which are only expressed in certain cell types. Examples of regulatable elements which make possible cell cycle-specific expression in eukaryotes are promoters of the following genes: cdc25A, cdc25B, cdc25C, cyclin A, cyclin E, cdc2, E2F-1 to E2F-5, B-myb or DHFR (see e.g., U.S. Pat. No. 6,856,18; U.S. Pat. No. 6,903,078; and Zwicker J. and Muller R., 1997, Trends Genet., 13, 3-5). The use of cell cycle regulated promoters may be used where expression of the polypeptides or nucleic acids used according to the invention is to be restricted to proliferating cells. In an embodiment, an example of an regulatable element which allows for keratinocyte-specific expression in the skin is the FIRE-element (Jaakkola el al., 2000, *Gen. Ther.*, 7, 1640-1647). The FIRE element is an AP-1-driven, FGF-inducible response element of the Syndecan-1 gene (Jaakkola et al., 1998, *FASEB J.*, 12, 959-9). Also, examples of elements which make possible metabolically specific expression in eukaryotes are promoters that are regulated by hypoxia (e.g., HIF-1-alpha), by glucose deficiency, by phosphate concentration or by heat shock.

In another embodiment, an enhancer element can be combined with a promoter sequence. Such enhancers may not only amplify, but also can regulate expression of the gene of interest. In an embodiment, the enhancer may be derived from a sequence that is normally positioned adjacent to a gene that encodes for a polypeptide (e.g., collagen) involved in the maintenance or function of cells involved in cosmetic appearance. Suitable enhancer elements for use in mammalian expression systems are, for example, those derived from viruses that have a broad host range, such as the SV40 early gene enhancer, the enhancer/promoters derived from the LTR of the Rous Sarcoma Virus, and from human cytomegalovirus. Additionally, other suitable enhancers include those that can be incorporated into promoter sequences that will become active only in the presence of an inducer, such as a hormone, a metal ion, or an enzyme substrate, as is known in the art.

In another embodiment of the present invention, a transcription termination sequence may be placed 3' to the translation stop codon of the coding sequence for the gene of interest. Thus, the terminator sequence, together with the promoter, would flank the coding sequence.

The expression vector may also contain an origin of replication such that it can be maintained as a replicon, capable of autonomous replication and stable maintenance in a host. Such an origin of replication includes those that enable an expression vector to be reproduced at a high copy number in the presence of the appropriate proteins within the cell, for example, the 2 μ and autonomously replicating sequences that are effective in yeast, and the origin of replication of the SV40 vital T- antigen, that is effective in COS-7 cells. Mammalian replication systems may include those derived from animal viruses that require trans-acting factors to replicate. For example, the replication system of papovaviruses, such as SV40, the polyomavirus that replicate to extremely high copy number in the presence of the appropriate vital T antigen may be used, or those derived from bovine papillomarvirus and Epstein-Barr virus may be used.

In some cases, the expression vector can have more than one replication system, thus, allowing it to be maintained, for example, in mammalian cells for expression and in a procaryotic host for cloning and amplification (see e.g., U.S. Pat. No. 5,677,278).

In one embodiment, the expression vector can be made to integrate into the host cell genome as an integrating vector. The integrating vector herein may contains at least one polynucleotide sequence that is homologous to the host cell genome that allows the vector to integrate. For example, in one embodiment, bacteriophage or transposon insertion sequences may be used. Optimization of the techniques described herein may be performed as described in e.g., in Branski et al., 2006, Gene Therapy, 2006, 1-10; and Hengge, 2006, Gene Therapy, 13:155-1563.

In certain embodiments of the present invention, one or more selectable markers can be included in the expression vector to allow for the selection of the host cells that have been transformed. Selectable markers that can be expressed in a host cell include genes that can render the host cell resistant to drugs such as tunicamycin, G418, ampicillin, chloramphenicol, erythromycin, kanamycin (neomycin), and tetracycline. Selectable markers also include biosynthetic genes, such as those in the histidine, tryptophan, and leucine biosynthetic pathways, such as adc2, his4, leu2, trp1, or that provide the host cells with the ability to grow in the presence of toxic compounds, such as a metal, may be used.

Thus, in an embodiment, the present invention comprises a method of making a polynucleotide encoding at least one of a nucleic acid or a polypeptide involved in maintaining the cells having cosmetic function such that the nucleic acid or polypeptide can be expressed in cells having cosmetic function to enhance and/or maintain a biochemical and/or physiological process that has a positive effect on cosmetic appearance. The method may also comprise inserting the polynucleotide into a vector for expression of the recombinant construct. Thus, in certain embodiments, the present invention comprises an expression vector comprising polynucleotide encoding at least one of a nucleic acid or a polypeptide involved in maintaining the cells having cosmetic function. Also, in certain embodiments, the present invention comprises a host cell transfected with such a vector.

For example, the method may also comprise the step of incorporating the DNA construct into an expression vector. The method may further comprise the step of transfecting a cell with the expression vector of the present invention. Thus, in an embodiment, the present invention comprises a cell transfected with the expression vector of the invention. For example, plasmids may be constructed to express a polypeptide involved in maintaining the cells having cosmetic function. The expression cassette sequences may be inserted into an expression vector such as pcDNA3.1 or the expression vector (Invitrogen, CA) using standard recombinant techniques.

As is known in the art, such nucleic acid constructs may be modified by mutation, as for example, by PCR amplification of a nucleic acid template with primers comprising the mutation of interest. In this way, polypeptides comprising varying levels of biological activity may be designed. In alternate embodiments, the mutated sequences may be 70%, 75%, 80%, 85%, or 90% or more identical to the starting DNA. As such, variants may include nucleotide sequences that hybridize under stringent conditions (i.e., equivalent to about 20-27° C. below the melting temperature (TM) of the DNA duplex in 1 molar salt).

Also, the method may comprise transfecting the expression vector into a host cell. In certain embodiments, the polypeptides of the present invention may be expressed in mammalian expression systems, including systems in which the expression constructs are introduced into the mammalian cells using virus such as retrovirus or adenovirus. Mammalian cell lines available as hosts for expression are well known in the art and include many immortalized cell lines available from the American Type Culture Collection (ATCC). These include, inter alia, Chinese hamster ovary (CHO) cells, NS0, SP2 cells, HeLa cells, baby hamster kidney (BHK) cells, monkey kidney cells (COS), human hepatocellular carcinoma cells (e.g., Hep G2), A549 cells, and a number of other cell lines. Cell lines may be selected through determining which cell lines have high expression levels of the polypeptide. Other cell lines that may be used are insect cell lines, such as Sf9 cells. Plant host cells may include, e.g., Nicotiana, Arabidopsis, duckweed, corn, wheat, potato, and the like. Bacterial host cells may include *E. coli* and Streptomyces species. Yeast host cells include *Schizosaccharomyces pombe, Saccharomyces cerevisiae* and *Pichia pastoris*.

When recombinant expression vectors encoding the genes of interest are introduced into mammalian host cells, the polypeptides of the present invention may be produced by culturing the host cells for a period of time sufficient to allow for expression of the polypeptide in the host cells or secretion of the polypeptide into the culture medium in which the host cells are grown. The expressed polypeptide may be recovered from the culture medium using standard protein purification methods.

Nucleic acid molecules encoding the polypeptide of the present invention and expression vectors comprising these nucleic acid molecules may be used for transfection of a suitable mammalian, plant, bacterial or yeast host cell. Transformation may be performed by any known method for introducing polynucleotides into a host cell. Methods for introduction of heterologous polynucleotides into mammalian cells are known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming plant cells are known in the art, including, e.g., Agrobacterium-mediated transformation, biolistic transformation, direct injection, electroporation and viral transformation. Methods of transforming bacterial and yeast cells are also known in the art.

An expression vector may also be delivered to an expression system using DNA biolistics, wherein the plasmid is precipitated onto microscopic particles, preferably gold, and the particles are propelled into a target cell or expression system. DNA biolistics techniques are well-known the art and devices, e.g., a "gene gun", are commercially available for delivery of the microparticles in to a cell (e.g., Helios Gene Gun, Bio-Rad Labs., Hercules, Calif.) and into the skin (PMED Device, PowderMed Ltd., Oxford, UK).

Expression of the polypeptides of the present invention from production cell lines may be enhanced using a number of known techniques. For example, the glutamine synthetase gene expression system (the GS system) and the plasma-encoded neomycin resistance system are common approaches for enhancing expression under certain conditions.

When the polypeptides of the present invention are expressed by different cell lines, they may have different glycosylation patterns from each other. However, all polypeptides encoded by the nucleic acid molecules as described herein, or comprising the amino acid sequences as described herein, are part of the instant invention, regardless of the glycosylation of the polypeptide.

In one embodiment, the recombinant DNA construct may be transfected into Chinese Hamster Ovary cells and expression optimized. In alternate embodiments, the cells may produce 0.1 to 20 grams/liter, or 0.5 to 10 grams/liter, 1 to 5 grams/liter, or about 1-2 grams/liter. For example, the recombinant vectors may be stably transfected into Chinese Hamster Ovary (CHO) cells, and cells expressing a polypeptide involved in the maintenance of cells having cosmetic function selected and cloned. In an embodiment, cells expressing the recombinant construct are selected for plasmid-encoded neomycin resistance by applying antibiotic G418. Individual clones may be selected and clones expressing high levels of recombinant protein as detected by Western Blot analysis of the cell supernatant may be expanded, and the gene product purified by affinity chromatography using Protein A columns.

Transfer of a Recombinant Construct Encoding a Polynucleotide or Polypeptide Involved in Skin Maintenance and/or Treatment into Cells Having Cosmetic Function A variety of methods may be used to transfer a polynucleotide encoding a polynucleotide or polypeptide involved in maintaining cells having cosmetic function so as to enhance and/or maintain a biochemical and/or physiological process that has a positive effect on cosmetic appearance. Thus, the formulations of the present invention may comprise specific components that facilitate transfer of proteins into cells.

To allow for the introduction of nucleic acids in a eukaryotic and/or prokaryotic cell by transfection, transformation or infection, the nucleic acid can be present as a plasmid, as part of a viral or non-viral vector. Suitable viral vectors may include baculoviruses, vaccinia viruses, lentiviruses (see e.g., Siprashvili and Khavari, *Mol. Ther.*, 2004, 9, 93-100), adenoviruses, adeno-associated viruses and herpesviruses. Examples of vectors having gene therapy activity are virus vectors, for example adenovirus vectors or retroviral vectors (Lindemann et al., 1997, *Mol. Med.*, 3, 466-76; Springer et al., 1998, *Mol. Cell.*, 2, 549-58). Also, eukaryotic expression vectors are suitable in isolated form for gene therapy use, as naked DNA can penetrate into cells having cosmetic function on topical application (Hengge et al., 1996, *J. Clin. Invest.*, 97, 2911-6; Yu et al., 1999, *J. Invest. Dermatol.*, 112, 370-5). Another form of gene therapy vectors can be obtained by applying the above described nucleic acid to gold particles and shooting these into tissue, preferably into the skin, or cells with the aid of the so-called gene gun (Wang et al., 1999, *J. Invest. Dermatol.*, 112, 775-81, Tuting et al., 1998, *J. Invest. Dermatol.*, 111, 183-8). Several methods of gene transfection that may be used with the methods and compositions of the present invention are described in more detail below.

Naked DNA

In an embodiment, the recombinant polynucleotide encoding at least one of a nucleic acid or a polypeptide involved in maintaining a cell having a cosmetic function so as to enhance and/or maintain a biochemical and/or physiological process that has a positive effect on cosmetic appearance is directly injected, as "naked DNA," into the cells having cosmetic function. Also, oligonucleotides (e.g., encoding RNAi) may be efficiently transferred to all cell layers in the epidermis after topical application.

In certain embodiments, the DNA may be administered in water or a buffer. Or, liposomes as described in more detail herein may be used. Also, in certain embodiments, the skin may be abraded, either by removing a portion of the hair (e.g., stripping), or by brushing, or by other methods known in the art (Choi et al., Skin Pharmacol. Appl Skin Physiol., 2003, 16:271-282; Choi et al., Current Drug Delivery, 2006, 3:37-45).

In other embodiments, gene delivery systems comprising peptides bound to DNA may be used (see e.g., Jensen, *Expert Opin. Biol. Ther.*, 2004, 4, 1-6). In yet another embodiment, the vector may be introduced as "naked" expression vectors into a biocompatible matrix, for example a collagen matrix (Goldstein and Banadio, U.S. Pat. No. 5,962,427).

Several studies have reported that naked plasmid DNA can be successfully delivered across the skin (Fan et al., 1999, Nature Biotech., 17:870-872; Yu et al., 1999, J. Invest. Dermatol., 112:370-375; Kang et al., 2004, J. Gene Med., 6:1238-1246). For example, it was reported that topical application of DNA in a phosphate buffered saline (PBS) solution generated antibodies against bacterial β-galactosidase, indicating the transdermal delivery of the naked plasmid DNA (Fan et al. (1999). By comparing this delivery in mice with and without normal hair follicles, Fan et al. (1999) suggested that delivery was via the hair follicles. However, others reported that delivery of naked plasmid DNA resulted in reporter gene expression in both the hair follicles and the superficial keratinocytes of the superficial epidermis (Yu et al., 1999). It has also been demonstrated that topical application of 300 μg of plasmid DNA results in the delivery of approximately 1,000 ng plasmid DNA/g of tissue after 2 hours and approximately 100 ng plasmid DNA/g of tissue after 24 hours and that mRNA was expressed as early as day 1 after topical application (Kang et al., 2004).

Early research suggests that plasmid DNA may penetrate the stratum corneum through a system of lacunae that transiently form into pore pathways under appropriate conditions (Menon and Elias, 1997, Skin Pharmacol., 10:235-246). It has also been demonstrated that pathways formed of aqueous regions surrounded by polar lipids may facilitate the intercellular transfer of polar materials (Sznitowska et al., 1998, J. Pharm. Sci., 87:1109-1114). Also, uptake of plasmid DNA intracellularly by keratinocytes has recently been shown to be primarily by macropinocytosies and may involve the DNA binding proteins ezrin and moesin (Basner-Tschakarjan et al., 2004, Gene Therapy 11:765-774).

The safety and distribution of naked plasmid DNA has been extensively reviewed (e.g., Hengge U R, Vol-Platzer B (eds), *The Skin and Gene Therapy*, Springer-Verlag: Berlin, 2001, pp. 67-80). Unlike viral vector deliver of DNA, naked plasmid cDNA does not elicit adverse immune responses, does not undergo insertional mutagenesis, and maintains promoter function. A potential concern has been the migration of plasmid DNA from the target site to other tissues and organs, however, it has been reported that integration of plasmid DNA into host DNA was not detected at any time point and that expression of the plasmid cDNA was transient such that 11 days after treatment, expressed RNA was only detectable in the treated skin and not in any other tissues (Hengge et al., 1995, Nat. Genet., 10:161-166). It is hypothesized that this loss of plasmid DNA is due to degradation via tissue nucleases and epidermal regeneration. Thus, gene therapy for the skin is considered safe due to the transient expression of the plasmid DNA and the rapid degradation of the plasmid DNA.

Liposome and Nanosome Mediated Transfer

For example, in alternate embodiments, liposomes and/or nanosomes may be used to facilitate transfer of a polynucleotide encoding a polypeptide involved in maintaining cells having cosmetic function so as to enhance and/or maintain a biochemical and/or physiological process that has a positive effect on cosmetic appearance. Liposomes are artificially-made small vesicles with a lipid bilayer membrane comprised of phospholipids (Jeschke, M. G. et al., *Gene Ther.*, 12, 1718-24 (2005); U.S. Pat. No. 6,576,618). Nanosomes are very small liposomes but may be made in essentially the same manner as liposomes.

Nucleic acids, proteins, and other biological materials can be enclosed in liposomes and/or nanosomes for delivery to mammalian cells through fusion with the cell's plasma membrane. Liposomes and/or nanosomes may be an attractive delivery system because they are non-viral, stable and can interact with the cell membrane. Administration of liposomes and/or nanosomes directly to the skin can allow for the molecules enclosed within the bilayer to be delivered into cells having cosmetic function via fusion with cell membranes. The mode of transfer may be through endocytosis or via a follicular pathway. For example, liposomes and/or nanosomes can be subcutaneously injected to transfect cells in the dermis, leading to localized protein expression in the skin. Pre-treatment of the skin with empty liposomes and/or nanosomes followed by naked DNA may also be employed.

Liposomes and/or nanosomes can be comprised of cationic, anionic, or neutral lipids, and mixtures thereof (Luo, D. & Saltzman, W. M., *Nat. Biotech.*, 18, 33-37 (1999)). For DNA transfer, the lipids can also be modified chemically to incorporate chemical groups to facilitate DNA condensation or release. Cationic lipids, such as quaternary ammonium detergents, cationic derivatives of cholesterol and diacylglycerol, and lipid derivatives of polyamines, may be favored for cell transfection because they decrease the net negative charge of the DNA and facilitate its interaction with cell membranes (Nishikawa, M. & Huang, L., 2001, *Hum. Gene Ther.*, 12, 861-70; Badca J. Biol. Gene Medi. 2005, 7:1200-1214). Other liposomes tha may be used include 1,2-dioleoyl-3-trimethylammonium-propane (DOTAP)/diolcylphosphatidylethanolamines (DOPEJ/DNA lipoplexes (see e.g., Paasonen et al., 2005, Int. J. of Pharmaceutics, 307:188-193).

Neutral lipids, such as dioltoylphospmtylethanotamine (DOPE), glycerol dilaurate, polyoxyethylene-10-stearyl ether (POE-10), and cholesterol, may be added as 'helper lipids' in cationic-lipid DNA complexes to facilitate the release of the DNA from the endosome after endocytic uptake of the complex. Auxiliaries that increase DNA transfer, such as polymers or proteins that are bound to the DNA or synthetic peptide-DNA molecules that make it possible to transport DNA into the nucleus of the cell more efficiently can also be used (see e.g., Niidome, T. & Huang, L., *Gene Ther.*, 9, 1647-52 (2002)). Thus, cationic polymers, such as polylysine or protamine, can be used in lipid-DNA complexes as they cause tight condensation of DNA, which prevents complex aggregation and nuclease degradation. For example, mixing 1,2-dioleoyl-3-(trimethylammonium)propane (DOTAP) liposomes with protamine sulfate prior to mixing with plasmid DNA produced small 135 nm particles that were stable and resulted in a high level of gene expression in a variety of tissues (e.g., lung., liver, heart) (Li, S. et al., *Gene Ther.*, 5, 930-37 (1998)). Inclusion of cholesterol as a helper lipid may increase the transfection efficiency of liposome-peptide-DNA complexes. Also, luciferase or β-galactosidase gene DNA may be precompacted with short peptides derived from human histone or protamine before addition of a cationic lipid (Lipofectamine RPR 115335 or RPR 120535) or polymer (polyethylenimine) to achieve enhanced transfection efficiency, even in the presence of serum (see e.g., Schwartz, B. et al., *Gene Ther.*, 6, 282-92 (1999)).

As is known in the art, liposomes may be made by heating lipids to form a lipid phase (Wu, H. et al., *Int. J. Pharmaceut.*, 221, 23-24 (2001)). An aqueous phase containing water, salts or buffer may then be mixed with the lipid phase by passing the mixture back and forth between syringes under cooling conditions, followed by sonication until a final liposome size of 100 to 140 nm is reached. The DNA or protein to be included in the liposome is then added (as a solution) by inversion mixing. This liposome preparation can then be applied directly to or injected into the skin. The choice of lipids used, their ratio, the concentration of DNA used in creating the liposomes and the amount of liposomes added to the skin will generally require empirical determination for optimization. Auxiliaries to facilitate DNA transfer, such as peptides, can be mixed with the DNA prior to adding to the liposome mixture but the DNA-auxiliary must maintain sufficiently high aqueous solubility to be properly encapsulated within the external lipid phase of the liposome.

Alternatively, small unilamellar vesicles can be prepared by ultrasonic treatment of a liposome suspension comprised of cationic lipids, such as Cytofectin GS 2888, mixed with 1,2-dioleyloxypropyl-3-trimethylammonium bromide (DOTMA) or dioleoylphosphati-dylethanolamine bromide (DPOE). After inversion mixing, the DNA or protein may be bound ionically to the surface of the liposomes, in a ratio that maintains a positive net charge on the complex while having DNA complexed to 100% of the liposomes. Also, dimerizable cationic thiol detergents may be used to prepare liposomes for delivery of DNA (see e.g., Dauty, E. et at., *J. Am. Chem. Soc.*, 123, 9227-34 (2001)). Upon oxidation, the thiol groups in the lipid can convert to disulfides and cause the DNA-lipid complex to form a stable nanometric particle that can bind electrostatically to cell surface anionic heparin sulfate proteoglycans for cellular uptake. The small size of the nanoparticle, and its lipid bilayer, can facilitate transfer of the DNA into cells having cosmetic function. Once inside the cell, the reductive environment provided by intracellular glutathione reduces the disulfides back to thiols and releases the DNA.

Water-In-Oil and Oil-In-Water Nanoemulsion-Mediated Transfer

In another embodiment, a water-in-oil and/or oil in water nanoemulsion may be used to deliver a polynucleotide or polypeptide involved in maintaining a cell having a cosmetic function so as to enhance and/or maintain a biochemical and/or physiological process that has a positive effect on cosmetic appearance. Water-in-oil and/or oil-in-water nanoemulsions are thermodynamically stable liquid isotropic dispersions, composed of water, oil and surfactants, and may comprise a technique for transferring DNA or proteins (or other biomolecules) into mammalian cells (Wu, H. et al., *Int. J. Pharmaceul.*, 221, 23-24 (2001); see also, U.S. Pat. Nos. 5,753,241, 6,274,150, 6,335,022, 6,464,990, 6,541,018, and 6,689,371).

Components that are considered biologically safe, such as polyoxyethylene 20 sorbitan monooleate (TWEEN® 80), sorbitan monooleate (Span® 80) and olive oil, can be used to minimize risk of irritation to human subjects. At defined stoichiometric ratios of the components, and with warming and gentle mixing, spontaneous formation of the nanoemulsion may occur upon. Thus, there may not be a need for high shear forces, thereby eliminating a significant cause of physical damage to the biomolecule to be delivered. This technique can be readily scalable and can encapsulate significant amounts of aqueous phase. Nanoemulsions can be applied directly to the skin to achieve transfer of biomolecules into cells having cosmetic function. For example, this technique has been used to successfully transfect excised murine skin with either chloramphenicol acetyltransferase or human interferon-α2 cDNA such that DNA deposition was primarily into follicular keratinocytes (Wu et al., 2001). Transgene expression after a single application was found to be highest at 24 hours, although expression was significantly higher with multiple daily doses. Microemulsions including ethanol-in-fluorocarbon can also be used in a similar fashion.

Particle-Mediated Transfer

In yet another embodiment, the method of transfer may comprise particle-mediated transfer (see e.g., Nishikawa, M. & Huang, L., *Hum. Gene Ther.*, 12, 861-70 (2001); Luo, D. & Saltzman, W. M., *Nat. Biotech.*, 18, 33-37 (1999)). For example, DNA-coated microparticles, composed of metals such as gold or tungsten and 1-5 μm in size, may be accelerated to high velocity using a so-called gene gun to penetrate cell membranes (Williams, R. S. et al., *Proc. Nat. Acad. Sci. U.S.A.*, 88, 2726-30 (1991)). Microparticles may be coated with DNA by mixing the particles in an aqueous slurry sequentially with the DNA solution, calcium chloride and free-base spermidine. The particles are then washed with an ethanol solution and spread onto the gene gun device applicator. Once the particles are dry and the ethanol has evaporated, the device can be fired to introduce the particles into the cell having a cosmetic function so as to enhance and/or maintain a biochemical and/or physiological process that has a positive effect on cosmetic appearance. This technique can introduce a biomolecule into many cells simultaneously, and may transfer the biomolecule through the cell membrane and into the cytoplasm or even the nucleus, thereby bypassing the endosomal compartment and potential enzymatic degradation. Also, in an embodiment, this technique may only achieve shallow penetration of the cell layer, which can be effective for limited local expression of the delivered DNA to the epidermis. Little cell damage or inflammation is caused by particle bombardment. For example, Oshikawa et al. used a helium-pulse PowderJect XR gene delivery device to project gold particles coated with interleukin 12 gene DNA into murine skin either overlying or distal to tumor locations (Oshikawa, K. et al., *Hum. Gene Ther.*, 12, 149-60 (2001)). It was found that transfection of skin cells overlying the tumor location was most effective at suppressing tumor growth, but that treatment had an antimetastatic effect irrespective of transfection site (Oshikawa et al., 2001). Similarly, a similar protocol was used to successfully transfect murine skin with DNA encoding the luciferase gene under the control of the human β-actin promoter such that 10-20% of the cells in the bombarded area expressed the transferred gene (Williams et al., 1991).

Voltage-Driven Transfer

Yet other methods of transfer such as electroporation, iontophoresis, and electroincorporation may be used (see e.g., Banga, A. K. et al., *Int. J. Pharmaceut.*, 179, 1-19 (1999); Banga A. J. & Prausnitz, M. R., *TIBTech.*, 16, 408, 12 (1998); André, F. & Mir, L. M., *Gene Ther.*, 11, S33-42 (2004)). In these methods, a current is used to facilitate the transfer of DNA into cells after the DNA has been injected into or applied to the skin, preferably in a high ionic strength medium. Skin is an optimal tissue for the use of these techniques due to ease of administration. Use of these techniques may entail optimization of the dose of DNA, electrode shape (e.g. needle, caliper) and number, and the electrical field strength and duration. Decreased permeation of cells after treatment suggests that any damage caused by these techniques is reversible. Additionally, these techniques can be combined to achieve a high degree of DNA transfer with less irritation as a result of exposure to current.

Electroporation:

Electroporation involves the use of very short (μs-ms) high voltage (typically>100 V) electrical pulses to transiently permeabilize cell membranes, permitting cellular uptake of macromolecules (see e.g., Nishikawa, M. & Huang, L., *Hum. Gene Ther.*, 12, 861-70 (2001)). The current can open up pores in cell membranes through which DNA or proteins can pass down a concentration gradient into the interior of the cell thereby enhancing and/or maintaining uptake of the biomolecule after injection/application. This technique has been used to transfect skin in vivo by intradermally injecting plasmids encoding reporter genes into porcine or murine skin and then administering electrical pulses using PulseAgile Electroporation equipment and software (CytoPulse Sciences, Hanover, Md.) (Drabick, J. J. et al., *Molec. Ther.*, 3, 249-55 (2000)). Transfected cells were primarily located in the dermis and included adipocytes, fibroblasts and endothelial cells, amongst others.

Iontophoresis:

Iontophoresis involves the use of low voltage (typically 10 V or less) electrical pulses administered in high frequency pulses or as a continuous constant current (typically 0.5 mA/cm$^3$ or less) to push a charged molecule into skin (Nishikawa, M. & Huang, L., *Hum. Gene Ther.*, 12, 861-70 (2001)). An electrode of the same polarity as the charge on the molecule may be used to drive the charged molecule into the skin. For example, a negatively charged anode can be used to transfer negatively charged DNA molecules. Electrodes are usually very small and may be incorporated into a matrix that is applied to the skin after application of the DNA solution (Mikszta, J. A. et al., *Nat. Med.*, 8, 415-19 (2002)). The technique creates new pores in the skin, similar to electroporation, in addition to using preexisting pathways, such as sweat glands, to effectuate transfer. In contrast to eletroporation, this technique is commonly used with humans. Delivery of the DNA is proportional to the current and the size of the electrode matrix applied to the skin. Thus, dosage is readily adjustable and can be optimized according to patient needs. Also, because iontophoresis is driven transfer, it may be less dependant on other biological variables, such as membrane penetration or intracellular components, than are other drug delivery systems (Banga, A. K. et al., Int. J. Pharmaceut., 179, 1-19 (1999)). In an embodiment, microenhancer arrays may be used to transfect the cells having cosmetic function of BALB/c mice with naked luciferase gene DNA with significant (e.g., up to 2,800-fold enhanced) transgene gene activity compared to topical application controls Mikszta, J. A. et al., 2002).

Electroincorporation:

Electroincorporation is a modification of iontophoresis and electrophoresis where molecules encapsulated in vesicles or particles, such as microspheres or gold particles, are delivered into the skin by applying a pulse which causes a breakdown of the upper layer of the skin. The electrodes may be placed directly onto the location of interest and the particles applied directly to the skin. Dielectrophoresis and/or pressure is thought to drive the particles into the skin after breakdown of the skin's top layer (Zhang et al., Bioelectrochem. Bioenerg., 42, 283-92 (1997)). Also, pressure-mediated electroincorporation may be used.

Radio Frequency Ablation-Mediated Transfer

Also, in an embodiment, the method of DNA and/or protein transfer may comprise radio frequency ablation mediated-transfer. Thus, microchannels, or transient microconduits, can be created in the cell having a cosmetic function by radio frequency ablation (Birchall, J. et al., Int. J. Pharmaceut., 312, 15-23 (2006)). These channels may be large enough and have sufficient morphology and depth to permit delivery of 100 nm nanoparticles. In yet another embodiment, the method of DNA or protein transfer may comprise ultrasound-mediated transfer, or phonophoresis. A device that has been used to achieve DNA transfer through radio frequency ablation creation of microchannels is ViaDerm™. The device has an electronic controller unit and a disposable array of stainless steel electrodes (100 or 50 μm in length) at a density of 100 electrodes/cm$^2$ in a total area of 1.4 cm$^2$. Microchannels may bee created by applying a voltage of 290 or 330 V and an RF frequency of 100 kHz for 1-5 bursts lasting 700 μs. The skin can be treated prior to and after the application of DNA to the skin to increase transfer. For example, the ViaDerm™ device was used to transfect excised human skin with plasmid DNA containing the beta-galactosidase or the green fluorescent protein reporter genes (Birchall et al., 2006).

Ultrasound

Ultrasound can also increase the permeability of cell membranes to macromolecules such as DNA (see e.g., Newman, C. M., et al., Echocardiography, 18, 339-47 (2001); Niidome, T. & Huang, L., Gene Ther., 9, 1647-52 (2002)). For example, after injection of DNA into the skin, an irradiating ultrasonic wave may be used to facilitate transfer of the DNA into cells. This technique is commonly used with humans, usually in musculature, and is both flexible and safe. Ultrasound has also been combined with microbubbles, or ultrasound contrast agents, such as perfluoropropane-filled albumin microbubbles, to lower the threshold for cavitation of cells by ultrasound energy (Teupe, C. et al., Circulation, 105, 1104-09 (2002)). For example, ultrasound-mediated destruction of plasmid-loaded albumin microbubbles was used to transfect porcine coronary arteries with DNA encoding an activated form of endothelial nitric oxide synthase (eNOS) with significant protein expression and enhanced nitrous oxide-mediated relaxation of bradykinin-stimulated arteries (Teupe et al., 2002).

Tissue-Specific, Self-Replicating and Integrating Plasmid Expression Systems to Facilitate Long-Lasting Gene Expression In an embodiment, the method of DNA transfer may comprise the use of self-replicating and integrating plasmid expression systems (reviewed in Newmand, C. M., et al., Echocardiography, 18, 339-47 (2001); Niidome, T. & Huang, L., Gene Ther., 9, 1647-52 (2002)). Also, in certain embodiments, the integration may be tissue or cell-type specific. Thus, at least some of the techniques described herein may be transient and may not be biologically targeted to specific cell types.

In an embodiment, tissue specific delivery can be achieved by incorporating protein or peptide ligands into DNA complexes to facilitate receptor-mediated targeting of cells that express certain receptors on their surface. Additionally or alternatively, DNA elements can be incorporated into the DNA transferred to cells such that the encoded gene can only be expressed in cells containing the corresponding protein factor. For example, a tissue-specific transcription factor binding site or promoter can be incorporated into the DNA molecule to be transferred. Such a technique was used to successfully transfected murine liver in vivo with plasmid DNA containing a human factor IX minigene sequence, including a portion of the first intron and 3'-untranslated region, under the control of the hepatic apolipoprotein E locus control region and α1-antitrypsin promoter and with the bovine growth hormone polyadenylation signal (Miao, C. H. et al., Mol. Ther., 1, 522-32 (2000)). Including these genetic elements in addition to the gene sequence itself resulted in increased gene expression in the therapeutic range that was sustained for at least ten months.

In other embodiments, long-lasting expression of transferred genes can be achieved by transfer of self-replicating DNA molecules into target cells. For example, Epstein Barr virus provides a system by which DNA plasmids can be maintained episomally and yet be heritable passed down through generations of cells (Shirakata M. & Hirai, K., J. Biochem., 123, 175-81 (1998)). This system may require that the transferred DNA contains the Epstein Barr Nuclear Antigen 1 (EBNA1) coding sequence and the oriP DNA element such that after transfer into cells, expression of the EBNA1 protein can result in replication of the transferred DNA in conjunction with the genomic DNA. For long-lasting expression of the desired protein in the skin, the transferred DNA may need to be introduced into basal cells. For example, this system as been used for suicide gene therapy in vitro and in vivo using plasmids encoding the EBV elements and the herpes simplex virus type 1 thymidine kinase (HSV-1 tk) gene, to increase cell sensitivity to the chemotherapeutic drug ganciclovir (Maruyama-Tabata, H. et al., Gene Ther., 7, 53-60 (2000)). Also, long term expression of $\beta_2$-adrenergic receptor was achieved by injecting plasmid DNA encoding the gene and carrying the EBV elements into hamster ventricle muscle (Tomiyasu, K. et al. Gene Ther., 7, 2087-93 (2000)).

If the transferred plasmid DNA is integrated into the chromosomal DNA of the basal cells of the skin or other cell having a cosmetic function, it can be heritably transmitted to daughter cells during cell division and, thus, provide a continual source for protein expression. Integration of the transferred DNA into the chromosomal DNA, may employ the use of an enzyme that cleaves the chromosomal DNA for insertion of the transferred DNA. One method of effecting DNA incorporation into the chromosome of a cell having a cosmetic function may be the use of transposons, such as the Sleeping Beauty (SB) transposon system. Thus, in an embodiment, transposons may direct the precise transfer of specific constructs from a donor plasmid into a mammalian chromosome (e.g., reviewed in Hackett, P. B., et al., *Adv. in Genet.*, 54, 189-232 (2005); see also, U.S. Pat. No. 6,489,458)). Using a transposon-based method, the DNA transferred may include the coding sequence for the transposase or, alternatively, the transposase mRNA, in addition to the DNA encoding the a nucleic acid or a polypeptide involved in maintaining a cell having a cosmetic function. For example, the SB transposon is comprised of two terminal repeats of approximately 340 base pairs each, and can mediate transfer of an exogenous nucleotide sequence nearly randomly into chromosomes at TA-dinucleotide base pairs (although flanking DNA sequences may influence the probability of integration at a given site). SB transposons have been used to ameliorate murine disorders that model human disease, and to facilitate somatic integration of an activated NRAS oncogene into mouse hepatocyte DNA (Carelson et al., *Proc. Nat. Acad. Sci. U.S.A.*, 102, 17059-64 (2005)).

In another embodiment, chromosomal integration can be achieved via phage integrases (reviewed in Groth, A. C. & Calos, M. P., *J. Biol Chem.*, 335(3), 667-678 (2004)). For example, a phage integrase may mediate efficient site-specific recombination between two different, relatively short sequences. Thus, the serine-catalyzed family φC31 integrase has been found to work efficiently in human cells to mediate integration at introduced recognition sites or native chromosomal sequences that bear partial identity to these sites (Sclimenti et al., *Nucl. Acid Res.*, 29, 5044-51 (2001)).

Formulations

The polynucleotide construct encoding at least one of a nucleic acid or a polypeptide involved in maintaining a cell having a cosmetic function so as to enhance and/or maintain a biochemical and/or physiological process that has a positive effect on cosmetic appearance may, in certain embodiments, be mixed with a pharmaceutically acceptable carrier to produce a therapeutic composition that can be administered for the treatment of a cell having a cosmetic function. A variety of formulations that may be used with the methods and/or compositions of the present invention are described in U.S. Patent Publication No. 2006/0058256 and U.S. Patent Publication No. 2006/0025363, both of which are incorporated by reference herein in their entireties.

In an embodiment, the compositions of the present invention may comprise a topical formulation. Topical formulations can be comprised of either dissolving or suspending the compositions in a media such as a gel, lotion, cream, suspension, dispersion, any may include, for example, mineral oil, petroleum, polyhyrodxy alcohols or other bases used for topical pharmaceutical formulations. Any other suitable formulation may be used for delivering the compositions, and the compositions may include any number of pharmaceutically acceptable excipients known to those skilled in the art, for instance, as described in *Remington's Pharmaceutical Sciences* (16th Edition, 1980). In certain embodiments, the addition of other ingredients, such as cocoa butter or aloe, to a composition may be desirable.

The formulations may include those suitable for oral, rectal, topical, nasal, ophthalmic or parenteral (including subcutaneous, intramuscular and intravenous) administration, all of which may be used as routes of administration for practicing the present invention.

The formulations may conveniently be presented in a dosage form and may be prepared by any of the methods well known in the art of pharmacy. The formulations may include bringing the active compound into association with a carrier which constitutes one or more accessory ingredients. In general, the formulations are prepared by uniformly and intimately bringing the active compound into association with a liquid carrier, a finely divided solid carrier, or both, and then, if necessary, shaping the product into desired formulations.

Formulations suitable for parenteral administration may conveniently comprise a sterile aqueous preparation of the active compound, which is preferably isotonic with the blood of the recipient.

Nasal spay formulations may comprise purified aqueous solutions of the active compound with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Ophthalmic formulations may be prepared by a similar method to the nasal spray, except that the pH and isotonic factors are preferably adjusted to match that of the eye.

Formulations of the present invention suitable for oral administration may be presented as discrete units such as capsules, cachets, tablets or lozenges, each containing a predetermined amount of a potentiating agent as a powder or granules; as liposomes; or as a suspension in an aqueous liquor or non-aqueous liquid such as a syrup, an elixir, an emulsion or a draught. For example, a tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tablets comprised of a mixture of the powdered active compound with a suitable carrier may be made by molding in a suitable machine. Or, a syrup may be made by adding the active compound to a concentrated aqueous solution of a sugar, for example sucrose to which may also be added any accessory ingredient(s). Such accessory ingredient(s) may include flavorings, suitable preservatives, an agent to retard crystallization of the sugar, and an agent to increase the solubility of any other ingredient, such as a polyhydric alcohol, for example glycerol or sorbitol.

In an embodiment, administration of the polynucleotide encoding at least one of a nucleic acid or a polypeptide involved in maintaining a cell having a cosmetic function may be topical. Topical formulations may comprise the active compound dissolved or suspended in one or more media such as mineral oil, petroleum, polyhydroxy alcohols or other bases used for topical pharmaceutical formulations. The addition of other accessory ingredients may be desirable. For example, the preparation of the present invention may be in the form of a skin cream, face cream, lotion, ointment, or any other suitable topical skin formulation (see e.g., U.S. Pat. No. 4,760,096 incorporated by reference herein in its entirety). Depending upon the intended use of the preparation, other components can be incorporated into it to prepare a skin preparation having desired rheological properties.

Thus, in an embodiment, the formulations of the present invention may be in the form of an aqueous mixture such as a solution, colloidal solution, emulsified lotion, oil-in-water cream (hydrophilic cream) or aqueous gel wherein the aqueous phase is the continuous phase. Alternatively, the formulation can be in the form of an oily mixture such as a solution, ointment, water-in-oil cream, gel base, absorption base or hydrophilic ointment wherein the oil phase is the continuous phase. Also, a non-aqueous water-soluble base such as a mixture with polyethylene glycol may be used. Also, in an embodiment, a suspension base such as a shaking lotion, in which a solid dispersing agent is added, can also be prepared. Oily components, emulsifiers, dispersing agents, gelatinizers and solid materials which can be used to prepare such formulations are well known for use in the preparation of cosmetics and topical products.

As is known in the art, the oily components may include hydrocarbons such as liquid paraffin, petrolatum, solid paraffin, or microcrystalline wax. Also, higher aliphatic alcohols such as cetyl alcohol, hexadecyl alcohol, stearyl alcohol, oleyl alcohol; esters of higher aliphatic alcohols such as bees wax; esters of higher aliphatic acids with lower alcohols such as isopropyl myristate or isopropyl palmitate; vegetable oils and modified vegetable oils; anhydrous lanolin and its derivatives; squalene, or squalane; and higher aliphatic acids such as palmitic acid, stearic acid may be used.

In an embodiment, the formulations can be used with physical (e.g. dermabrasion and occlusion), and/or chemical permeation/penetration enhancers (Azone, DMSO, alcohols, fatty acids and terpenes), as such penetration enhancers have been shown to increase permeability by disordering or 'fluidising' the lipid structure of the stratum corneum). Alternatively or additionally, the formulations of the present invention may be used with other penetration enhancing methods, for instance, electroporation; ultrasound; agents affecting cellular osmolarity; nanoparticles; and any other suitable technique or method that is effective in enhancing the penetration of the formulations of the present invention, e.g., for topical administration.

In one embodiment, L-serine, L-hydroxyproline, or other amino acids that may potentiate and/or synergize with growth factor action may be included in the formulations of the present invention.

In another embodiment, a topical formulation of the present invention may comprise useful emulsifiers and dispersing agents including anionic, cationic and nonionic surfactants. Nonionic surfactants may be preferred because of their low level of irritation to skin. Typical of nonionic surfactants may include monoglycerides such as glyceryl monostearate; sorbitan aliphatic esters such as sorbitan monolaurate; sucrose aliphatic esters; polyoxyethylene aliphatic esters such as polyoxyethylene stearate; and polyoxyethylene higher alcohol ethers such as polyoxyethylene cetyl ether, polyoxyethylene oleyl ether, polyoxyethylene fatty ethers and the like (see e.g., U.S. Pat. No. 4,760,096). Also, gelatinizers such as carboxymethylcellulose, cellulose gel, polyvinyl alcohol, polyethylene glycol and various gums may be used. These oily components, emulsifiers, dispersing agents and gelatinizers can be used alone or in combination with each other. Also, nanoemulsions may be used.

In addition to the aforementioned ingredients, the formulations of this invention may further include one or more accessory ingredient(s) selected from diluents, buffers, flavoring agents, binders, disintegrants, surface active agents, thickeners, lubricants, preservatives (including antioxidants) and the like.

Dosages

The polynucleotide construct may be administered in an amount to deliver the amount of polypeptide or polynucleotide that is required to maintain and/or improve cells having cosmetic function. For topical application of the polypeptide, in alternate embodiments, a dose administration of from about 1 $ng/cm^3$ to 1 $mg/cm^2$ of tissue area, or from about 10 $ng/cm^2$ to 100 $\mu g/cm^2$ of tissue area, or from about 100 $ng/cm^2$ to 10 $\mu g/cm^2$ of tissue area, or from about 500 $ng/cm^2$ to 10 $\mu g/cm^2$ of tissue area, or from about 1 $\mu g/cm^2$ to 5 $\mu g/cm^2$ of tissue area, or from about 1 $\mu g/cm^2$ to 2 $\mu g/cm^2$ of tissue area may be used.

Or, for systemic administration (e.g., intraperitoneal) the dose may range from about 1 ng/kg/day to 100 mg/kg/day, or from about 10 ng/kg/day to 10 mg/kg/day, or from about 100 ng/kg/day to 5 mg/kg/day, or from about 1 $\mu$g/kg/day to 1 mg/kg/day, or from about 100 $\mu$g/kg/day to 500 $\mu$g/kg/day, or from about 10 $\mu$g/kg/day to 100 $\mu$g/kg/day. Or, ranges within these ranges may be used.

In alternate embodiments, the polynucleotide may provide the equivalent to a dose administration of polypeptide that ranges from about 1 $ng/cm^2$ to 1 $mg/cm^2$ of tissue area, or from about 10 $ng/cm^2$ to 100 $\mu g/cm^2$ of tissue area, or from about 100 $ng/cm^2$ to 10 $\mu g/cm^2$ of tissue area, or from about 500 $ng/cm^2$ to 10 $\mu g/cm^2$ of tissue area, or from about 1 $\mu g/cm^2$ to 5 $\mu g/cm^2$ of tissue area, or from about 10 $\mu g/cm^2$ to 2 $\mu g/cm^2$ of tissue area. Or, ranges within these ranges may be used.

For example, vector constructs may be applied as naked DNA doses that range from about 1 $ng/cm^2$ to 1 $mg/cm^2$ of tissue area, or from about 10 $ng/cm^2$ to 10 $mg/cm^2$ of tissue area, or from about 100 $ng/cm^2$ to 100 $\mu g/cm^2$ of tissue area, or from about 500 $ng/cm^2$ to 10 $\mu g/cm^2$ of tissue area, or from about 1 $\mu g/cm^2$ to 5 $\mu g/cm^2$ of tissue area, or from about 10 $\mu g/cm^2$ to 2 $\mu g/cm^2$ of tissue area. Or, ranges within these ranges may be used.

These dose ranges may be determined by performing in vitro and animal studies to precisely characterize the efficiency of gene transfection in the cosmetic cell of interest. Similarly, dose ranges for other carriers, such as liposomes, nanosomes, nanoemulsions, particle-mediated transfer, and voltage driven transfer may be determined using methods specific to each of these applications as is known in the art.

In studies for evaluating the genetic modification of cells having cosmetic function, a plasmid may be administered at any dosage range that produces a desired effect on cosmetic function in the cells. For instance, a plasmid may be administered via a topical route of administration, in a suitable formulation, at individual dosages within a range of about 5 to about 2000 micrograms/milliliter ($\mu$g/ml); preferably at individual dosages within a range of about 50 to about 1000 $\mu$g/ml; and more preferably at individual dosages within a range of about 100 to about 500 $\mu$g/ml. According to one example, sub-therapeutic microdermabrasion is performed for enhancement of KGF-1 pDNA delivery to porcine skin; and KGF-1 pDNA is delivered to the porcince skin at individual dosages within a range of about 100 to about 500 $\mu$g/ml of the KGF-1 pDNA. According to one embodiment, plasmid is delivered at concentrations of 100, 250, 500, 750, 1000, 1500, and 2000 micrograms/milliliter ($\mu$g/ml).

Thus, embodiments of the present invention allow for genetic modification of cells having cosmetic function to enhance and/or maintain expression of genes that may stimulate production of skin proteins for a more youthful appearance. In certain embodiments, the methods and compositions of the present invention may have distinct advantages over currently available cosmetic enhancers including plastic surgery, BOTOX® (injectable botulinum toxin), laser resurfacing, microdermabrasion, pulsed light therapy, injectable fillers/connective tissue substitutes, autologous fibroblast injection, skin care topical products and other methods.

In one advantage, the methods and compositions of the present invention provide improved constant delivery of therapeutic molecules to cells having cosmetic function as compared to topical application of compositions to the such tissues.

Also, in some cases, topically applied compounds, including growth factors, may be rapidly digested by proteases thus limiting the duration of their beneficial effects, or stimulate an immunogenic response. Embodiments of the present invention may stimulate production of the cells having cosmetic function to increase production of the cell's own proteins, and thus, there may be a reduced activation of proteases or an immunogenic response.

Unlike topically applied growth factor protein products which recommend twice daily topical application to achieve improved cosmetic appearance, embodiments of the methods and compositions of the present invention may offer once weekly or once monthly dosing (i.e., the standard daily or twice daily application may not be required for full cosmetic benefits), or in the case of stem cell transfection, one time dosing, to improve cosmetic appearance. Constant round-the-clock steady expression of a cosmetic enhancing polypeptide, for example a plasmid encoding keratinocyte growth factor (KGF), for a seven day period, would have obvious advantages over the very temporal peak and troughs of twice daily topical KGF polypeptide application. In effect, this method turns the skin into a bioreactor producing constant cosmetically beneficial polypeptides with distinct advantages. Also, because the methods and compositions of the present invention are administered much less frequently than standard topical treatments, the methods and compositions of the present invention can eliminate or reduces the need for invasive, and sometimes complicated, surgical, injectable and laser/light therapies which produce skin damage as an inherit part of the treatment, and with improved compliance with less frequent dosing.

Sub-Therapeutic Microdermabrasion

In studies to determine whether expression and/or levels of skin proteins and other biomolecules such as collagen, elastin, extracellular matrix proteins, proteoglycans, growth factors has a cosmetic rejuvenation effect on the skin, and in methods for evaluating the cosmetic genetic modification of substantially intact cells having a cosmetic function, it is preferred to use sub-therapeutic microdermabrasion.

Plasmid DNA (pDNA) delivery through intact skin has been intensively studied utilizing a variety of penetration enhancing techniques including barrier disruption (e.g. microdermabrasion and tape stripping), lipid-based delivery systems (e.g. liposomes), and membrane-destabilizing techniques such as electroporation (Choi M J and Maibach H I. Topical Vaccination of DNA Antigens: Topical Delivery of DNA Antigens, Skin Pharmacol. Appl. Skin Physiol. 2003; 16:271-282). High-molecular weight pDNA needs to penetrate the uppermost stratum corneum to reach viable keratinocytes. Physical disruption of the stratum corneum with tape-stripping and brushing enhances delivery of macromolecules and plasmid DNA across animal skin (Yu W H, Kashani-Sabet M, Liggitt D, Moore D, Heath T D, Debs R J. Topical gene delivery to murine skin. J Invest Dermatol 1999; 112:370-375).

Lee et al. (Microdermabrasion as a novel tool to enhance drug delivery via the skin: an animal study. Dermatol Surg. 2006 August; 32(8):1013-22) found that sub-therapeutic microdermabrasion (i.e., using very low suction pressures and short treatment durations [15 cmHg for 10 seconds=20 kPa]) increased drug delivery 8-fold to 24-fold in mice and pigs. These sub-therapeutic microdermabrasion treatment parameters are less intense than the microdermabrasion parameters intended for therapeutic purposes (i.e. wrinkle reduction), and do not elicit an inflammatory reaction in the skin. With sub-therapeutic microdermabrasion, microscopic analysis has demonstrated no observable damage to the whole skin with only a slight thinning of the stratum corneum (SC). The SC layers appeared to be concentrated and focally compacted. No change was seen in the layers of epidermis and dermis, and results obtained with sub-therapeutic microdermabrasion are controllable and reproducible.

Increased macromolecule delivery is also seen in primates and humans following microdermabrasion (Prausnitz M R, et al. Transdermal drug delivery. Nat Biotechnol. 2008 November;26(11):1261-8; Gill H S, et al. Selective removal of stratum corneum by microdermabrasion to increase skin permeability. Eur J Pharm Sci. 2009). Gill et al (2009) found that that degree of stratum corneum removal was controllable by the number of skin passes by the microdermabrasion head in monkeys and humans. However, variable pressure (25 kPa versus 50 kPa) did not show a difference.

As described in the Examples herein, sub-therapeutic microdermabrasion can be used reliably in different mammalian species, for example, in mice or pigs. It should be understood that the experimental studies described herein (e.g., as set forth in the Examples), including the studies employing sub-therapeutic microdermabrasion, can also be performed in other mammalian species, for instance, to determine whether expression of other growth factors, e.g., PDGF (platelet derived growth factor), has a cosmetic rejuvenation effect on skin. Sub-therapeutic microdermabrasion can also be employed in studies for evaluating the cosmetic genetic modification of substantially intact cells having a cosmetic function.

Moreover, it should also be understood that techniques other than sub-therapeutic microdermabrasion can be utilized to assess whether expression of other growth factors, e.g., PDGF (platelet derived growth factor), has a cosmetic rejuvenation effect on skin.

Histologic and Other Analytical Procedures

In animal studies to determine whether expression and/or levels of skin proteins and other biomolecules such as collagen, elastin, extracellular matrix proteins, proteoglycans, growth factors has a cosmetic rejuvenation effect on the skin, and in methods for evaluating the cosmetic genetic modification of substantially intact cells having a cosmetic function, results can be analyzed by standard and well-known histological procedures, e.g., by histological analysis of tissue sections before and after expression of one or more biomolecules. Histological procedures are also employed since issue has little inherent contrast in either the light or electron microscope, and since staining gives both contrast to the tissue as well as highlighting particular features of interest.

For instance, in studies that involve delivery of KGF-1 pDNA to an animal's skin, and to determine whether expression of the KGF-1 has a cosmetic rejuvenation effect on the skin, standard and well-known histological procedures can be utilized. Similar histologic procedures can also be utilized to evaluate whether expression of one or more other biomolecules also has a cosmetic rejuvenation effect on skin.

Examples of histologic procedures that can be used include the use of light microscopical stains, such as hematoxylin and eosin (H&E) stains. It is to be understood that other well-known and established procedures in histology and histopathology can also be utilized for evaluating whether expression of one or more other biomolecules has a cosmetic rejuvenation effect on the skin.

Other exemplary staining techniques that can be employed include, for instance, Masson's trichrome stain, which is typically a three-color staining protocol often used in histology, and also Von Gieson staining. Staining using H&E, Mason Trichrome and Von Gieson can be used for various histological measurements, including analysis of the thickness of the skin, the collagen and elastic fibers contents.

In another exemplary embodiment, H&E stains can be used for evaluating changes in epidermis thickness, number of keratinocytes, collagen thickness and density in the dermis, e.g., before and after delivery of KGF-1 pDNA to an animal's skin.

Staining is employed to give both contrast to the tissue as well as highlighting particular features of interest. Hematoxylin, a basic dye, stains nuclei blue due to an affinity to nucleic acids in the cell nucleus; eosin, an acidic dye, stains the cytoplasm pink. Uranyl acetate and lead citrate are commonly used to impart contrast to tissue in the electron microscope. There are also various other techniques that can be used to selectively stain cells and cellular components. Other compounds that can be used to color tissue sections include, for instance, safranin, Congo red, fast green FCF, silver salts, and numerous natural and artificial dyes.

Tissue samples can also be analyzed by other procedures to determine whether expression and/or levels of skin proteins and other biomolecules such as collagen, elastin, extracellular matrix proteins, proteoglycans, and/or growth factors has a cosmetic rejuvenation effect on the skin, and in methods for evaluating the cosmetic genetic modification of substantially intact cells having a cosmetic function. For instance, antibodies can be used to specifically visualize biomolecules, for instance, using immunohistochemistry, or when utilizing a fluorescent stain with immunofluorescence. Other techniques, such as nonradioactive in situ hybridization, can be combined with immunochemistry to identify specific DNA or RNA molecules with fluorescent probes or tags that can be used for immunofluorescence and enzyme-linked fluorescence amplification. Different imaging techniques can be used to study the histological samples, for instance, after staining the tissue sample or after immunofluorescence with a fluorescent stain. In certain embodiments, fluorescence microscopy and confocal microscopy can be used to detect fluorescent signals with good intracellular detail. Digital cameras can also be used to capture histological and histopathological images.

Animal Models

In accordance with the embodiments described herein, any suitable animal model can be used to determine whether expression and/or levels of skin proteins and other biomolecules such as collagen, elastin, extracellular matrix proteins, proteoglycans, and/or growth factors has a cosmetic rejuvenation effect on the skin, and in methods for evaluating the cosmetic genetic modification of substantially intact cells having a cosmetic function. The term "animal" is intended to include, but is not limited to, any mammalian species. Examples of such mammals include, but are not limited to, different species of porcine (pig) and murine (mouse). It is known to those skilled in the art that porcine animal models, for instance, offer certain advantages, given known similarities between porcine and human skin physiology and morphology. The choice of animal model can involve an assessment of many different factors. Some of the factors considered in selecting a suitable animal model include the skin layer thickness and ability for drug penetration across the skin.

The stratum corneum (SC), which is the outer protective layer of the epidermis, is hydrophobic, and it is difficult for negatively charged pDNA to penetrate this layer (Branski L K, et al., Gene Ther. 2007 January;14(1):1-10). Mouse dorsal skin has only 1-2 cell layers of the stratum corneum, and the rabbit has 1-2 dorsal SC cell layers. In contrast, pigs and humans have similar stratum corneum thickness and skin (Meyer, W., et al., 1978, Curr. Prob. Dermatol. 7:39-52; Bronaugh, R., et al., 1982, Toxicol. Appl. Pharmacol. 62: 481-488; Kiritsy C P, et al. Crit Rev Oral Biol Med. 1993; 4(5):729-60). Human facial skin has 9±2 such layers; many fewer hair follicles; and 14-17 cell layers in non-facial areas. Mice have a thinner dermal layer and a less cornified stratum corneum (Hengge, U. R., et al. J. Clin. Invest. (1996) 97, 2911-2916). Permeability of the skin (usually 10-100 times higher permeability than in human skin) is thus one consideration in selecting an animal model, such as hairless mice and rats (Paasonen L., et al. Int. J. Pharm. 2006 Jan. 13:307 (2):188-93).

The normal-healing pig model has been used widely in studies with induced partial-thickness skin wounds because of their similarity of skin integumen to that of humans and their relative hairlessness. Also, pigs, like humans, are considered tight-skinned animals, in contrast to loose-skinned rodents, rabbits, and guinea pigs. Loosely skinned animals contain a panniculus carnosus, that is, a muscle layer underneath and attached to the skin. Hengge et al (J. Clin. Invest., (1996) 97, 2911-2916) reported that mouse skin, after naked pDNA intradermal injection, exhibited expression in epidermis, dermis, and underlying fat and muscle. In contrast, pig and human skin showed only epidermal expression. Similarly, Glasspool-Malone et al (Mol. Ther. 2000; 2: 140-146) reported that transgene expression of injected pDNA into pigs and rhesus monkeys was restricted largely to the epidermis. Minipigs are an attractive model for cutaneous testing because of their smaller size and close resemblance to human skin (Mortensen J T, et al. Scand. J. Lab. Anim. Sci. Suppl. 1. 1998. Vol. 25). The epidermis is rather thick in both species, being approximately 70-140 mm in pigs and 20-120 mm in humans, with large variations from site to site. The epidermis of the pig resembles that of man with a reticulated dermal-epidermal junction. Skin permeability in various animal models is ranked generally as follows: rabbit>rat>guinea pig>swine>rhesus monkey>man. The skin of minipigs is less sensitive to irritants than rabbit skin. Based on a evaluation of numerous factors, pigs are thus one suitable animal model for testing topically applied pDNA. As stated elsewhere Example 1

Amplification, Cloning, and Expression of Human Collagen α1 Type 1, Collagen α2 Type 1, TIMP-1, and Elastin from Normal Tissue cDNAs First strand cDNAs generated from normal human tissues were purchased from BioChain Institute (Hayward, Calif.). Collagen α1 Type 1 (COLA1A), Collagen α2 Type 1 (COL1A2), and Elastin were amplified from normal human skin (Cat No. C1234218-10) cDNAs, whereas TIMP-1 was amplified from both normal human lung (Cat No. C1234152-10) and brain (Cat. No. C1244035-10) cDNAs. Gene amplifications were performed with high fidelity Platinum Pfx Polymerase (Invitrogen, Carlsbad, Calif.), according to manufacturer's instructions, with gene specific oligonucleotides. Table 1 summarizes oligonucleotide sequences used for amplification of each gene, as well as Polymerase Chain Reaction (PCR) conditions. Table 1 shows the oligonucleotide sequences and PCR parameters used in the amplification of COLA1A, COL1A2, Elastin, and TIMP-1 from normal human tissue cDNAs.

TABLE 1

Primers and PCR parameters for cloning COLA1A, COL1A2, Elastin and TIMP-1 cDNAs from normal tissue

| | Tissue source | 5' oligo | 3' oligo | Anneal temp. | Ext. time |
|---|---|---|---|---|---|
| COLA1A | Skin | GATC<u>GCTAGC</u>GCCGCCACC<u>ATG</u>TTCAGCTTTGTGGACCTCCGGCTCCTGC (SEQ ID NO: 3) | CGAT<u>AAGCTT</u>TTACAGGAAGCAGACAGGGCCAACGTCGAAGCCG (SEQ ID NO: 4) | 56° C. | 6 min. |
| COL1A2 | Skin | GATC<u>GCTAGC</u>GCCGCCACC<u>ATG</u>CTCAGCTTTGTGGATACGCGGACTTTGTTGCTGCTT (SEQ ID NO: 20) | CGAT<u>AAGCTT</u>TTATTTGAAACAGACTGGGCCAATGTCCACAAAGAATTCCT (SEQ ID NO: 21) | 56° C. | 6 min. |
| Elastin | Skin | GATC<u>GCTAGC</u>GCCGCCACC<u>ATG</u>GCGGGTCTGACGGCGGCGGCCCCGCGG SEQ ID NO: 7) | GCTA<u>AGATCT</u>TCATTTTCTCTTCCGGCCACAAGCTTTCCCAGG (SEQ ID NO: 8) | 56° C. | 3 min. |
| TIMP-1 | Brain; lung | GATC<u>GCTAGC</u>GCCGCCACC<u>ATG</u>GCCCCCTTTGAGCCCCTGGCTTCTGGCATCCTG (SEQ ID NO: 15) | CGAT<u>AAGCTT</u>TCAGGCTATCTGGGACCGCAGGGACTGCCAGGTGCA (SEQ ID NO: 16) | 56° C. | 1.5 min. |

5' oligonucleotides were designed with an NheI restriction endonuclease (REN) site for cloning into the mammalian expression vector pcDNA3.1+zeo:intA immediately downstream of the PCMV promoter. Kozak sequences for optimal translation initiation were engineered immediately following each NheI site (GCCGCCACC<u>ATG</u>) (i.e., nucleotides 11-22 of SEQ ID NO:3). 3' oligonucleotides were designed with HindII Restriction Endonuclease Sites (REN sites) for COLA1A, COL1A2, and TIMP-1, and with BglII REN for Elastin for cloning into the same vector immediately preceding the bovine growth hormone polyadenylation (BGHpA) signal sequence. REN sites are underlined, and translation initiation codons (ATG) are double underlined. Stop codons native to each gene (e.g., 5'-TAA-3' or 5'-TGA-3') immediately precede the REN site in the 3' oligonucleotide sequences, and are bolded.

PCR reactions were setup on ice, and contained final concentration of each component, as follows: 1× Pfx Amplification Buffer, 0.3 mM each of dATP, dTTP, dCTP, dGTP, 1 mM MgSO$_4$, 0.3 μM each oligonucleotide, 1 μL of first strand cDNA template, 1.0-2.5 units Platinum Pfx DNA Polymerase, and nuclease-free distilled water to a final volume of 50 μL. Each reaction was subjected to three-step PCR cycling, using the following parameters: 94° C. for 15 seconds, 56° C. for 30 seconds, and 68° C. for the amount of time indicated in Table 1 above for each gene. Each amplification was performed for 35 cycles, following by a final extension cycle at 72° C. for 7 minutes, and cooling at +4° C. until analysis. A positive control was run alongside each experimental PCR reaction by using the same first strand cDNA template and a set of primers specific for human beta actin (BioChain). Following PCR each reaction was analyzed by Tris-Acetate EDTA (TAE) agarose gel electrophoresis to determine extend and integrity of amplified cDNA. For each analysis 10 μL of each reaction were mixed with Blue Juice loading buffer (Invitrogen) and loaded per lane of a 1% TAE agarose gel. TriDye 1 kb DNA ladder (New England Biolabs, Ipswich, Mass.) was used to estimate the size of amplified cDNAs. Following confirmation of PCR amplification for each cDNA each reaction was immediately cloned into the Zero Blunt TOPO PCR Cloning system (Invitrogen), according to manufacturer's instructions. Colonies were screened either by PCR or REN analysis of purified DNAs from overnight bacterial cultures, or both. pCR-Blunt II-TOPO clones containing fragments of expected sizes were subsequently restricted with the appropriate RENs for isolation and cloning of the full length genes into the mammalian expression vector pcDNA3.1+zeo:intA. The expression vector was constructed from pcDNA3.1+zeo (Invitrogen) by adding the human CMV intron A sequence to the 3' end of the minimal promoter. CMV intron A sequence has been extensively characterized and shown to greatly enhance the expression of recombinant genes in mammalian cells when compared with an intronless CMV promoter counterpart. The intron A sequence was PCR amplified from the vector pWRG7077 (kindly provided by Dr. Jay Hooper, United States Army Medical Research Institute of Infectious Diseases [USAMRIID]), and was cloned into pcDNA3.1+zeo as a NdeI-NheI sites. pcDNA3.1+zeo:intA is a 6.5 kb plasmid with the expression elements outlined in FIG. 8. TIMP-1 was amplified from both brain and lung tissue cDNAs. For this work TIMP-1 from brain cDNAs was used for all subsequent cloning and expression experiments.

Cloning reactions were performed as described in Maniatis and Sambrook, 1988, followed by transformation into subcloning efficiency *Escherichia coli* (*E. coli*) strain DH5α, for propagation of cloned DNAs. Colonies were screened either by PCR or REN analysis of purified DNAs from overnight bacterial cultures, or both. pcDNA3.1+zeo:intA clones containing fragments of expected sizes were subsequently restricted with unique RENs for confirmation of gene identities. For each construct highly pure midiprep plasmid DNAs were isolated form 50 mL *E. coli* cultures growth overnight in selective broth. DNAs were assayed for purity and concentration by A280 and A260. Expression of each gene was confirmed by lipofectamine-mediated transfection of the human endothelial kidney cell line HEK-293T/17, and subsequent analysis of cell extracts and supernatants. For each construct to be analyzed, 1×10$^6$ HEK-293T/17 cells were seeded per well of a Poly-D-Lysine coated 6 well plate in 2 mL of growth medium (DMEM, high glucose; 2 mM L-Glutamine; 1× Non Essential Amino Acids [NEAA]; 10% heat inactivated Fetal Bovine Serum [FBS]) the night prior to transfection, and cultured at 37° C., 5% CO$_2$, 90% relative humidity (Rh). The following day cultures were fed with 2 mL of fresh growth medium prior to transfection. Four µg of each plasmid DNA construct were gently mixed in 250 µL of Opti-MEM Reduced Serum Medium (Invitrogen) and combined with an additional 250 µL of the same medium supplemented with 10 µL of Lipofectamine 2000 transfection reagent (Invitrogen). The reaction was incubated at room temperature for 20 minutes to allow DNA:lipofectamine complexes to form. The entire reaction was then gently pipetted into the corresponding well containing HEK-293T/17 cells and was gently swirled to evenly distribute the transfection mix. Plates were then returned to the incubator and were cultured for 72 hours prior to harvesting and analysis. Expression of each gene construct was performed on transfected HEK-293T/17 cell extracts and culture supernatants.

Following the 72 hour transfection supernatants were harvested and cleared by centrifugation. One mL of each supernatant was transferred to a polypropylene microcentifuge tube and kept on ice until analysis. Cells were scraped from wells and were pelleted by brief centrifugation in polypropylene microcentrifuge tubes. Supernatants were carefully decanted and pellets were resuspended in 1× Phosphate Buffered Saline (PBS), pH 7.4, and pelleted by brief centrifugation. PBS was decanted and each cell pellet was resuspended in 100 µL of Mammalian Cell Lysis Buffer (Sigma-Aldrich, St. Louis, Mo.), according to manufacturer's instructions. Lysis buffer was prepared with TRIS buffer, Sodium Chloride, Sodium Dodecyl Sulfate (SDS), Igepal, Deoxycholate, and protease inhibitors. Lysis reactions were incubated at room temperature for 10 minutes, followed by centrifugation at 14,000× g for 10 minutes at room temperature. Supernatants were transferred to fresh polypropylene microcentrifuge tubes and were kept on ice until analysis. SDS-Polyacryiamide Gel Electrophoresis (SDS-PAGE) and Western Blot analysis were performed on each set of transfected HEK-293T/17 cell extracts and supernatants. One hundred thousand cell equivalents (~10 µL) were mixed with NuPage LDS Sample Buffer, NuPAGE Reducing Agent, and deionized water, heated at 90° C. for 5 minutes and were loaded per lane of a 10% NuPage Novex Bis-Tris Gel. Likewise, 30 µL of corresponding supernatant were similarly prepared and loaded alongside cell extracts. SeeBlue Plus-2 Protein molecular weight marker (Invitrogen) was used to estimate protein sizes. Gels were run in 1× SDS NuPAGE MES Running Buffer at 200 V, for 45 minutes. Following electrophoresis proteins were transferred to 0.45 µm Nitrocellulose membrane using an X-Cell II Blot Module, according to manufacturer's instructions (Invitrogen). Western blots were performed with a Protein Detector TMB Western Blot Kit (KPL, Gaithersburg, Md.), according to manufacturer's instructions, using primary antisera and secondary detection reagents, as outlined in Table 2. Rabbit antisera to COLA1A, COL1A2, TIMP-1, and Elastin were purchased from Santa Cruz Biotechnology (Santa Cruz, Calif.). Horseradish Peroxidase (HRP)-labeled Goat anti-Rabbit IgG (H+L) (Santa Cruz Biotechnology) was used as secondary detection reagent. Immunological complexes were detected with TMB membrane substrate for 2-5 minutes, and reactions were stopped by immersing the blots in distilled water. Permanent records were generated by high resolution scanning of developed blots. Table 2 shows detection reagents for Western Blot analysis of COLA1A, COL1A2, TIMP-1, and Elastin transiently expressed in HEK-293T/17 cells.

TABLE 2

Sera Used for Western Blot Detection of Expressed Recombinant Proteins

| | Primary antisera | Source | Secondary detection reagent |
|---|---|---|---|
| COLA1A | Rabbit polyclonal antibody to amino acids 1021-1217 of Human Collagen α1 Type 1 | Collagen Type 1 (H-197): sc-28657 | Goat anti-Rabbit IgG (H + L)-HRP: sc-2004 |
| COL1A2 | Rabbit polyclonal antibody to amino acids 1021-1090 of Human Collagen α2 Type 1 | Collagen Type 1 (H-70): sc-28655 | |
| Elastin | Rabbit polyclonal antibody to amino acids 431-730 of Human Elastin | Elastin (H-300): sc-25736 | |
| TIMP-1 | Rabbit polyclonal antibody to amino acids 58-207 of Human TIMP-1 | TIMP-1 (H-150): sc-5538 | |

Figure 8:
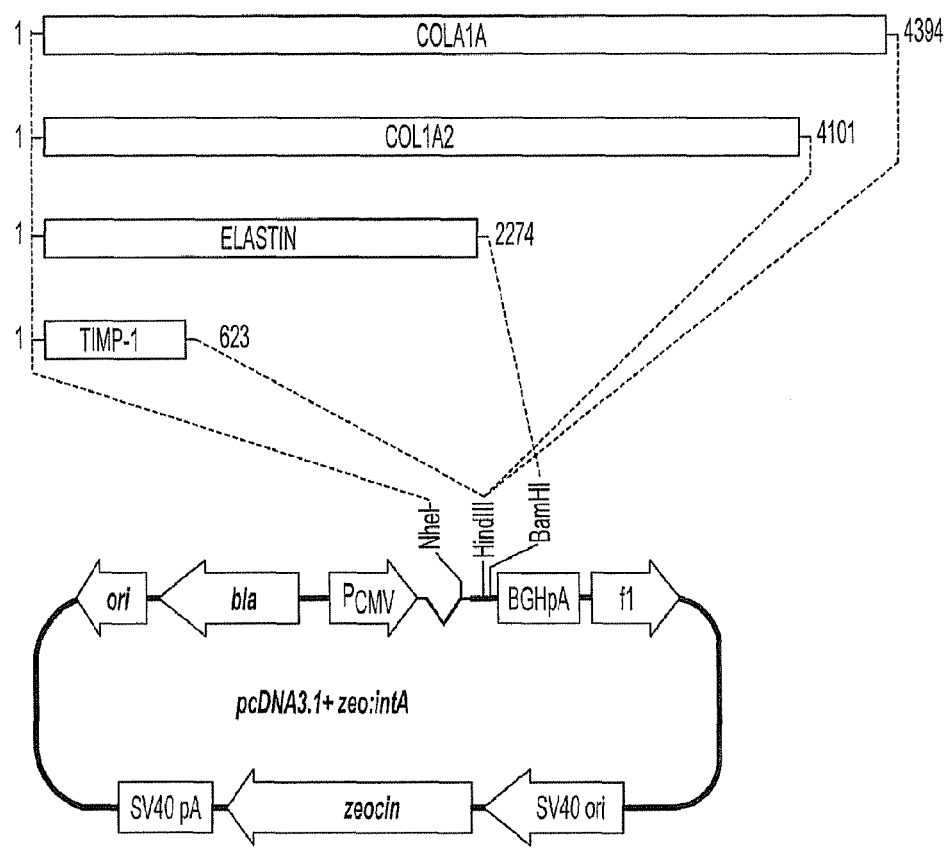
FIG. 8 depicts the cloning strategy for expression of human proteins COLA1A, COL1A2, Elastin, and TIMP-1 in mammalian cells using the CMV promoter-driven eukaryotic vector pcDNA3.1+zeo:intA in accordance with alternate embodiments of the present invention.

FIG. 8 show the cloning strategy for expression of human proteins COLA1A, COL1A2, Elastin, and TIMP-1 in mammalian cells using the CMV promoter-driven eukaryotic vector pcDNA3.1+zeo:intA. Genes were PCR amplified from normal human tissue cDNAs and cloned as described in Materials and Methods. COLA1A, COL1A2, and TIMP-1 were directionally cloned into the mammalian vector's NheI-HindIII REN sites, whereas Elastin was cloned into NheI-BamHI sites. The BglII site on the 3' end of Elastin was directionally cloned into the unique isoschizomer site BamHI. Relevant expression elements are bacterial origin of replication (ori), beta-lactamase gene (bla), cytomegalovirus early promoter ($P_{CMV}$), bovine growth hormone polyadenylation signal (BGHpA), single-stranded philamentous phage origin (f1), simian virus 40 origin of replication (SV40 ori), simian virus 40 polyadenylation signal (SV40 pA), zeocin antibiotic resistance gene (zeocin).

Figure 9:
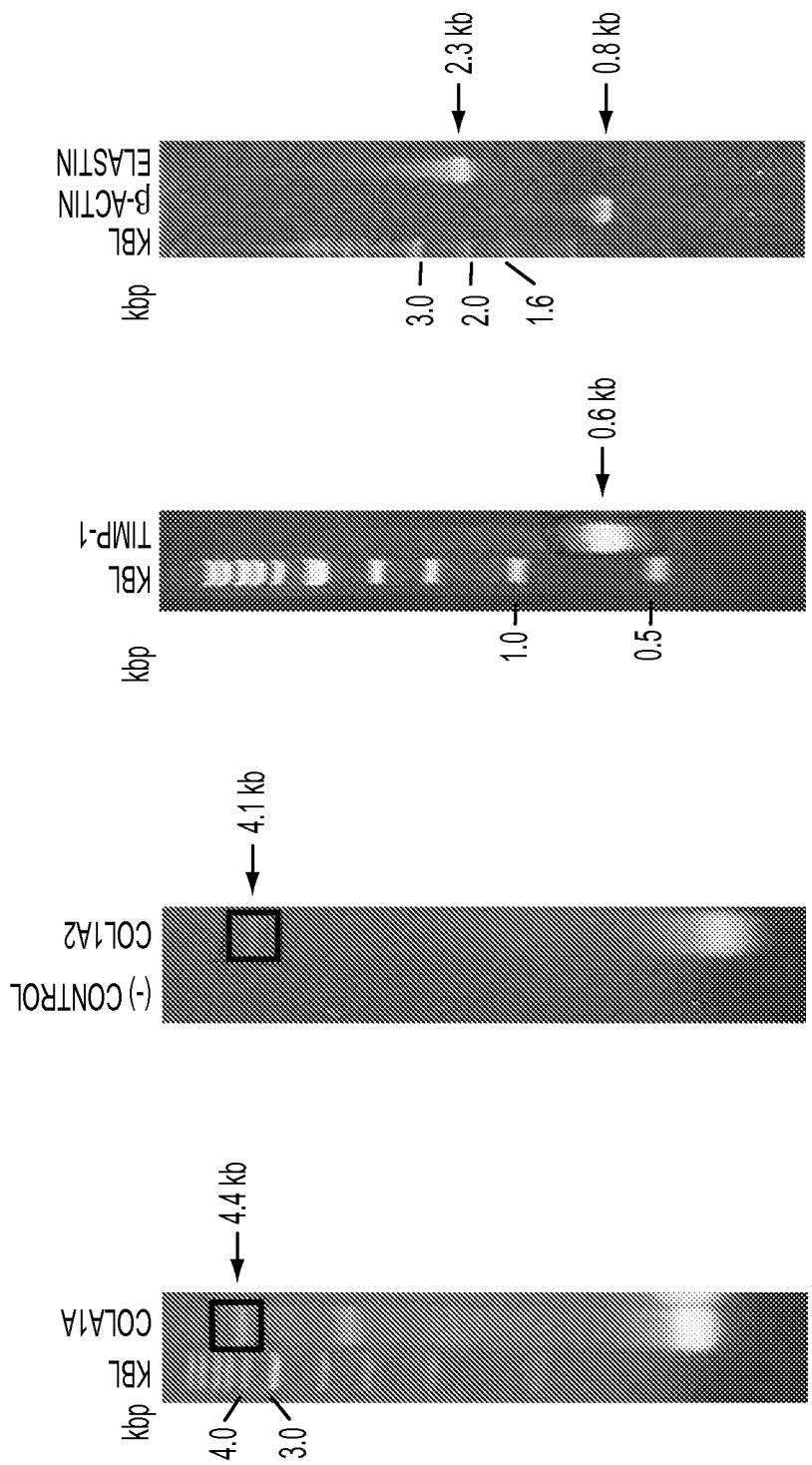
FIG. 9 depicts PCR amplification of COLA1A, COL1A2, TIMP-1, and Elastin from normal human tissue cDNAs in accordance with alternate embodiments of the present invention.

FIG. 9 shows PCR amplification of COLA1A, COL1A2, TIMP-1, and Elastin from normal human tissue cDNAs. Each gene was amplified as described in Materials and Methods using gene-specific oligonucleotide primers. Amplified gene sequences of interested are marked by arrows, and corresponding sizes are indicated: (a) COLA1A; (b) COL1A2; (c) TIMP-1; (d) Elastin. KBL, kilobase ladder; kbp, kilobase pairs.

Figure 10:
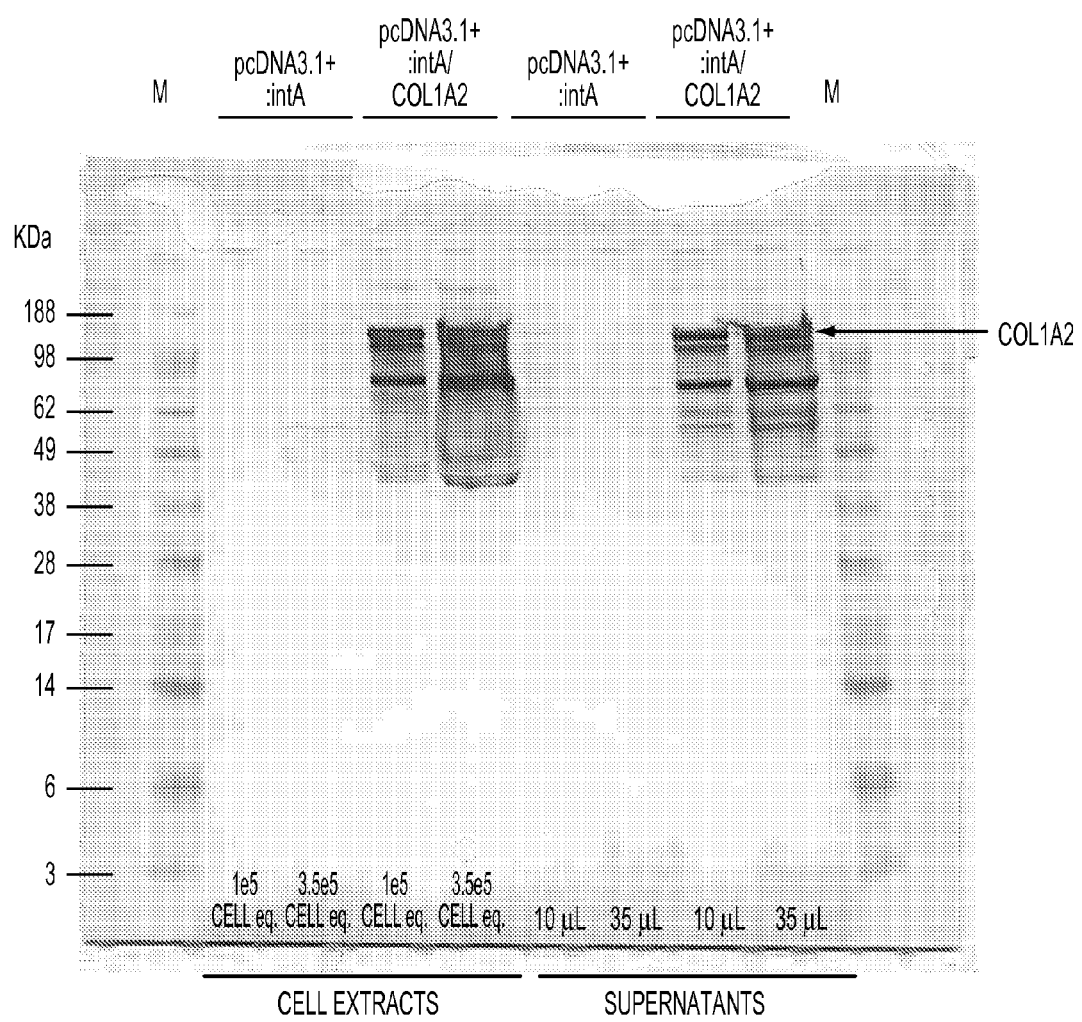
FIG. 10 depicts transient expression analysis of human COL1A2 in HEK-293T/17 cells in accordance with an embodiment of the present invention. The 138.9 KDa COL1A2 protein is indicated by an arrow.
Figure 11:
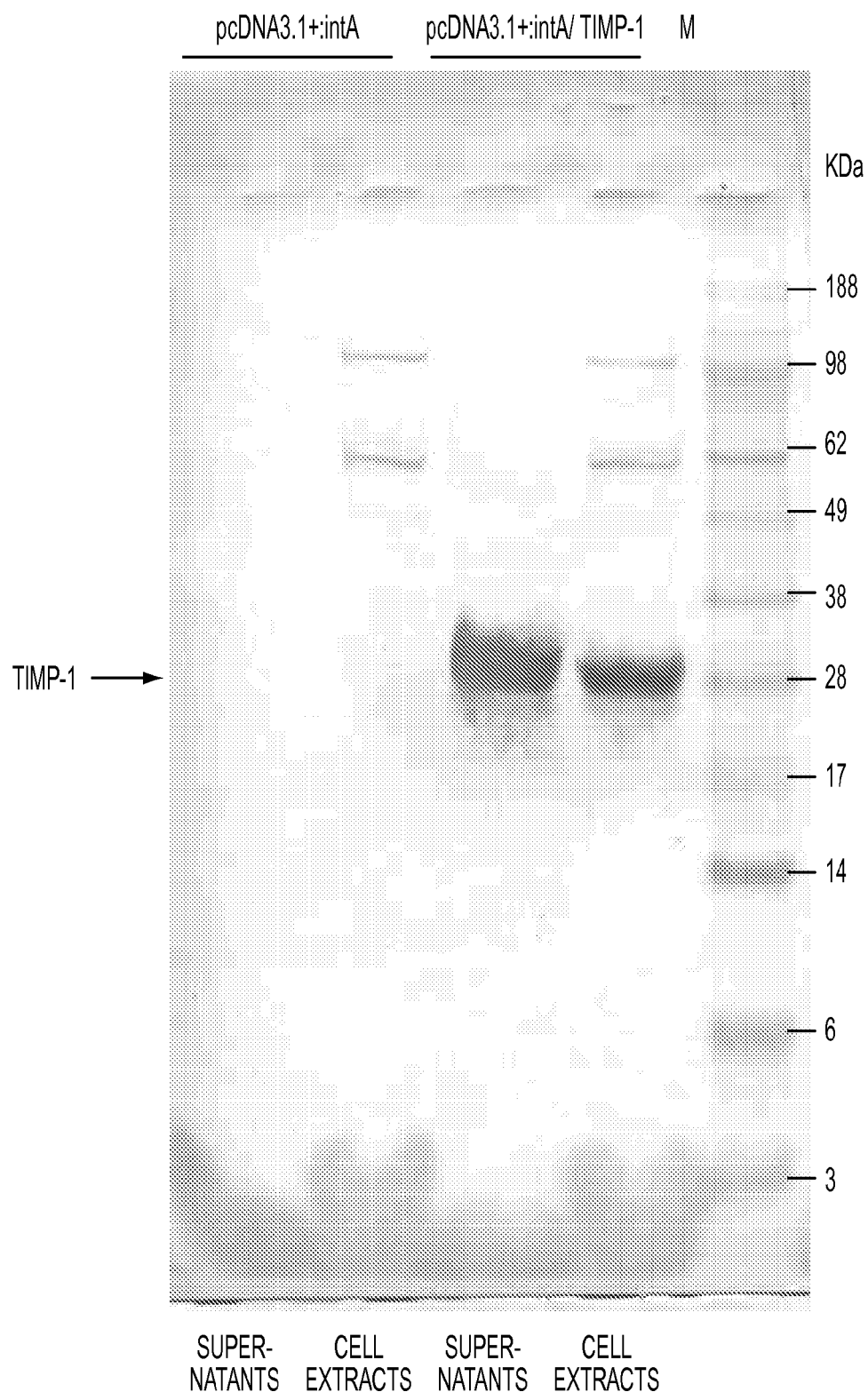
FIG. 11 depicts transient expression analysis of human TIMP-1 in HEK-293T/17 cells in accordance with an embodiment of the present invention. The 23.2 KDa TIMP-1 protein is indicated by an arrow.
Figure 12:
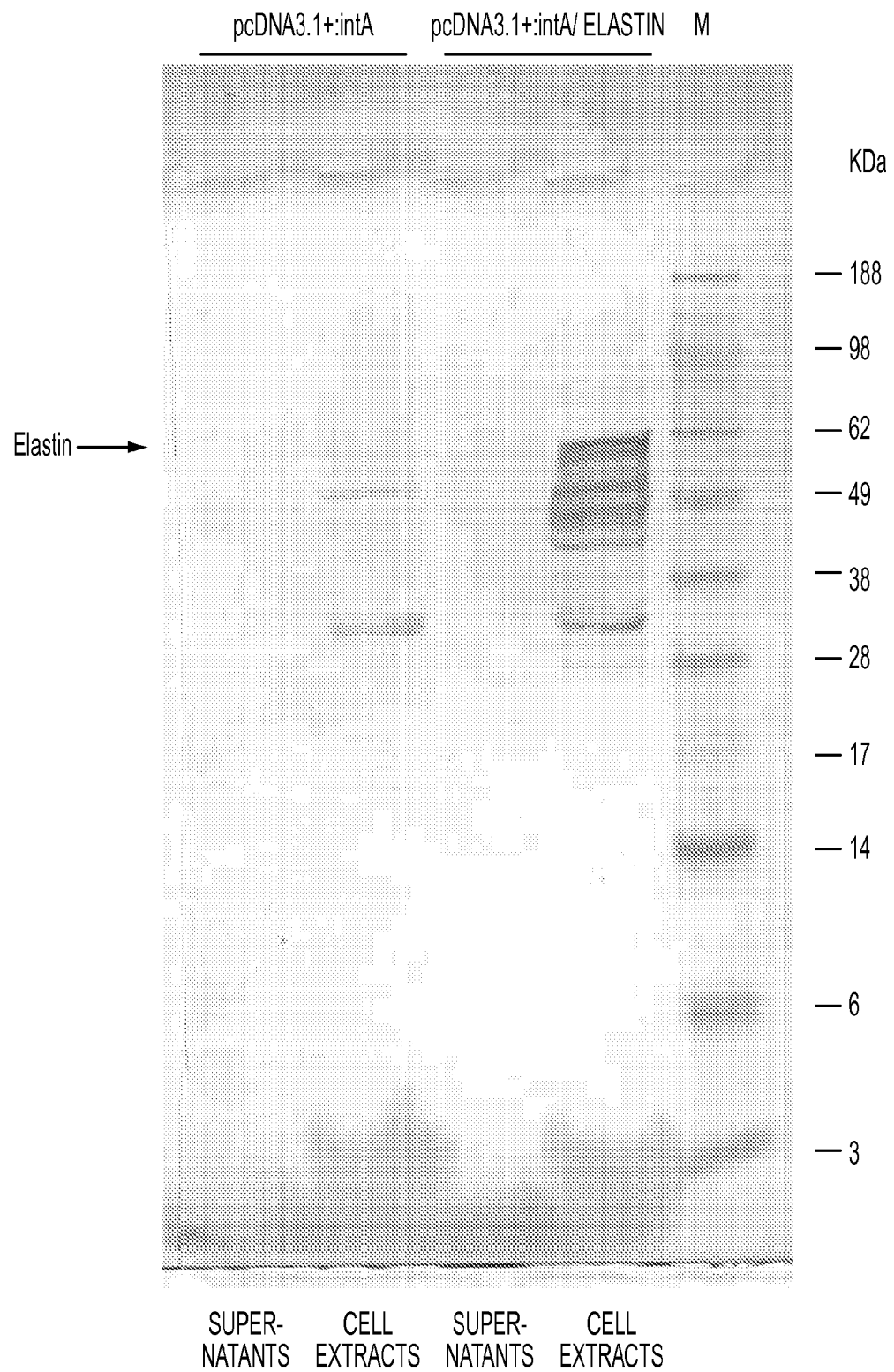
FIG. 12 depicts transient expression analysis of human Elastin in HEK-293T/17 cells in accordance with an embodiment of the present invention. The 66.1 KDa Elastin protein is indicated by an arrow.

Results showing expression of the cloned proteins (COL1A2, TIMP-1, and Elastin) are shown in FIGS. 10-12. FIG. 10 shows transient expression analysis of human COL1A2 in HEK-293T/17 cells. The 138.9 KDa COL1A2 protein is indicated by an arrow. Minor fragments detected by the COL1A2-specrfic antiserum may be incomplete translation products and degraded protein. FIG. 11 shows transient expression analysis of human TIMP-1 in HEK-293T/17 cells. The 23.2 KDa TIMP-1 protein is indicated by an arrow. TIMP-1 runs higher than its predicted protein molecular weight of 23 KDa likely due to predicted N-linked and Asn-Xaa-Ser/Thr glycosylation of this protein in mammalian cells. FIG. 12 shows transient expression analysis of human Elastin in HEK-293T/17 cells. The 66.1 KDa Elastin protein is indicated by an arrow. Minor fragments detected by the Elastin-specific antiserum may be incomplete translation products and degraded protein. Expression results indicate that in HEK-293T/17 cells this Elastin construct is not secreted, and is only expressed intracellularly.

Example 2

Amplification, Cloning, and Expression of Human Keratinocyte Growth Factor-1 (KGF-1, FGF-7) from Normal Lung Tissue cDNAs Materials and Methods First strand cDNAs generated from normal human tissues were purchased from BioChain Institute (Hayward, Calif.). Keratinocyte Growth Factor-1 was amplified from normal normal human lung cDNAs (Cat. No. C1234152-10). Gene amplifications were performed with high fidelity Platinum Pfx Polymerase (Invitrogen, Carlsbad, Calif.), according to manufacturer's instructions, with gene specific oligonucleotides. Table 3 summarizes oligonucleotide sequences used for amplification of the KGF-1 gene, as well as Polymerase Chain Reaction (PCR) conditions.

TABLE 3

Oligonucleotide sequences and PCR parameters used in the amplification of KGF-1 from normal human lung tissue cDNAs

| Gene | Tissue source | 5' oligo | 3' oligo | Anneal temp | Extension time |
|---|---|---|---|---|---|
| KGF-1 | lung | 5'-GATCGCTAGCGCCGCCA CCATGCACAAATGGA TACTGACATGGATC-3' 46-mer (SEQ ID NO: 21) | 5'-CGATAAGCTTTTAAGTTATT GCCATAGGAAGAAAGTGGG CTGTTTTTTGT-3' 50-mer (SEQ ID NO: 22) | 55° C. | 1 min. |

5' oligonucleotides were designed with an NheI restriction endonuclease (REN) site for cloning into the mammalian expression vector pcDNA3.1+zeo:intA immediately downstream of the PCMV promoter. Kozak sequences for optimal translation initiation were engineered immediately following each NheI site (GCCGCCACCATG). 3' oligonucleotides were designed with HindIII RENs (underlined) for cloning into the same vector immediately preceding the bovine growth hormone polyadenylation (BGHpA) signal sequence. REN sites are underlined, and translation initiation codons (ATG) are double underlined. A stop codons native to the gene immediately precedes the REN site in the 3' oligonucleotide sequence and is bolded.

PCR reactions were setup on ice, and contained final concentration of each component, as follows: 1× Pfx Amplification Buffer, 0.3 mM each of dATP, dTTP, dCTP, dGTP, 1 mM MgSO$_4$, 0.3 μM each oligonucleotide. 1 μL of first strand cDNA template, 1.0-2.5 units Platinum Pfx DNA Polymerase, and nuclease-free distilled water to a final volume of 50 μL. Each reaction was subjected to three-step PCR cycling, using the following parameters: 94° C. for 15 seconds, 56° C. for 30 seconds, and 68° C. for the amount of time indicated in table 1 above. Each amplification was performed for 35 cycles, following by a final extension cycle at 72° C. for 7 minutes, and cooling at +4° C. until analysis. A positive control was run alongside each experimental PCR reaction by using the same first strand cDNA template and a set of primers specific for human beta actin (BioChain). Following PCR each reaction was analyzed by Tris-Acetate EDTA (TAE) agarose gel electrophoresis to determine extend and integrity of amplified cDNA. For each analysis 10 μL of each reaction were mixed with Blue Juice loading buffer (Invitrogen) and loaded per lane of a 1% TAE agarose gel. TriDye 1 kb DNA ladder (New England Biolabs, Ipswich, Mass.) was used to estimate the size of amplified cDNAs. Following confirmation of PCR amplification for each cDNA each reaction was immediately cloned into the Zero Blunt TOPO PCR Cloning system (Invitrogen), according to manufacturer's instructions. Colonies were screened either by PCR or REN analysis of purified DNAs from overnight bacterial cultures, or both. pCR-Blunt II-TOPO clones containing fragments of expected sizes were subsequently restricted with the appropriate RENs for isolation and cloning of the full length genes into the mammalian expression vector pcDNA3.1+zeo:intA.

The expression vector was constructed from pcDNA3.1+zeo (Invitrogen) by adding the human CMV intron A sequence to the 3' end of the minimal promoter. CMV intron A sequence has been extensively characterized and shown to greatly enhance the expression of recombinant genes in mammalian cells when compared with an intronless CMV promoter counterpart. The intron A sequence was PCR amplified from the vector pWRG7077 (kindly provided by Dr. Jay Hooper, United States Army Medical Research Institute of Infectious Diseases [USAMARIID]), and was cloned into pcDNA3.1+zeo as NdeI-NheI sites. pcDNA3.1+zeo:intA is a 6.5 kb plasmid with the expression elements outlined in FIG. 13. Cloning reactions were performed as described in Maniatis and Sambrook, 1988, followed by transformation into subcloning efficiency *Escherichia coli* (*E. coli*) strain DH5α, for propagation of cloned DNAs. Colonies were screened either by PCR or REN analysis of purified DNAs from overnight bacterial cultures, or both.

Figure 13:
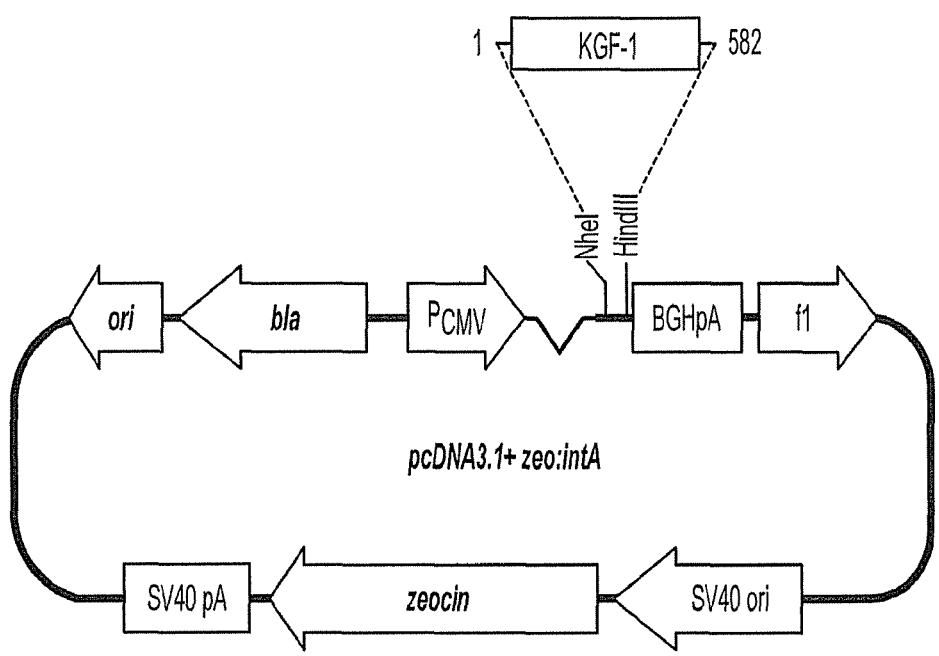
FIG. 13 depicts the cloning strategy for expression of human protein KGF-1 in mammalian cells using the CMV promoter-driven eukaryotic vector pcDNA3.1+zeo:intA in accordance with an embodiment of the present invention.

FIG. 13 shows shows the cloning strategy for expression of human protein KGF-1 in mammalian cells using the CMV promoter-driven eukaryotic vector pcDNA3.1+zeo:intA. Genes were PCR amplified from normal human tissue cDNAs and cloned as described in Materials and Methods. KGF-1 was directionally cloned into the mammalian vector's NheI-HindIII REN sites. Relevant expression elements are bacterial origin of replication (ori), beta-lactamase gene (bla), cytomegalovirus early promoter (P$_{CMV}$), bovine growth hormone polyadenylation signal (BGHpA), single-stranded philamentous phage origin (f1), simian virus 40 origin of replication (SV40 ori), simian virus 40 polyadenylation signal (SV40 pA), zeocin antibiotic resistance gene (zeocin).

pcDNA3.1+zeo:intA clones containing fragments of expected sizes were subsequently restricted with unique RENs for confirmation of gene identities. For each construct highly pure midiprep plasmid DNAs were isolated form 50 mL *E. coli* cultures growth overnight in selective broth. DNAs were assayed for purity and concentration by A280 and A260. Expression of each gene was confirmed by lipofectamine-mediated transfection of the human endothelial kidney cell line HEK-293T/17, and subsequent analysis of cell extracts and supernatants. For each construct to be analyzed, 1×10$^5$ HEK-293T/17 cells were seeded per well of a Poly-D-Lysine coated 6 well plate in 2 mL of growth medium (DMEM, high glucose; 2 mM L-Glutamine; 1× Non Essential Amino Acids [NEAA]; 10% heat inactivated Fetal Bovine Serum [FBS]) the night prior to transfection, and cultured at 37° C., 5% $CO_2$, 90% relative humidity (Rh). The following day cultured were fed with 2 mL of fresh growth medium prior to transfection. Four μg of each plasmid DNA construct were gently mixed in 250 μL of Opti-MEM Reduced Serum Medium (Invitrogen) and combined with an additional 250 μL of the same medium supplemented with 10 μL of Lipofectamine 2000 transfection reagent (Invitrogen). The reaction was incubated at room temperature for 20 minutes to allow DNA:lipofectamine complexes to form. The entire reaction was then gently pipetted into the corresponding well containing HEK-293T/17 cells and was gently swirled to evenly distribute the transfection mix. Plates were then returned to the incubator and were cultured for 72 hours prior to harvesting and analysis.

Expression of each gene construct was performed and measure for transfected HEK-293T/17 cell extracts and culture supernatants. Following the 72 hour transfection supernatants were harvested and cleared by centrifugation. One mL of each supernatant was transferred to a polypropylene microcentrifuge tube and kept on ice until analysis. Cells were scraped from wells and were pelleted by brief centrifugation in polypropylene microcentrifuge tubes. Supernatants were carefully decanted and pellets were resuspended in 1× Phosphate Buffered Saline (PBS), pH 7.4, and pelleted by brief centrifugation. PBS was decanted and each cell pellet was resuspended in 100 μL of Mammalian Cell Lysis Buffer (Sigma-Aldrich, St. Louis, Mo.), according to manufacturer's instructions. Lysis buffer was prepared with TRIS buffer, Sodium Chloride, Sodium Dodecyl Sulfate (SDS), Igepal, Deoxycholate, and protease inhibitors. Lysis reactions were incubated at room temperature for 10 minutes, followed by centrifugation at 14,000× g for 10 minutes at room temperature. Supernatants were transferred to fresh polypropylene microcentrifuge tubes and were kept on ice until analysis.

For determination and quantitation of expressed proteins, SDS-Polyacrylamide Gel Electrophoresis (SDS-PAGE) and Western Blot analysis were performed on each set of transfected HEK-293T/17 cell extracts and supernatants. One hundred thousand cell equivalents (~10 μL) were mixed with NuPage LDS Sample Buffer, NuPAGE Reducing Agent, and deionized water, heated at 90° C. for 5 minutes and were loaded per lane of a 10% NuPage Novex Bis-Tris Gel. Likewise, 30 μL of corresponding supernatant were similarly prepared and loaded alongside cell extracts. SeeBlue Plus-2 Protein molecular weight marker (Invitrogen) was used to estimate protein sizes. Gels were run in 1× SDS NuPAGE MES Running Buffer at 200 V, for 45 minutes. Following electrophoresis proteins were transferred to 0.45 μm Nitrocellulose membrane using an X-Cell II Blot Module, according to manufacturer's instructions (Invitrogen). Western blots were performed with a Protein Detector TMB Western Blot Kit (KPL, Gaithersburg, Md.), according to manufacturer's instructions, using primary antisera and secondary detection reagents, as outlined in Table 4. Rabbit antisera to COLA1A, COL1A2, and KGF-1 were purchased from Santa Cruz Biotechnology (Santa Cruz, Calif.). Horseradish Peroxidase (HRP)-labeled Goat anti-Rabbit IgG (H+L) (Santa Cruz Biotechnology) was used as secondary detection reagent. Immunological complexes were detected with TMB membrane substrate for 2-5 minutes, and reactions were stopped by immersing the blots in distilled water. Permanent records were generated by high resolution scanning of developed blots.

TABLE 4

Detection reagents for Western Blot analysis of COLA1A, COL1A2, and KGF-1 transiently expressed in HEK-293T/17 cells

|  | Primary antisera | Source | Secondary detection reagent |
| --- | --- | --- | --- |
| COLA1A | Rabbit polyclonal antibody to amino acids 1021-1217 of Human Collagen α1 Type 1 | Collagen Type 1 (H-197): sc-28657 | Goat anti-Rabbit IgG (H + L)-HRP: sc-2004 |
| COL1A2 | Rabbit polyclonal antibody to amino acids 1021-1090 of Human Collagen α2 Type 1 | Collagen Type 1 (H-70): sc-28655 | |
| KGF-1 | Rabbit polyclonal antibody to amino acids 32-104 of Human KGF-1 | FGF-7 (H-73): sc-7882 | |

Results

Figure 14:
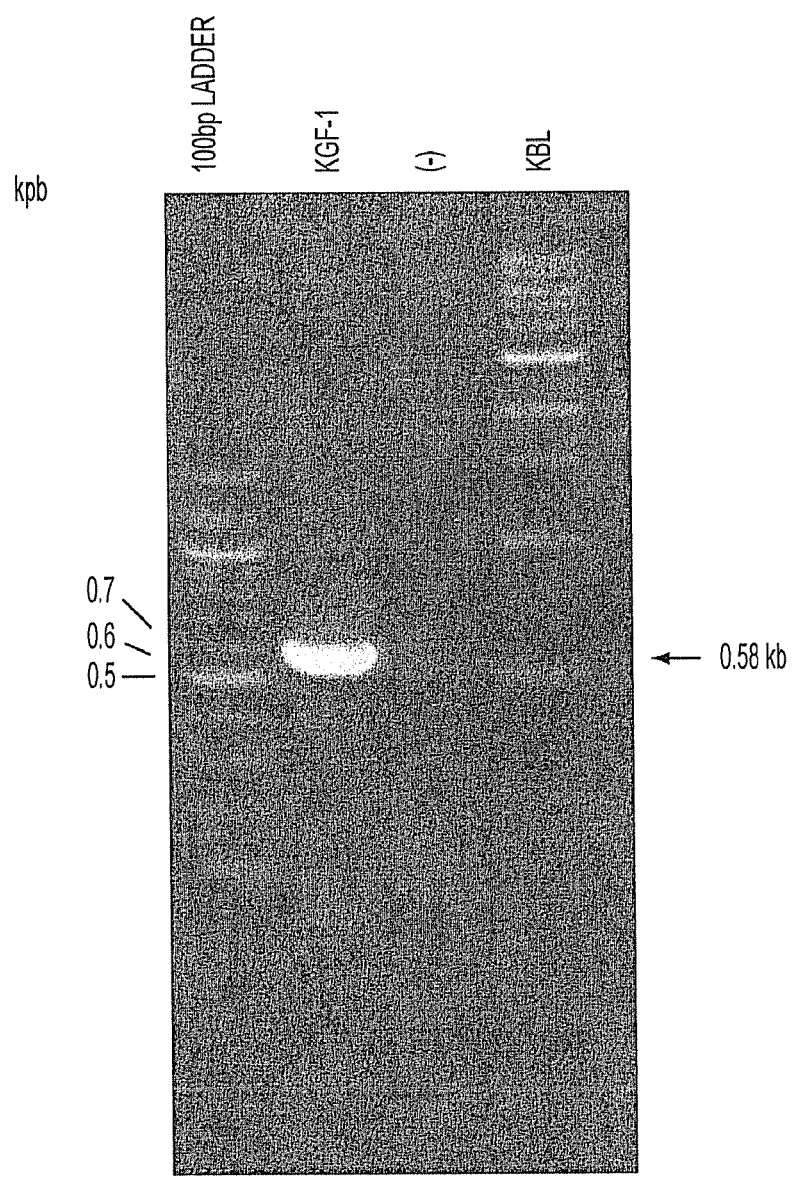
FIG. 14 depicts PCR amplification of KGF-1 from normal human lung tissue cDNAs in accordance with an embodiment of the present invention. Amplified gene sequences of interested are marked by arrows, and corresponding sizes are indicated. KBL, kilobase ladder; kbp, kilobase pairs.

FIG. 14 shows PCR amplification of KGF-1 from normal human lung tissue cDNAs in accordance with an embodiment of the present invention. The gene was amplified as described in Materials and Methods using gene-specific oligonucleotide primers. Amplified gene sequences of interested are marked by arrows, and corresponding sizes are indicated. KBL, kilobase ladder; kbp, kilobase pairs.

Figure 15A:
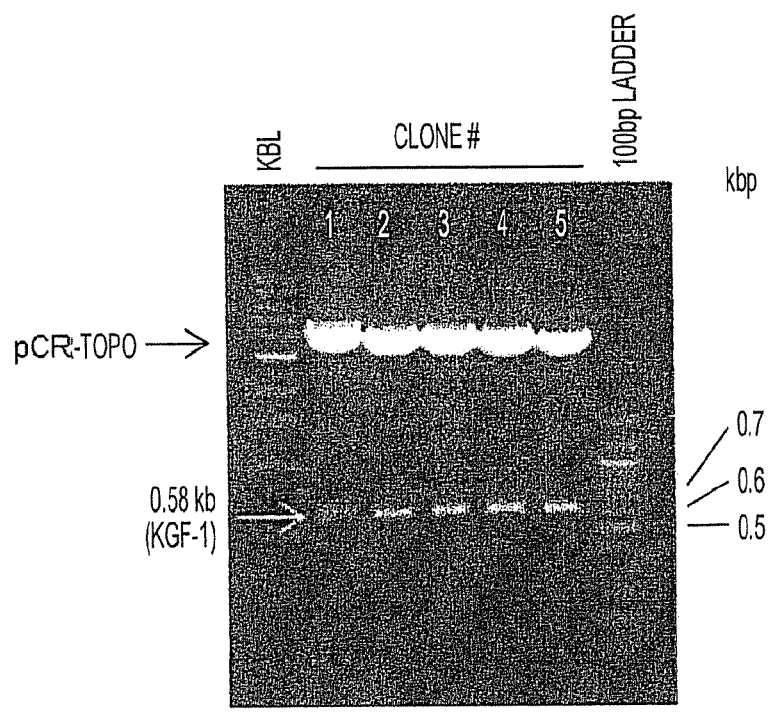
FIGS. 15A-15B depict the following: cloning of human KGF-1 cDNA (0.58 kb insert) in the interim pCR-TOPO vector (FIG. 15A) and subsequent cloning in the mammalian expression vector pcDNA3.1+zeo:intA (FIG. 15B) in accordance with an embodiment of the present invention. The KGF-1 gene was excised from pCR TOPO with NheI and HindIII, and was then directionally cloned in pcDNA3.1+zeo:intA restricted with the same endonucleases. Amplified gene sequences of interest are marked by arrows, and corresponding sizes are indicated. Shown in FIG. 15B are five separate subclones (1-5) where lanes 1, 2 are uncut and NheI and HindIII digested miniprep DNAs for clone 1 (lanes 1 and 2, respectively), clone 2 (lanes 3 and 4, respectively), clone 3 (lanes 5 and 6, respectively), clone 4 (lanes 7 and 8, respectively), and clone 5 (lanes 9 and 10, respectively). Also shown are size markers kilobase ladder (KBL) (lane 11) and a 100 base pair (bp) ladder (lane 12); kbp=kilobase pairs.
Figure 15B:
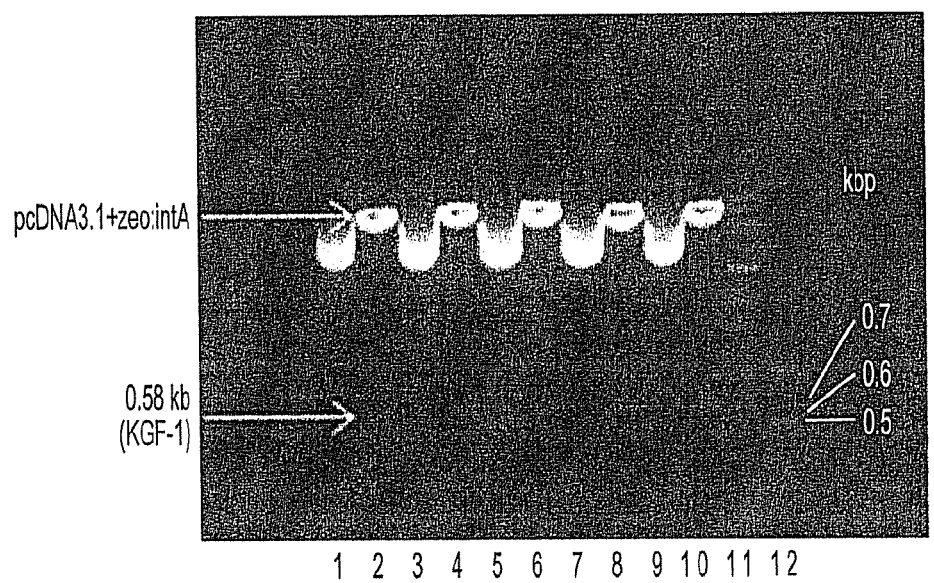

FIG. 15 shows cloning of human KGF-1 cDNA in the interim pCR-TOPO vector (FIG. 15A) and subsequent cloning in the mammalian expression vector pcDNA3.1+zeo:intA (FIG. 15B). The KGF-1 gene was excised from pCR TOPO with NheI and HindIII, and was then directionally cloned in pcDNA3.1+zeo:intA restricted with the same endonucleases. Amplified KGF-1 gene sequences of interested are marked by arrows, and corresponding sizes are indicated where KBL=kilobase ladder; kbp=kilobase pairs.

FIG. 16 shows the protein sequence of KGF-1 (FIG. 16A) and the nucleotide sequence for KGF-1/FGF-7 (FIG. 16B). For FIG. 16B, the DNA sequence for KGF-1 corresponds to basepairs 446 to 1030 of SEQ ID NO: 24 (bold font). The additional flanking sequence (not bold) corresponds to flanking genomic DNA sequence. Only the sequence from 446 to 1030 of SEQ ID NO: 24 was cloned.

Figure 17A:
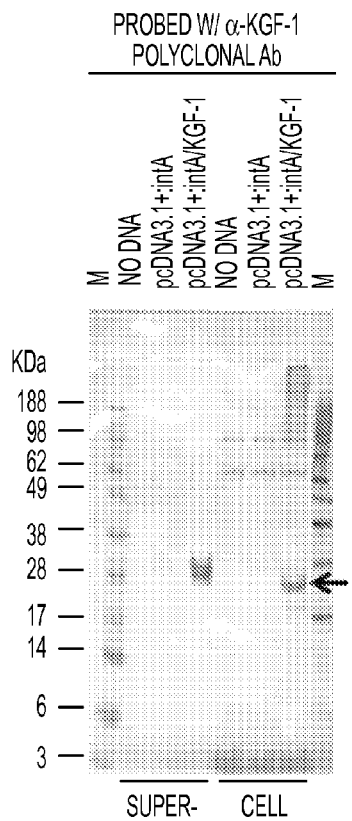
FIG. 17 depicts transient expression analysis of human KGF-1 (a), COLA1A (b), and COL1A2 (c) in cell extracts and supernatants of HEK-293T/17 cells transfected with pcDNA3.1+:intA/KGF-1, vector alone (pcDNA3.1+:intA), or no DNA control in accordance with an embodiment of the present invention. The KGF-1 protein is indicated by a black arrow. M=molecular weight marker; KDa=kilodaltons.
Figure 17B:
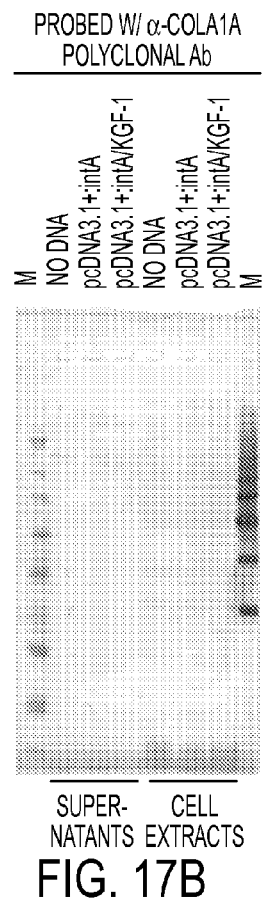
Figure 17C:
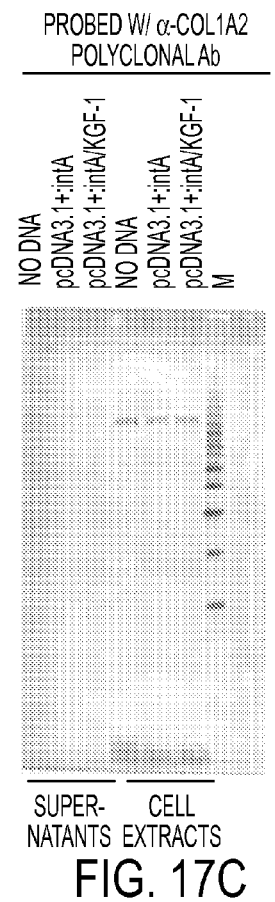

Results of western blotting showed that KGF-1 was expressed in 293T cells. For example, FIG. 17 shows transient expression analysis of human KGF-1 protein (a), COLA1A protein (b), and COL1A2 protein (c) in cell extracts (C) and supernatants (S) of HEK-293T/17 cells transfected with pcDNA3.1+:intA/KGF-1, vector alone (pcDNA3.1+:intA), or no DNA control in accordance with an embodiment of the present invention. It can be seen that the expressed KGF-1 gene is present in cell extracts and supernatants of 293T/17 cells transfected with pcDNA3.1+:intA/KGF-1 only. The KGF-1 protein is indicated by a black arrow (M=molecular weight marker; KDa=kilodaltons). It can be seen that there is additional staining in the higher molecular weight ranges for cells transfected with KGF and stained for COL1A1 and COL1A2 proteins indicating that expression of KGF in the transfected cells may increase expression of collagen.

Example 3

Evaluating a KGF Plasmid Applied Topically in Mice

This experimental study was carried out in BALB/C mice to determine whether a KGF plasmid topically applied had a cosmetic rejuvenation effect on skin.

The experimental design was as follows: in the treated groups, the BALB/C mouse skin had the stratum corneum removed by brushing 100 strokes with a nylon brush. Brushing was utilized as a sub-therapeutic microdermabrasion technique. Control BALB/C mice had the hair clipped but were not "brushed."

Two different vehicles were tested:

Vehicle A: 94% TE buffer (10 mM Tris); 5% Glycerin; and 1% Hydroxypropyl Methylcellulose.

Vehicle B: 88% TE buffer (10 mM Tris); 5% Glycerin; 5% Propylene Glycol; and 1% Hydroxypropyl Methylcellulose.

Two different plasmids were tested: The gWiz-KGF1 plasmid and the NTX-KGF1 plasmid were each tested at a single concentration of 2000 micrograms per ml for each plasmid. A single dose of 4 microlitres was applied on each mouse.

Test groups using KGF1 plasmids:

|  | vehicle A | | vehicle B | |
| --- | --- | --- | --- | --- |
|  | brush | no brush | brush | no brush |
| gWiz-KGF1 | N = 5 | n = 2 | n = 1 | n = 0 |
| NTX-KGF1 | N = 5 | n = 2 | n = 1 | n = 0 |

Control groups included:
no treatment;
Vehicle A alone;
Vehicle B alone;
the gWiz-KGF1 plasmid without vehicle; and
the NTX-KGF1 plasmid without vehicle.

Control groups using no plasmid: The same mouse had 2 spots treated with either vehicle A or B; and a remote, brushed but vehicle-free skin area on the same mouse was taken as "no vehicle."

|  | vehicle A | vehicle B | no vehicle |
| --- | --- | --- | --- |
| brush | n = 1 | n = 1 | n = 1 |
| no brush | n = 1 | n = 1 | n = 1 |

Control groups using no vehicle:
naked plasmid (with no vehicle) was applied on the skin.

|  | brush | no brush |
| --- | --- | --- |
| gWiz-KGF1 | n = 1 | n = 0 |
| NTX-KGF1 | n = 1 | n = 0 |

All groups detailed:

| Groups | treatment | n = | Harvest time | Tissue ID |
| --- | --- | --- | --- | --- |
| Group 1 Control "brush" 1-BR | Brush 3 spots Vehicle A Vehicle B No vehicle | 1 | All mice at Day 3 | 1-BR-A 1-BR-B 1-BR-N |
| Group 1 Control "no brush" 1-NBR | No brushing Vehicle A Vehicle B No vehicle | 1 | All mice at Day 3 | 1-NBR-A 1-NBR-B 1-NBR-N |
| Group 2 2-BR-gWiz-A | Topical A gWiz-KGF1 "brush" | 5 | 3 mice day 3 1 mouse day 7 1 mouse day 10 | 2-BR-A-gWiz-D3 (samples 1 to 3) 2-BR-A-gWiz-D7 2-BR-A-gWiz-D10 |
| Group 2 2-NBR-gWiz-A | Topical A gWiz-KGF1 "no brush" | 2 | All 2 mice day 3 | 2-NBR-A-gWiz-D3 (samples 1 and 2) |
| Group 2 2-BR-NTX-A | Topical A NTX-KGF1 "brush" | 5 | 3 mice day 3 1 mouse day 7 1 mouse day 10 | 2-BR-A-NTX-D3 (samples 1 to 3) 2-BR-A-NTX-D7 2-BR-A-NTX-D10 |
| Group 2 2-NBR-NTX-A | Topical A NTX-KGF1 "no brush" | 2 | All 2 mice day 3 | 2-NBR-A-NTX-D3 (samples 1 and 2) |
| Group 2 2-BR-gWiz-B | Topical B gWiz-KGF1 "brush" | 1 | day 3 | 2-BR-B-gWiz-D3 |
| Group 2 2-BR-NTX-B | Topical B NTX-KGF1 "brush" | 1 | day 3 | 2-BR-B-NTX-D3 |
| Group 2 2-BR-NV-gWiz-20 | No vehicle 20 ug gWiz In 5 ul (no dilution) | 1 | Day 3 | 2-BR-NV-gWiz-20 |
| Group 2 2-BR-NV-NTX-20 | No vehicle 20 ug NTX In 3 ul (no dilution) | 1 | Day 3 | 2-BR-NV-NTX-20 |

Materials and Methods

Plasmids

Plasmids and vehicles were obtained from Aaron Tabor, Gene Facelift, LLC.

Animals

20 BALB/C mice were obtained from Jackson labs and acclimated before the start of the experiment.

Plasmid Administration

Mice were anesthetized with a mix of Ketamine/Xylazine (1/10) by intraperitoneal injection. Their backs were shaved but not depilated with Nair®. The treatment zone was brushed firmly with a nylon brush (3 rows of nylon fibers 4 cm×1 cm). 100 strokes (50 strokes in 2 perpendicular directions) were applied to obtain erythema without bleeding that would evidence a break in the skin barrier. The intersection of these 2 perpendicular sets of strokes created a treatment zone of approximately 1 square cm. The treatment compounds (i.e., the gWiz-KGF1 plasmid or the NTX-KGF1 plasmid) were applied on the brushed zone with a P10 pipette (GILSON, France) and gently spread on the skin without rubbing and left to dry before the animal was returned to the cage. Animals were housed in single cages.

Histological Assessment After Plasmid Administration

Results were assessed in each animal at day 0 and daily until sacrifice.

Skin biopsy samples were taken with a 12 mm punch biopsy that included the treatment zone and 1 mm out of the treatment zone on each side. The skin biopsy samples were laid flat in a cassette and put in 10% formalin for histology. Staining was performed using H&E, Mason Trichrome and Von Gieson to analyze the thickness of the skin, the collagen and elastic fibers contents.

Summary of Results

Based on histological analysis, no effect on cosmetic skin rejuvenation was observed in animals that were brushed, and that were administered the gWiz-KGF1 plasmid, with no vehicle.

The gWiz-KGF1 plasmid was observed to work, i.e., to have some positive effect on cosmetic skin rejuvenation, only in Vehicle B when there was microdermabrasion. These results suggest that propylene glycol, which is a known penetration enhancer, enabled the gWiz-KGF1 plasmid to produce a positive effect on cosmetic skin rejuvenation.

The NTX-KGF1 plasmid produced a positive effect on cosmetic skin rejuvenation when administered in Vehicle A, Vehicle B, and also when administered with no vehicle (saline), but only when there was sub-therapeutic microdermabrasion.

Neither the gWiz-KGF1 plasmid nor the NTX-KGF1 plasmids produced any effect on cosmetic skin rejuvenation without the microdermabrasion or the brushing.

The phrase "positive effect on cosmetic skin rejuvenation," as used herein, includes a number of desirable changes observed after treatment with the KGF1 plasmids, as described herein; and which were assessed by histological analysis; these changes include:
1. Increased epidermis thickness with greater number of keratinocytes (H&E stain);
2. Increased collagen thickness and density in the dermis (Masson's Trichome stain);
3. Increased elastin fibers with more perpendicular orientation to dermal-epidermal junction (Luna Stain); and
4. Increased basal cell proliferation (Ki-67 Stain).

Example 4

Sub-Therapeutic Microdermabrasion Validation Studies in Mice

The general purpose of this study was to validate the sub-therapeutic microdermabrasion settings for the studies in mice. For this study, SV129 mice were used. Dermabrasion was performed on the SV129 mice. An evaluator marked the locations where biopsies would be performed on each mouse; and then the biopsies were completed. The biopsies were taken immediately after dermabrasion.

In performing the dermabrasion, two different types of brushes were used. Each brush had a different type of bristle, which was used to "brush" the skin of the mouse.

The two different types of bristles were as follows:

Brushes with medium, softer (not coarse) bristles had a nylon green (G) tip; and Brushes with medium, coarse bristles had a nylon yellow (Y) tip.

The following is the code used for the labeling:
1st letter: color of the tip used (G for green and Y for yellow)
Next numbers: pressure in "in Hg" (10, 15 or 20)
Next single number sample ID (1 to 4)
Codes for pathology samples

| GROUPS | VACUUM PRESSURE | | |
|---|---|---|---|
| | 10 in Hg | 15 in Hg | 20 in Hg |
| Medium Softer bristles (nylon green tip) | G-10/1 | G-15/1 | G-20/1 |
| | G-10/2 | G-15/2 | G-20/2 |
| | G-10/3 | G-15/3 | G-20/3 |
| | G-10/4 | G-15/4 | G-20/4 |
| Medium Coarse bristles (nylon yellow tip) | Y-10/1 | Y-15/1 | Y-20/1 |
| | Y-10/2 | Y-15/2 | Y-20/2 |
| | Y-10/3 | Y-15/3 | Y-20/3 |
| | Y-10/4 | Y-15/4 | Y-20/4 |
| Control samples No dermabrasion | C-1 | | |
| | C-2 | | |
| | C-3 | | |
| | C-4 | | |

Based on the results obtained from this study, the Yellow tip (brushes with medium, coarse bristles had a nylon yellow tip) at 20 in Hg was selected for the microdermabrasion settings.

Example 5

Dose-Escalation Studies in Mice

The overall purpose of this study was to evaluate the effects of topical application of different concentrations of the NTX-KGF1 pDNA plasmid in mice.

This experiment was performed according to the microdermabrasion settings selected from the study in Example 4. Based on the results described in Example 4, the Yellow tip (brushes with medium, coarse bristles had a nylon yellow tip) at 20 in Hg was selected for the microdermabrasion settings.

A total of 26 "SV129 mice"—also referred to as "GFP mice" or Green Fluorescence Protein mice (since these mice express GFP in their cytoplasm)—were used in this study.

In this study, only the NTX plasmid (specifically, the NTX-KGF1 pDNA plasmid) was evaluated. The gWiz-KGF1 plasmid was not evaluated in this study. The specific NTX-KGF1 plasmid used was NTC8385-KGF1 lot # NTC-011007 (manufactured Oct. 27, 2009 by Nature Technology Corporation). This NTX-KGF1 plasmid was obtained at a stock concentration of 3.18 mg/ml.

Six different dosages of the NTX-KGF1 pDNA plasmid were tested, namely: 50, 100, 250, 500, 750, and 1000 micrograms/milliliter (µg/ml) of the NTX-KGF1 plasmid.

The only vehicle used in this study was Vehicle A. As described elsewhere herein. Vehicle A includes: 94% TE buffer (10 mM Tris); 5% Glycerin; and 1% Hydroxypropyl Methylcellulose.

One mouse died shortly after anesthesia and during the handling for dermabrasion.

The control groups consisted of the following groups of mice:
Dermabrasion alone (2 mice)
Dermabrasion+Vehicle A (2 mice)
Vehicle A alone (no plasmid, no dermabrasion) (2 mice)
Vehicle A+NTX plasmid at six different concentrations (50, 100, 250, 500, 750, 1000 micrograms/milliliter) but no dermabrasion (1 mouse per concentration)

To test the different dosages, two different types of treatment were used:
some mice received the full treatment (dermabrasion, with plasmid in vehicle A at different concentrations); and
other mice received the plasmid in vehicle A at different concentrations without dermabrasion.

The mice were anesthetized by a mix of Ketamine/Xylazine (9/1) intraperitoneal. Their dorsum was shaved with a clipper but not depilated.

The sub-therapeutic dermabrasion was performed with a DermaSweep-brand Mini MicroResurfacing device (Dermasweep Inc. Rocklin, Calif., USA) using the yellow tip at 20 in Hg vacuum pressure.

Dermasweep Mini Microdermabrasion Machine

The DermaSweep-brand Mini MicroResurfacing device ("Dermasweep Mini") features a closed system with a variable level vacuum pump that gently lifts the skin as the bristles "sweep away" the dead layer of skin in a precise and controlled manner. The bristle tips eliminate the mess and hazards associated with traditional crystal systems. The Dermasweep Mini is an FDA-registered medical device.

Application of the NTX-KGF1 pDNA Plasmid in Mice

The NTX-KGF1 pDNA plasmids were applied at different dosages shortly after the sub-therapeutic dermabrasion (maximum 5 minutes after) with a micropipette and left to dry before the animals were returned to their facility. The anesthesia lasted long enough to observe the compound drying on the mice dorsum.

Control groups without plasmid:

| Treatment description | Mice tag numbers |
|---|---|
| Dermabrasion alone | 831, 830 |
| Dermabrasion + vehicle A | 160, 161 (deep scratch on dorsal skin) |
| Vehicle A alone | 829, 166 |

Test groups receiving different dosages of the NTX-KGF1 pDNA plasmid:

| Dosage (μg/ml) | With dermabrasion | Without dermabrasion |
|---|---|---|
| 50 | 164, 165 | 163, 833 (extra mouse) |
| 100 | 828, 159 | 155 |
| 250 | 162, 900 | 156 |
| 500 | 826, 170 | 169 |
| 750 | 827, 158 | 832 |
| 1000 | 167, 157 | 171 |

Summary of Results for Example 5

After completion of the study, histological analysts was performed to evaluate the effects of the different treatment groups. At all dosages of the NTX-KGF1 pDNA plasmid, and particularly at 100, 250, and 500 micrograms per milliliter (μg/ml), the following observations were made based on histologic evaluation:

1. There was increased epidermis thickness with greater number of keratinocytes (observed using an H&E stain);
2. There was increased collagen thickness and density in the dermis (observed using an H&E stain); and
3. Some inflammation/toxicity was observed at dosages above 500 micrograms/milliliter.

Example 6

Microdermabrasion Validation Study in Pigs

The general purpose of this study was to evaluate and validate the sub-therapeutic microdermabrasion settings for enhancement of KGF-1 pDNA delivery to porcine skin.

The species and strain used in this study was the Yorkshire pig; the animals tested were healthy; with an approximate 200 lbs. starting weight.

For this study, it was hypothesized that 1) sub-therapeutic microdermabrasion can be performed in a controlled and reproducible manner; 2) sub-therapeutic microdermabrasion plus KGF-1 pDNA will produce cosmetic skin rejuvenation; and, 3) sub-therapeutic microdermabrasion alone plus/minus vehicles does not produce cosmetic skin rejuvenation.

Study Goals:

Determine the optimal microdermabrasion settings (tip grade, number of passes, and vacuum pressure) for effective removal (or near removal) of stratum corneum without disruption or inflammation of the underlying viable epidermis.

Demonstrate that the sub-therapeutic microdermabrasion procedure is controllable and reproducible.

Determine dose-effect of topically applied KGF-1 pDNA administered in conjunction with an optimized sub-therapeutic microdermabrasion procedure.

EXPERIMENT #1

Optimizing the Sub-Therapeutic Microdermabrasion Procedure

Treatment and Tissue Collection: One Yorkshire pig was used. The Dermasweep Mini microdermabrasion instrument (described elsewhere herein) was used for validation to determine the extent and reproducibility of stratum corneum removal. After electrically clipping and gently cleansing the treatment area of the Yorkshire pig, the vacuum pressure and number of passes was varied to generate the treatment array.

Skin punch biopsies were taken and H&E stained to examine the percentage of stratum corneum removed.

In this experiment, different instrument settings of the Dermasweep Mini microdermabrasion instrument were evaluated, to determine which settings produced a sub-therapeutic removal of the stratum corneum without disrupting or inflaming the underlying viable epidermis. The treatment zone was approximately 2×2 centimeters=4 square centimeters. Tissues were collected immediately after microdermabrasion. The animal was euthanized at the end of surgery.

The lowest Dermasweep Mini vacuum setting analyzed was 3 in Hg and the highest was 27 in Hg. In most cases while treating humans with the instrument, a vacuum setting in the range of 15 to 20 in Hg is used during 1 vertical and 1 horizontal pass using a medium (green) or medium coarse (yellow) treatment tip. The medium coarse (yellow) treatment tip has firmer nylon bristles compared to the medium (green) treatment tip. The rate of tip movement across the skin was assessed at 10 cm per second. Control skin areas with no microdermabrasion treatment were also harvested for analysis.

| MICRODERMABRASION TREATMENT ARRAY | | | | | |
|---|---|---|---|---|---|
| GROUP | VACUUM PRESSURE | | | | |
| 1. Medium (green tip) Two passes total (1 vertical pass + 1 horizontal pass) × 2 areas | 5 in Hg | 10 in Hg | 15 in Hg | 20 in Hg | 25 in Hg |
| TISSUE ID: + Control (no micro; adjacent; serves as control for all 3 tx's) | PIG1 PIG2 PIG3 | PIG4 PIG5 PIG6 | PIG7 PIG8 PIG9 | PIG10 PIG11 PIG12 | PIG13 PIG14 PIG15 |
| 2. Medium Coarse (yellow tip) Two passes total (1 vertical pass + 1 horizontal pass) × 2 areas | 5 in Hg | 10 in Hg | 15 in Hg | 20 in Hg | 25 in Hg |
| TISSUE ID: | PIG16 PIG17 | PIG18 PIG19 | PIG20 PIG21 | PIG22 PIG23 | PIG24 PIG25 |

-continued

| MICRODERMABRASION TREATMENT ARRAY | | | | | |
|---|---|---|---|---|---|
| GROUP | VACUUM PRESSURE | | | | |
| 3. Medium (green tip) Four passes total (2 vertical pass + 2 horizontal pass) × 1 area | 5 in Hg | 10 in Hg | 15 in Hg | 20 in Hg | 25 in Hg |
| TISSUE ID: | PIG26 | PIG27 | PIG28 | PIG29 | PIG30 |

Materials and Methods

Dermasweep Mini Microdermabrasion Machine

As described elsewhere herein, the Dermasweep Mini Microdermabrasion Machine (the "Dermasweep Mini") used in this study features a closed system with a variable level vacuum pump that gently lifts the skin as the bristles "sweep away" the dead layer of skin in a precise and controlled manner. The bristle tips fully eliminate the mess and hazards associated with traditional crystal systems. Dermasweep Mini is an FDA-registered medical device.

Microdermabrasion Procedure

The Yorkshire Pig was anethesized. Treatment areas were electrically clipped and cleansed, but not depilated, before procedure at varying instrument settings as specified above.

Tissue Collection

All tissues were collected at a single time on Day 0. Skin biopsy samples were taken immediately after the microdermabrasion procedure with a 12 mm punch biopsy. Animals were euthanized at the end of surgery.

Biopsy Samples Nomenclature: Flank Biopsies

| | 5 in Hg | 10 in Hg | 15 in Hg | 20 in Hg | 25 in Hg |
|---|---|---|---|---|---|
| Green Tip | G5-1 | G10-1 | G15-1 | G20-1 | G25-1 |
| | G5-2 | G10-2 | G15-2 | G20-2 | G25-2 |
| Yellow Tip | Y5-1 | Y10-1 | Y15-1 | Y20-1 | Y25-1 |
| | Y5-2 | Y10-2 | Y15-2 | Y20-2 | Y25-2 |

Two control samples were designated C1 and C2

Biopsy Samples Nomenclature: Abdomen Biopsises

| | 5 in Hg | 10 in Hg | 15 in Hg | 20 in Hg | 25 in Hg |
|---|---|---|---|---|---|
| Green Tip | G5-B | G10-B | G15-B | G20-B | G25-B |
| Yellow Tip | Y5-B | Y10-B | Y15-B | Y20-B | Y25-B |

"B" for "belly"

Assessment

The tissue samples were laid flat in a cassette and put in 10% formalin for histology. Staining was performed using H&E to analyze the thickness of the stratum corneum/epidermis/dermis and presence of any inflammation indicators.

Summary of Results of Experiment 1

1. The Green (G) tip at 25 in Hg×2 passes produced the smoothest removal of stratum corneum. There was no observed epithelial damage with the Green (G) tip at any pressure setting. The Yellow (Y) tip produced a much more coarse surface, and started significantly damaging the epidermis at 20 in Hg.

2. The flank of the pig was determined to be the optimal treatment area. The abdomen was determined to be highly convoluted with big peaks and valleys in the skin. The "valleys" in the abdomen skin didn't appear to have any stratum corneum removed. The flank was much smoother skin.

3. Tattooing for the pigs was used to make sure the samples were collected from the precise microdermabrasion and treatment area.

EXPERIMENT #2

Sub-Therapeutic Microdermabrasion Followed by KGF-1 pDNA Topical Application

Treatment and Tissue Collection: 1 Yorkshire pig was used. Prior to test application on Day 0, the skin treatment areas were electrically clipped to remove hair, gently cleansed, and then subjected to a mild microdermabrasion procedure (as determined in the prior experiment) to remove the stratum corneum. The treatment zone was approximately 2×2 centimeters=4 square centimeters. Tissues were collected at a single time on Day 4 (96 hours after treatment). The animal was euthanized at the end of surgery on Day 4.

Vehicle:

Vehicle A: 94% TE buffer (10 mM Tris); 5% Glycerin; and 1% Hydroxypropyl Methylcellulose.

Plasmid: NTX-KGF1 pDNA plasmid was tested at various concentrations of 100, 250, 500, 750, 1000, 1500, and 2000 micrograms/milliliter. Since NTX-KGF1 showed such potent macroscopic effects in mice, a wide range (20-fold variation) of concentrations was evaluated. A volume of 4 microliters was applied to each square centimeter of treated area (i.e. 16 microliters pipetted onto the 4 square centimeter treatment area).

Control groups consisted of: 1) no microdermabrasion or pDNA treatment (harvested adjacent to treatment area); 2) microdermabrasion alone; and 3) the vehicles alone after microdermabrasion. See treatment table below.

MICRODERMABRASION PLUS NTX-KGF-1 pDNA TREATMENT ARRAY
58 total treatment areas of 4 square centimeters = 232 square centimeters.
Treatment areas were evaluated pre-treatment, post-treatment, Day 1, Day 2, Day 3, and Day 4

| Groups | pDNA CONCENTRATION (micrograms/milliliter) | | | | | | | Harvest Time |
|---|---|---|---|---|---|---|---|---|
| 1. NTX-KGF1 Microdermabrasion x2 areas Vehicle A | 100 | 250 | 500 | 750 | 1000 | 1500 | 2000 | |
| Tissue ID | PIG31 | PIG35 | PIG37 | PIG39 | PIG41 | PIG43 | PIG45 | Day 4 (96 |
| Treatment | PIG32 | PIG36 | PIG38 | PIG40 | PIG42 | PIG44 | PIG46 | hours post-treatment) |
| 2. NTX-KGF1 No Microdermabrasion x2 areas Vehicle A | | | 500 | | 1000 | | 2000 | |

MICRODERMABRASION PLUS NTX-KGF-1 pDNA TREATMENT ARRAY
58 total treatment areas of 4 square centimeters = 232 square centimeters.
Treatment areas were evaluated pre-treatment, post-treatment, Day 1, Day 2, Day 3, and Day 4

| Groups | pDNA CONCENTRATION (micrograms/milliliter) | | | Harvest Time |
|---|---|---|---|---|
| Tissue ID | | PIG47 | PIG49 | PIG51 Day 4 |
| Treatment | | PIG48 | PIG50 | PIG52 |
| 3. CONTROLS | | | | Day 4 |
| No NTX-KGF1 on | | | | |
| any of these. | | | | |
| x2 areas | | | | |
| No Microderm | PIG53 | | | |
| Microdermabrasion | PIG54 | | | |
| Microdermabrasion | PIG55 | | | |
| plus Vehicle A | PIG56 | | | |
| | PIG57 | | | |
| | PIG58 | | | |

Plasmids

Plasmid and vehicles were obtained from Aargon Tabor, gene Facelift, LLC.

Animals

One Yorkshire pig was obtained and acclimated before the start of the experiment.

Microdermabrasion Procedure and Plasmid Administration

The pig was anethesized. The animal's back was electrically clipped and cleansed, but not depilated, before the sub-therapeutic microdermabrasion procedure was applied, as determined in Experiment #1.

The treatment zone was microdermabraded to remove the stratum corneum. The treatment zone was approximately 2×2 centimeters=4 square centimeters.

The treatments were applied on the microdermabraded zones with a pipette and were gently spread on the skin with a disposable serum fan brush (or spatula) without rubbing; and were left to dry before the animal was returned to the cage.

The animal was housed in a single cage.

Tissue Collection

All tissues were collected at a single time on Day 3. On Day 3, the animal was anesthesized. Skin biopsy samples were taken with a 12 mm punch biopsy. The animal was euthanized at the end of surgery.

Assessment

Evaluation was performed at Day 0 before and after microdermabrasion, and daily until sacrifice.

The tissue samples were laid flat in a cassette and put in 10% formalin for histology. Staining was performed using H&E±Selective Ki67, and Collagen and Elastin stains were used for additional histologic analysis.

Summary of Exemplary Experiment: Sub-therapeutic Microdermabrasion and Gene Therapy in Pigs—Dose Escalation Study Animal model: A large female Yorkshire pig 8 month old (275 pounds) was used and sedated under general anesthesia.

Mapping the treatment areas: Treatment spots were identified with a pen on the dorsum and on the flanks of the animal.

Mapping the treatment areas: The treatment codes were written directly on the skin Relevance of the pig skin model: On the dorsum and the flanks the pig skin has major similarities with the human skin.

Method for planning the samples collection: Around and next to the planned treatment areas (black dots) round circles were traced with black ink using a dull 12 mm punch bipsy and the skin was tattooed (red spots) at a fixed distance of 24 mm (twice the diameter of the 12 mm punch biopsy to be used for collection) in a vertical direction.

The tattoo machine used was the Spaulding Special Electric Tattoo Marker, Model SSEMK, Spaulding & Rogers MFG, Inc. Voorheesville, N.Y. USA. The power was set between 17 and 21. After tattooing and washing the ink away, the microdermabrasion was performed at 25 in Hg with the green tip and the vehicle (vehicle A) with or without plasmid was applied.

Treatment Description

| Control groups | # samples |
|---|---|
| Nothing | 6 (3 dorsum and 3 flanks) |
| Dermabrasion alone | 6 (3 dorsum and 3 flanks) |
| Vehicle alone | 6 (3 dorsum and 3 flanks) |
| Dermabrasion + vehicle, no plasmid | 6 (3 dorsum and 3 flanks) |

| | Test groups | | | | | | | |
|---|---|---|---|---|---|---|---|---|
| | 50 | 100 | 250 | 500 | 750 | 1000 | 1500 | 2000 |
| | Dermabrasion + Vehicle A + NTX-KGF pDNA (# of samples) | | | | | | | |
| dorsum | 3 | 3 | 3 | 3 | 3 | 3 | 3 | 3 |
| flank | 3 | 3 | 3 | 3 | 3 | 3 | 3 | 3 |
| | Vehicle A + NTX-KGF pDNA but NO dermabrasion (# of samples) | | | | | | | |
| flank | 2 | 2 | 2 | 2 | 2 | 2 | 2 | 2 |

Treatment Areas Nomenclature

Rank of treatment performance (from left to right and up to down)

| rank | treatment description |
|---|---|
| 1 | Nothing |
| 2 | Dermabrasion alone |
| 3 | Vehicle alone |
| 4 | Dermabrasion + vehicle, no plasmid |
| 5 | 50 micrograms/milliliter NTX |
| 6 | 100 micrograms/milliliter NTX |

-continued

| rank | treatment description |
|---|---|
| 7 | 250 micrograms/milliliter NTX |
| 8 | 500 micrograms/milliliter NTX |
| 9 | 750 micrograms/milliliter NTX |
| 10 | 1000 micrograms/milliliter NTX |
| 11 | 1500 micrograms/milliliter NTX |
| 12 | 2000 micrograms/milliliter NTX |

This ranking system was repeated for each body area (dorsum and flank) except for the controls with NTX but no dermabrasion. The 3 samples of each treatment regimen were labeled A, B and C. The body area was labeled D for dorsum, F for flank.

For the series of treatments with NTX but without dermabrasion the codes were:

First the dosage and second the sample number (A or B)
Examples:
50-A: 50 micrograms/milliliter plasmid with no dermabrasion, first sample.
100-B: 1000 micrograms/milliliter plasmid with no dermabrasion, second sample.
Pathology Slides Nomenclature (Sample IDs)

| Vehicle A + NTX-KGF but NO dermabrasion (samples IDs) | | | | | | | | |
|---|---|---|---|---|---|---|---|---|
| 50 | 100 | 250 | 500 | 750 | 1000 | 1500 | 2000 | Dosage |
| 50-A | 100-A | 250-A | 500-A | 750-A | 1000-A | 1500-A | 2000-A | left flank |
| 50-B | 100-B | 250-B | 500-B | 750-B | 1000-B | 1500-B | 2000-B | right flank |

| Control groups: | Samples IDs |
|---|---|
| Nothing | Dorsum: D-1-A/D-1-B/D-1-C |
| | Flank: F-1-A/F-1-B/F-1-C |
| Dermabrasion alone | Dorsum: D-2-A/D-2-B/D-2-C |
| | Flank: F-2-A/F-2-B/F-2-C |
| Vehicle alone | Dorsum: D-3-A/D-3-B/D-3-C |
| | Flank: F-3-A/F-3-B/F-3-C |
| Dermabrasion + vehicle, no plasmid | Dorsum: D-4-A/D-4-B/D-4-C |
| | Flank: F-4-A/F-4-B/F-4-C |

| | Dermabrasion + Vehicle A + NTX-KGF (samples IDs) | |
|---|---|---|
| | Dorsum | Flank |
| 50 | D-50-A/D-50-B/D-50-C | F-50-A/F-50-B/F-50-C |
| 100 | D-100-A/D-100-B/D-100-C | F-100-A/F-100-B/F-100-C |
| 250 | D-250-A/D-250-B/D-250-C | F-250-A/F-250-B/F-250-C |
| 500 | D-500-A/D-500-B/D-500-C | F-500-A/F-500-B/F-500-C |
| 750 | D-750-A/D-750-B/D-750-C | F-750-A/F-750-B/F-750-C |
| 1000 | D-1000-A/D-1000-B/D-1000-C | F-1000-A/F-1000-B/F-1000-C |
| 1500 | D-1500-A/D-1500-B/D-1500-C | F-1500-A/F-1500-B/F-1500-C |
| 2000 | D-2000-A/D-2000-B/D-2000-C | F-2000-A/F-2000-B/F-2000-C |

Embedding of Skin Samples in Paraffin

The skin sample was sliced in half passing through the center of the sample. The sample was then introduced in a parafin mold with the cut surface facing down and held in straight position until the hot parafin began to solidify.

Summary of Results (Analyzed Histologically)

1) At 50 micrograms/milliliter dose treatment with NTX-KGF1 pDNA, there was no observed difference compared to controls.

2) At 100 to 250 micrograms/milliliter dose treatment with NTX-KGF1 pDNA, there was good epidermal and dermal proliferation with a very dense collagen band laid down directly under the dermal-epidermal junction. This is a key structural area (collagen IV/VII and collagen I/III) to protect skin integrity against wrinkles. The epidermis was also thickened with improved rete pegs (interdigitation) thus increasing epidermal/dermal surface area. Basal stem cells (right above dermis) stained much darker (greater proliferation).

3) At 500 micrograms/milliliter dose treatment with NTX-KGF1 pDNA, some hyperkeratosis was observed (which may indicate an inflammatory over-response).

4) At 750 to 2000 micrograms/milliliter dose treatment with NTX-KGF1 pDNA, there was hyperkeratosis without much of the dense collagen layer.

5) After treatment with single dose at 250 micrograms/milliliter of NTX-KGF1 plasmid, the epidermis was thickened with increased number of keratinocytes. Thick band of fibrous collagen has been deposited directly below the dermal-epidermal junction.

Significant Effects on Cosmetic Skin Rejuvenation

The results of the studies described herein, as described in further detail in the Examples, indicate that gene therapy to the superficial skin layers using plasmid DNA has surprising and unexpected effects on cosmetic skin rejuvenation. These results indicate that administration of KGF1 pDNA via the delivery routes and methods described herein, are surprisingly advantageous in cosmetic skin rejuvenation. Thus, such administration in humans may analogously be advantageous in correcting the signs of aging, and removing undesirable changes in cosmetic appearance, such as wrinkling, sagging, thinning, dryness, dullness, roughness, and discoloration of the skin which are often the result of UV exposure and aging. The embodiments described herein are only illustrative, and are not intended to limit the scope of the present invention. Expression of one or more other biomolecules such as, for example, PDGF or other growth factors, structural biomolecules (e.g., collagen 1; collagen 3), and antioxidant molecules (e.g., superoxide dismutase), are also within the scope of the present invention, and can also be evaluated for effects on removing undesirable changes in cosmetic appearance, such as wrinkling, sagging, thinning, dryness, dullness, roughness, and discoloration of the skin which are often the result of UV exposure and aging.

These results further indicate that a topical anti-wrinkle gene therapy treatment may be developed, e.g., for the plastic surgery, dermatology, and medical spa markets. In effect, deteriorated growth factor genes are replaced with new growth factor genes to restart collagen and elastin production, and restore skin thickness.

The compositions and methods described herein can thus be used to correct underlying causes of skin aging; namely, to correct broken or mutated genes. In general, the compositions and methods described herein can be used to produce an increase in skin thickness, to increase collagen and elastin; and thus the gene therapy described herein can be reliably and effectively used to restore cosmetic properties to the skin. Certain growth factors, such as KGF, may thus be used in other mammalian species, even humans, to produce desirable cosmetic effects on photoaged, wrinkled skin.

Additional surprising and unexpected advantages of the compositions and methods of the present invention include, but are not limited to, 1) improved quality of skin without irritation, in contrast to Botox treatment (i.e., which often paralyzes muscles) and Juvéderm (temporarily distends skin); 2) sustained desired effects are achieved with each application because of gene therapy for a stronger cosmetic effect, in contrast to a short-lived effect produced by peptides; 3) the compositions and methods of the present invention are usable in more ways, as compared to other cosmetic drugs; such desired uses include, for example, treatment of wrinkles, under-eye circles, back of hands, neck sagging.

All patents, publications, abstracts and other references cited herein are incorporated herein by reference in their entireties. It should be understood that the foregoing relates only to certain embodiments of the present invention and that numerous modifications or alterations may be made therein without departing from the spirit and the scope of the present invention as defined in the following claims.

That which is claimed is:

1. A method for the cosmetic genetic modification of skin cells having a cosmetic function in a subject comprising: topically administering a NTX-keratinocyte growth factor-1 plasmid to the skin cells of the subject, wherein the plasmid comprises an isolated polynucleotide encoding a keratinocyte growth factor-1 polypeptide, such that the keratinocyte growth factor-1 polypeptide is expressed in the skin cells having cosmetic function to enhance or maintain a biochemical or physiological process or both that has a positive effect on cosmetic appearance.

2. The method of claim 1, wherein the polynucleotide comprises at least one sequence selected from the group consisting of: (i) nucleotides 446 to 1030 of SEQ ID NO: 24; (ii) a sequence that is at least 90% identical to nucleotides 446 to 1030 of SEQ ID NO: 24; and (iii) a polynucleotide that encodes a protein having the sequence of SEQ ID NO: 23.

3. The method of claim 1, wherein the polynucleotide is maintained as a extrachromosomal plasmid.

4. The method of claim 1, wherein the polynucleotide is operably linked to a constitutive or an inducible promoter.

5. The method of claim 4, wherein the promoter is not ubiquitously expressed, but is expressed in the cells having cosmetic function.

6. The method of claim 1, wherein the polynucleotide is operably linked to an enhancer.

7. The method of claim 1, wherein the polynucleotide is operably linked to at least one of a functional poly A sequence, an intron, a cleavage sequence, a stop sequence, and a cap site.

8. The method of claim 1, wherein the polynucleotide is introduced as naked DNA into the cells having a cosmetic function.

9. The method of claim 1, wherein the polynucleotide is introduced into the cells having a cosmetic function via at least one of liposomes, nanoparticles, an emulsion, a thixogel, and an organoleptic gel.

10. The method of claim 1, wherein the polynucleotide is introduced into the cells having a cosmetic function via a water-in-oil emulsion or an oil-in-water emulsion.

11. The method of claim 1, wherein the polynucleotide is introduced into the cells having a cosmetic function via at least one of particle mediated transfer, voltage driven transfer, radio frequency ablation-mediated transfer, ultrasound, and microneedles.

12. The method of claim 1, wherein the plasmid comprising the isolated polynucleotide is topically administered in a composition comprising TE buffer, glycerin, and hydroxypropyl methylcellulose.

13. The method of claim 12, wherein the composition further comprises propylene glycol.

* * * * *

SEQUENCE LISTING

```
<160> NUMBER OF SEQ ID NOS: 24

<210> SEQ ID NO 1
<211> LENGTH: 5921
<212> TYPE: DNA
<213> ORGANISM: Homo sapiens

<400> SEQUENCE: 1
agcagacggg agtttctcct cggggtcgga gcaggaggca cgcggagtgt gaggccacgc      60
atgagcggac gctaaccccc tccccagcca caaagagtct acatgtctag ggtctagaca     120
tgttcagctt tgtggacctc cggctcctgc tcctcttagc ggccaccgcc ctcctgacgc     180
acggccaaga ggaaggccaa gtcgagggcc aagacgaaga catcccacca atcacctgcg     240
tacagaacgg cctcaggtac catgaccgag acgtgtggaa acccgagccc tgccggatct     300
gcgtctgcga caacggcaag gtgttgtgcg atgacgtgat ctgtgacgag accaagaact     360
gccccggcgc cgaagtcccc gagggcgagt gctgtcccgt ctgccccgac ggctcagagt     420
cacccaccga ccaagaaacc accggcgtcg agggacccaa gggagacact ggcccccgag     480
gcccaagggg acccgcaggc ccccctggcc gagatggcat ccctggacag cctggacttc     540
ccggaccccc cggaccccccc ggacctcccg gacccccctgg cctcggagga aactttgctc     600
cccagctgtc ttatggctat gatgagaaat caaccggagg aatttccgtg cctggcccca     660
tgggtcccct tggtcctcgt ggtctccctg gccccccctg tgcacctggt ccccaaggct     720
tccaaggtcc ccctggtgag cctggcgagc ctggagcttc aggtcccatg ggtccccgag     780
gtcccccagg tccccctgga aagaatggag atgatgggga agctggaaaa cctggtcgtc     840
ctggtgagcg tgggcctcct gggcctcagg gtgctcgagg attgccgga acagctggcc     900 tccctggaat gaagggacac agaggtttca gtggtttgga tggtgccaag ggagatgctg     960
gtcctgctgg tcctaagggt gagcctggca gccctggtga aaatggagct cctggtcaga    1020
tgggcccccg tggcctgcct ggtgagagag gtcgccctgg agccctggc cctgctggtg    1080 ctcgtggaaa tgatggtgct actggtgctg ccgggcccccc tggtcccacc ggccccgctg    1140
gtcctcctgg cttccctggt gctgttggtg ctaagggtga agctggtccc caagggcccc    1200
gaggctctga aggtccccag ggtgtgcgtg gtgagcctgg ccccccctggc cctgctggtg    1260 ctgctggccc tgctggaaac cctggtgctg atggacagcc tggtgctaaa ggtgccaatg    1320
gtgctcctgg tattgctggt gctcctggct tccctggtgc ccgaggcccc tctggacccc    1380
agggcccccg cggccctcct ggtcccaagg gtaacagcgg tgaacctggt gctcctggca    1440
gcaaaggaga cactggtgct aagggagagc ctggccctgt tggtgttcaa ggaccccctg    1500
gccctgctgg agaggaagga aagcgaggag ctcgaggtga acccggaccc actggcctgc    1560 ccggacccc tggcgagcgt ggtggacctg gtagccgtgg tttccctggc gcagatggtt    1620
ttgctggtcc caagggtccc gctggtgaac gtggttctcc tggcccccgct ggccccaaag    1680
```

```
gatctcctgg tgaagctggt cgtcccggtg aagctggtct gcctggtgcc aagggtctga   1740
ctggaagccc tggcagccct ggtcctgatg gcaaaactgg ccccctggt cccgccggtc    1800 aagatggtcg ccccggaccc ccaggcccac ctggtgcccg tggtcaggct ggtgtgatgg   1860
gattccctgg acctaaaggt gctgctggag agcccggcaa ggctggagag cgaggtgttc   1920
ccggaccccc tggcgctgtc ggtcctgctg gcaaagatgg agaggctgga gctcagggac   1980
cccctggccc tgctggtccc gctggcgaga gaggtgaaca aggccctgct ggctccccg    2040 gattccaggg tctccctggt cctgctggtc ctccaggtga agcaggcaaa cctggtgaac   2100
agggtgttcc tggagacctt ggcgcccctg gcccctctgg agcaagaggc gagagaggtt   2160
tccctggcga gcgtggtgtg caaggtcccc ctggtcctgc tggaccccga ggggccaacg   2220
gtgctcccgg caacgatggt gctaagggtg atgctggtgc ccctggagct cccggtagcc   2280
agggcgcccc tggccttcag ggaatgcctg gtgaacgtgg tgcagctggt cttccagggc   2340
ctaagggtga cagaggtgat gctggtccca aggtgctga tggctctcct ggcaaagatg    2400
gcgtccgtgg tctgaccggc cccattggtc ctcctggccc tgctggtgcc cctggtgaca   2460
agggtgaaag tggtcccagc ggccctgctg gtcccactgg agctcgtggt gcccccggag   2520
accgtggtga gcctggtccc cccggccctg ctggctttgc tggcccccct ggtgctgacg   2580
gccaacctgg tgctaaaggc gaacctggtg atgctggtgc caaggcgat gctggtcccc    2640 ctgggcctgc cggacccgct ggaccccctg gccccattgg taatgttggt gctcctggag   2700
ccaaaggtgc tcgcggcagc gctggtcccc ctggtgctac tggtttccct ggtgctgctg   2760
gccgagtcgg tcctcctggc ccctctggaa atgctggacc cctggcct ctggtcctg     2820 ctggcaaaga aggcggcaaa ggtccccgtg gtgagactgg ccctgctgga cgtcctggtg   2880
aagttggtcc cctggtccc cctggccctg ctggcgagaa aggatcccct ggtgctgatg    2940
gtcctgctgg tgctcctggt actccgggc ctcaaggtat gctggacag cgtggtgtgg    3000 tcggcctgcc tggtcagaga ggagagagag gcttccctgg tcttcctggc cctctggtg   3060 aacctggcaa acaaggtccc tctggagcaa gtggtgaacg tggtccccc ggtcccatgg    3120 gcccccctgg attggctgga ccccctggtg aatctggacg tgagggggct cctgctgccg   3180
aaggttcccc tggacgagac ggttctcctg gcgccaaggg tgaccgtggt gagaccggcc   3240
ccgctggacc ccctggtgct cctggtgctc ctggtgcccc tggccccgtt ggccctgctg   3300
gcaagagtgg tgatcgtggt gagactggtc ctgctggtcc cgccggtccc gtcggccccg   3360
tcggcgcccg tggccccgcc ggaccccaag gcccccgtgg tgacaagggt gagacaggcg   3420
aacagggcga cagaggcata aagggtcacc gtggcttctc tggcctccag ggtccccctg   3480
gccctcctgg ctctcctggt gaacaaggtc cctctggagc ctctggtcct gctggtcccc   3540
gaggtccccc tggctctgct ggtgctcctg gcaaagatgg actcaacggt ctccctggcc   3600
ccattgggcc cctggtcct cgcggtcgca ctggtgatgc tggtcctgtt ggtccccccg    3660
gccctcctgg acctcctggt cccctggtc ctcccagcgc tggtttcgac ttcagcttcc    3720
tgccccagcc acctcaagag aaggctcacg atggtggccg ctactaccgg gctgatgatg   3780
ccaatgtggt tcgtgaccgt gacctcgagg tggacaccac cctcaagagc ctgagccagc   3840
agatcgagaa catccggagc ccagagggaa gccgcaagaa ccccgcccgc acctgccgtg   3900
acctcaagat gtgccactct gactggaaga gtggagagta ctggattgac cccaaccaag   3960
gctgcaacct ggatgccatc aaagtcttct gcaacatgga gactggtgag acctgcgtgt   4020
```

| | |
|---|---|
| acccccactca gcccagtgtg gcccagaaga actggtacat cagcaagaac cccaaggaca | 4080 |
| agaggcatgt ctggttcggc gagagcatga ccgatggatt ccagttcgag tatggcggcc | 4140 |
| agggctccga ccctgccgat gtggccatcc agctgacctt cctgcgcctg atgtccaccg | 4200 |
| aggcctccca gaacatcacc taccactgca agaacagcgt ggcctacatg gaccagcaga | 4260 |
| ctggcaacct caagaaggcc ctgctcctca agggctccaa cgagatcgag atccgcgccg | 4320 |
| agggcaacag ccgcttcacc tacagcgtca ctgtcgatgg ctgcacgagt cacaccggag | 4380 |
| cctggggcaa gacagtgatt gaatacaaaa ccaccaagtc ctcccgcctg cccatcatcg | 4440 |
| atgtggcccc cttggacgtt ggtgcccag accaggaatt cggcttcgac gttggccctg | 4500 |
| tctgcttcct gtaaactccc tccatcccaa cctggctccc tcccacccaa ccaactttcc | 4560 |
| ccccaacccg gaaacagaca agcaacccaa actgaacccc cccaaaagcc aaaaaatggg | 4620 |
| agacaatttc acatggactt tggaaaatat ttttttcctt tgcattcatc tctcaaactt | 4680 |
| agttttatc tttgaccaac cgaacatgac caaaaaccaa aagtgcattc aaccttacca | 4740 |
| aaaaaaaaaa aaaaaaaaaa agaataaata aataagtttt taaaaaagga agcttggtcc | 4800 |
| acttgcttga agacccatgc gggggtaagt ccctttctgc ccgttgggtt atgaaacccc | 4860 |
| aatgctgccc tttctgctcc tttctccaca cccccccttgg cctcccctcc actccttccc | 4920 |
| aaatctgtct ccccagaaga cacaggaaac aatgtattgt ctgcccagca atcaaaggca | 4980 |
| atgctcaaac acccaagtgg ccccacccct cagcccgctc ctgcccgccc agcaccccca | 5040 |
| ggccctgggg acctgggtt ctcagactgc caaagaagcc ttgccatctg gcgctcccat | 5100 |
| ggctcttgca acatctcccc ttcgtttttg aggggtcat gccggggag ccaccagccc | 5160 |
| ctcactgggt tcggaggaga gtcaggaagg gccacgacaa agcagaaaca tcggatttgg | 5220 |
| ggaacgcgtg tcatcccttg tgccgcaggc tgggcgggag agactgttct gttctgttcc | 5280 |
| ttgtgtaact gtgttgctga aagactacct cgttcttgtc ttgatgtgtc accggggcaa | 5340 |
| ctgcctgggg gcggggatgg gggcagggtg gaagcggctc cccatttta taccaaaggt | 5400 |
| gctacatcta tgtgatgggt ggggtgggga gggaatcact ggtgctatag aaattgagat | 5460 |
| gcccccccag gccagcaaat gttccttttt gttcaaagtc tatttttatt ccttgatatt | 5520 |
| ttttctttct ttttttttt ttttgtggat ggggacttgt gaattttct aaaggtgcta | 5580 |
| tttaacatgg gaggagagcg tgtgcgctcc agcccagccc gctgctcact ttccacccct | 5640 |
| tctccacctg cctctggctt tcaggcctc tgctctccga cctctctcct ctgaaccct | 5700 |
| cctccacagc tgcagcccat cctcccggct ccctcctagt ctgtcctgcg tcctctgtcc | 5760 |
| ccgggtttca gagacaactt cccaaagcac aaagcagttt ttccctaggg gtgggaggaa | 5820 |
| gcaaaagact ctgtacctat tttgtatgtg tataataatt tgagatgttt ttaattattt | 5880 |
| tgattgctgg aataaagcat gtggaaatga cccaaacata a | 5921 |

<210> SEQ ID NO 2
<211> LENGTH: 1464
<212> TYPE: PRT
<213> ORGANISM: Homo sapiens

<400> SEQUENCE: 2

Met Phe Ser Phe Val Asp Leu Arg Leu Leu Leu Leu Leu Ala Ala Thr
1               5                   10                  15

Ala Leu Leu Thr His Gly Gln Glu Glu Gly Gln Val Glu Gly Gln Asp
            20                  25                  30

Glu Asp Ile Pro Pro Ile Thr Cys Val Gln Asn Gly Leu Arg Tyr His

```
            35                  40                  45
Asp Arg Asp Val Trp Lys Pro Glu Pro Cys Arg Ile Cys Val Cys Asp
            50                  55                  60
Asn Gly Lys Val Leu Cys Asp Val Ile Cys Asp Glu Thr Lys Asn
 65                  70                  75                  80
Cys Pro Gly Ala Glu Val Pro Glu Gly Glu Cys Cys Pro Val Cys Pro
                85                  90                  95
Asp Gly Ser Glu Ser Pro Thr Asp Gln Glu Thr Thr Gly Val Glu Gly
                100                 105                 110
Pro Lys Gly Asp Thr Gly Pro Arg Gly Pro Arg Gly Pro Ala Gly Pro
                115                 120                 125
Pro Gly Arg Asp Gly Ile Pro Gly Gln Pro Gly Leu Pro Gly Pro Pro
                130                 135                 140
Gly Pro Pro Gly Pro Pro Gly Pro Pro Gly Leu Gly Gly Asn Phe Ala
145                 150                 155                 160
Pro Gln Leu Ser Tyr Gly Tyr Asp Glu Lys Ser Thr Gly Gly Ile Ser
                165                 170                 175
Val Pro Gly Pro Met Gly Pro Ser Gly Pro Arg Gly Leu Pro Gly Pro
                180                 185                 190
Pro Gly Ala Pro Gly Pro Gln Gly Phe Gln Gly Pro Pro Gly Glu Pro
                195                 200                 205
Gly Glu Pro Gly Ala Ser Gly Pro Met Gly Pro Arg Gly Pro Pro Gly
                210                 215                 220
Pro Pro Gly Lys Asn Gly Asp Asp Gly Glu Ala Gly Lys Pro Gly Arg
225                 230                 235                 240
Pro Gly Glu Arg Gly Pro Pro Gly Pro Gln Gly Ala Arg Gly Leu Pro
                245                 250                 255
Gly Thr Ala Gly Leu Pro Gly Met Lys Gly His Arg Gly Phe Ser Gly
                260                 265                 270
Leu Asp Gly Ala Lys Gly Asp Ala Gly Pro Ala Gly Pro Lys Gly Glu
                275                 280                 285
Pro Gly Ser Pro Gly Glu Asn Gly Ala Pro Gly Gln Met Gly Pro Arg
                290                 295                 300
Gly Leu Pro Gly Glu Arg Gly Arg Pro Gly Ala Pro Gly Pro Ala Gly
305                 310                 315                 320
Ala Arg Gly Asn Asp Gly Ala Thr Gly Ala Ala Gly Pro Pro Gly Pro
                325                 330                 335
Thr Gly Pro Ala Gly Pro Pro Gly Phe Pro Gly Ala Val Gly Ala Lys
                340                 345                 350
Gly Glu Ala Gly Pro Gln Gly Pro Arg Gly Ser Glu Gly Pro Gln Gly
                355                 360                 365
Val Arg Gly Glu Pro Gly Pro Pro Gly Pro Ala Gly Ala Ala Gly Pro
                370                 375                 380
Ala Gly Asn Pro Gly Ala Asp Gly Gln Pro Gly Ala Lys Gly Ala Asn
385                 390                 395                 400
Gly Ala Pro Gly Ile Ala Gly Ala Pro Gly Phe Pro Gly Ala Arg Gly
                405                 410                 415
Pro Ser Gly Pro Gln Gly Pro Gly Pro Pro Gly Pro Lys Gly Asn
                420                 425                 430
Ser Gly Glu Pro Gly Ala Pro Gly Ser Lys Gly Asp Thr Gly Ala Lys
                435                 440                 445
Gly Glu Pro Gly Pro Val Gly Val Gln Gly Pro Pro Gly Pro Ala Gly
                450                 455                 460
```

-continued

```
Glu Glu Gly Lys Arg Gly Ala Arg Gly Glu Pro Gly Pro Thr Gly Leu
465                 470                 475                 480

Pro Gly Pro Pro Gly Glu Arg Gly Gly Pro Gly Ser Arg Gly Phe Pro
                485                 490                 495

Gly Ala Asp Gly Val Ala Gly Pro Lys Gly Pro Ala Gly Glu Arg Gly
            500                 505                 510

Ser Pro Gly Pro Ala Gly Pro Lys Gly Ser Pro Gly Glu Ala Gly Arg
        515                 520                 525

Pro Gly Glu Ala Gly Leu Pro Gly Ala Lys Gly Leu Thr Gly Ser Pro
    530                 535                 540

Gly Ser Pro Gly Pro Asp Gly Lys Thr Gly Pro Pro Gly Pro Ala Gly
545                 550                 555                 560

Gln Asp Gly Arg Pro Gly Pro Pro Gly Pro Pro Gly Ala Arg Gly Gln
                565                 570                 575

Ala Gly Val Met Gly Phe Pro Gly Pro Lys Gly Ala Ala Gly Glu Pro
            580                 585                 590

Gly Lys Ala Gly Glu Arg Gly Val Pro Gly Pro Pro Gly Ala Val Gly
        595                 600                 605

Pro Ala Gly Lys Asp Gly Glu Ala Gly Ala Gln Gly Pro Pro Gly Pro
    610                 615                 620

Ala Gly Pro Ala Gly Glu Arg Gly Glu Gln Gly Pro Ala Gly Ser Pro
625                 630                 635                 640

Gly Phe Gln Gly Leu Pro Gly Pro Ala Gly Pro Pro Gly Glu Ala Gly
                645                 650                 655

Lys Pro Gly Glu Gln Gly Val Pro Gly Asp Leu Gly Ala Pro Gly Pro
            660                 665                 670

Ser Gly Ala Arg Gly Glu Arg Gly Phe Pro Gly Glu Arg Gly Val Gln
        675                 680                 685

Gly Pro Pro Gly Pro Ala Gly Pro Arg Gly Ala Asn Gly Ala Pro Gly
    690                 695                 700

Asn Asp Gly Ala Lys Gly Asp Ala Gly Ala Pro Gly Ala Pro Gly Ser
705                 710                 715                 720

Gln Gly Ala Pro Gly Leu Gln Gly Met Pro Gly Glu Arg Gly Ala Ala
                725                 730                 735

Gly Leu Pro Gly Pro Lys Gly Asp Arg Gly Asp Ala Gly Pro Lys Gly
            740                 745                 750

Ala Asp Gly Ser Pro Gly Lys Asp Gly Val Arg Gly Leu Thr Gly Pro
        755                 760                 765

Ile Gly Pro Pro Gly Pro Ala Gly Ala Pro Gly Asp Lys Gly Glu Ser
    770                 775                 780

Gly Pro Ser Gly Pro Ala Gly Pro Thr Gly Ala Arg Gly Ala Pro Gly
785                 790                 795                 800

Asp Arg Gly Glu Pro Gly Pro Pro Gly Pro Ala Gly Phe Ala Gly Pro
                805                 810                 815

Pro Gly Ala Asp Gly Gln Pro Gly Ala Lys Gly Glu Pro Gly Asp Ala
            820                 825                 830

Gly Ala Lys Gly Asp Ala Gly Pro Pro Gly Pro Ala Gly Pro Ala Gly
        835                 840                 845

Pro Pro Gly Pro Ile Gly Asn Val Gly Ala Pro Gly Ala Lys Gly Ala
    850                 855                 860

Arg Gly Ser Ala Gly Pro Pro Gly Ala Thr Gly Phe Pro Gly Ala Ala
865                 870                 875                 880
```

```
Gly Arg Val Gly Pro Pro Gly Ser Gly Asn Ala Gly Pro Pro Gly
            885                 890                 895

Pro Pro Gly Pro Ala Gly Lys Glu Gly Gly Lys Gly Pro Arg Gly Glu
        900                 905                 910

Thr Gly Pro Ala Gly Arg Pro Gly Glu Val Gly Pro Pro Gly Pro Pro
        915                 920                 925

Gly Pro Ala Gly Glu Lys Gly Ser Pro Gly Ala Asp Gly Pro Ala Gly
        930                 935                 940

Ala Pro Gly Thr Pro Gly Pro Gln Gly Ile Ala Gly Gln Arg Gly Val
945                 950                 955                 960

Val Gly Leu Pro Gly Gln Arg Gly Glu Arg Gly Phe Pro Gly Leu Pro
        965                 970                 975

Gly Pro Ser Gly Glu Pro Gly Lys Gln Gly Pro Ser Gly Ala Ser Gly
        980                 985                 990

Glu Arg Gly Pro Pro Gly Pro Met Gly Pro Pro Gly Leu Ala Gly Pro
        995                 1000                1005

Pro Gly Glu Ser Gly Arg Glu Gly Ala Pro Ala Glu Gly Ser
    1010                1015                1020

Pro Gly Arg Asp Gly Ser Pro Gly Ala Lys Gly Asp Arg Gly Glu
    1025                1030                1035

Thr Gly Pro Ala Gly Pro Pro Gly Ala Pro Gly Ala Pro Gly Ala
    1040                1045                1050

Pro Gly Pro Val Gly Pro Ala Gly Lys Ser Gly Asp Arg Gly Glu
    1055                1060                1065

Thr Gly Pro Ala Gly Pro Ala Gly Pro Val Gly Pro Val Gly Ala
    1070                1075                1080

Arg Gly Pro Ala Gly Pro Gln Gly Pro Arg Gly Asp Lys Gly Glu
    1085                1090                1095

Thr Gly Glu Gln Gly Asp Arg Gly Ile Lys Gly His Arg Gly Phe
    1100                1105                1110

Ser Gly Leu Gln Gly Pro Pro Gly Pro Pro Gly Ser Pro Gly Glu
    1115                1120                1125

Gln Gly Pro Ser Gly Ala Ser Gly Pro Ala Gly Pro Arg Gly Pro
    1130                1135                1140

Pro Gly Ser Ala Gly Ala Pro Gly Lys Asp Gly Leu Asn Gly Leu
    1145                1150                1155

Pro Gly Pro Ile Gly Pro Pro Gly Pro Arg Gly Arg Thr Gly Asp
    1160                1165                1170

Ala Gly Pro Val Gly Pro Pro Gly Pro Pro Gly Pro Pro Gly Pro
    1175                1180                1185

Pro Gly Pro Pro Ser Ala Gly Phe Asp Phe Ser Phe Leu Pro Gln
    1190                1195                1200

Pro Pro Gln Glu Lys Ala His Asp Gly Gly Arg Tyr Tyr Arg Ala
    1205                1210                1215

Asp Asp Ala Asn Val Val Arg Asp Arg Asp Leu Glu Val Asp Thr
    1220                1225                1230

Thr Leu Lys Ser Leu Ser Gln Gln Ile Glu Asn Ile Arg Ser Pro
    1235                1240                1245

Glu Gly Ser Arg Lys Asn Pro Ala Arg Thr Cys Arg Asp Leu Lys
    1250                1255                1260

Met Cys His Ser Asp Trp Lys Ser Gly Glu Tyr Trp Ile Asp Pro
    1265                1270                1275

Asn Gln Gly Cys Asn Leu Asp Ala Ile Lys Val Phe Cys Asn Met
```

```
                       1280              1285              1290
Glu Thr Gly Glu Thr Cys Val Tyr Pro Thr Gln Pro Ser Val Ala
           1295              1300              1305
Gln Lys Asn Trp Tyr Ile Ser Lys Asn Pro Lys Asp Lys Arg His
       1310              1315              1320
Val Trp Phe Gly Glu Ser Met Thr Asp Gly Phe Gln Phe Glu Tyr
   1325              1330              1335
Gly Gly Gln Gly Ser Asp Pro Ala Asp Val Ala Ile Gln Leu Thr
   1340              1345              1350
Phe Leu Arg Leu Met Ser Thr Glu Ala Ser Gln Asn Ile Thr Tyr
   1355              1360              1365
His Cys Lys Asn Ser Val Ala Tyr Met Asp Gln Gln Thr Gly Asn
   1370              1375              1380
Leu Lys Lys Ala Leu Leu Leu Lys Gly Ser Asn Glu Ile Glu Ile
   1385              1390              1395
Arg Ala Glu Gly Asn Ser Arg Phe Thr Tyr Ser Val Thr Val Asp
   1400              1405              1410
Gly Cys Thr Ser His Thr Gly Ala Trp Gly Lys Thr Val Ile Glu
   1415              1420              1425
Tyr Lys Thr Thr Lys Ser Ser Arg Leu Pro Ile Ile Asp Val Ala
   1430              1435              1440
Pro Leu Asp Val Gly Ala Pro Asp Gln Glu Phe Gly Phe Asp Val
   1445              1450              1455
Gly Pro Val Cys Phe Leu
   1460
```

<210> SEQ ID NO 3
<211> LENGTH: 50
<212> TYPE: DNA
<213> ORGANISM: Artificial
<220> FEATURE:
<223> OTHER INFORMATION: Artificial sequence = synthetic construct

<400> SEQUENCE: 3
gatcgctagc gccgccacca tgttcagctt tgtggacctc cggctcctgc          50

<210> SEQ ID NO 4
<211> LENGTH: 44
<212> TYPE: DNA
<213> ORGANISM: Artificial
<220> FEATURE:
<223> OTHER INFORMATION: Artificial sequence = synthetic construct

<400> SEQUENCE: 4
cgataagctt ttacaggaag cagacagggc aacgtcgaa gccg                 44

<210> SEQ ID NO 5
<211> LENGTH: 2274
<212> TYPE: DNA
<213> ORGANISM: Homo sapiens

<400> SEQUENCE: 5
atggcgggtc tgacggcggc ggccccgcgg cccggagtcc tcctgctcct gctgtccatc     60
ctccacccct ctcggcctgg agggtccct ggggccattc ctggtggagt tcctggagga    120
gtcttttatc caggggctgg tctcggagcc cttggaggag gagcgctggg gcctggaggc    180
aaacctctta agccagttcc cggagggctt gcgggtgctg gccttggggc agggctcggc    240
gccttccccg cagttaccct tccgggggct ctggtgcctg gtggagtggc tgacgctgct    300

```
gcagcctata aagctgctaa ggctggcgct gggcttggtg gtgtcccagg agttggtggc    360
ttaggagtgt ctgcaggtgc ggtggttcct cagcctggac ccggagtgaa gcctgggaaa    420
gtgccgggtg tggggctgcc aggtgtatac ccaggtggcg tgctcccagg agctcggttc    480
cccggtgtgg gggtgctccc tggagttccc actggagcag gagttaagcc caaggctcca    540
ggtgtaggtg gagcttttgc tggaatccca ggagttggac cctttggggg accgcaacct    600
ggagtcccac tggggtatcc catcaaggcc cccaagctgc ctggtggcta tggactgccc    660
tacaccacag ggaaactgcc ctatggctat gggcccggag gagtggctgg tgcagcgggc    720
aaggctggtt acccaacagg gacaggggtt ggccccccagg cagcagcagc agcggcagct    780
aaagcagcag caaagttcgg tgctggagca gccggagtcc tccctggtgt tggagggggct    840 ggtgttcctg gcgtgcctgg ggcaattcct ggaattggag gcatcgcagg cgttgggact    900
ccagctgcag ctgcagctgc agcagcagcc gctaaggcag ccaagtatgg agctgctgca    960
ggcttagtgc ctggtgggcc aggctttggc ccgggagtag ttggtgtccc aggagctggc   1020
gttccaggtg ttggtgtccc aggagctggg attccagttg tccaggtgc tgggatccca   1080 ggtgctgcgg ttccaggggt tgtgtcacca gaagcagctg ctaaggcagc tgcaaaggca   1140
gccaaatacg gggccaggcc cggagtcgga gttggaggca ttcctactta cggggttgga   1200
gctgggggct ttcccggctt tggtgtcgga gtcggaggta tccctggagt cgcaggtgtc   1260
cctagtgtcg gaggtgttcc cggagtcgga ggtgtcccgg gagttggcat ttcccccgaa   1320
gctcaggcag cagctgccgc caaggctgcc aagtacggag tggggacccc agcagctgca   1380
gctgctaaag cagccgccaa agccgcccag tttgggttag ttcctggtgt cggcgtggct   1440
cctggagttg gcgtggctcc tggtgtcggt gtggctcctg gagttggctt ggctcctgga   1500
gttggcgtgg ctcctggagt tggtgtggct cctggcgttg gcgtggctcc cggcattggc   1560
cctggtggag ttgcagctgc agcaaaatcc gctgccaagg tggctgccaa agcccagctc   1620
cgagctgcag ctgggcttgg tgctggcatc cctggacttg gagttggtgt cggcgtccct   1680
ggacttggag ttggtgctgg tgttcctgga cttggagttg gtgctggtgt tcctggcttc   1740
ggggcaggtg cagatgaggg agttaggcgg agcctgtccc ctgagctcag ggaaggagat   1800
ccctcctcct ctcagcacct ccccagcacc ccctcatcac ccagggtacc tggagccctg   1860
gctgccgcta aagcagccaa atatggagca gcagtgcctg gggtccttgg agggctcggg   1920
gctctcggtg gagtaggcat cccaggcggt gtggtgggag ccggacccgc cgccgccgct   1980
gccgcagcca aagctgctgc caaagccgcc cagtttggcc tagtgggagc cgctgggctc   2040
ggaggactcg gagtcggagg gcttggagtt ccaggtgttg gggccttgg aggtataacct   2100 ccagctgcag ccgctaaagc agctaaatac ggtgctgctg gccttggagg tgtcctaggg   2160
ggtgccgggc agttcccact tggaggagtg gcagcaagac ctggcttcgg attgtctccc   2220
attttcccag gtggggcctg cctggggaaa gcttgtggcc ggaagagaaa atga         2274
```

<210> SEQ ID NO 6
<211> LENGTH: 757
<212> TYPE: PRT
<213> ORGANISM: Homo sapiens

<400> SEQUENCE: 6

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Gly Val Pro Gly Ala

```
                20              25              30
Ile Pro Gly Gly Val Pro Gly Gly Val Phe Tyr Pro Gly Ala Gly Leu
                35              40              45
Gly Ala Leu Gly Gly Gly Ala Leu Gly Pro Gly Gly Lys Pro Leu Lys
        50              55              60
Pro Val Pro Gly Gly Leu Ala Gly Ala Gly Leu Gly Ala Gly Leu Gly
65              70              75              80
Ala Phe Pro Ala Val Thr Phe Pro Gly Ala Leu Val Pro Gly Gly Val
                85              90              95
Ala Asp Ala Ala Ala Ala Tyr Lys Ala Ala Lys Ala Gly Ala Gly Leu
            100             105             110
Gly Gly Val Pro Gly Val Gly Gly Leu Gly Val Ser Ala Gly Ala Val
            115             120             125
Val Pro Gln Pro Gly Ala Gly Val Lys Pro Gly Lys Val Pro Gly Val
            130             135             140
Gly Leu Pro Gly Val Tyr Pro Gly Gly Val Leu Pro Gly Ala Arg Phe
145             150             155             160
Pro Gly Val Gly Val Leu Pro Gly Val Pro Thr Gly Ala Gly Val Lys
                165             170             175
Pro Lys Ala Pro Gly Val Gly Gly Ala Phe Ala Gly Ile Pro Gly Val
            180             185             190
Gly Pro Phe Gly Gly Pro Gln Pro Gly Val Pro Leu Gly Tyr Pro Ile
            195             200             205
Lys Ala Pro Lys Leu Pro Gly Gly Tyr Gly Leu Pro Tyr Thr Thr Gly
            210             215             220
Lys Leu Pro Tyr Gly Tyr Gly Pro Gly Gly Val Ala Gly Ala Ala Gly
225             230             235             240
Lys Ala Gly Tyr Pro Thr Gly Thr Gly Val Gly Pro Gln Ala Ala Ala
            245             250             255
Ala Ala Ala Ala Lys Ala Ala Lys Phe Gly Ala Gly Ala Ala Gly
            260             265             270
Val Leu Pro Gly Val Gly Gly Ala Gly Val Pro Gly Val Pro Gly Ala
            275             280             285
Ile Pro Gly Ile Gly Gly Ile Ala Gly Val Gly Thr Pro Ala Ala Ala
            290             295             300
Ala Ala Ala Ala Ala Ala Ala Lys Ala Ala Lys Tyr Gly Ala Ala Ala
305             310             315             320
Gly Leu Val Pro Gly Gly Pro Gly Phe Gly Pro Gly Val Val Gly Val
                325             330             335
Pro Gly Ala Gly Val Pro Gly Val Gly Val Pro Gly Ala Gly Ile Pro
            340             345             350
Val Val Pro Gly Ala Gly Ile Pro Gly Ala Ala Val Pro Gly Val Val
            355             360             365
Ser Pro Glu Ala Ala Ala Lys Ala Ala Ala Lys Ala Ala Lys Tyr Gly
            370             375             380
Ala Arg Pro Gly Val Gly Val Gly Gly Ile Pro Thr Tyr Gly Val Gly
385             390             395             400
Ala Gly Gly Phe Pro Gly Phe Gly Val Gly Val Gly Gly Ile Pro Gly
            405             410             415
Val Ala Gly Val Pro Ser Val Gly Gly Val Pro Gly Val Gly Gly Val
            420             425             430
Pro Gly Val Gly Ile Ser Pro Glu Ala Gln Ala Ala Ala Ala Ala Lys
            435             440             445
```

```
Ala Ala Lys Tyr Gly Val Gly Thr Pro Ala Ala Ala Lys Ala
            450                 455                 460

Ala Ala Lys Ala Ala Gln Phe Gly Leu Val Pro Gly Val Gly Val Ala
465                 470                 475                 480

Pro Gly Val Gly Val Ala Pro Gly Val Gly Val Ala Pro Gly Val Gly
                485                 490                 495

Leu Ala Pro Gly Val Gly Val Ala Pro Gly Val Gly Val Ala Pro Gly
                500                 505                 510

Val Gly Val Ala Pro Gly Ile Gly Pro Gly Gly Val Ala Ala Ala
            515                 520                 525

Lys Ser Ala Ala Lys Val Ala Ala Lys Ala Gln Leu Arg Ala Ala
            530                 535                 540

Gly Leu Gly Ala Gly Ile Pro Gly Leu Gly Val Gly Val Gly Val Pro
545                 550                 555                 560

Gly Leu Gly Val Gly Ala Gly Val Pro Gly Leu Gly Val Gly Ala Gly
                565                 570                 575

Val Pro Gly Phe Gly Ala Gly Ala Asp Glu Gly Val Arg Arg Ser Leu
                580                 585                 590

Ser Pro Glu Leu Arg Glu Gly Asp Pro Ser Ser Gln His Leu Pro
            595                 600                 605

Ser Thr Pro Ser Ser Pro Arg Val Pro Gly Ala Leu Ala Ala Lys
            610                 615                 620

Ala Ala Lys Tyr Gly Ala Ala Val Pro Gly Val Leu Gly Gly Leu Gly
625                 630                 635                 640

Ala Leu Gly Gly Val Gly Ile Pro Gly Gly Val Val Gly Ala Gly Pro
                645                 650                 655

Ala Ala Ala Ala Ala Ala Lys Ala Ala Lys Ala Ala Gln Phe
            660                 665                 670

Gly Leu Val Gly Ala Ala Gly Leu Gly Gly Leu Gly Val Gly Gly Leu
                675                 680                 685

Gly Val Pro Gly Val Gly Gly Leu Gly Gly Ile Pro Pro Ala Ala Ala
690                 695                 700

Ala Lys Ala Ala Lys Tyr Gly Ala Ala Gly Leu Gly Gly Val Leu Gly
705                 710                 715                 720

Gly Ala Gly Gln Phe Pro Leu Gly Gly Val Ala Ala Arg Pro Gly Phe
                725                 730                 735

Gly Leu Ser Pro Ile Phe Pro Gly Gly Ala Cys Leu Gly Lys Ala Cys
                740                 745                 750

Gly Arg Lys Arg Lys
            755

<210> SEQ ID NO 7
<211> LENGTH: 49
<212> TYPE: DNA
<213> ORGANISM: Artificial
<220> FEATURE:
<223> OTHER INFORMATION: Artificial sequence = synthetic construct

<400> SEQUENCE: 7
gatcgctagc gccgccacca tggcgggtct gacggcggcg gccccgcgg              49

<210> SEQ ID NO 8
<211> LENGTH: 44
<212> TYPE: DNA
<213> ORGANISM: Artificial
<220> FEATURE:
```

<223> OTHER INFORMATION: Artificial sequence = synthetic construct

<400> SEQUENCE: 8

| | |
|---|---|
| gctaagatct tcattttctc ttccggccac aagctttccc cagg | 44 |

<210> SEQ ID NO 9
<211> LENGTH: 1984
<212> TYPE: DNA
<213> ORGANISM: Homo sapiens

<400> SEQUENCE: 9

| | |
|---|---|
| ggatccagag atttagattt tttataagct ttcctgccac cgaaacgggt gtttgggacc | 60 |
| tcacgaggcc ctgttcattc ttcgtcgctg cgctccccac tctgtactgg atgcatttac | 120 |
| tgacgttgtt gtctccgtcc ccagagtatg aaccccaag gtgactcatg cagctgtggg | 180 |
| tgcccggcat acagcatggt gactggaatg gatgagcacc caataaacat tgttgcagg | 240 |
| aatgcaggag gacgggcagg ccagcaagca ggctgcctgg tttttccac atgggctttt | 300 |
| ctgggaaaga agagcttcta ttttttggaaa gggctgctat gattgagaaa agttcatggc | 360 |
| agcaaaaaaa ggacagacgt cgggagggaa acactcctag ttctcccaga caacacattt | 420 |
| tttaaaaaga ctccttcatc tctttaataa taacggtaac gacaatgaca atgatgatta | 480 |
| cttatgagtg cggctagtgc cagccactgt gttgtcactg ggcgagtaat gatctcattg | 540 |
| gatcttcacg gtgggcgtgc ggggctccag ggacagcctg cgttcctggg ctggctgggt | 600 |
| gcagctctct tttcaggaga gaaagctctc ttggaggagc tggaaaggtg cccgactcca | 660 |
| gccatgctgg cgctactgtg ttcctgcctg ctcctggcag ccggtgcctc ggacgcctgg | 720 |
| acgggcgagg actcggcgga gcccaactct gactcggcgg agtggatccg agacatgtac | 780 |
| gccaaggtca cggagatctg gcaggaggtc atgcagcggc gggacgacga cggcacgctc | 840 |
| cacgccgcct gccaggtgca gccgtcggcc acgctggacg ccgcgcagcc ccgggtgacc | 900 |
| ggcgtcgtcc tcttccggca gcttgcgccc gcgccaagc tcgacgcctt cttcgccctg | 960 |
| gagggcttcc cgaccgagcc gaacagctcc agccgcgcca tccacgtgca ccagttcggg | 1020 |
| gacctgagcc agggctgcga gtccaccggg cccactaca acccgctggc cgtgccgcac | 1080 |
| ccgcagcacc cgggcgactt cggcaacttc gcggtccgcg acggcagcct ctggaggtac | 1140 |
| cgcgccggcc tggccgcctc gctcgcgggc ccgcactcca tcgtgggccg ggccgtggtc | 1200 |
| gtccacgctg gcgaggacga cctgggccgc ggcggcaacc aggccagcgt ggagaacggg | 1260 |
| aacgcgggcc ggcggctggc ctgctgcgtg gtgggcgtgt gcgggcccgg gctctgggag | 1320 |
| cgccaggcgc gggagcactc agagcgcaag aagcggcggc gcgagagcga gtgcaaggcc | 1380 |
| gcctgagcgc ggcccccacc cggcggcggc cagggacccc cgaggccccc ctctgccttt | 1440 |
| gagcttctcc tctgctccaa cagacacctt ccactctgag gtctcacctt cgcctctgct | 1500 |
| gaagtctccc cgcagccctc tccacccaga ggtctcccta taccgagacc caccatcctt | 1560 |
| ccatcctgag gaccgcccca accctcggag ccccccactc agtaggtctg aaggcctcca | 1620 |
| tttgtaccga aacacccgc tcacgctgac agcctcctag gctccctgag gtaccttccc | 1680 |
| acccagaccc tccttcccca ccccataagc cctgagactc ccgcctttga cctgacgatc | 1740 |
| ttccccttc ccgccttcag gttcctccta ggcgctcaga ggcgctctg gggggttgcc | 1800 |
| tcgagtcccc ccaccctcc ccaccacca ccgctcccgc ggcaagccag cccgtgcaac | 1860 |
| ggaagccagg ccaactgccc cgcgtcttca gctgtttcgc atccaccgcc accccactga | 1920 |
| gagctgctcc tttgggggaa tgtttggcaa cctttgtgtt acagattaaa aattcagcaa | 1980 | ttca                                                                                    1984

<210> SEQ ID NO 10
<211> LENGTH: 240
<212> TYPE: PRT
<213> ORGANISM: Homo sapiens

<400> SEQUENCE: 10

Met Leu Ala Leu Leu Cys Ser Cys Leu Leu Ala Ala Gly Ala Ser
1               5                   10                  15

Asp Ala Trp Thr Gly Glu Asp Ser Ala Glu Pro Asn Ser Asp Ser Ala
            20                  25                  30

Glu Trp Ile Arg Asp Met Tyr Ala Lys Val Thr Glu Ile Trp Gln Glu
                35                  40                  45

Val Met Gln Arg Arg Asp Asp Gly Thr Leu His Ala Ala Cys Gln
    50                  55                  60

Val Gln Pro Ser Ala Thr Leu Asp Ala Ala Gln Pro Arg Val Thr Gly
65                  70                  75                  80

Val Val Leu Phe Arg Gln Leu Ala Pro Arg Ala Lys Leu Asp Ala Phe
                85                  90                  95

Phe Ala Leu Glu Gly Phe Pro Thr Glu Pro Asn Ser Ser Arg Ala
                100                 105                 110

Ile His Val His Gln Phe Gly Asp Leu Ser Gln Gly Cys Glu Ser Thr
                115                 120                 125

Gly Pro His Tyr Asn Pro Leu Ala Val Pro His Pro Gln His Pro Gly
                130                 135                 140

Asp Phe Gly Asn Phe Ala Val Arg Asp Gly Ser Leu Trp Arg Tyr Arg
145                 150                 155                 160

Ala Gly Leu Ala Ala Ser Leu Ala Gly Pro His Ser Ile Val Gly Arg
                165                 170                 175

Ala Val Val Val His Ala Gly Glu Asp Asp Leu Gly Arg Gly Asn
                180                 185                 190

Gln Ala Ser Val Glu Asn Gly Asn Ala Gly Arg Arg Leu Ala Cys Cys
                195                 200                 205

Val Val Gly Val Cys Gly Pro Gly Leu Trp Glu Arg Gln Ala Arg Glu
                210                 215                 220

His Ser Glu Arg Lys Lys Arg Arg Arg Glu Ser Glu Cys Lys Ala Ala
225                 230                 235                 240

<210> SEQ ID NO 11
<211> LENGTH: 56
<212> TYPE: DNA
<213> ORGANISM: Artificial
<220> FEATURE:
<223> OTHER INFORMATION: Artificial sequence = synthetic construct

<400> SEQUENCE: 11
gatcgctagc gccgccacca tgctggcgct actgtgttcc tgcctgctcc tggcag      56

<210> SEQ ID NO 12
<211> LENGTH: 46
<212> TYPE: DNA
<213> ORGANISM: Artificial
<220> FEATURE:
<223> OTHER INFORMATION: Artificial sequence = synthetic construct

<400> SEQUENCE: 12
cgataagctt tcaggcggcc ttgcactcgc tctcgcgccg ccgctt                  46

<210> SEQ ID NO 13
<211> LENGTH: 931
<212> TYPE: DNA
<213> ORGANISM: Homo sapiens

<400> SEQUENCE: 13

```
tttcgtcggc cgcccttg gcttctgcac tgatggtggg tggatgagta atgcatccag      60
gaagcctgga ggcctgtggt ttccgcaccc gctgccaccc ccgcccctag cgtggacatt    120
tatcctctag cgctcaggcc ctgccgccat cgccgcagat ccagcgccca gagagacacc    180
agagaaccca ccatggcccc cttgagccc tggcttctg gcatcctgtt gttgctgtgg      240
ctgatagccc ccagcagggc ctgcacctgt gtcccacccc acccacagac ggccttctgc    300
aattccgacc tcgtcatcag ggccaagttc gtggggacac cagaagtcaa ccagaccacc    360
ttataccagc gttatgagat caagatgacc aagatgtata aagggttcca agccttaggg    420
gatgccgctg acatccggtt cgtctacacc cccgccatgg agagtgtctg cggatacttc    480
cacaggtccc acaaccgcag cgaggagttt ctcattgctg aaaactgca ggatggactc    540
ttgcacatca ctacctgcag ttttgtggct ccctggaaca gcctgagctt agctcagcgc    600
cggggcttca ccaagaccta cactgttggc tgtgaggaat gcacagtgtt ccctgtttta    660
tccatcccct gcaaactgca gagtggcact cattgcttgt ggacggacca gctcctccaa    720
ggctctgaaa agggcttcca gtcccgtcac cttgcctgcc tgcctcggga gccagggctg    780
tgcacctggc agtccctgcg gtcccagata gcctgaatcc tgcccggagt ggaagctgaa    840
gcctgcacag tgtccaccct gttcccactc ccatctttct tccggacaat gaaataaaga    900
gttaccaccc agcagaaaaa aaaaaaaaaa a                                   931
```

<210> SEQ ID NO 14
<211> LENGTH: 207
<212> TYPE: PRT
<213> ORGANISM: Homo sapiens

<400> SEQUENCE: 14

Met Ala Pro Phe Glu Pro Leu Ala Ser Gly Ile Leu Leu Leu Leu Trp
1               5                   10                  15

Leu Ile Ala Pro Ser Arg Ala Cys Thr Cys Val Pro His Pro Gln
            20                  25                  30

Thr Ala Phe Cys Asn Ser Asp Leu Val Ile Arg Ala Lys Phe Val Gly
        35                  40                  45

Thr Pro Glu Val Asn Gln Thr Thr Leu Tyr Gln Arg Tyr Glu Ile Lys
    50                  55                  60

Met Thr Lys Met Tyr Lys Gly Phe Gln Ala Leu Gly Asp Ala Ala Asp
65                  70                  75                  80

Ile Arg Phe Val Tyr Thr Pro Ala Met Glu Ser Val Cys Gly Tyr Phe
                85                  90                  95

His Arg Ser His Asn Arg Ser Glu Glu Phe Leu Ile Ala Gly Lys Leu
            100                 105                 110

Gln Asp Gly Leu Leu His Ile Thr Thr Cys Ser Phe Val Ala Pro Trp
        115                 120                 125

Asn Ser Leu Ser Leu Ala Gln Arg Arg Gly Phe Thr Lys Thr Tyr Thr
    130                 135                 140

Val Gly Cys Glu Glu Cys Thr Val Phe Pro Cys Leu Ser Ile Pro Cys
145                 150                 155                 160

```
Lys Leu Gln Ser Gly Thr His Cys Leu Trp Thr Asp Gln Leu Leu Gln
            165                 170                 175

Gly Ser Glu Lys Gly Phe Gln Ser Arg His Leu Ala Cys Leu Pro Arg
        180                 185                 190

Glu Pro Gly Leu Cys Thr Trp Gln Ser Leu Arg Ser Gln Ile Ala
        195                 200                 205

<210> SEQ ID NO 15
<211> LENGTH: 55
<212> TYPE: DNA
<213> ORGANISM: Artificial
<220> FEATURE:
<223> OTHER INFORMATION: Artificial sequence = synthetic construct

<400> SEQUENCE: 15
gatcgctagc gccgccacca tggccccctt tgagcccctg gcttctggca tcctg        55

<210> SEQ ID NO 16
<211> LENGTH: 46
<212> TYPE: DNA
<213> ORGANISM: Artificial
<220> FEATURE:
<223> OTHER INFORMATION: Artificial sequence = synthetic construct

<400> SEQUENCE: 16
cgataagctt tcaggctatc tgggaccgca gggactgcca ggtgca                  46

<210> SEQ ID NO 17
<211> LENGTH: 4101
<212> TYPE: DNA
<213> ORGANISM: Homo sapiens

<400> SEQUENCE: 17
atgctcagct ttgtggatac gcggactttg ttgctgcttg cagtaacctt atgcctagca     60
acatgccaat ctttacaaga ggaaactgta agaaagggcc cagccggaga tagaggacca    120
cgtggagaaa ggggtccacc aggccccca ggcagagatg gtgaagatgg tcccacaggc    180
cctcctggtc cacctggtcc tcctggcccc cctggtctcg gtgggaactt tgctgctcag    240
tatgatggaa aaggagttgg acttggccct ggaccaatgg gcttaatggg acctagaggc    300
ccacctggtg cagctggagc cccaggccct caaggtttcc aaggacctgc tggtgagcct    360
ggtgaacctg gtcaaactgg tcctgcaggt gctcgtggtc cagctggccc tcctggcaag    420
gctggtgaag atggtcaccc tggaaaaccc ggacgacctg gtgagagagg agttgttgga    480
ccacagggtc tcgtggtttt ccctggaact cctggactc ctggcttcaa aggcattagg    540
ggacacaatg gtctggatgg attgaaggga cagcccggtg ctcctggtgt aagggtgaa    600 cctggtgccc ctggtgaaaa tggaactcca ggtcaaacag agcccgtgg gcttcctggt    660 gagagaggac gtgttggtgc cctggcccca gctggtgccc gtggcagtga tggaagtgtg    720
ggtcccgtgg gtcctgctgg tcccattggg tctgctggcc ctccaggctt cccaggtgcc    780 cctggccccca agggtgaaat tggagctgtt ggtaacgctg gtcctgctgg tcccgccggt    840
ccccgtggtg aagtgggtct tccaggcctc tccggccccg ttggacctcc tggtaatcct    900
ggagcaaacg gccttactgg tgccaagggt gctgctggct tcccggcgt tgctgggct    960 cccggcctcc ctggaccccg cggtattcct ggcccgttg gtgctgccgg tgctactggt   1020
gccagaggac ttgttggtga gcctggtcca gctggctcca aggagagag cggtaacaag   1080 ggtgagcccg gctctgctgg gccccaaggt cctcctggtc ccagtggtga agaaggaaag   1140
```

```
agaggccctα atggggaagc tggatctgcc ggccctccag gacctcctgg gctgagaggt    1200
agtcctggtt ctcgtggtct tcctggagct gatggcagag ctggcgtcat gggccctcct    1260
ggtagtcgtg gtgcaagtgg ccctgctgga gtccgaggac ctaatggaga tgctggtcgc    1320
cctggggagc ctggtctcat gggacccaga ggtcttcctg gttccctgg aaatatcggc     1380
cccgctggaa agaaggtcc tgtcggcctc cctggcatcg acggcaggcc tggcccaatt    1440
ggcccagctg gagcaagagg agagcctggc aacattggat ccctggacc caaaggcccc    1500
actggtgatc ctggcaaaaa cggtgataaa ggtcatgctg gtcttgctgg tgctcggggt    1560
gctccaggtc ctgatggaaa caatggtgct cagggacctc ctggaccaca gggtgttcaa    1620
ggtggaaaag gtgaacaggg tccccctggt cctccaggct tccagggtct gcctggcccc    1680
tcaggtcccg ctggtgaagt tggcaaacca ggagaaaggg gtctccatgg tgagtttggt    1740
ctccctggtc ctgctggtcc aagaggggaa cgcggtcccc caggtgagag tggtgctgcc    1800
ggtcctactg gtcctattgg aagccgaggt ccttctggac ccccagggcc tgatggaaac    1860
aagggtgaac ctggtgtggt tggtgctgtg ggcactgctg gtccatctgg tcctagtgga    1920
ctcccaggag agaggggtgc tgctggcata cctggaggca agggagaaaa gggtgaacct    1980
ggtctcagag gtgaaattgg taaccctggc agagatggtg ctcgtggtgc tcctggtgct    2040
gtaggtgccc ctggtcctgc tggagccaca ggtgaccggg gcgaagctgg ggctgctggt    2100
cctgctggtc ctgctggtcc tcggggaagc cctggtgaac gtggtgaggt cggtcctgct    2160
ggccccaatg gatttgctgg tcctgctggt gctgctggtc aacctggtgc taaaggagaa    2220
agaggagcca agggcctaa gggtgaaaac ggtgttgttg gtcccacagg ccccgttgga    2280
gctgctggcc cagctggtcc aaatggtccc ccggtcctg ctggaagtcg tggtgatgga     2340
ggccccctg gtatgactgg tttccctggt gctgctggac ggactggtcc cccaggaccc    2400
tctggtattt ctggccctcc tggtccccct ggtcctgctg ggaagaagg gcttcgtggt    2460
cctcgtggtg accaaggtcc agttggccga actggagaag taggtgcagt tggtccccct    2520
ggcttcgctg gtgagaaggg tccctctgga gaggctggta ctgctggacc tctggcact    2580
ccaggtcctc agggtcttct tggtgctcct ggtattctgg gtctccctgg ctcgagaggt    2640
gaacgtggtc taccaggtgt tgctggtgct gtgggtaaac ctggtcctct ggcattgcc     2700
ggccctcctg gggcccgtgg tcctcctggt gctgtgggta gtcctggagt caacggtgct    2760
cctggtgaag ctggtcgtga tggcaaccct gggaacgatg gtccccagg tcgcgatggt    2820
caacccggac acaagggaga gcgcggttac cctggcaata ttggtcccgt tggtgctgca    2880
ggtgcacctg gtcctcatgg ccccgtgggt cctgctggca acatggaaa ccgtggtgaa     2940
actggtcctt ctggtcctgt tggtcctgct ggtgctgttg gcccaagagg tcctagtggc    3000
ccacaaggca ttcgtggcga taagggagag ccccggtgaaa aggggcccag aggtcttcct    3060
ggcttaaagg gacacaatgg attgcaaggt ctgcctggta tcgctggtca ccatggtgat    3120
caaggtgctc ctggctccgt gggtcctgct ggtcctaggg gccctgctgg tccttctggc    3180
cctgctggaa agatggtcg cactggacat cctggtacag ttggacctgc tggcattcga    3240
ggccctcagg tcaccaagg ccctgctggc ccccctggtc ccctggccc tcctggacct     3300
ccaggtgtaa gcggtggtgg ttatgacttt ggttacgatg gagacttcta cagggctgac    3360
cagcctcgct cagcaccttc tctcagaccc aaggactatg aagttgatgc tactctgaag    3420
tctctcaaca accagattga gacccttctt actcctgaag ctctagaaa gaacccagct    3480
cgcacatgcc gtgacttgag actcagccac ccagagtgga gcagtggtta ctactggatt    3540
```

-continued

```
gaccctaacc aaggatgcac tatggatgct atcaaagtat actgtgattt ctctactggc    3600
gaaacctgta tccgggccca acctgaaaac atcccagcca gaactggta taggagctcc     3660 aaggacaaga aacacgtctg gctaggagaa actatcaatg ctggcagcca gtttgaatat    3720
aatgtagaag gagtgacttc caaggaaatg gctacccaac ttgccttcat gcgcctgctg    3780
gccaactatg cctctcagaa catcacctac cactgcaaga acagcattgc atacatggat    3840
gaggagactg caacctgaa aaaggctgtc attctacagg gctctaatga tgttgaactt     3900
gttgctgagg caacagcag gttcacttac actgttcttg tagatggctg ctctaaaaag    3960
acaaatgaat ggggaaagac aatcattgaa tacaaaacaa ataagccatc acgcctgccc    4020
ttccttgata ttgcaccttt ggacatcggt ggtgctgacc aggaattctt tgtggacatt    4080
ggcccagtct gtttcaaata a                                              4101
```

<210> SEQ ID NO 18
<211> LENGTH: 1366
<212> TYPE: PRT
<213> ORGANISM: Homo sapiens

<400> SEQUENCE: 18

```
Met Leu Ser Phe Val Asp Thr Arg Thr Leu Leu Leu Ala Val Thr
1               5                   10                  15

Leu Cys Leu Ala Thr Cys Gln Ser Leu Gln Glu Glu Thr Val Arg Lys
            20                  25                  30

Gly Pro Ala Gly Asp Arg Gly Pro Arg Gly Glu Arg Gly Pro Pro Gly
        35                  40                  45

Pro Pro Gly Arg Asp Gly Glu Asp Gly Pro Thr Gly Pro Pro Gly Pro
    50                  55                  60

Pro Gly Pro Pro Gly Pro Gly Leu Gly Gly Asn Phe Ala Ala Gln
65                  70                  75                  80

Tyr Asp Gly Lys Gly Val Gly Leu Gly Pro Gly Pro Met Gly Leu Met
                85                  90                  95

Gly Pro Arg Gly Pro Pro Gly Ala Ala Gly Ala Pro Gly Pro Gln Gly
            100                 105                 110

Phe Gln Gly Pro Ala Gly Glu Pro Gly Glu Pro Gly Gln Thr Gly Pro
        115                 120                 125

Ala Gly Ala Arg Gly Pro Ala Gly Pro Pro Gly Lys Ala Gly Glu Asp
    130                 135                 140

Gly His Pro Gly Lys Pro Gly Arg Pro Gly Glu Arg Gly Val Val Gly
145                 150                 155                 160

Pro Gln Gly Ala Arg Gly Phe Pro Gly Thr Pro Gly Leu Pro Gly Phe
                165                 170                 175

Lys Gly Ile Arg Gly His Asn Gly Leu Asp Gly Leu Lys Gly Gln Pro
            180                 185                 190

Gly Ala Pro Gly Val Lys Gly Glu Pro Gly Ala Pro Gly Glu Asn Gly
        195                 200                 205

Thr Pro Gly Gln Thr Gly Ala Arg Gly Leu Pro Gly Glu Arg Gly Arg
    210                 215                 220

Val Gly Ala Pro Gly Pro Ala Gly Ala Arg Gly Ser Asp Gly Ser Val
225                 230                 235                 240

Gly Pro Val Gly Pro Ala Gly Pro Ile Gly Ser Ala Gly Pro Pro Gly
                245                 250                 255

Phe Pro Gly Ala Pro Gly Pro Lys Gly Glu Ile Gly Ala Val Gly Asn
            260                 265                 270
```

```
Ala Gly Pro Ala Gly Pro Ala Gly Pro Arg Gly Glu Val Gly Leu Pro
        275                 280                 285
Gly Leu Ser Gly Pro Val Gly Pro Pro Gly Asn Pro Gly Ala Asn Gly
        290                 295                 300
Leu Thr Gly Ala Lys Gly Ala Ala Gly Leu Pro Gly Val Ala Gly Ala
305                 310                 315                 320
Pro Gly Leu Pro Gly Pro Arg Gly Ile Pro Gly Pro Val Gly Ala Ala
                325                 330                 335
Gly Ala Thr Gly Ala Arg Gly Leu Val Gly Glu Pro Gly Pro Ala Gly
            340                 345                 350
Ser Lys Gly Glu Ser Gly Asn Lys Gly Glu Pro Gly Ser Ala Gly Pro
        355                 360                 365
Gln Gly Pro Pro Gly Pro Ser Gly Glu Glu Gly Lys Arg Gly Pro Asn
        370                 375                 380
Gly Glu Ala Gly Ser Ala Gly Pro Pro Gly Pro Pro Gly Leu Arg Gly
385                 390                 395                 400
Ser Pro Gly Ser Arg Gly Leu Pro Gly Ala Asp Gly Arg Ala Gly Val
                405                 410                 415
Met Gly Pro Pro Gly Ser Arg Gly Ala Ser Gly Pro Ala Gly Val Arg
            420                 425                 430
Gly Pro Asn Gly Asp Ala Gly Arg Pro Gly Glu Pro Gly Leu Met Gly
        435                 440                 445
Pro Arg Gly Leu Pro Gly Ser Pro Gly Asn Ile Gly Pro Ala Gly Lys
        450                 455                 460
Glu Gly Pro Val Gly Leu Pro Gly Ile Asp Gly Arg Pro Gly Pro Ile
465                 470                 475                 480
Gly Pro Ala Gly Ala Arg Gly Glu Pro Gly Asn Ile Gly Phe Pro Gly
                485                 490                 495
Pro Lys Gly Pro Thr Gly Asp Pro Gly Lys Asn Gly Asp Lys Gly His
            500                 505                 510
Ala Gly Leu Ala Gly Ala Arg Gly Ala Pro Gly Pro Asp Gly Asn Asn
        515                 520                 525
Gly Ala Gln Gly Pro Pro Gly Pro Gln Gly Val Gln Gly Gly Lys Gly
        530                 535                 540
Glu Gln Gly Pro Ala Gly Pro Pro Gly Phe Gln Gly Leu Pro Gly Pro
545                 550                 555                 560
Ser Gly Pro Ala Gly Glu Val Gly Lys Pro Gly Glu Arg Gly Leu His
                565                 570                 575
Gly Glu Phe Gly Leu Pro Gly Pro Ala Gly Pro Arg Gly Glu Arg Gly
            580                 585                 590
Pro Pro Gly Glu Ser Gly Ala Ala Gly Pro Thr Gly Pro Ile Gly Ser
        595                 600                 605
Arg Gly Pro Ser Gly Pro Pro Gly Pro Asp Gly Asn Lys Gly Glu Pro
        610                 615                 620
Gly Val Val Gly Ala Val Gly Thr Ala Gly Pro Ser Gly Pro Ser Gly
625                 630                 635                 640
Leu Pro Gly Glu Arg Gly Ala Ala Gly Ile Pro Gly Gly Lys Gly Glu
                645                 650                 655
Lys Gly Glu Pro Gly Leu Arg Gly Glu Ile Gly Asn Pro Gly Arg Asp
            660                 665                 670
Gly Ala Arg Gly Ala Pro Gly Ala Val Gly Ala Pro Gly Pro Ala Gly
        675                 680                 685
```

-continued

```
Ala Thr Gly Asp Arg Gly Glu Ala Gly Ala Gly Pro Ala Gly Pro
    690                 695                 700
Ala Gly Pro Arg Gly Ser Pro Gly Glu Arg Gly Glu Val Gly Pro Ala
705                 710                 715                 720
Gly Pro Asn Gly Phe Ala Gly Pro Ala Gly Ala Ala Gly Gln Pro Gly
                725                 730                 735
Ala Lys Gly Glu Arg Gly Ala Lys Gly Pro Lys Gly Glu Asn Gly Val
            740                 745                 750
Val Gly Pro Thr Gly Pro Val Gly Ala Ala Gly Pro Ala Gly Pro Asn
        755                 760                 765
Gly Pro Pro Gly Pro Ala Gly Ser Arg Gly Asp Gly Gly Pro Pro Gly
    770                 775                 780
Met Thr Gly Phe Pro Gly Ala Ala Gly Arg Thr Gly Pro Pro Gly Pro
785                 790                 795                 800
Ser Gly Ile Ser Gly Pro Pro Gly Pro Pro Gly Pro Ala Gly Lys Glu
                805                 810                 815
Gly Leu Arg Gly Pro Arg Gly Asp Gln Gly Pro Val Gly Arg Thr Gly
            820                 825                 830
Glu Val Gly Ala Val Gly Pro Pro Gly Phe Ala Gly Glu Lys Gly Pro
        835                 840                 845
Ser Gly Glu Ala Gly Thr Ala Gly Pro Pro Gly Thr Pro Gly Pro Gln
    850                 855                 860
Gly Leu Leu Gly Ala Pro Gly Ile Leu Gly Leu Pro Gly Ser Arg Gly
865                 870                 875                 880
Glu Arg Gly Leu Pro Gly Val Ala Gly Ala Val Gly Glu Pro Gly Pro
                885                 890                 895
Leu Gly Ile Ala Gly Pro Pro Gly Ala Arg Gly Pro Pro Gly Ala Val
            900                 905                 910
Gly Ser Pro Gly Val Asn Gly Ala Pro Gly Glu Ala Gly Arg Asp Gly
        915                 920                 925
Asn Pro Gly Asn Asp Gly Pro Pro Gly Arg Asp Gly Gln Pro Gly His
    930                 935                 940
Lys Gly Glu Arg Gly Tyr Pro Gly Asn Ile Gly Pro Val Gly Ala Ala
945                 950                 955                 960
Gly Ala Pro Gly Pro His Gly Pro Val Gly Pro Ala Gly Lys His Gly
                965                 970                 975
Asn Arg Gly Glu Thr Gly Pro Ser Gly Pro Val Gly Pro Ala Gly Ala
            980                 985                 990
Val Gly Pro Arg Gly Pro Ser Gly Pro Gln Gly Ile Arg Gly Asp Lys
        995                 1000                1005
Gly Glu Pro Gly Glu Lys Gly Pro Arg Gly Leu Pro Gly Leu Lys
    1010                1015                1020
Gly His Asn Gly Leu Gln Gly Leu Pro Gly Ile Ala Gly His His
    1025                1030                1035
Gly Asp Gln Gly Ala Pro Gly Ser Val Gly Pro Ala Gly Pro Arg
    1040                1045                1050
Gly Pro Ala Gly Pro Ser Gly Pro Ala Gly Lys Asp Gly Arg Thr
    1055                1060                1065
Gly His Pro Gly Thr Val Gly Pro Ala Gly Ile Arg Gly Pro Gln
    1070                1075                1080
Gly His Gln Gly Pro Ala Gly Pro Pro Gly Pro Pro Gly Pro Pro
    1085                1090                1095
Gly Pro Pro Gly Val Ser Gly Gly Gly Tyr Asp Phe Gly Tyr Asp
```

```
                   1100                1105                1110

Gly Asp Phe Tyr Arg Ala Asp Gln Pro Arg Ser Ala Pro Ser Leu
    1115                1120                1125

Arg Pro Lys Asp Tyr Glu Val Asp Ala Thr Leu Lys Ser Leu Asn
    1130                1135                1140

Asn Gln Ile Glu Thr Leu Leu Thr Pro Glu Gly Ser Arg Lys Asn
    1145                1150                1155

Pro Ala Arg Thr Cys Arg Asp Leu Arg Leu Ser His Pro Glu Trp
    1160                1165                1170

Ser Ser Gly Tyr Tyr Trp Ile Asp Pro Asn Gln Gly Cys Thr Met
    1175                1180                1185

Asp Ala Ile Lys Val Tyr Cys Asp Phe Ser Thr Gly Glu Thr Cys
    1190                1195                1200

Ile Arg Ala Gln Pro Glu Asn Ile Pro Ala Lys Asn Trp Tyr Arg
    1205                1210                1215

Ser Ser Lys Asp Lys Lys His Val Trp Leu Gly Glu Thr Ile Asn
    1220                1225                1230

Ala Gly Ser Gln Phe Glu Tyr Asn Val Glu Gly Val Thr Ser Lys
    1235                1240                1245

Glu Met Ala Thr Gln Leu Ala Phe Met Arg Leu Leu Ala Asn Tyr
    1250                1255                1260

Ala Ser Gln Asn Ile Thr Tyr His Cys Lys Asn Ser Ile Ala Tyr
    1265                1270                1275

Met Asp Glu Glu Thr Gly Asn Leu Lys Lys Ala Val Ile Leu Gln
    1280                1285                1290

Gly Ser Asn Asp Val Glu Leu Val Ala Glu Gly Asn Ser Arg Phe
    1295                1300                1305

Thr Tyr Thr Val Leu Val Asp Gly Cys Ser Lys Lys Thr Asn Glu
    1310                1315                1320

Trp Gly Lys Thr Ile Ile Glu Tyr Lys Thr Asn Lys Pro Ser Arg
    1325                1330                1335

Leu Pro Phe Leu Asp Ile Ala Pro Leu Asp Ile Gly Gly Ala Asp
    1340                1345                1350

Gln Glu Phe Phe Val Asp Ile Gly Pro Val Cys Phe Lys
    1355                1360                1365

<210> SEQ ID NO 19
<211> LENGTH: 58
<212> TYPE: DNA
<213> ORGANISM: Artificial
<220> FEATURE:
<223> OTHER INFORMATION: Artificial sequence = synthetic construct

<400> SEQUENCE: 19
gatcgctagc gccgccacca tgctcagctt tgtggatacg cggactttgt tgctgctt         58

<210> SEQ ID NO 20
<211> LENGTH: 51
<212> TYPE: DNA
<213> ORGANISM: Artificial
<220> FEATURE:
<223> OTHER INFORMATION: Artificial sequence = synthetic construct

<400> SEQUENCE: 20
cgataagctt ttatttgaaa cagactgggc caatgtccac aaagaattcc t                51

<210> SEQ ID NO 21
```

```
<211> LENGTH: 46
<212> TYPE: DNA
<213> ORGANISM: Artificial Sequence
<220> FEATURE:
<223> OTHER INFORMATION: Artificial sequence = synthetic construct

<400> SEQUENCE: 21
gatcgctagc gccgccacca tgcacaaatg gatactgaca tggatc            46

<210> SEQ ID NO 22
<211> LENGTH: 50
<212> TYPE: DNA
<213> ORGANISM: Artificial Sequence
<220> FEATURE:
<223> OTHER INFORMATION: Artificial sequence = artificial construct

<400> SEQUENCE: 22
cgataagctt ttaagttatt gccataggaa gaaagtgggc tgttttttgt         50

<210> SEQ ID NO 23
<211> LENGTH: 194
<212> TYPE: PRT
<213> ORGANISM: Homo sapiens

<400> SEQUENCE: 23

Met His Lys Trp Ile Leu Thr Trp Ile Leu Pro Thr Leu Leu Tyr Arg
1               5                   10                  15

Ser Cys Phe His Ile Ile Cys Leu Val Gly Thr Ile Ser Leu Ala Cys
            20                  25                  30

Asn Asp Met Thr Pro Glu Gln Met Ala Thr Asn Val Asn Cys Ser Ser
        35                  40                  45

Pro Glu Arg His Thr Arg Ser Tyr Asp Tyr Met Glu Gly Gly Asp Ile
    50                  55                  60

Arg Val Arg Arg Leu Phe Cys Arg Thr Gln Trp Tyr Leu Arg Ile Asp
65                  70                  75                  80

Lys Arg Gly Lys Val Lys Gly Thr Gln Glu Met Lys Asn Asn Tyr Asn
                85                  90                  95

Ile Met Glu Ile Arg Thr Val Ala Val Gly Ile Val Ala Ile Lys Gly
            100                 105                 110

Val Glu Ser Glu Phe Tyr Leu Ala Met Asn Lys Glu Gly Lys Leu Tyr
        115                 120                 125

Ala Lys Lys Glu Cys Asn Glu Asp Cys Asn Phe Lys Glu Leu Ile Leu
    130                 135                 140

Glu Asn His Tyr Asn Thr Tyr Ala Ser Ala Lys Trp Thr His Asn Gly
145                 150                 155                 160

Gly Glu Met Phe Val Ala Leu Asn Gln Lys Gly Ile Pro Val Arg Gly
                165                 170                 175

Lys Lys Thr Lys Lys Glu Gln Lys Thr Ala His Phe Leu Pro Met Ala
            180                 185                 190

Ile Thr

<210> SEQ ID NO 24
<211> LENGTH: 1440
<212> TYPE: DNA
<213> ORGANISM: Homo sapiens

<400> SEQUENCE: 24
acgcgctcac acacagagag aaaatccttc tgcctgttga tttatggaaa caattatgat    60
tctgctggag aacttttcag ctgagaaata gtttgtagct acagtagaaa ggctcaagtt   120
```

```
gcaccaggca gacaacagac atggaattct tatatatcca gctgttagca acaaaacaaa    180
agtcaaatag caaacagcgt cacagcaact gaacttacta cgaactgttt ttatgaggat    240
ttatcaacag agttatttaa ggaggaatcc tgtgttgtta tcaggaacta aaaggataag    300
gctaacaatt tggaaagagc aagtactctt tcttaaatca atctacaatt cacagatagg    360
aagaggtcaa tgacctagga gtaacaatca actcaagatt cattttcatt atgttattca    420
tgaacacccg gagcactaca ctataatgca caaatggata ctgacatgga tcctgccaac    480
tttgctctac agatcatgct ttcacattat ctgtctagtg ggtactatat ctttagcttg    540
caatgacatg actccagagc aaatggctac aaatgtgaac tgttccagcc ctgagcgaca    600
cacaagaagt tatgattaca tggaaggagg ggatataaga gtgagaagac tcttctgtcg    660
aacacagtgg tacctgagga tcgataaaag aggcaaagta aaagggaccc aagagatgaa    720
gaataattac aatatcatgg aaatcaggac agtggcagtt ggaattgtgg caatcaaagg    780
ggtggaaagt gaattctatc ttgcaatgaa caaggaagga aaactctatg caagaaaaga    840
atgcaatgaa gattgtaact tcaaagaact aattctggaa aaccattaca acacatatgc    900
atcagctaaa tggacacaca acggagggga aatgtttgtt gccttaaatc aaaaggggat    960
tcctgtaaga ggaaaaaaaa cgaagaaaga acaaaaaaca gcccactttc ttcctatggc   1020
aataacttaa ttgcatatgg tatataaaga acccagttcc agcagggaga tttcttaag    1080 tggactgttt tctttcttct caaaatttc tttcctttta tttttagta atcaagaaag    1140 gctggaaaaa ctactgaaaa actgatcaag ctggacttgt gcattatgt ttgttttaag    1200 acactgcatt aaagaaagat ttgaaaagta tacacaaaaa tcagatttag taactaaagg    1260
ttgtaaaaaa ttgtaaaact ggttgtacaa tcatgatgtt agtaacagta attttttct    1320 taaattaatt taccctttaag agtatgttag atttgattat ctgataatga ttatttaaat    1380
attcctatct gcttataaaa tggctgctat aataataata atacagatgt tgttatataa    1440
```